US011535849B2

(12) United States Patent
Monia et al.

(10) Patent No.: US 11,535,849 B2
(45) Date of Patent: Dec. 27, 2022

(54) MODULATION OF TRANSTHYRETIN EXPRESSION

(71) Applicant: Ionis Pharmaceuticals, Inc., Carlsbad, CA (US)

(72) Inventors: Brett P. Monia, Encinitas, CA (US); Susan M. Freier, San Diego, CA (US); Andrew M. Siwkowski, Carlsbad, CA (US); Shuling Guo, Carlsbad, CA (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/889,470

(22) Filed: Jun. 1, 2020

(65) Prior Publication Data

US 2021/0095281 A1 Apr. 1, 2021

Related U.S. Application Data

(60) Continuation of application No. 16/229,643, filed on Dec. 21, 2018, now abandoned, which is a continuation of application No. 15/729,860, filed on Oct. 11, 2017, now abandoned, which is a continuation of application No. 15/190,533, filed on Jun. 23, 2016, now Pat. No. 9,816,092, which is a continuation of application No. 14/717,746, filed on May 20, 2015, now Pat. No. 9,399,774, which is a division of application No. 14/184,984, filed on Feb. 20, 2014, now Pat. No. 9,061,044, which is a division of application No. 13/944,786, filed on Jul. 17, 2013, now Pat. No. 8,697,860, which is a continuation of application No. 13/098,303, filed on Apr. 29, 2011, now abandoned.

(60) Provisional application No. 61/405,163, filed on Oct. 20, 2010, provisional application No. 61/329,538, filed on Apr. 29, 2010.

(51) Int. Cl.
C12N 15/113 (2010.01)
A61K 31/712 (2006.01)

(52) U.S. Cl.
CPC .......... *C12N 15/113* (2013.01); *A61K 31/712* (2013.01); *C12N 2310/11* (2013.01); *C12N 2310/14* (2013.01); *C12N 2310/315* (2013.01); *C12N 2310/321* (2013.01); *C12N 2310/3341* (2013.01); *C12N 2310/341* (2013.01); *C12N 2310/52* (2013.01); *C12N 2320/30* (2013.01)

(58) Field of Classification Search
CPC .............. C12N 15/113; C12N 2310/11; C12N 2310/315; C12N 2310/321; C12N 2310/3341; C12N 2310/341
See application file for complete search history.

(56) References Cited

U.S. PATENT DOCUMENTS

| | | |
|---|---|---|
| 3,687,808 A | 8/1972 | Merigan, Jr. et al. |
| 4,426,330 A | 1/1984 | Sears |
| 4,469,863 A | 9/1984 | Ts'o et al. |
| 4,476,301 A | 10/1984 | Imbach et al. |
| 4,534,899 A | 8/1985 | Sears |
| 4,587,044 A | 5/1986 | Miller et al. |
| 4,605,735 A | 8/1986 | Miyoshi et al. |
| 4,667,025 A | 5/1987 | Miyoshi et al. |
| 4,762,779 A | 8/1988 | Snitman |
| 4,789,737 A | 12/1988 | Miyoshi et al. |
| 4,824,941 A | 4/1989 | Gordon et al. |
| 4,828,979 A | 5/1989 | Klevan et al. |
| 4,835,263 A | 5/1989 | Nguyen et al. |
| 4,845,205 A | 7/1989 | Huynh Dinh et al. |
| 4,876,335 A | 10/1989 | Yamane et al. |
| 4,904,582 A | 2/1990 | Tullis |
| 4,948,882 A | 8/1990 | Ruth |
| 4,958,013 A | 9/1990 | Letsinger et al. |
| 4,981,957 A | 1/1991 | Lebleu et al. |
| 5,013,556 A | 5/1991 | Woodle et al. |
| 5,013,830 A | 5/1991 | Ohtsuka et al. |
| 5,023,243 A | 6/1991 | Tullis |
| 5,034,506 A | 7/1991 | Summerton et al. |
| 5,082,830 A | 1/1992 | Brakel et al. |
| 5,108,921 A | 4/1992 | Low et al. |
| 5,109,124 A | 4/1992 | Ramachandran et al. |
| 5,112,963 A | 5/1992 | Pieles et al. |
| 5,118,800 A | 6/1992 | Smith et al. |
| 5,118,802 A | 6/1992 | Smith et al. |
| 5,130,302 A | 7/1992 | Spielvogel et al. |
| 5,134,066 A | 7/1992 | Rogers et al. |
| 5,138,045 A | 8/1992 | Cook et al. |
| 5,149,797 A | 9/1992 | Pederson |
| 5,166,315 A | 11/1992 | Summerton |
| 5,175,273 A | 12/1992 | Bischofberger |
| 5,177,196 A | 1/1993 | Meyer, Jr. et al. |

(Continued)

FOREIGN PATENT DOCUMENTS

| | | |
|---|---|---|
| RU | 2007119777 | 10/2005 |
| WO | WO 1993/007883 | 4/1993 |

(Continued)

OTHER PUBLICATIONS

U.S. Appl. No. 09/315,298, filed May 20, 1999, Teng et al.

(Continued)

*Primary Examiner* — Brian Whiteman

(74) *Attorney, Agent, or Firm* — Knobbe, Martens, Olsen & Bear, LLP

(57) ABSTRACT

Provided herein are methods, compounds, and compositions for reducing expression of transthyretin mRNA and protein in an animal. Such methods, compounds, and compositions are useful to treat, prevent, delay, or ameliorate transthyretin amyloidosis, or a symptom thereof.

10 Claims, No Drawings

Specification includes a Sequence Listing.

(56) References Cited

U.S. PATENT DOCUMENTS

| | | |
|---|---|---|
| 5,177,198 A | 1/1993 | Spielvogel et al. |
| 5,185,444 A | 2/1993 | Summerton et al. |
| 5,188,897 A | 2/1993 | Suhadolnik et al. |
| 5,194,599 A | 3/1993 | Froehler et al. |
| 5,213,804 A | 5/1993 | Martin et al. |
| 5,214,134 A | 5/1993 | Weis et al. |
| 5,214,136 A | 5/1993 | Lin et al. |
| 5,216,141 A | 6/1993 | Benner |
| 5,218,105 A | 6/1993 | Cook et al. |
| 5,220,007 A | 6/1993 | Pederson et al. |
| 5,223,618 A | 6/1993 | Cook et al. |
| 5,227,170 A | 7/1993 | Sullivan |
| 5,235,033 A | 8/1993 | Summerton et al. |
| 5,245,022 A | 9/1993 | Weis et al. |
| 5,254,469 A | 10/1993 | Warren, III et al. |
| 5,256,775 A | 10/1993 | Froehler |
| 5,258,506 A | 11/1993 | Urdea et al. |
| 5,262,536 A | 11/1993 | Hobbs, Jr. |
| 5,264,221 A | 11/1993 | Tagawa et al. |
| 5,264,423 A | 11/1993 | Cohen et al. |
| 5,264,562 A | 11/1993 | Matteucci |
| 5,264,564 A | 11/1993 | Matteucci |
| 5,272,250 A | 12/1993 | Spielvogel et al. |
| 5,276,019 A | 1/1994 | Cohen et al. |
| 5,278,302 A | 1/1994 | Caruthers et al. |
| 5,286,717 A | 2/1994 | Cohen et al. |
| 5,292,873 A | 3/1994 | Rokita et al. |
| 5,317,098 A | 5/1994 | Shizuya et al. |
| 5,319,080 A | 6/1994 | Leumann |
| 5,321,131 A | 6/1994 | Agrawal et al. |
| 5,354,844 A | 10/1994 | Beug et al. |
| 5,356,633 A | 10/1994 | Woodle et al. |
| 5,359,044 A | 10/1994 | Cook et al. |
| 5,366,878 A | 11/1994 | Pederson et al. |
| 5,367,066 A | 11/1994 | Urdea et al. |
| 5,371,241 A | 12/1994 | Brush |
| 5,378,825 A | 1/1995 | Cook et al. |
| 5,386,023 A | 1/1995 | Sanghvi et al. |
| 5,391,723 A | 2/1995 | Priest |
| 5,393,878 A | 2/1995 | Leumann |
| 5,395,619 A | 3/1995 | Zalipsky et al. |
| 5,399,676 A | 3/1995 | Froehler |
| 5,403,711 A | 4/1995 | Walder et al. |
| 5,405,938 A | 4/1995 | Summerton et al. |
| 5,405,939 A | 4/1995 | Suhadolnik et al. |
| 5,414,077 A | 5/1995 | Lin et al. |
| 5,416,016 A | 5/1995 | Low et al. |
| 5,416,203 A | 5/1995 | Letsinger |
| 5,417,978 A | 5/1995 | Tari et al. |
| 5,432,272 A | 7/1995 | Benner |
| 5,434,257 A | 7/1995 | Matteucci et al. |
| 5,446,137 A | 8/1995 | Maag et al. |
| 5,451,463 A | 9/1995 | Nelson et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,127 A | 10/1995 | Felgner et al. |
| 5,459,255 A | 10/1995 | Cook et al. |
| 5,462,854 A | 10/1995 | Coassin et al. |
| 5,466,677 A | 11/1995 | Baxter et al. |
| 5,466,786 A | 11/1995 | Buhr et al. |
| 5,469,854 A | 11/1995 | Unger et al. |
| 5,470,967 A | 11/1995 | Huie et al. |
| 5,476,925 A | 12/1995 | Letsinger et al. |
| 5,484,908 A | 1/1996 | Froehler et al. |
| 5,486,603 A | 1/1996 | Buhr |
| 5,489,677 A | 2/1996 | Sanghvi et al. |
| 5,491,133 A | 2/1996 | Walder et al. |
| 5,502,177 A | 3/1996 | Matteucci et al. |
| 5,508,270 A | 4/1996 | Baxter et al. |
| 5,510,475 A | 4/1996 | Agrawal et al. |
| 5,512,295 A | 4/1996 | Kornberg et al. |
| 5,512,439 A | 4/1996 | Hornes et al. |
| 5,512,667 A | 4/1996 | Reed et al. |
| 5,514,785 A | 5/1996 | Van Ness et al. |
| 5,519,126 A | 5/1996 | Hecht |
| 5,519,134 A | 5/1996 | Acevedo et al. |
| 5,521,291 A | 5/1996 | Curiel et al. |
| 5,525,465 A | 6/1996 | Haralambidis et al. |
| 5,525,711 A | 6/1996 | Hawkins et al. |
| 5,527,528 A | 6/1996 | Allen et al. |
| 5,527,899 A | 6/1996 | Froehler et al. |
| 5,534,259 A | 7/1996 | Zalipsky et al. |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,541,313 A | 7/1996 | Ruth |
| 5,543,152 A | 8/1996 | Webb et al. |
| 5,543,158 A | 8/1996 | Gref et al. |
| 5,545,730 A | 8/1996 | Urdea et al. |
| 5,547,932 A | 8/1996 | Curiel et al. |
| 5,550,111 A | 8/1996 | Suhadolnik et al. |
| 5,552,538 A | 9/1996 | Urdea et al. |
| 5,552,540 A | 9/1996 | Haralambidis |
| 5,556,948 A | 9/1996 | Tagawa et al. |
| 5,561,225 A | 10/1996 | Maddry et al. |
| 5,563,253 A | 10/1996 | Agrawal et al. |
| 5,565,350 A | 10/1996 | Kmiec |
| 5,565,552 A | 10/1996 | Magda et al. |
| 5,565,555 A | 10/1996 | Froehler et al. |
| 5,567,810 A | 10/1996 | Weis et al. |
| 5,567,811 A | 10/1996 | Misiura et al. |
| 5,571,799 A | 11/1996 | Tkachuk et al. |
| 5,574,142 A | 11/1996 | Meyer, Jr. et al. |
| 5,576,427 A | 11/1996 | Cook et al. |
| 5,578,717 A | 11/1996 | Urdea et al. |
| 5,578,718 A | 11/1996 | Cook et al. |
| 5,580,575 A | 12/1996 | Unger et al. |
| 5,580,731 A | 12/1996 | Chang et al. |
| 5,583,020 A | 12/1996 | Sullivan |
| 5,585,481 A | 12/1996 | Arnold, Jr. et al. |
| 5,587,361 A | 12/1996 | Cook et al. |
| 5,587,371 A | 12/1996 | Sessler et al. |
| 5,587,469 A | 12/1996 | Cook et al. |
| 5,591,584 A | 1/1997 | Chang et al. |
| 5,591,721 A | 1/1997 | Agrawal et al. |
| 5,591,722 A | 1/1997 | Montgomery et al. |
| 5,594,121 A | 1/1997 | Froehler et al. |
| 5,595,726 A | 1/1997 | Magda et al. |
| 5,595,756 A | 1/1997 | Bally et al. |
| 5,596,086 A | 1/1997 | Matteucci et al. |
| 5,596,091 A | 1/1997 | Switzer |
| 5,597,696 A | 1/1997 | Linn et al. |
| 5,597,909 A | 1/1997 | Urdea et al. |
| 5,599,923 A | 2/1997 | Sessler et al. |
| 5,599,928 A | 2/1997 | Hemmi et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,623,065 A | 4/1997 | Cook et al. |
| 5,623,070 A | 4/1997 | Cook et al. |
| 5,625,050 A | 4/1997 | Beaton et al. |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,652,355 A | 7/1997 | Metelev et al. |
| 5,652,356 A | 7/1997 | Agrawal |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,681,941 A | 10/1997 | Cook et al. |
| 5,688,941 A | 11/1997 | Cook et al. |
| 5,700,920 A | 12/1997 | Altmann et al. |
| 5,700,922 A | 12/1997 | Cook |

(56) References Cited

U.S. PATENT DOCUMENTS

| | | |
|---|---|---|
| 5,714,331 A | 2/1998 | Buchardt et al. |
| 5,719,262 A | 2/1998 | Buchardt et al. |
| 5,721,218 A | 2/1998 | Froehler |
| 5,744,368 A | 4/1998 | Goldgaber et al. |
| 5,750,692 A | 5/1998 | Cook et al. |
| 5,763,588 A | 6/1998 | Matteucci et al. |
| 5,792,608 A | 8/1998 | Swaminathan et al. |
| 5,792,747 A | 8/1998 | Schally et al. |
| 5,801,154 A | 9/1998 | Baracchini et al. |
| 5,830,653 A | 11/1998 | Froehler et al. |
| 5,951,455 A | 9/1999 | Cowsert |
| 6,005,096 A | 12/1999 | Matteucci et al. |
| 6,040,179 A | 3/2000 | Cowsert |
| 6,143,037 A | 11/2000 | Goldstein et al. |
| 6,165,728 A | 12/2000 | Ward et al. |
| 6,248,720 B1 | 6/2001 | Mathiowitz et al. |
| 6,268,490 B1 | 7/2001 | Imanishi |
| 6,287,860 B1 | 9/2001 | Monia et al. |
| 6,369,209 B1 | 4/2002 | Manoharan |
| 6,383,809 B1 | 5/2002 | Bennett et al. |
| 6,410,324 B1 | 6/2002 | Bennet et al. |
| 6,426,220 B1 | 7/2002 | Bennett et al. |
| 6,468,796 B1 | 10/2002 | Watt |
| 6,525,191 B1 | 2/2003 | Ramasamy |
| 6,582,908 B2 | 6/2003 | Fodor et al. |
| 6,656,730 B1 | 12/2003 | Manoharan |
| 6,670,461 B1 | 12/2003 | Wengel et al. |
| 6,770,748 B2 | 8/2004 | Imanishi et al. |
| 6,794,499 B2 | 9/2004 | Wengel et al. |
| 6,887,906 B1 | 5/2005 | Teng et al. |
| 7,034,133 B2 | 4/2006 | Wengel et al. |
| 7,053,207 B2 | 5/2006 | Wengel |
| 7,078,196 B2 | 7/2006 | Tuschl et al. |
| 7,122,527 B2 | 10/2006 | Yoon et al. |
| 7,205,283 B2 | 4/2007 | Yoon et al. |
| 7,250,496 B2 | 7/2007 | Bentwich |
| 7,399,845 B2 | 7/2008 | Seth et al. |
| 7,547,684 B2 | 6/2009 | Seth et al. |
| 7,655,785 B1 | 2/2010 | Bentwich |
| 7,696,334 B1 | 4/2010 | Bentwich |
| 7,696,342 B1 | 4/2010 | Bentwich |
| 7,696,345 B2 | 4/2010 | Allerson et al. |
| 7,888,497 B2 | 2/2011 | Bentwich et al. |
| 8,090,542 B2 | 1/2012 | Khvorova et al. |
| 8,101,743 B2 | 1/2012 | Brown-Driver et al. |
| 8,168,775 B2 | 5/2012 | Sah et al. |
| 8,697,860 B1 | 4/2014 | Monia et al. |
| 8,741,866 B2 | 6/2014 | Sah et al. |
| 9,061,044 B2 | 6/2015 | Freier et al. |
| 9,234,196 B2 | 1/2016 | Sah et al. |
| 9,399,774 B2 | 7/2016 | Monia et al. |
| 9,399,775 B2 | 7/2016 | Zimmerman et al. |
| 9,816,092 B2 | 11/2017 | Monia et al. |
| 10,208,307 B2 | 2/2019 | Zimmerman et al. |
| 2001/0053519 A1 | 12/2001 | Fodor et al. |
| 2002/0058638 A1 | 5/2002 | Monia et al. |
| 2002/0160394 A1 | 10/2002 | Wu |
| 2003/0004120 A1 | 1/2003 | McKay et al. |
| 2003/0027780 A1 | 2/2003 | Hardee et al. |
| 2003/0143732 A1 | 7/2003 | Fosnaugh et al. |
| 2003/0203862 A1 | 10/2003 | Miraglia et al. |
| 2003/0228597 A1 | 12/2003 | Cowsert et al. |
| 2004/0002153 A1 | 1/2004 | Monia et al. |
| 2004/0009946 A1 | 1/2004 | Lewis et al. |
| 2004/0018176 A1 | 1/2004 | Tolentino et al. |
| 2004/0048249 A1 | 3/2004 | Tang et al. |
| 2004/0115716 A1 | 6/2004 | Freier et al. |
| 2004/0138163 A1 | 7/2004 | McSwiggen et al. |
| 2004/0171570 A1 | 9/2004 | Allerson et al. |
| 2004/0226056 A1 | 11/2004 | Roch et al. |
| 2004/0266707 A1 | 12/2004 | Leake et al. |
| 2005/0038117 A1 | 2/2005 | Kong et al. |
| 2005/0058982 A1 | 3/2005 | Han et al. |
| 2005/0130923 A1 | 6/2005 | Bhat et al. |
| 2005/0244869 A1 | 11/2005 | Brown-Driver et al. |
| 2005/0245475 A1 | 11/2005 | Khorova et al. |
| 2005/0246794 A1 | 11/2005 | Khvorova et al. |
| 2005/0261365 A1 | 11/2005 | Kelly et al. |
| 2006/0003322 A1 | 1/2006 | Bentwich |
| 2007/0031844 A1 | 2/2007 | Khvorova et al. |
| 2007/0207974 A1 | 9/2007 | Khvorova et al. |
| 2007/0299027 A1 | 12/2007 | Hung et al. |
| 2008/0039418 A1 | 2/2008 | Freier et al. |
| 2008/0039618 A1 | 2/2008 | Allerson et al. |
| 2009/0012281 A1 | 1/2009 | Swayze et al. |
| 2009/0092981 A1 | 4/2009 | Swayze et al. |

FOREIGN PATENT DOCUMENTS

| | | |
|---|---|---|
| WO | WO 1994/002499 | 2/1994 |
| WO | WO 1994/017093 | 8/1994 |
| WO | WO 1998/039352 | 9/1998 |
| WO | WO 1999/014226 | 3/1999 |
| WO | WO 2002/029103 | 4/2002 |
| WO | WO 2002/036743 | 5/2002 |
| WO | WO 2002/059621 | 8/2002 |
| WO | WO 2003/004602 | 1/2003 |
| WO | WO 2003/070969 | 8/2003 |
| WO | WO 2004/106356 | 12/2004 |
| WO | WO 2005/021570 | 3/2005 |
| WO | WO 2005/049806 | 6/2005 |
| WO | WO 2006/034348 | 3/2006 |
| WO | WO 2006/048291 | 5/2006 |
| WO | WO 2007/134181 | 11/2007 |
| WO | WO 2008/150729 | 11/2008 |
| WO | WO 2008/154401 | 12/2008 |
| WO | WO 2009/006478 | 1/2009 |
| WO | WO 2009/086539 | 7/2009 |
| WO | WO 2010/000372 | 1/2010 |
| WO | WO 2010/017509 | 2/2010 |
| WO | WO 2010/048228 | 4/2010 |

OTHER PUBLICATIONS

U.S. Appl. No. 60/989,574 filed Nov. 21, 2007, Seth et al.
U.S. Appl. No. 61/026,995, filed Feb. 7, 2008, Bhat et al.
U.S. Appl. No. 61/026,998, filed Feb. 7, 2008, Seth et al.
U.S. Appl. No. 61/056,564, filed May 28, 2008, Seth et al.
U.S. Appl. No. 61/086,231, filed Aug. 5, 2008, Migawa et al.
U.S. Appl. No. 61/097,787, filed Sep. 17, 2008, Seth et al.
U.S. Appl. No. 61/099,844, filed Sep. 24, 2008, Seth et al.
Adamski-Werner et al., "Diflunisal Analogues Stabilize the Native State of Transthyretin. Potent Inhibition of Amyloidogenesis" J. Med. Chem. (2004) 47:355-374.
Albaek et al., "Analogues of a Locked Nucleic Acid wit Three-Carbon 2',4'-Linkages: Synthesis by Ring-Closing Metathesis and Influence on Nucleic Acid Duplex Stability and Structure" J. Org. Chem. (2006) 71:7731-7740.
Altland et al., "Potential treatment of transthyretin-type amyloidoses by sulfite" Neurogenetics (1999) 2:183-188.
Altmann et al., "Second Generation of Antisense Oligonucleotides: From Nuclease Resistance to Biological Efficacy in Animals" Chimia (1996) 50:168-176.
Altmann et al., "Second-generation antisense oligonucleotides: structure-activity relationships and the design of improved signal-transduction inhibitors" Biochem. Soc. Trans. (1996) 24:630-637.
Altmann et al., "Second Generation Antisense Oligonucleotides— Inhibition of PKC-a and c-RAF Kinase Expression by Chimeric Oligonucleotides Incorporating 6'-Substituted Carbocyclic Nucleosides and 2'-O-Ethylene Glycol Substituted Ribonucleosides" Nucleosides Nucleotides (1997) 16(7-9):917-926.
Altschul et al., "Basic local alignment search tool" J. Mol. Biol. (1990) 215(3):403-410.
Amarzguioui et al., "Tolerance for mutations and chemical modifications in a siRNA" Nucleic Acids Research (2003) 31:589-595.
Applicant's arguments filed on Oct. 29, 2007 in U.S. Appl. No. 10/946,498 p. 1-6.
Applicant's arguments in U.S. Appl. No. 12/488,394 p. 1-13 (2011).
Aukunuru et al., "Nanoparticle formulation enhances the delivery and activity of a vascular endothelial growth factor antisense

(56) References Cited

OTHER PUBLICATIONS oligonucleotide in human retinal pigment epithelial cells" J Pharm Pharmacol (2003) 55(9): 1199-1206.
Baker et al., "2'-O-(2-Methoxy)ethyl-modified Anti-intercellular Adhesion Molecule 1 (ICAM-1) Oligonucleotides Selectively Increase the ICAM-1 mRNA Level and Inhibit Formation of the ICAM-1 Translation Initiation Complex in Human Umbilical Vein Endothelial Cells" J. Biol. Chem. (1997) 272(18):11944-12000.
Baker et al., "Discovery and analysis of antisense oligonucleotide activity in cell culture" Methods (2001) 23:191-198.
Beaucage et al., "Deoxynucleoside Phosphoramidites—A New Class of Key Intermediates for Deoxypolynucleotide Synthesis" Tetrahedron Lett. (1981) 22:1859-1862.
Benson et al., Suppression of transthyretin synthesis by antisense oligonucleotides, international Symposium on Amyloidoisis, 10th, Tours, France, Meeting date: Apr. 18-22, 2004, Meeting abstract published in Amyloid and amyloidosis, CRC Press, 2004, pp. 500-502.
Benson et al., "Targeted suppression of an amyloidogenic transthyretin with antisense oligonucleotides" Muscle and Nerve (2006) 33:609-618.
Benson et al., "The molecular biology of clinical features of amyloid neuropathy" Muscle & Nerve (2007) 36(4):411-423.
Blast results for selected nucleotides of TTR (NM_000371)., accessed www.ncbi.nlm.nih.gov/BLAST on May 16, 2008.
Borish et al., "Transthyretin is an Inhibitor of Monocyte and Endothelial Cell Interleukin-1 Production" Inflammation (1992) 16:471-484.
Braasch et al., "Locked nucleic acid (LNA): fine-tuning the recognition of DNA and RNA" Chem. Biol. (2001) 8:1-7.
Branch et al., "A good antisense molecule is hard to find," TIBS (1998) 23:45-50.
Brazma et al., "Gene Expression Data Analysis" FEBS Lett., Minireview, (2000) 480:17-24.
Brouwer et al., "Binding of a Metabolite of 3.4.3',4'-Tetrachlorobiphenyl to Transthyretin Reduces Serum Vitamin A Transport by Inhibiting the Formation of the Protein Complex Carrying Both Retinol and Thyroxin" Toxicol. Appl. Pharmacol. (1986) 85:301-312.
Buxbaum et al., "Transthyretin protects Alzheimer's mice from the behavioral and biochemical effects of Abeta toxicity" PNAS (2008) 105:2681-2686.
Byrom et al., "Visualizing siRNA in Mammalian Cells: Fluorescence Analysis of the RNAi Effect" Ambion TechNotes (2002) vol. 9:30. Accessed http://www.ambion.com/techlib/tn/93/935.html on Jun. 13, 2008. 11 print-out pages.
Carulli et al., "High Throughput Analysis of Differential Gene Expression" J. Cell Biochem. Suppl. (1998) 30/31:286-96.
Celis et al., "Gene expression profiling: monitoring transcription and translation products using DNA microarrays and proteomics" FEBS Lett. (2000) 480:2-16.
Chiang et al., "Antisense Oligonucleotides Inhibit Intercellular Adhesion Molecule 1 Expression by Two Distinct Mechanisms" J. Biol. Chem. (1991) 266:18162-18171.
Chin, "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
Cornwell et al., "Evidence that the Amyloid Fibril Protein in Senile Systemic Amyloidosis is Derived from Normal Prealbumin" Biochem. Biophys. Res. Commun. (1988) 154:648-653.
Costa et al., "Amyloid fibril protein related to prealbumin in familial amyloidotic polyneuropathy" PNAS (1978) 75:4499-4503.
Crooke et al., "Basic Principles of Antisense Therapeutics" Antisense Research and Application (1998) Chapter 1:1-50.
Dahl et al., "A Highly Reactive, Odourless Substitute for Thiophenol/Triethylamine as a Deprotection Reagent in the Synthesis of Oligonucleotides and their Analogues" Acta Chem. Scand. (1990) 44:639-641.

Dean et al., "Antisense oligonucleotide-based therapeutics for cancer" Oncogene (2003) 22:9087-9096.
Dharmacon siDESIGN Cneter Custom siRNA Design Tool, http://www.dharmacon.com/DesignCenter/DesignCenterPage.aspx, the URL accessed on Sep. 18, 2007.
Dickson et al., "Rat Choroid Plexus Specialized in the Synthesis and the Secretion of Transthyretin" J. Biol. Chem. (1986) 261:3475-3478.
Elayadi et al., "Application of PNA and LNA oligomers to chemotherapy" Curr. Opinion Invest. Drugs (2001) 2:558-561.
Elbashir et al., "RNA interference is mediated by 21- and 22-nucleotide RNAs" Genes Dev. (2001) 15:188-200.
Elbashir et al., "Duplexes of 21-nucleotide RNAs mediate RNA interference in cultured mammalian cells" Nature (2001) 411:494-498.
Elbashir et al., Analysis of gene function in somatic mammalian cells using small interfering RNAs (2002) Methods, vol. 26, pp. 199-213.
Englisch et al., "Chemically Modified Oligonucleotides as Probes and Inhibitors" Angewandte Chemie International Edition (1991) 30:613.
Episkopou et al., "Disruption of the transthyretin gene results in mice with depressed levels of plasma retinol and thyroid hormone" PNAS (1993) 90:2375-2379.
Ernstrom et al., "A yellow component associated with human transthyretin has properties like a pterin derivative, 7,8-dihydropterin-6-carboxaldehyde" FEBS Lett. (1995) 360:177-182.
Fire et al., "Potent and specific genetic interference by double-stranded RNA in Caenorhabditis elegans" Nature (1998) 391:806-811.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Fromageot et al., "The synthesis of oligoribonucleotides. 3. Monoacylation of ribonucleosides and derivatives via orthoester exchange." Tetrahedron (1967) 23:2315-2331.
Fuchs et al., "Identification of Differentially Expressed Genes by Mutually Subtracted RNA Fingerprinting" Anal. Biochem. (2000) 286:91-98.
Gautschi et al., "Activity of a Novel bcl-2/bcl-xL-Bispecific Antisense Oligonucleotide Against Tumors of Diverse Histologic Origins" J. Natl. Cancer Inst. (2001) 93(6):463-471.
Genbank Accession No. NM_000371 Nucleotide—*Homo sapiens* transthyretin (TTR) mRNA accessed http://www.ncbi.nlm.nih.gov/nusccore/221136767 on Feb. 23, 2009. 6 print-out pages inclosed.
Going et al., "Molecular Pathology and Future Developments" Eur. J. Cancer (1999) 35:1895-1904.
Griffin et al., "The Synthesis of Oligoribonucleotides—II: Methoxymethylidene Derivatives of Ribonucleosides and 5'-Ribonucleotides" Tetrahedron (1967) 23:2301-2313.
Grunweller et al., "Comparison of different antisense strategies in mammalian cells using locked nucleic acids, 2'-O-methyl RNA, phosphorothioates and small interfering RNA" Nucleic Acids Research (2003) 31: 3185-3193.
Jacobsson et al., "Transthyretin Immunoreactivity in Human and Porcine Liver, Choroid Plexus, and Pancreatic Islets" J. Histochem. Cytochem. (1989) 37:31-37.
Jiang et al., "The V1221 cardiomyopathy variant of transthyretin increases the velocity of rate-limiting tetramer dissociation, resulting in accelerated amyloidosis" PNAS (2001) 98:14943-14948.
Joao et al., "Transthyretin Mutations in Hyperthyroxinemia and Amyloid Diseases" Human Mutation (2001) 17: 493-503.
Jones et al., "RNA Quantitation by Fluorescence-Based Solution Assay: RiboGreen Reagent Characterization" Analytical Biochemistry (1998) 265:368-374.
Jungblut et al., "Proteomics in human disease: Cancer, heart and infectious diseases" Electrophoresis (1999) 20:2100-2110.
Jurecic et al., "Long-distance DD-PCR and cDNA microarrays" Curr. Opin. Microbiol. (2000) 3:316-321.

(56) References Cited

OTHER PUBLICATIONS

Kohno et al., "Analysis of Amyloid Deposition in a Transgenic Mouse Model of Homozygous Familial Amyloidotic Polyneuropathy" Am J Pathol (1997) 150: 1497-1508.
Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition" Tetrahedron (1998) 54:3607-3630.
Kroschwitz, "The Concise Encyclopedia of Polymer Science and Engineering" pp. 858-859, John Wiley & Sons, 1990.
Kumar et al., "The First Analogues of LNA (Locked Nucleic Acids): Phosphorothioate-LNA and 2'-Thio-LNA" Bioorg. Med. Chem. Lett. (1998) 8:2219-2222.
Kurosawa et al., "Selective silencing of a mutant tranthyretin allele by small interfering RNAs" Biochemical and Biophysical Research Communications (2005) 337(3): 1012-1018.
Larson et al., "Rapid DNA Fingerprinting of Pathogens by Flow Cytometry" Cytometry (2000) 41:203-208.
Larsson et al., "High-throughput protein expression of cDNA products as a tool in functional genomics" J. Biotechnol. (2000) 80:143-57.
Lassus et al., "Confirming specificity of RNAi in mammalian cells" Science's Signaling, The Transduction Knowledge Environment (2002) 147(13):1-9.
Lee et al., "Mammalian APH-1 interacts with presenilin and nicastrin and is required for intramembrane proteolysis of amyloid-beta precursor protein and Notch" The Journal of Biological Chemistry (2002) 277:45013-45019.
Leumann, "DNA Analogues: From Supramolecular Principles to Biological Properties" Bioorg. Med. Chem. (2002) 10:841-854.
Liz et al., "Transthyretin: A New Cryptic Protease" J. Biol. Chem. (2004).
Love, et al. "Lipid-like materials for low dose, in vivo gene silencing" PNAS (2010) 107:1864-1869.
Madden et al., "Serial analysis of gene expression: from gene discovery to target identification" Drug Discov. Today (2000) 5:415-425.
Maher et al., "Comparative hybrid arrest by tandem antisense oligodeoxyribonucleotides or oligodeoxyribonucleoside methylpbosphonates in a cell-free system" Nuc. Acid. Res. (1988) 16(8):3341-3358.
Martin et al., "Ein neuer Zugang zu 2'-O-Alkylribonucleosiden und Eigenschaften deren Oligonucleotide" Helv. Chem. Acta (1995) 78:486-504.
Martinez et al., "Single-stranded antisense siRNAs guide target RNA cleavage in RNAi" Cell (2002) 110:563-574.
Martone et al., "Transthyretin is Synthesized in the Mammalian Eye" Biochem. Biophys. Res. Commun. (1988) 151:905-912.
Matteucci et al., "Synthesis of Deoxyoligonucleotides on a Polymer Support" J. Am. Chem. Soc. (1981) 103:3185-3191.
Mazumder et al., "Translational control by the 3'-UTR: the ends specify the means" Trends in Biochemical Science (2003) 28:91-98.
Mita et al., "Cloning and Sequence Analysis of cDNA for Human Prealbumin" Biochem. Biophys. Res. Commun. (1984) 124:558-564.
Miyagishi et al., "Comparison of the suppressive effects of antisense oligonucleotides and siRNAs directed against the same targets in mammalian cells" Antisense and Nucleic Acid Drug Development (2003) 13:1-7.
Montgomery et al., "RNA as a target of double-stranded RNA-mediated genetic interference in Caenorhabditis elegans" PNAS (1998) 95:15502-15507.
Myers et al., "Sensible use of antisense: how to use oligonucleotides as research tools" Trends Pharmacol Sci (2000) 21(1): 19-23.
Nakamura et al., "Applications of gene therapy for familial amyloidotic polyneuropathy" Expert Opinion of Biological Therapy (2004) 4(10): 1621-1627.
Nakamura et al., "Targeted conversion of the transthyretin gene in vitro and in vivo" Gene Ther. 1-9 (2004).
New England Biolabs 1998/99 Catalog (cover page and pp. 121 and 284).
Nielsen et al., "Sequence-Selective Recognition of DNA by Strand Displacement with a Thymine-Substituted Polyamide" Science (1991) 254:14971-1500.
Niemietz et al., "Therapeutic Oligonucleotides Targeting Liver Disease: TTR Amyloidosis" Molecules (2015) 20: 17944-17975.
Ong et al., "Synthesis and Secretion of Retinol-Binding Protein and Transthyretin by Cultured Retinal Pigment Epithelium" Biochemistry (1994) 33:1835-1842.
Orum et al., "Locked nucleic acids: A promising molecular family for gene-function analysis and antisense drug development" Curr. Opinion Mol. Ther. (2001) 3:239-243.
Oza et al., "Synthesis, Structure, and Activity of Diclofenac Analogues as Transthyretin Amyloid Fibril Formation Inhibitors" J Med Chem (2002) 45: 321-332.
Palha, "Transthyretin as a Thyroid Hormone Carrier: Function Revisited" Clin. Chem. Lab. Med. (2002) 40:1292-1300.
Peng et al., "Silencing expression of the catalytic subunit of DNA-dependent protein kinase by small interfering RNA sensitizes human cells for radiation-induced chromosome damage, cell killing, and mutation" Cancer Research (2002) 62:6400-6404.
Prashar et al., "READS: A Method for Display of 3'-End Fragments of Restriction Enzyme-Digested cDNAs for Analysis of Differential Gene Expression" Methods Enzymol. (1999) 303:258-272.
Propsting et al., "Inosine 15.1 Hammerhead Ribozymes for Targeting the Transthyretin-30 Mutation" Biochem. Biophys. Res. Commun. (1999) 260:313-317.
Propsting et al., "Inhibition of transthyretin-met30 expression using isosine 15.1-hammerhead ribozymes in cell culture" Biochemical and Biophysical Research Communications (2000) 279:970-973.
Randall et al., "Clearance of replicating hepatitis C virus replicon RNAs in cell culture by small interfering RNAs" PNAS (2003) 100:235-240.
Reddy et al., "Fast Cleavage and Deprotection of Oligonucleotides" Tetrahedron Lett. (1994) 35:4311-4314.
Reixach et al., "Tissue damage in the amyloidoses: Transthyretin monomers and nonnative oligomers are the major cytotoxic species in tissue culture" PNAS (2004) 101:2817-2822.
Reynolds et al., "Rational siRNA design for RNA interference" Nature Biotechnology (2004) 22:326-330.
Sakaki et al., "Human transthyretin (prealbumin) gene and molecular genetics of familial amyloidotic polyneuropathy." Mol. Biol. Med. (1989) 6(2):161-168.
Sanghvi, "Antisense Research and Applications" Chapter 15, pp. 289-302, Crooke and Lebleu, CRC Press, 1993.
Saraiva et al., "Amyloid Fibril Protein" J. Clin. Invest. (1984) 74:104-119.
Scaringe et al., "Novel RNA Synthesis Method Using 5'-O-Silyl-2'-O-orthoester Protecting Groups" J. Am. Chem. Soc. (1998) 120:11820-11821.
Schmidt, Negotiating the RNAi patent thicket, Mar. 2007, Nature Biotechnology, vol. 25, pp. 273-275.
Sekijima et al., "Energetic characteristics of the new transthyretin variant A25T may explain its atypical central nervous system pathology" Laboratory Investigation (2003) 83(3):409-417.
Sekijima et al., "Pathogenesis of and Therapeutic Strategies to Ameliorate the Transthyretin Amyloidoses" Current Pharmaceutical Design (2008) 14(30): 3219-3230.
Siebert, "Electrophoretic study of the blood protein response in tuberculosis" J. Biol. Chem. (1942) 143:29-38.
Singh et al., "LNA (locked nucleic acids): synthesis and high-affinity nucleic acid recognition" Chem. Commun. (1998) 4:455-456.
Singh et al., "Synthesis of 2'-Amino-LNA: A Novel Conformationally Restricted High-Affinity Oligonucleotide Analogue with a Handle" J. Org. Chem. (1998) 63:10035-10039.
Soprano et al., "Retinol-binding protein and transthyretin mRNA levels in visceral yolk sac and liver during fetal development in the rat" PNAS (1986) 83:7330-7334.
Sousa et al., "Evidence for the Role of Megalin in Renal Uptake of Transthyretin" J. Biol. Chem. (2000) 275:38176-38181.

(56) References Cited

OTHER PUBLICATIONS

Sousa et al., "Evidence of a Novel Yet Unidentified Receptor-Associated Protein (RAP)-Sensitive Receptor" J. Biol. Chem. (2001) 276:14420-14425.

Sousa et al., "Neurodegeneration in familial amyloid polyneuropathy: from pathology to molecular signaling" Prog. Neurobiol. (2003) 71:385-400.

Sparkes et al., "Assignment of the prealbumin (PALB) gene (familial amyloidotic polynueropathy) to human chromosome region 18q11.2-q12.1" Hum, Genet. (1987) 75:151-154.

Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8363-8379.

Stein et al., "Neutralization of transthyretin reverses the neuroprotective effects of secreted amyloid precursor protein (APP) in APPSW mice resulting in Tau phosphorylation and loss of hippocampal neurons: Support for the amyloid hypothesis" The Journal of Neuroscience (2004) 24:7707-7717.

Sutcliffe et al., "TOGA: An automated parsing technology for analyzing expression of nearly all genes" PNAS (2000) 97:1976-1981.

Tabara et al., "RNAi in C. elegans: Soaking in the Genome Sequence" Science (1998) 282:430-431.

Tanaka et al., "Suppression of transthyretin expression by ribozymes: a possible therapy for familial amyloidotic polyneuropathy" J. Neurol. Sci. (2001) 183:79-84.

Tanskanen et al., "Senile systemic amyloidosis affects 25% of the very aged and associates with genetic variation in alpha2-macroglobulin and tau: A population-based autopsy study" Ann. Med. (2008) 40(3):232-239.

Tasaki et al., "siRNA therapy for TTR-related ocular amyloidosis" Amyloid: The International Journal of Experiental and Clinical Investigation (2010) 17(suppl. 1): 52-53.

Tijsterman et al., "RNA Helicase MUT-14-Dependent Gene Silencing Triggered in C. elegans by Short Antisense RNAs" Science (2002) 295:694-697.

Timmons et al., "Ingestion of bacterially expressed dsRNAs can produce specific and potent genetic interference in Caenorhabditis elegans" Gene (2001) 263:103-112.

Timmons et al., "Specific interference by ingested dsRNA" Nature (1998) 395:854.

To, "Identification of Differential Gene Expression by High Throughput Analysis" Comb. Chem. High Throughput Screen (2000) 3:235-241.

Torner et al., "Anxiolytic and anti-stress effects of brain prolactin: Improved efficacy of antisense targeting of the prolactin receptor by molecular modeling" The Journal of Neuroscience (2001) 21:3207-3214.

Tsuzuki et al., "Structure of the human prealbumin gene" J Biol Chem (1985) 260(22): 12224-12227.

Tuschl et al., "Targeted mRNA degradation by double-stranded RNA in vitro" Genes Dev. (1999) 13:3191-3197.

Ui-Tei et al., "Guidelines for the selction of highly effective siRNA sequences for mammalian and chick RNA interference" Nucleic Acids Research (2004) 32(3): 936-948.

Valoczi et al., "Sensitive and specific detection of microRNAs by northern blot analysis using LNA-modified oligonucleotide probes" Nucleic Acids Research (2004) 32(e175):1-7.

Vickers et al., "Efficient reduction of target RNAs by small interfering RNA and Rnase H-dependent antisense agents" The Journal of Biological Chemistry (2003) 278:7108-7118.

Wahlestedt et al., "Potent and nontoxic antisense oligonucleotides containing locked nucleic acids" PNAS (2000) 97:5633-5638.

Watts et al., "Gene silencing by siRNAs and antisense oligonucleotides in the laboratory and the clinic" J Pathol (2012) 226(2): 365-379.

Whitehead et al., "Cloning of Human Prealbumin Complementary DNA: Localization of the Gene to Chromosome 18 and Detection of a Variant Prealbumin Allele in a Family with Familial Amyloid Polyneuropathy" Mol. Biol. Med. (1984) 2:411-423.

Whitesell et al., "Stability, clearance, and disposition of intraventricularly administered oligodeoxynucleotides: implications for therapeutic application within the central nervous system" PNAS (1993) 90:4665-4669.

Wincott et al., "Synthesis, deprotection, analysis and purification of RNA and ribozymes" Nucleic Acids Res. (1995) 23:2677-2684.

Woolf et al., "Specificity of antisense oligonucleotides in vivo" PNAS (1992) 89(16):7305-7309.

Yazaki et al., "Contribution of Wild-Type Transthyretin to Hereditary Peripheral Nerve Amyloid" Muscle Nerve (2003) 28:438-442.

Zhang et al., "PowerBLAST: A New Network BLAST Application for Interactive or Automated Sequence Analysis and Annotation" Genome Res. (1997) 7:649-656.

Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.

"siDESIGN Center" Gene Name: SRC, Accession: NM_198291, Retrieved from www.dharmacon.com/DesignCenter on May 13, 2008: total 3 print-out pages.

BPAI decision, U.S. Appl. No. 11/083,583; Appeal No. 2011-009971, Mail date: Nov. 28, 2012.

European Search Report for application EP 09805627.8 dated Jun. 21, 2012.

International Search Report for application PCT/US09/53202 dated Sep. 28, 2009.

European Search Report for application EP 11778071.8 dated Oct. 13, 2014.

International Search Report for application PCT/US11/34661 dated Aug. 30, 2011.

MODULATION OF TRANSTHYRETIN EXPRESSION

SEQUENCE LISTING

The present application is being filed along with a Sequence Listing in electronic format. The Sequence Listing is provided as a file entitled BIOL0123USC6SEQ_ST25.txt created Jun. 1, 2020 which is 64 Kb in size. The information in the electronic format of the sequence listing is incorporated herein by reference in its entirety.

FIELD OF THE INVENTION

Provided herein are methods, compounds, and compositions for reducing expression of transthyretin mRNA and protein in an animal. Such methods, compounds, and compositions are useful, for example, to treat, prevent, or ameliorate transthyretin amyloidosis.

BACKGROUND OF THE INVENTION

Transthyretin (TTR), (also known as prealbumin, hyperthytoxinemia, dysprealbuminemic, thyroxine; senile systemic amyloidosis, amyloid polyneuropathy, amyloidosis I, PALB; dystransthyretinemic, HST2651; TBPA; dysprealbuminemic euthyroidal hyperthyroxinemia) is a serum/plasma and cerebrospinal fluid protein responsible for the transport of thyroxine and retinol (Sakaki et al, Mol Biol Med. 1989, 6:161-8). Structurally, TTR is a homotetramer; point mutations and misfolding of the protein leads to deposition of amyloid fibrils and is associated with disorders, such as senile systemic amyloidosis (SSA), familial amyloid polyneuropathy (FAP), and familial amyloid cardiopathy (FAC).

TTR is synthesized primarily by the liver and the choroid plexus of the brain and, to a lesser degree, by the retina in humans (Palha, *Clin Chem Lab Med,* 2002, 40, 1292-1300). Transthyretin that is synthesized in the liver is secreted into the blood, whereas transthyretin originating in the choroid plexus is destined for the CSF. In the choroid plexus, transthyretin synthesis represents about 20% of total local protein synthesis and as much as 25% of the total CSF protein (Dickson et al., *J Biol Chem,* 1986, 261, 3475-3478).

With the availability of genetic and immunohistochemical diagnostic tests, patients with TTR amyloidosis have been found in many nations worldwide. Recent studies indicate that TTR amyloidosis is not a rare endemic disease as previously thought, and may affect as much as 25% of the elderly population (Tanskanen et al, Ann Med. 2008; 40(3): 232-9).

At the biochemical level, TTR was identified as the major protein component in the amyloid deposits of FAP patients (Costa et al, *Proc. Natl. Acad. Sci. USA* 1978, 75:4499-4503) and later, a substitution of methionine for valine at position 30 of the protein was found to be the most common molecular defect causing the disease (Saraiva et al, *J. Clin. Invest.* 1984, 74: 104-119). In FAP, widespread systemic extracellular deposition of TTR aggregates and amyloid fibrils occurs throughout the connective tissue, particularly in the peripheral nervous system (Sousa and Saraiva, *Prog. Neurobiol.* 2003, 71: 385-400). Following TTR deposition, axonal degeneration occurs, starting in the unmyelinated and myelinated fibers of low diameter, and ultimately leading to neuronal loss at ganglionic sites.

The compounds and treatment methods described herein provide significant advantages over the treatments options currently available for TTR related disorders. TTR amyloidosis typically lead to death within ten years, and until recently, was considered incurable. Liver transplantation is an effective means of replacing the disease-associated allele by a wild type (WT) allele in familial cases because the liver is typically the source of amyloidogenic TTR. While liver transplantation is effective as a form of gene therapy it is not without its problems. Transplantation is complicated by the need for invasive surgery for the recipient and the donor, long-term post-transplantation immunosuppressive therapy, a shortage of donors, its high cost, and the large number of TTR amyloidosis patients that are not good candidates because of their disease progression. Unfortunately, cardiac amyloidosis progresses in some familial patients even after liver transplantation because WT TTR often continues to deposit. Central nervous system (CNS) deposition of TTR is also not relieved by transplantation owing to its synthesis by the choroid plexus. Transplantation is not a viable option for the most prevalent TTR disease, senile systemic amyloidosis (SSA), affecting approximately 25% of those over 80 due to the deposition of WT TTR.

Antisense technology is emerging as an effective means for reducing the expression of specific gene products and may therefore prove to be uniquely useful in a number of therapeutic, diagnostic, and research applications for the modulation of TTR expression (See U.S. Patent Publication Nos. 2008/0039418 and 2007/0299027.

The present invention provides compositions and methods for modulating transthyretin expression. Antisense compounds for modulating expression of transthyretin are disclosed in the aforementioned published patent applications. However, there remains a need for additional such compounds.

SUMMARY OF THE INVENTION

Provided herein are methods, compounds, and compositions for modulating expression of transthyretin (TTR) mRNA and protein. In certain embodiments, compounds useful for modulating expression of TTR mRNA and protein are antisense compounds. In certain embodiments, the antisense compounds are antisense oligonucleotides.

In certain embodiments, modulation can occur in a cell or tissue. In certain embodiments, the cell or tissue is in an animal. In certain embodiments, the animal is a human. In certain embodiments, TTR mRNA levels are reduced. In certain embodiments, TTR protein levels are reduced. Such reduction can occur in a time-dependent manner or in a dose-dependent manner.

Provided herein are methods, compounds, and compositions for modulating expression of transthyretin and treating, preventing, delaying or ameliorating transthyretin amyloidosis and or a symptom thereof. In certain embodiments are methods, compounds, and compositions for modulating expression of transthyretin and treating, preventing, delaying or ameliorating transthyretin amyloid disease or transthyretin amyloidosis or transthyretin related amyloidosis (e.g., hereditary TTR amyloidosis, leptomeningeal amyloidosis, transthyretin amyloid polyneuropathy, familial amyloid polyneuropathy, familial amyloid cardiomyopathy, or senile systemic amyloidosis).

In certain embodiments, an animal at risk for transthyretin amyloidosis is treated by administering to the animal a therapeutically effective amount of a compound comprising a modified oligonucleotide consisting of 8 to 80 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 8 to 80 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, 87, 115, 120, 122, or 124.

In certain embodiments, an animal at risk for transthyretin amyloidosis is treated by administering to the animal a therapeutically effective amount of a compound comprising a modified oligonucleotide consisting of 12 to 50 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 12 to 50 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, 87, 115, 120, 122, or 124.

In certain embodiments, an animal at risk for transthyretin amyloidosis is treated by administering to the animal a therapeutically effective amount of a compound comprising a modified oligonucleotide consisting of 12 to 30 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 12 to 30 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, 87, 115, 120, 122, or 124.

In certain embodiments, an animal at risk for transthyretin amyloidosis is treated by administering to the animal a therapeutically effective amount of a compound comprising a modified oligonucleotide consisting of 15 to 25 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 15 to 25 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, 87, 115, 120, 122, or 124.

In certain embodiments, an animal at risk for transthyretin amyloidosis is treated by administering to the animal a therapeutically effective amount of a compound comprising a modified oligonucleotide consisting of 18 to 21 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 18 to 21 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, 87, 115, 120, 122, or 124.

In certain embodiments, an animal at risk for transthyretin amyloidosis is treated by administering to the animal a therapeutically effective amount of a compound comprising a modified oligonucleotide consisting of 20 to 30 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 20 to 30 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, 87, 115, 120, 122, or 124.

In certain embodiments, an animal having transthyretin amyloidosis is treated by administering to the animal a therapeutically effective amount of a compound comprising a modified oligonucleotide consisting of 8 to 80 linked nucleosides, wherein the modified oligonucleotide is complementary to a transthyretin nucleic acid as shown in SEQ ID NO: 1 or SEQ ID NO: 2, or a therapeutically effective amount of a compound comprising a modified oligonucleotide consisting of 8 to 80 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, 87, 115, 120, 122, or 124.

In certain embodiments, an animal having transthyretin amyloidosis is treated by administering to the animal a therapeutically effective amount of a compound comprising a modified oligonucleotide consisting of 12 to 50 linked nucleosides, wherein the modified oligonucleotide is complementary to a transthyretin nucleic acid as shown in SEQ ID NO: 1 or SEQ ID NO: 2, or a therapeutically effective amount of a compound comprising a modified oligonucleotide consisting of 12 to 50 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, 87, 115, 120, 122, or 124.

In certain embodiments, an animal having transthyretin amyloidosis is treated by administering to the animal a therapeutically effective amount of a compound comprising a modified oligonucleotide consisting of 12 to 30 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 12 to 30 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, 87, 115, 120, 122, or 124.

In certain embodiments, an animal having transthyretin amyloidosis is treated by administering to the animal a therapeutically effective amount of a compound comprising a modified oligonucleotide consisting of 15 to 25 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 15 to 25 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, 87, 115, 120, 122, or 124.

In certain embodiments, an animal having transthyretin amyloidosis is treated by administering to the animal a therapeutically effective amount of a compound comprising a modified oligonucleotide consisting of 18 to 21 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 18 to 21 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, 87, 115, 120, 122, or 124.

In certain embodiments, an animal at risk for transthyretin amyloidosis or having transthyretin amyloidosis is treated by administering to the animal a therapeutically effective amount of a compound comprising a modified oligonucleotide consisting of 8 to 80 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 8 to 80 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, or 87.

In certain embodiments, an animal at risk for transthyretin amyloidosis or having transthyretin amyloidosis is treated by administering to the animal a therapeutically effective amount of a compound comprising a modified oligonucleotide consisting of 12 to 50 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 12 to 50 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, or 87.

In certain embodiments, an animal at risk for transthyretin amyloidosis or having transthyretin amyloidosis is treated by administering to the animal a therapeutically effective amount of a compound comprising a modified oligonucleotide consisting of 12 to 30 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 12 to 30 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, or 87.

In certain embodiments, an animal at risk for transthyretin amyloidosis or having transthyretin amyloidosis is treated by administering to the animal a therapeutically effective amount of a compound comprising a modified oligonucleotide consisting of 15 to 25 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 15 to 25 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, or 87.

In certain embodiments, an animal at risk for transthyretin amyloidosis or having transthyretin amyloidosis is treated by administering to the animal a therapeutically effective amount of a compound comprising a modified oligonucleotide consisting of 18 to 21 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 18 to 21 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, or 87.

In certain embodiments, an animal at risk for transthyretin amyloidosis or having transthyretin amyloidosis is treated by administering to the animal a therapeutically effective amount of a compound comprising a modified oligonucleotide consisting of 20 to 30 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 20 to 30 linked nucleosides and having a nucleobase sequence comprising at least 8, 9, 10, 11, 12, 13, 14, 15, 16, 17, 18, 19 or 20 contiguous nucleobases of a nucleobase sequence selected from any one of nucleobase sequences recited in SEQ ID NOs: 25, 80, 86, or 87.

In certain embodiments, an animal at risk for transthyretin amyloidosis or having transthyretin amyloidosis is treated by administering to the animal a therapeutically effective amount of a compound comprising a modified oligonucleotide consisting of 8 to 80 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 8 to 80 linked nucleosides and having a nucleobase sequence comprising at least 8, 9, 10, 11, 12, 13, 14, 15, 16, 17, 18, 19 or 20 contiguous nucleobases of the nucleobase sequence recited in SEQ ID NO: 80.

In certain embodiments, an animal at risk for transthyretin amyloidosis or having transthyretin amyloidosis is treated by administering to the animal a therapeutically effective amount of a compound comprising a modified oligonucleotide consisting of 12 to 50 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 12 to 50 linked nucleosides and having a nucleobase sequence comprising at least 8, 9, 10, 11, 12, 13, 14, 15, 16, 17, 18, 19 or 20 contiguous nucleobases of the nucleobase sequence recited in SEQ ID NO: 80.

In certain embodiments, an animal at risk for transthyretin amyloidosis or having transthyretin amyloidosis is treated by administering to the animal a therapeutically effective amount of a compound comprising a modified oligonucleotide consisting of 12 to 30 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 12 to 30 linked nucleosides and having a nucleobase sequence comprising at least 8, 9, 10, 11, 12, 13, 14, 15, 16, 17, 18, 19 or 20 contiguous nucleobases of the nucleobase sequence recited in SEQ ID NO: 80.

In certain embodiments, an animal at risk for transthyretin amyloidosis or having transthyretin amyloidosis is treated by administering to the animal a therapeutically effective amount of a compound comprising a modified oligonucleotide consisting of 15 to 25 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 15 to 25 linked nucleosides and having a nucleobase sequence comprising at least 8, 9, 10, 11, 12, 13, 14, 15, 16, 17, 18, 19 or 20 contiguous nucleobases of the nucleobase sequence recited in SEQ ID NO: 80.

In certain embodiments, an animal at risk for transthyretin amyloidosis or having transthyretin amyloidosis is treated by administering to the animal a therapeutically effective amount of a compound comprising a modified oligonucleotide consisting of 18 to 21 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 18 to 21 linked nucleosides and having a nucleobase sequence comprising at least 8, 9, 10, 11, 12, 13, 14, 15, 16, 17, 18, 19 or 20 contiguous nucleobases of the nucleobase sequence recited in SEQ ID NO: 80.

In certain embodiments, an animal at risk for transthyretin amyloidosis or having transthyretin amyloidosis is treated by administering to the animal a therapeutically effective amount of a compound comprising a modified oligonucleotide consisting of 20 to 30 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 20 to 30 linked nucleosides and having a nucleobase sequence comprising at least 8, 9, 10, 11, 12, 13, 14, 15, 16, 17, 18, 19 or 20 contiguous nucleobases of the nucleobase sequence recited in SEQ ID NO: 80.

In certain embodiments, an animal at risk for transthyretin amyloidosis or having transthyretin amyloidosis is treated by administering to the animal a therapeutically effective amount of a compound comprising a modified oligonucleotide consisting of 20 linked nucleosides, wherein the modified oligonucleotide is complementary to a transthyretin nucleic acid as shown in SEQ ID NO: 1 or SEQ ID NO: 2; or a therapeutically effective amount of a compound comprising a modified oligonucleotide consisting of 20 linked nucleosides and having a nucleobase sequence comprising at least 8, 9, 10, 11, 12, 13, 14, 15, 16, 17, 18, 19, or 20 contiguous nucleobases of the nucleobase sequence recited in SEQ ID NO: 80.

In certain embodiments, an animal having transthyretin amyloidosis is treated by administering to the animal a therapeutically effective amount of a compound comprising a modified oligonucleotide consisting of 20 linked nucleosides, wherein the modified oligonucleotide is 100% complementary to a transthyretin nucleic acid as shown in SEQ ID NO: 1 or SEQ ID NO: 2; or a therapeutically effective amount of a compound comprising a modified oligonucleotide consisting of 20 linked nucleosides and having the nucleobase sequence recited in SEQ ID NO: 80.

In certain embodiments, an animal having transthyretin amyloidosis is treated by administering to the animal a therapeutically effective amount of a compound comprising a modified oligonucleotide consisting of 20 linked nucleosides, wherein the modified oligonucleotide is 100% complementary to a transthyretin nucleic acid as shown in SEQ ID NO: 1; and wherein the compound comprises a modified oligonucleotide consisting of 20 linked nucleosides having the nucleobase sequence recited in SEQ ID NO: 80.

In certain embodiments, an animal having transthyretin amyloidosis is treated by administering to the animal a therapeutically effective amount of a compound comprising a modified oligonucleotide consisting of 20 linked nucleosides, wherein the modified oligonucleotide is 100% complementary to a transthyretin nucleic acid as shown in SEQ ID NO: 1; wherein the compound comprises a modified oligonucleotide consisting of 20 linked nucleosides having the nucleobase sequence recited in SEQ ID NO: 80; and wherein the modified oligonucleotides has a gap segment of 10 linked deoxynucleosides between two wing segments that independently have 5 linked modified nucleosides. In certain embodiments, one or more modified nucleosides in the wing segment have a modified sugar. In certain embodiments, the modified nucleoside is a 2'-substituted nucleoside. In certain embodiments, the modified nucleoside is a 2'-MOE nucleoside.

In certain embodiments, modulation can occur in a cell, tissue, organ or organism. In certain embodiments, the cell, tissue or organ is in an animal. In certain embodiments, the animal is a human. In certain embodiments, transthyretin mRNA levels are reduced. In certain embodiments, transthyretin protein levels are reduced. Such reduction can occur in a time-dependent manner or in a dose-dependent manner.

Also provided are methods, compounds, and compositions useful for preventing, treating, and ameliorating diseases, disorders, and conditions related to transthyretin amyloidosis. In certain embodiments, such diseases, disorders, and conditions are transthyretin amyloidosis related diseases disorders or conditions.

In certain embodiments, methods of treatment include administering a TTR antisense compound to an individual in need thereof. In certain embodiments, methods of treatment include administering a TTR antisense oligonucleotide to an individual in need thereof.

In certain embodiments, methods of treatment include administering a transthyretin antisense oligonucleotide and an additional therapy to an individual in need thereof.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to transthyretin is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" refers to a lessening of at least one indicator, sign, or symptom of an associated disease, disorder, or condition. The severity of indicators may be determined by subjective or objective measures, which are known to those skilled in the art.

"Amyloidosis" is a group of diseases or disorders resulting from abnormal protein (amyloid or amyloid fibril) deposits in various body tissues. The amyloid proteins may either be deposited in one particular area of the body (localized amyloidosis) or they may be deposited throughout the body (systemic amyloidosis). There are three types of systemic amyloidosis: primary (AL), secondary (AA), and familial (ATTR). Primary amyloidosis is not associated with any other diseases and is considered a disease entity of its own. Secondary amyloidosis occurs as a result of another illness. Familial Mediterranean Fever is a form of familial (inherited) amyloidosis.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Central nervous system (CNS)" refers to the vertebrate nervous system which is enclosed in meninges. It contains the majority of the nervous system, and consists of the brain (in vertebrates which have brains), and the spinal cord. The CNS is contained within the dorsal cavity, with the brain within the cranial cavity, and the spinal cord in the spinal cavity. The brain is also protected by the skull, and the spinal cord is, in vertebrates, also protected by the vertebrae.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Choroid plexus" is the area on the ventricles of the brain where cerebrospinal fluid (CSF) is produced.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Familial amyloidosis" or "hereditary amyloidosis" is a form of inherited amyloidosis.

"Familial amyloid polyneuropathy" or "FAP" is a neurodegenerative genetically transmitted disorder, characterized by systemic depositions of amyloid variants of transthyretin proteins, causing progressive sensory and motorial polyneuropathy.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hereditary transthyretin (TTR) amyloidosis" is a systemic disease caused by mutations in transthyretin, a plasma transport protein for thyroxine and vitamin A. It is most frequently associated with peripheral neuropathy and restrictive cardiomyopathy, but amyloid deposits in blood vessel walls and connective tissue structures throughout the body often cause dysfunction of other organ systems. Gastrointestinal motility abnormalities are common in this disease with constipation, diarrhea and early satiety from delayed gastric-emptying. Connective tissue deposits of amyloid in the wrist may cause carpal tunnel syndrome. Amyloid deposits in spinal blood vessels and surrounding structures cause spinal stenosis with symptoms of claudication.

"Hybridization" means the annealing of complementary nucleic acid molecules. In certain embodiments, complementary nucleic acid molecules include an antisense compound and a target nucleic acid.

"Immediately adjacent" means there are no intervening elements between the immediately adjacent elements.

"Individual" means a human or non-human animal selected for treatment or therapy.

"Intracerebroventricular administration" or "cerebral intraventricular administration" or "cerebral ventricular administration" means administration through injection or infusion into the ventricular system of the brain.

"Intraperitoneal administration" means administration to the peritoneal cavity.

"Intrathecal administration" means administration through injection or infusion into the cerebrospinal fluid bathing the spinal cord and brain.

"Intravenous administration" means administration into a vein.

"Intraventricular administration" means administration into the ventricles of either the brain or heart.

"Internucleoside linkage" refers to the chemical bond between nucleosides.

"Leptomeningeal" means having to do with the leptomeninges, the two innermost layers of tissues that cover the brain and spinal cord. "Leptomeningeal amyloidosis" refers to amyloidosis of the leptomeninges resulting from transthyretin amyloid deposition within the leptomeninges.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid may also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intracerebral administration, intrathecal administration, intraventricular administration, ventricular administration, intracerebroventricular administration, cerebral intraventricular administration or cerebral ventricular administration. Administration can be continuous, or chronic, or short or intermittent.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Transthyretin-specific inhibitor" or "Transthyretin inhibitor" means any compound capable of decreasing transthyretin mRNA or protein expression. Examples of such compounds include a nucleic acid, a peptide, an antibody, or a histone deacetylase inhibitor.

"Transthyretin specific modulator" or "transthyretin modulator" means any compound capable of increasing or decreasing transthyretin mRNA or protein expression.

"Transthyretin-related amyloidosis" or "transthyretin amyloidosis" or "Transthyretin amyloid disease", as used herein, is any pathology or disease associated with dysfunction or dysregulation of transthyretin that result in formation of transthyretin-containing amyloid fibrils. Transthyretin amyloidosis includes, but is not limited to, hereditary TTR amyloidosis, leptomeningeal amyloidosis, familial amyloid polyneuropathy (FAP), familial amyloid cardiomyopathy, familial oculoleptomeningeal amyloidosis, senile cardiac amyloidosis, or senile systemic amyloidosis.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting transthyretin expression.

Certain embodiments provide antisense compounds targeted to a transthyretin nucleic acid. In certain embodiments, the transthyretin nucleic acid is any of the sequences set forth in GENBANK Accession No. NM_000371.2 (incorporated herein as SEQ ID NO: 1), GENBANK Accession No. NT_010966.10 truncated from nucleotides 2009236 to 2017289 (incorporated herein as SEQ ID NO: 2); exons 1-4 extracted from the rhesus monkey genomic sequence GENBANK Accession No. NW_001105671.1, based on similarity to human exons; and GENBANK Accession No. NW_001105671.1 truncated from nucleotides 628000 to 638000 (incorporated herein as SEQ ID NO: 4).

Certain embodiments provide compounds comprising a modified oligonucleotide consisting of 8 to 80 linked nucleosides wherein the linked nucleosides comprise at least 8 contiguous nucleobases of a sequence selected from among the nucleobase sequences recited in SEQ ID NOs: 25, 80, 86, 87, 115, 120, 122, and 124. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 25, 80, 86, 87, 115, 120, 122, and 124.

Certain embodiments provide compounds comprising a modified oligonucleotide consisting of 12 to 50 linked nucleosides wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 25, 80, 86, 87, 115, 120, 122, and 124. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 25, 80, 86, 87, 115, 120, 122, and 124.

Certain embodiments provide compounds comprising a modified oligonucleotide consisting of 12 to 30 linked nucleosides wherein the linked nucleosides comprise at least 8 contiguous nucleobases of a sequence selected from among the nucleobase sequences recited in SEQ ID NOs: 25, 80, 86, 87, 115, 120, 122, and 124. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 25, 80, 86, 87, 115, 120, 122, and 124.

Certain embodiments provide compounds comprising a modified oligonucleotide consisting of 15 to 25 linked nucleosides wherein the linked nucleosides comprise at least 8 contiguous nucleobases of a sequence selected from among the nucleobase sequences recited in SEQ ID NOs: 25, 80, 86, 87, 115, 120, 122, and 124.

Certain embodiments provide compounds comprising a modified oligonucleotide consisting of 18 to 21 linked nucleosides wherein the linked nucleosides comprise at least 8 contiguous nucleobases of a sequence selected from among the nucleobase sequences recited in SEQ ID NOs: 25, 80, 86, 87, 115, 120, 122, and 124. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 25, 80, 86, 87, 115, 120, 122, and 124.

Certain embodiments provide compounds comprising a modified oligonucleotide consisting of 8 to 80 linked nucleosides wherein the linked nucleosides comprise at least 8 contiguous nucleobases of a sequence selected from among the nucleobase sequences recited in SEQ ID NOs: 25, 80, 86, and 87. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 25, 80, 86, and 87.

Certain embodiments provide compounds comprising a modified oligonucleotide consisting of 12 to 50 linked nucleosides wherein the linked nucleosides comprise at least 8 contiguous nucleobases of a sequence selected from among the nucleobase sequences recited in SEQ ID NOs: 25, 80, 86, and 87. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 25, 80, 86, and 87.

Certain embodiments provide compounds comprising a modified oligonucleotide consisting of 12 to 30 linked nucleosides wherein the linked nucleosides comprise at least 8 contiguous nucleobases of a sequence selected from among the nucleobase sequences recited in SEQ ID NOs: 25, 80, 86, and 87. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 25, 80, 86, and 87.

Certain embodiments provide compounds comprising a modified oligonucleotide consisting of 15 to 25 linked nucleosides wherein the linked nucleosides comprise at least 8 contiguous nucleobases of a sequence selected from among the nucleobase sequences recited in SEQ ID NOs: 25, 80, 86, and 87. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 25, 80, 86, and 87.

Certain embodiments provide compounds comprising a modified oligonucleotide consisting of 18 to 21 linked nucleosides wherein the linked nucleosides comprise at least 8 contiguous nucleobases of a sequence selected from among the nucleobase sequences recited in SEQ ID NOs: 25, 80, 86, and 87. In certain embodiments, the modified oligonucleotide comprises at least 9, at least 10, at least 11, at least 12, at least 13, at least 14, at least 15, at least 16, at least 17, at least 18, at least 19 or at least 20 contiguous nucleobases of a sequence selected from among the nucleobase sequences recited in SEQ ID NOs: 25, 80, 86, and 87.

Certain embodiments provide compounds comprising a modified oligonucleotide consisting of 8 to 80 linked nucleosides wherein the linked nucleosides comprise at least 8 contiguous nucleobases of the nucleobase sequence recited in SEQ ID NO: 80. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 80.

Certain embodiments provide compounds comprising a modified oligonucleotide consisting of 12 to 50 linked nucleosides wherein the linked nucleosides comprise at least 8 contiguous nucleobases of the nucleobase sequence recited in SEQ ID NO: 80. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 80.

Certain embodiments provide compounds comprising a modified oligonucleotide consisting of 12 to 30 linked nucleosides wherein the linked nucleosides comprise at least 8 contiguous nucleobases of the nucleobase sequence recited in SEQ ID NO: 80. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 80.

Certain embodiments provide compounds comprising a modified oligonucleotide consisting of 15 to 25 linked nucleosides wherein the linked nucleosides comprise at least 8 contiguous nucleobases of the nucleobase sequence recited in SEQ ID NO: 80. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 80.

Certain embodiments provide compounds comprising a modified oligonucleotide consisting of 18 to 21 linked nucleosides wherein the linked nucleosides comprise at least 8 contiguous nucleobases of the nucleobase sequence recited in SEQ ID NO: 80. In certain embodiments, the modified oligonucleotide comprises at least 9, at least 10, at least 11, at least 12, at least 13, at least 14, at least 15, at least 16, at least 17, at least 18, at least 19, or at least 20 contiguous nucleobases of a sequence selected from among the nucleobase sequences recited in SEQ ID NOs: 80.

Certain embodiments provide compounds comprising a modified oligonucleotide consisting of 20 to 30 linked nucleosides wherein the linked nucleosides comprise at least 8 contiguous nucleobases of the nucleobase sequence recited in SEQ ID NO: 80. In certain embodiments, the modified oligonucleotide comprises at least 9, at least 10, at least 11, at least 12, at least 13, at least 14, at least 15, at least 16, at least 17, at least 18, or at least 19 contiguous nucleobases of the nucleobase sequence recited in SEQ ID NO: 80.

In certain embodiments, the compound comprises a modified oligonucleotide consisting of 20 linked nucleosides recited in SEQ ID NO: 80.

Certain embodiments provide compounds comprising a modified oligonucleotide consisting of 12 to 30 linked nucleosides wherein the linked nucleosides comprise at least an 8 contiguous nucleobase portion that is complementary to an equal length nucleobase portion within the region selected from nucleotides 120-139, 212-236, 226-245, 293-468, 293-326, 347-381, 425-468, 425-467, 452-478, 452-474, 459-478, 461-519, 462-500, 500-519, 501-535, 502-531, 505-524, 507-526, 508-527, 514-540, 514-539, 515-534, 516-535, 523-542, 544-606, 544-564, 564-583, 578-601, 580-608, 580-599, 584-606, 585-604, 587-606, or 597-617 of SEQ ID NO: 1. In certain embodiments the region is selected from 507-526, 508-527, 515-534, 516-535, 580-599, 585-604, 587-606 and 589-608 of SEQ ID NO: 1. In certain embodiments the region is selected from 501-535 or 580-608 of SEQ ID NO: 1. In certain embodiments, the modified oligonucleotide has at least a 9, at least a 10, at least an 11, at least an 12, at least an 13, at least an 14, at least an 15, at least an 16, at least an 17, at least an 18, at least an 19 or at least a 20 contiguous nucleobase portion of which is complementary within a region described herein.

Certain embodiments provide compounds comprising a modified oligonucleotide consisting of 12 to 30 linked nucleosides wherein the linked nucleosides comprise at least an 8 contiguous nucleobase portion that is complementary to an equal length nucleobase portion within the region selected from nucleotides 501-535 or 580-608 of SEQ ID NO: 1. In certain embodiments, the modified oligonucleotide has at least a 9, at least a 10, at least an 11, at least an 12, at least an 13, at least an 14, at least an 15, at least an 16, at least an 17, at least an 18, at least an 19 or at least a 20 contiguous nucleobase portion of which is complementary within a region described herein.

Certain embodiments provide compounds comprising a modified oligonucleotide consisting of 12 to 30 linked nucleosides wherein the linked nucleosides comprise at least an 8 contiguous nucleobase portion that is complementary to an equal length nucleobase portion within the region selected from nucleotides 508-527 of SEQ ID NO: 1. In certain embodiments, the modified oligonucleotide has at least a 9, at least a 10, at least an 11, at least an 12, at least an 13, at least an 14, at least an 15, at least an 16, at least an 17, at least an 18, at least an 19 or at least a 20 contiguous nucleobase portion of which is complementary within a region described herein.

Certain embodiments provide compounds comprising a modified oligonucleotide consisting of 15 to 25 linked nucleosides wherein the linked nucleosides comprise at least an 8 contiguous nucleobase portion that is complementary to an equal length nucleobase portion within the region selected from nucleotides 507-526, 508-527, 515-534, 516-535, 580-599, 585-604, 587-606 and 589-608 of SEQ ID NO: 1. In certain embodiments, the modified oligonucleotide has at least a 9, at least a 10, at least an 11, at least an 12, at least an 13, at least an 14, at least an 15, at least an 16, at least an 17, at least an 18, at least an 19 or at least a 20 contiguous nucleobase portion of which is complementary within a region described herein.

Certain embodiments provide compounds comprising a modified oligonucleotide consisting of 18 to 21 linked nucleosides wherein the linked nucleosides comprise at least an 8 contiguous nucleobase portion that is complementary to an equal length nucleobase portion within the region selected from nucleotides 507-526, 508-527, 515-534, 516-535, 580-599, 585-604, 587-606 and 589-608 of SEQ ID NO: 1. In certain embodiments, the modified oligonucleotide has at least a 9, at least a 10, at least an 11, at least an 12, at least an 13, at least an 14, at least an 15, at least an 16, at least an 17, at least an 18, at least an 19 or at least a 20 contiguous nucleobase portion of which is complementary within a region described herein.

Certain embodiments provide compounds comprising a modified oligonucleotide consisting of 20 linked nucleosides wherein the linked nucleosides comprise at least an 8 contiguous nucleobase portion that is complementary to an equal length nucleobase portion within the region selected from nucleotides 507-526, 508-527, 515-534, 516-535, 580-599, 585-604, 587-606 and 589-608 of SEQ ID NO: 1. In certain embodiments, the modified oligonucleotide has at least a 9, at least a 10, at least an 11, at least a 12, at least a 13, at least a 14, at least a 15, at least a 16, at least a 17, at least an 18, at least 19 or at least a 20 contiguous nucleobase portion of which is complementary within a region described herein. In certain embodiments, the modified oligonucleotide is 90%, 95%, 99%, or 100% complementary to a nucleic acid encoding human transthyretin (TTR), eg. SEQ ID No: 1.

Certain embodiments provide compounds comprising a modified oligonucleotide consisting of 20 linked nucleosides wherein the linked nucleosides comprise at least an 8 contiguous nucleobase portion that is complementary to an equal length nucleobase portion within the region selected from nucleotides 508-527 of SEQ ID NO: 1. In certain embodiments, the modified oligonucleotide has at least a 9, at least a 10, at least an 11, at least a 12, at least a 13, at least a 14, at least a 15, at least a 16, at least a 17, at least an 18, at least 19 or at least a 20 contiguous nucleobase portion of which is complementary to an equal length portion within the region selected from nucleotides 508-527 of SEQ ID NO: 1. In certain embodiments, the modified oligonucleotide is 90%, 95%, 99%, or 100% complementary to a nucleic acid encoding human transthyretin (TTR), eg. SEQ ID No: 1

Certain embodiments provide compounds comprising a modified oligonucleotide consisting of 20 linked nucleosides 60% complementary within the region selected from nucleotides 507-526, 508-527, 515-534, 516-535, 580-599, 585-604, 587-606 and 589-608 of SEQ ID NO: 1.

Certain embodiments provide compounds comprising a modified oligonucleotide consisting of 20 linked nucleosides 70% complementary within the region selected from nucleotides 507-526, 508-527, 515-534, 516-535, 580-599, 585-604, 587-606 and 589-608 of SEQ ID NO: 1.

Certain embodiments provide compounds comprising a modified oligonucleotide consisting of 20 linked nucleosides 80% complementary within the region selected from nucleotides 507-526, 508-527, 515-534, 516-535, 580-599, 585-604, 587-606 and 589-608 of SEQ ID NO: 1.

Certain embodiments provide compounds comprising a modified oligonucleotide consisting of 20 linked nucleosides 90% complementary within the region selected from nucleotides 507-526, 508-527, 515-534, 516-535, 580-599, 585-604, 587-606 and 589-608 of SEQ ID NO: 1.

Certain embodiments provide compounds comprising a modified oligonucleotide consisting of 20 linked nucleosides 95% complementary within the region selected from nucleotides 507-526, 508-527, 515-534, 516-535, 580-599, 585-604, 587-606 and 589-608 of SEQ ID NO: 1.

Certain embodiments provide compounds comprising a modified oligonucleotide consisting of 20 linked nucleosides 99% complementary within the region selected from nucleotides 507-526, 508-527, 515-534, 516-535, 580-599, 585-604, 587-606 and 589-608 of SEQ ID NO: 1.

Certain embodiments provide compounds comprising a modified oligonucleotide consisting of 20 linked nucleosides 100% complementary within the region selected from nucleotides 507-526, 508-527, 515-534, 516-535, 580-599, 585-604, 587-606 and 589-608 of SEQ ID NO: 1.

Certain embodiments provide compounds comprising a modified oligonucleotide consisting of 20 linked nucleosides 60% complementary within nucleotides 508-527 of SEQ ID NO: 1.

Certain embodiments provide compounds comprising a modified oligonucleotide consisting of 20 linked nucleosides 70% complementary within nucleotides 508-527 of SEQ ID NO: 1.

Certain embodiments provide compounds comprising a modified oligonucleotide consisting of 20 linked nucleosides 80% complementary within nucleotides 508-527 of SEQ ID NO: 1.

Certain embodiments provide compounds comprising a modified oligonucleotide consisting of 20 linked nucleosides 90% complementary within nucleotides 508-527 of SEQ ID NO: 1.

Certain embodiments provide compounds comprising a modified oligonucleotide consisting of 20 linked nucleosides 95% complementary within nucleotides 508-527 of SEQ ID NO: 1.

Certain embodiments provide compounds comprising a modified oligonucleotide consisting of 20 linked nucleosides 99% complementary within nucleotides 508-527 of SEQ ID NO: 1.

Certain embodiments provide compounds comprising a modified oligonucleotide consisting of 20 linked nucleosides 100% complementary within nucleotides 508-527 of SEQ ID NO: 1.

In certain embodiments, an antisense compound or modified oligonucleotide targeted to a transthyretin nucleic acid targets the following nucleotide regions of SEQ ID NO: 1: 120-139, 212-236, 226-245, 293-468, 293-326, 347-381, 425-468, 425-467, 452-478, 452-474, 459-478, 461-519, 462-500, 500-519, 502-531, 507-526, 505-524, 508-527, 514-540, 514-539, 515-534, 516-535, 523-542, 544-606, 544-564, 564-583, 578-601, 580-599, 584-606, 585-604, 587-606, or 597-617.

In certain embodiments, antisense compounds or modified oligonucleotides targets a region of a transthyretin nucleic acid. In certain embodiments, such compounds or oligonucleotides targeted to a region of a transthyretin nucleic acid have a contiguous nucleobase portion that is complementary to an equal length nucleobase portion of the region. For example, the portion can be at least an 8, 9, 10, 11, 12, 13, 14, 15, 16, 17, 18, 19 or 20 contiguous nucleobases portion complementary to an equal length portion of a region recited herein. In certain embodiments, such compounds or oligonucleotide target the following nucleotide regions of SEQ ID NO: 1: 120-139, 212-236, 226-245, 293-381, 293-366, 353-381, 293-468, 425-468, 425-467, 452-476, 461-481, 461-500, 500-519, 461-519, 502-531, 502-539, 504-536, 505-525, 506-530, 507-527, 508-527, 508-536, 514-540, 523-542, 544-606, 544-564, 544-583, or 597-617.

In certain embodiments, such compounds or oligonucleotides targeted to a region of a transthyretin nucleic acid have a contiguous nucleobase portion that is complementary to an equal length nucleobase portion of the region 501-535 or 580-608 of SEQ ID NO: 1.

In certain embodiments, the following nucleotide regions of SEQ ID NO: 1, when targeted by antisense compounds or oligonucleotides, displays at least 60% inhibition: 226-245, 293-366, 357-467, 452-474, 457-476, 459-478, 462-500, 500-519, 502-531, 504-536, 505-525, 506-530, 507-527, 508-527, 508-536, 514-539, 544-564, 564-583, 578-601, 584-606, or 597-617.

In certain embodiments, the following nucleotide regions of SEQ ID NO: 1, when targeted by antisense compounds or oligonucleotides, displays at least 65% inhibition: 293-366, 357-376, 425-449, 432-467, 452-474, 459-478, 462-500, 500-519, 502-531, 504-536, 505-525, 506-530, 507-527, 508-527, 508-536, 514-539, 544-563, 564-583, 578-601, 585-606, or 597-617.

In certain embodiments, the following nucleotide regions of SEQ ID NO: 1, when targeted by antisense compounds or oligonucleotides, displays at least 70% inhibition: 293-366, 425-449, 432-467, 452-474, 459-478, 462-500, 500-519, 502-531, 504-536, 505-525, 506-530, 507-527, 508-527, 508-536, 514-539, 564-583, 578-598, 581-600, or 597-617.

In certain embodiments, the following nucleotide regions of SEQ ID NO: 1, when targeted by antisense compounds or oligonucleotides, displays at least 75% inhibition: 293-322, 347-366, 425-449, 432-467, 452-474, 459-478, 462-500, 500-519, 503-531, 504-536, 505-525, 506-530, 507-527, 508-527, 508-536, 514-539, 578-598, 581-600, or 597-616.

In certain embodiments, the following nucleotide regions of SEQ ID NO: 1, when targeted by antisense compounds or oligonucleotides, displays at least 80% inhibition: 303-322, 425-449, 432-460, 443-467, 452-473, 481-500, 500-519, 503-531, 504-536, 505-525, 506-530, 507-527, 508-527, 508-536, 514-536, 519-539, 579-598, 581-600, or 597-616.

In certain embodiments, the following nucleotide regions of SEQ ID NO: 1, when targeted by antisense compounds or oligonucleotides, displays at least 85% inhibition: 427-449, 432-458, 441-460, 443-467, 452-473, 504-531, 504-536, 505-525, 506-530, 507-527, 508-527, 508-536, 514-536, 519-539, or 581-600.

In certain embodiments, the following nucleotide regions of SEQ ID NO: 1, when targeted by antisense compounds or oligonucleotides, displays at least 90% inhibition: 428-449, 432-456, 439-458, 441-460, 445-466, 452-473, 504-525, 508-527, or 515-536.

In certain embodiments, the following nucleotide regions of SEQ ID NO: 1, when targeted by antisense compounds or oligonucleotides, displays at least 95% inhibition: 434-453, 436-456, 441-460, 445-465, 505-524, or 516-535.

In certain embodiments, the following antisense compounds target a region of a SEQ ID NO: 1, a nucleic acid encoding human transthyretin, and demonstrate at least 60% inhibition of a transthyretin mRNA: ISIS NOs: 420954, 420904, 304286, 420874, 420948, 420883, 420955, 420952, 420956, 420957, 420882, 420947, 420950, 304312, 304307, 420879, 420910, 420902, 420908, 420924, 420877, 420880, 304309, 304289, 420906, 304311, 420878, 420911, 304284, 304288, 420909, 304296, 420949, 304290, 304299, 420898, 420920, 420925, 420951, 304287, 420894, 420916, 420918, 420926, 304285, 420919, 420923, 420886, 420900, 420912, 420915, 420917, 420921, 420884, 420885, 420887, 420889, 420892, 420901, 420914, 420897, 420899, 420888, 420895, 420896, 420913, 420922, 420893, 420890, or 420891.

In certain embodiments, the following antisense compounds target a region of a SEQ ID NO: 1, a nucleic acid encoding human transthyretin and demonstrate at least 65% inhibition of a transthyretin mRNA: ISIS NOs: 420955, 420952, 420956, 420957, 420882, 420947, 420950, 304312, 304307, 420879, 420910, 420902, 420908, 420924, 420877, 420880, 304309, 304289, 420906, 304311, 420878, 420911, 304284, 304288, 420909, 304296, 420949, 304290, 304299, 420898, 420920, 420925, 420951, 304287, 420894, 420916, 420918, 420926, 304285, 420919, 420923, 420886, 420900, 420912, 420915, 420917, 420921, 420884, 420885, 420887, 420889, 420892, 420901, 420914, 420897, 420899, 420888, 420895, 420896, 420913, 420922, 420893, 420890, or 420891.

In certain embodiments, the following antisense compounds target a region of a SEQ ID NO: 1, a nucleic acid encoding human transthyretin and demonstrate at least 70% inhibition of a transthyretin mRNA: ISIS NOs: 304312, 304307, 420879, 420910, 420902, 420908, 420924, 420877, 420880, 304309, 304289, 420906, 304311, 420878, 420911, 304284, 304288, 420909, 304296, 420949, 304290, 304299, 420898, 420920, 420925, 420951, 304287, 420894, 420916, 420918, 420926, 304285, 420919, 420923, 420886, 420900, 420912, 420915, 420917, 420921, 420884, 420885, 420887, 420889, 420892, 420901, 420914, 420897, 420899, 420888, 420895, 420896, 420913, 420922, 420893, 420890, or 420891.

In certain embodiments, the following antisense compounds target a region of a SEQ ID NO: 1, a nucleic acid encoding human transthyretin and demonstrate at least 75% inhibition of a transthyretin mRNA: ISIS NOs: 420877, 420878, 420880, 304284, 304285, 420884, 420885, 420886, 420887, 420888, 420889, 420890, 420891, 304287, 420892, 304288, 420893, 304289, 304290, 420894, 420895, 420896, 420897, 420898, 420899, 420900, 420901, 420902, 420906, 420908, 304296, 420909, 420911, 420912, 420913, 420914, 304299, 420915, 420916, 420917, 420918, 420919, 420920, 420921, 420922, 420923, 420924, 420925, 420926, 304309, 420949, 420951, or 304311.

In certain embodiments, the following antisense compounds target a region of a SEQ ID NO: 1, a nucleic acid encoding human transthyretin and demonstrate at least 80% inhibition of a transthyretin mRNA: ISIS NOs: 304311, 420878, 420911, 304284, 304288, 420909, 304296, 420949, 304290, 304299, 420898, 420920, 420925, 420951, 304287, 420894, 420916, 420918, 420926, 304285, 420919, 420923, 420886, 420900, 420912, 420915, 420917, 420921, 420884, 420885, 420887, 420889, 420892, 420901, 420914, 420897, 420899, 420888, 420895, 420896, 420913, 420922, 420893, 420890, or 42089.

In certain embodiments, the following antisense compounds target a region of a SEQ ID NO: 1, a nucleic acid encoding human transthyretin and demonstrate at least 85% inhibition of a transthyretin mRNA: ISIS NOs: 304290, 304299, 420898, 420920, 420925, 420951, 304287, 420894, 420916, 420918, 420926, 304285, 420919, 420923, 420886, 420900, 420912, 420915, 420917, 420921, 420884, 420885, 420887, 420889, 420892, 420901, 420914, 420897, 420899, 420888, 420895, 420896, 420913, 420922, 420893, 420890, or 420891.

In certain embodiments, the following antisense compounds target a region of a SEQ ID NO: 1, a nucleic acid encoding human transthyretin and demonstrate at least 90% inhibition of a transthyretin mRNA: ISIS NOs: 420923, 420886, 420900, 420912, 420915, 420917, 420921, 420884, 420885, 420887, 420889, 420892, 420901, 420914, 420897, 420899, 420888, 420895, 420896, 420913, 420922, 420893, 420890, or 420891.

In certain embodiments, the following antisense compounds target a region of a SEQ ID NO: 1, a nucleic acid encoding human transthyretin and demonstrate at least 95% inhibition of a transthyretin mRNA: ISIS NOs: 420888, 420895, 420896, 420913, 420922, 420893, 420890, or 420891.

In certain embodiments, a target region is nucleotides 120-139 of SEQ ID NO: 1. In certain embodiments, an antisense compound is targeted to nucleotides 120-139 of SEQ ID NO: 1. In certain embodiments, an antisense compound targeted to a transthyretin nucleic acid comprises a nucleobase sequence selected from SEQ ID NO: 37. In certain such embodiments, an antisense compound targeted to nucleotides 120-139 of SEQ ID NO: 1 is selected from ISIS NO: 420872.

In certain embodiments, a target region is nucleotides 212-236 of SEQ ID NO: 1. In certain embodiments, an antisense compound is targeted to nucleotides 212-236 of SEQ ID NO: 1. In certain embodiments, an antisense compound targeted to a transthyretin nucleic acid comprises a nucleobase sequence selected from SEQ ID NOs: 8 and 38. In certain such embodiments, an antisense compound targeted to nucleotides 212-236 of SEQ ID NO: 1 is selected from ISIS NOs: 420873 or 304267.

In certain embodiments, a target region is nucleotides 226-245 of SEQ ID NO: 1. In certain embodiments, an antisense compound is targeted to nucleotides 226-245 of SEQ ID NO: 1. In certain embodiments, an antisense compound targeted to a transthyretin nucleic acid comprises a nucleobase sequence selected from SEQ ID NO: 39. In certain such embodiments, an antisense compound targeted to nucleotides 226-245 of SEQ ID NO: 1 is selected from ISIS NO: 420874.

In certain embodiments, a target region is nucleotides 293-381 of SEQ ID NO: 1. In certain embodiments, an antisense compound is targeted to nucleotides 293-381 of SEQ ID NO: 1. In certain embodiments, an antisense compound targeted to a transthyretin nucleic acid comprises a nucleobase sequence selected from SEQ ID NOs: 10, 42-48. In certain such embodiments, an antisense compound targeted to nucleotides 293-381 of SEQ ID NO: 1 is selected from ISIS NOs: 420877, 420878, 420879, 420880, 304280, 420881, 420882, or 420883.

In certain embodiments, a target region is nucleotides 293-366 of SEQ ID NO: 1. In certain embodiments, an antisense compound is targeted to nucleotides 293-366 of SEQ ID NO: 1. In certain embodiments, an antisense compound targeted to a transthyretin nucleic acid comprises a nucleobase sequence selected from SEQ ID NOs: 42-45. In certain such embodiments, an antisense compound targeted to nucleotides 293-366 of SEQ ID NO: 1 is selected from ISIS NOs: 420877, 420878, 420879, or 420880.

In certain embodiments, a target region is nucleotides 353-381 of SEQ ID NO: 1. In certain embodiments, an antisense compound is targeted to nucleotides 353-381 of SEQ ID NO: 1. In certain embodiments, an antisense compound targeted to a transthyretin nucleic acid comprises a nucleobase sequence selected from SEQ ID NOs: 10, 46-48. In certain such embodiments, an antisense compound targeted to nucleotides 353-381 of SEQ ID NO: 1 is selected from ISIS NOs: 304280, 420881, 420882, or 420883.

In certain embodiments, a target region is nucleotides 293-468 of SEQ ID NO: 1. In certain embodiments, an antisense compound is targeted to nucleotides 293-468 of SEQ ID NO: 1. In certain embodiments, an antisense compound targeted to a transthyretin nucleic acid comprises a nucleobase sequence selected from SEQ ID NOs: 10-18, 42-63. In certain such embodiments, an antisense compound targeted to nucleotides 293-468 of SEQ ID NO: 1 is selected from ISIS NOs: 420877, 420878, 420879, 420880, 304280, 420881, 420882, 420883, 304284, 304285, 420884, 420885, 304286, 420886, 420887, 420888, 420889, 420890, 420891, 304287, 420892, 304288, 420893, 304289, 304290, 420894, 420895, 420896, 420897, 420898, or 304291.

In certain embodiments, a target region is nucleotides 425-468 of SEQ ID NO: 1. In certain embodiments, an antisense compound is targeted to nucleotides 425-468 of SEQ ID NO: 1. In certain embodiments, an antisense compound targeted to a transthyretin nucleic acid comprises a nucleobase sequence selected from SEQ ID NOs: 11-18, 49-63. In certain such embodiments, an antisense compound targeted to nucleotides 425-468 of SEQ ID NO: 1 is selected from ISIS NOs: 304284, 304285, 420884, 420885, 304286, 420886, 420887, 420888, 420889, 420890, 420891, 304287, 420892, 304288, 420893, 304289, 304290, 420894, 420895, 420896, 420897, 420898, or 304291.

In certain embodiments, a target region is nucleotides 425-467 of SEQ ID NO: 1. In certain embodiments, an antisense compound is targeted to nucleotides 425-468 of SEQ ID NO: 1. In certain embodiments, an antisense compound targeted to a transthyretin nucleic acid comprises a nucleobase sequence selected from SEQ ID NOs: 11-17, 49-63. In certain such embodiments, an antisense compound targeted to nucleotides 425-468 of SEQ ID NO: 1 is selected from ISIS NOs: 304284, 304285, 420884, 420885, 304286, 420886, 420887, 420888, 420889, 420890, 420891, 304287, 420892, 304288, 420893, 304289, 304290, 420894, 420895, 420896, 420897, or 420898.

In certain embodiments, a target region is nucleotides 452-476 of SEQ ID NO: 1. In certain embodiments, an antisense compound is targeted to nucleotides 452-476 of SEQ ID NO: 1. In certain embodiments, an antisense compound targeted to a transthyretin nucleic acid comprises a nucleobase sequence selected from SEQ ID NOs: 64-69. In certain such embodiments, an antisense compound targeted to nucleotides 452-476 of SEQ ID NO: 1 is selected from ISIS NOs: 420889, 420890, 420891, 304287, 420892, 304288, 420893, 304289, 304290, 420894, 420895, 420896, 420897, 420898, 304291, 304292, 304293, 420899, 420900, 420901, 420902, 420903, or 420904.

In certain embodiments, a target region is nucleotides 461-481 of SEQ ID NO: 1. In certain embodiments, an antisense compound is targeted to nucleotides 461-481 of SEQ ID NO: 1. In certain embodiments, an antisense compound targeted to a transthyretin nucleic acid comprises a nucleobase sequence selected from SEQ ID NOs: 72-73. In certain such embodiments, an antisense compound targeted to nucleotides 461-481 of SEQ ID NO: 1 is selected from ISIS NOs: 420907 or 420908.

In certain embodiments, a target region is nucleotides 461-500 of SEQ ID NO: 1. In certain embodiments, an antisense compound is targeted to nucleotides 461-500 of SEQ ID NO: 1. In certain embodiments, an antisense compound targeted to a transthyretin nucleic acid comprises a nucleobase sequence selected from SEQ ID NOs: 22, 72 and 73. In certain such embodiments, an antisense compound targeted to nucleotides 461-500 of SEQ ID NO: 1 is selected from ISIS NOs: 420907, 420908 or 304296.

In certain embodiments, a target region is nucleotides 500-519 of SEQ ID NO: 1. In certain embodiments, an antisense compound is targeted to nucleotides 500-519 of SEQ ID NO: 1. In certain embodiments, an antisense compound targeted to a transthyretin nucleic acid comprises a nucleobase sequence selected from SEQ ID NO: 74. In certain such embodiments, an antisense compound targeted to nucleotides 500-519 of SEQ ID NO: 1 is selected from ISIS NO: 420909.

In certain embodiments, a target region is nucleotides 461-519 of SEQ ID NO: 1. In certain embodiments, an antisense compound is targeted to nucleotides 461-519 of SEQ ID NO: 1. In certain embodiments, an antisense compound targeted to a transthyretin nucleic acid comprises a nucleobase sequence selected from SEQ ID NOs: 22, 23, 72-74. In certain such embodiments, an antisense compound targeted to nucleotides 461-519 of SEQ ID NO: 1 is selected from ISIS NOs: 420907, 420908, 304296, or 420909.

In certain embodiments, a target region is nucleotides 502-531 of SEQ ID NO: 1. In certain embodiments, an antisense compound is targeted to nucleotides 502-531 of SEQ ID NO: 1. In certain embodiments, an antisense compound targeted to a transthyretin nucleic acid comprises a nucleobase sequence selected from SEQ ID NOs: 25, 75-84. In certain such embodiments, an antisense compound targeted to nucleotides 502-531 of SEQ ID NO: 1 is selected from ISIS NOs: 420910, 420911, 420912, 420913, 420914, 304299, 420915, 420916, 420917, 420918, or 420919.

In certain embodiments, a target region is nucleotides 502-539 of SEQ ID NO: 1. In certain embodiments, an antisense compound is targeted to nucleotides 502-539 of SEQ ID NO: 1. In certain embodiments, an antisense compound targeted to a transthyretin nucleic acid comprises a nucleobase sequence selected from SEQ ID NOs: 25, 26, 75-91. In certain such embodiments, an antisense compound targeted to nucleotides 502-539 of SEQ ID NO: 1 is selected from ISIS NOs: 420910, 420911, 420912, 420913, 420914, 304299, 420915, 420916, 420917, 420918, 420919, 304300, 420920, 420921, 420922, 420923, 420924, 420925, or 420926.

In certain embodiments, a target region is nucleotides 504-536 of SEQ ID NO: 1. In certain embodiments, an antisense compound is targeted to nucleotides 504-536 of SEQ ID NO: 1. In certain embodiments, an antisense compound targeted to a transthyretin nucleic acid comprises a nucleobase sequence selected from SEQ ID NOs: 25, 26, 77-88. In certain such embodiments, an antisense compound targeted to nucleotides 504-536 of SEQ ID NO: 1 is selected from ISIS NOs: 420912, 420913, 420914, 304299, 420915, 420916, 420917, 420918, 420919, 304300, 420920, 420921, 420922, or 420923.

In certain embodiments, a target region is nucleotides 505-535 of SEQ ID NO: 1. In certain embodiments, an antisense compound is targeted to nucleotides 505-535 of SEQ ID NO: 1. In certain embodiments, an antisense compound targeted to a transthyretin nucleic acid comprises a nucleobase sequence selected from SEQ ID NOs: 25, 26, 78-87. In certain such embodiments, an antisense compound targeted to nucleotides 505-535 of SEQ ID NO: 1 is selected from ISIS NOs: 420913, 420914, 304299, 420915, 420916, 420917, 420918, 420919, 304300, 420920, 420921, or 420922.

In certain embodiments, a target region is nucleotides 506-530 of SEQ ID NO: 1. In certain embodiments, an antisense compound is targeted to nucleotides 506-530 of SEQ ID NO: 1. In certain embodiments, an antisense compound targeted to a transthyretin nucleic acid comprises a nucleobase sequence selected from SEQ ID NOs: 25, 79-83. In certain such embodiments, an antisense compound targeted to nucleotides 506-530 of SEQ ID NO: 1 is selected from ISIS NOs: 420913, 420914, 304299, 420915, 420916, 420917, 420918, or 420919.

In certain embodiments, a target region is nucleotides 507-527 of SEQ ID NO: 1. In certain embodiments, an antisense compound is targeted to nucleotides 507-527 of SEQ ID NO: 1. In certain embodiments, an antisense compound targeted to a transthyretin nucleic acid comprises a nucleobase sequence selected from SEQ ID NOs: 25 or 80. In certain such embodiments, an antisense compound targeted to nucleotides 507-527 of SEQ ID NO: 1 is selected from ISIS NO: 304299 or 420915.

In certain embodiments, a target region is nucleotides 508-527 of SEQ ID NO: 1. In certain embodiments, an antisense compound is targeted to nucleotides 508-527 of SEQ ID NO: 1. In certain embodiments, an antisense compound targeted to a transthyretin nucleic acid comprises a nucleobase sequence selected from SEQ ID NO: 80. In certain such embodiments, an antisense compound targeted to nucleotides 508-527 of SEQ ID NO: 1 is selected from ISIS NO: 420915.

In certain embodiments, a target region is nucleotides 514-540 of SEQ ID NO: 1. In certain embodiments, an antisense compound is targeted to nucleotides 514-540 of SEQ ID NO: 1. In certain embodiments, an antisense compound targeted to a transthyretin nucleic acid comprises a nucleobase sequence selected from SEQ ID NOs: 85-92. In certain such embodiments, an antisense compound targeted to nucleotides 514-540 of SEQ ID NO: 1 is selected from ISIS NOs: 420920, 420921, 420922, 420923, 420924, 420925, 420926, or 420927.

In certain embodiments, a target region is nucleotides 523-542 of SEQ ID NO: 1. In certain embodiments, an antisense compound is targeted to nucleotides 523-542 of SEQ ID NO: 1. In certain embodiments, an antisense compound targeted to a transthyretin nucleic acid comprises a nucleobase sequence selected from SEQ ID NO: 94. In certain such embodiments, an antisense compound targeted to nucleotides 523-542 of SEQ ID NO: 1 is selected from ISIS NO: 420929.

In certain embodiments, a target region is nucleotides 544-606 of SEQ ID NO: 1. In certain embodiments, an antisense compound is targeted to nucleotides 544-606 of SEQ ID NO: 1. In certain embodiments, an antisense compound targeted to a transthyretin nucleic acid comprises a nucleobase sequence selected from SEQ ID NOs: 30-33, 112-122. In certain such embodiments, an antisense compound targeted to nucleotides 544-606 of SEQ ID NO: 1 is selected from ISIS NOs: 420947, 420948, 304304, 304307, 304308, 304309, 420949, 420950, 420951, 420952, 420953, 420954, 420955, 420956, or 420957.

In certain embodiments, a target region is nucleotides 544-564 of SEQ ID NO: 1. In certain embodiments, an antisense compound is targeted to nucleotides 544-564 of SEQ ID NO: 1. In certain embodiments, an antisense compound targeted to a transthyretin nucleic acid comprises a nucleobase sequence selected from SEQ ID NOs: 112-113. In certain such embodiments, an antisense compound targeted to nucleotides 544-564 of SEQ ID NO: 1 is selected from ISIS NOs: 420947 or 420948.

In certain embodiments, a target region is nucleotides 544-583 of SEQ ID NO: 1. In certain embodiments, an antisense compound is targeted to nucleotides 544-583 of SEQ ID NO: 1. In certain embodiments, an antisense compound targeted to a transthyretin nucleic acid comprises a nucleobase sequence selected from SEQ ID NOs: 30, 31, 112, and 113. In certain such embodiments, an antisense compound targeted to nucleotides 544-583 of SEQ ID NO: 1 is selected from ISIS NOs: 420947, 420948, 304304, or 304307.

In certain embodiments, a target region is nucleotides 597-617 of SEQ ID NO: 1. In certain embodiments, an antisense compound is targeted to nucleotides 597-617 of SEQ ID NO: 1. In certain embodiments, an antisense compound targeted to a transthyretin nucleic acid comprises a nucleobase sequence selected from SEQ ID NOs: 34-35. In certain such embodiments, an antisense compound targeted to nucleotides 597-617 of SEQ ID NO: 1 is selected from ISIS NOs: 304311 or 304312.

In certain embodiments, the modified oligonucleotide consists of a single-stranded modified oligonucleotide.

In certain embodiments, the modified oligonucleotide consists of 20 linked nucleosides.

In certain embodiments, the nucleobase sequence of the modified oligonucleotide is at least 90% complementary over its entire length to a nucleobase sequence of SEQ ID NO: 1, 2, or 4. In certain embodiments, the nucleobase sequence of the modified oligonucleotide is at least 95% complementary over its entire length to a nucleobase sequence of SEQ ID NO: 1, 2, or 4. In certain embodiments, the modified oligonucleotide is at least 99% complementary over its entire length to SEQ ID NO: 1, 2, or 4. In certain embodiments, the nucleobase sequence of the modified oligonucleotide is 100% complementary over its entire length to a nucleobase sequence of SEQ ID NO: 1, 2, or 4.

In certain embodiments, the compound has at least one modified internucleoside linkage. In certain embodiments, the internucleoside linkage is a phosphorothioate internucleoside linkage.

In certain embodiments, the compound has at least one nucleoside comprising a modified sugar. In certain embodiments, the at least one modified sugar is a bicyclic sugar. In certain embodiments, the at least one bicyclic sugar comprises a 4'-CH(CH$_3$)—O-2' bridge. In certain embodiments, the at least one modified sugar comprises a 2'-O-methoxyethyl.

In certain embodiments, the compound comprises at least one at least one tetrahydropyran modified nucleoside wherein a tetrahydropyran ring replaces the furanose ring. In certain embodiments, the at least one tetrahydropyran modified nucleoside has the structure:

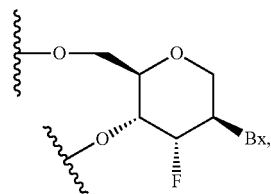

wherein Bx is an optionally protected heterocyclic base moiety.

In certain embodiments, the compound has at least one nucleoside comprising a modified nucleobase. In certain embodiments, the modified nucleobase is a 5-methylcytosine.

In certain embodiments, the modified oligonucleotide of the compound comprises:
(i) a gap segment consisting of linked deoxynucleosides;
(ii) a 5' wing segment consisting of linked nucleosides;
(iii) a 3' wing segment consisting of linked nucleosides, wherein the gap segment is positioned between the 5' wing segment and the 3' wing segment and wherein each nucleoside of each wing segment comprises a modified sugar.

In certain embodiments, the modified oligonucleotide of the compound comprises:
(i) a gap segment consisting of ten linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
(i) a gap segment consisting of eight linked deoxynucleosides;
(ii) a 5' wing segment consisting of six linked nucleosides;
(iii) a 3' wing segment consisting of six linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
(i) a gap segment consisting of eight linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
(i) a gap segment consisting of ten linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage; and wherein the nucleobase sequence comprises at least 8 contiguous nucleobases of the nucleobase sequence recited in SEQ ID NO: 80.

In certain embodiments, the modified oligonucleotide of the compound comprises:
(i) a gap segment consisting of ten linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage; and wherein the nucleobase sequence is recited in SEQ ID NO: 80.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 25, 80, 86, 87, 115, 120, 122, and 124 or a salt thereof and a pharmaceutically acceptable carrier or diluent.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of the nucleobase sequences recited in SEQ ID NO: 80 or a salt thereof and a pharmaceutically acceptable carrier or diluent.

Certain embodiments provide a composition comprising a compound as described herein, wherein the viscosity level is less than 40 cP. In certain embodiments, the composition has a viscosity level less than 15 cP. In certain embodiments, the composition has a viscosity level less than 12 cP. In certain embodiments, the composition has a viscosity level less than 10 cP.

Certain embodiments provide methods of treating, preventing, or ameliorating transthyretin amyloidosis.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 25, 80, 86, 87, 115, 120, 122, and 124.

Certain embodiments provide methods comprising administering to an animal a compound as described herein to an animal. In certain embodiments, the method comprises administering to an animal a compound or modified oligonucleotide consisting 12 to 30 linked nucleosides, wherein the linked nucleosides comprise at least an 8 contiguous nucleobase portion complementary to an equal length portion within the region selected from nucleotides 501-535 or 580-608 of SEQ ID NO: 1.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence recited in SEQ ID NO: 80.

Certain embodiments provide methods comprising administering to an animal a compound as described herein to an animal. In certain embodiments, the method comprises administering to an animal a compound or modified oligonucleotide consisting 12 to 30 linked nucleosides, wherein the linked nucleosides comprise at least an 8 contiguous nucleobase portion complementary to an equal length portion within the region selected from nucleotides 508-527 of SEQ ID NO: 1.

In certain embodiments, the animal is a human.

In certain embodiments, the administering prevents, treats, ameliorates, or slows progression of transthyretin amyloidosis as described herein.

In certain embodiments, the compound is co-administered with a second agent.

In certain embodiments, the compound and the second agent are administered concomitantly.

In certain embodiments, the administering is parenteral administration. In certain embodiments, the parenteral administration is subcutaneous administration. In certain embodiments, the formulation for administering is the compound in saline. In certain embodiments, the compound comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 25, 80, 86, 87, 115, 120, 122, and 124 or a salt thereof and saline. In certain embodiments, the formulation does not include any stabilizing agents or additional stabilizing agents including lipid agents.

In certain embodiments, the administering is parenteral administration. In certain embodiments, the parenteral administration is intracranial administration. In certain embodiments, the intracranial administration is intracerebral, intrathecal, intraventricular, ventricular, intracerebroventricular, cerebral intraventricular or cerebral ventricular administration.

Certain embodiments further provide a method to reduce transthyretin mRNA or protein expression in an animal comprising administering to the animal a compound or composition as described herein to reduce transthyretin mRNA or protein expression in the animal. In certain embodiments, the animal is a human. In certain embodiments, reducing transthyretin mRNA or protein expression prevents, treats, ameliorates, or slows progression of transthyretin amyloidosis.

Certain embodiments provide a method for treating a human with a transthyretin related disease comprising identifying the human with the disease and administering to the human a therapeutically effective amount of a compound or composition as described herein. In certain embodiments, the treatment reduces a symptom selected from the group consisting of restlessness, lack of coordination, nystagmus, spastic paraparesis, lack of muscle coordination, impaired vision, insomnia, unusual sensations, myoclonus, blindness, loss of speech, Carpal tunnel syndrome, seizures, subarachnoid hemorrhages, stroke and bleeding in the brain, hydrocephalus, ataxia, and spastic paralysis, coma, sensory neuropathy, parathesia, hypesthesia, motor neuropathy, autonomic neuropathy, orthostatic hypotension, cyclic constipation, cyclic diarrhea, nausea, vomiting, reduced sweating, impotence, delayed gastric emptying, urinary retention, urinary incontinence, progressive cardiopathy, fatigue, shortness of breath, weight loss, lack of appetite, numbness, tingling, weakness, enlarged tongue, nephrotic syndrome, congestive heart failure, dyspnea on exertion, peripheral edema, arrhythmias, palpitations, light-headedness, syncope, postural hypotension, peripheral nerve problems, sensory motor impairment, lower limb neuropathy, upper limb neuropathy, hyperalgesia, altered temperature sensation, lower extremity weakness, cachexia, peripheral edema, hepatomegaly, purpura, diastolic dysfunction, premature ventricular contractions, cranial neuropathy, diminished deep tendon reflexes, amyloid deposits in the corpus vitreum, vitreous opacity, dry eyes, glaucoma, scalloped appearance in the pupils, swelling of the feet due to water retention. In certain embodiments, the symptom is a cognitive symptom selected from the group consisting of impaired memory, impaired judgment, and thinking, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of dementia; anxiety, depression, blunted affect, egocentrisms, aggression, compulsive behavior, irritability, personality changes, including, impaired memory, judgment, and thinking and suicidal ideation.

Further embodiments provide a method of treating a human with transthyretin amyloidosis leading to cardiac amyloidosis and administering to the human a therapeutically effective amount of a compound or composition as described herein. In certain embodiments, the treatment reduces a symptom selected from the group consisting of congestive heart failure, cardiomegaly, dyspnea on exertion, peripheral edema, arrhythmias, palpitations, lightheadedness, syncope, deposition in the subendothelium of the peripheral vasculature can lead to severe postural hypotension, diastolic dysfunction, heart block, premature ventricular contractions, and various tachyarrhythmias.

Further embodiments provide a method of treating a human with transthyretin amyloidosis leading to peripheral neuropathic disorders and administering to the human a therapeutically effective amount of a compound or composition as described herein. In certain embodiments, the treatment reduces a symptom selected from the group consisting of peripheral nerve problems, sensorimotor impairment, lower-limb neuropathy, upper-limb neuropathy, hyperalgesia, altered temperature sensation, lower extremity weakness, pain, autonomic dysfunction, often manifested as sexual or urinary dysfunction, symmetric sensory impairment and weakness, orthostatic hypotension, diarrhea, and/or impotence.

Further embodiments provide a method of treating a human with transthyretin amyloidosis leading to gastrointestinal disorders and administering to the human a therapeutically effective amount of a compound or composition a described herein. In certain embodiments, the treatment reduces a symptom selected from the group consisting of diarrhea, constipation, nausea, vomiting, and related kidney and liver disorders.

Further provided is a method for reducing or preventing transthyretin amyloidosis comprising administering to a human a therapeutically effective amount compound or composition as described herein, thereby reducing or preventing transthyretin amyloidosis.

Further provided is a method for reducing or preventing a cardiac disease comprising administering to a human a therapeutically effective amount compound or composition as described herein, thereby reducing or preventing a cardiac disease. Further provided is a method for reducing or preventing a neuropathic disease comprising administering to a human a therapeutically effective amount compound or composition as described herein, thereby reducing or preventing a neuropathic disease. Further provided is a method for reducing or preventing a gastrointestinal disease comprising administering to a human a therapeutically effective amount compound or composition as described herein, thereby reducing or preventing a gastrointestinal disease.

Further provided is a method for ameliorating a symptom of transthyretin amyloidosis, comprising administering to a human in need thereof a compound comprising a modified oligonucleotide consisting of 12 to 30 linked nucleosides, wherein said modified oligonucleotide specifically hybridizes to SEQ ID NO: 1, 2, or 4, thereby ameliorating a symptom of transthyretin amyloidosis in the human.

Further provided is a method for reducing the rate of progression of a symptom associated with transthyretin amyloidosis, comprising administering to a human in need thereof a compound comprising a modified oligonucleotide consisting of 12 to 30 linked nucleosides, wherein said modified oligonucleotide specifically hybridizes to SEQ ID NO: 1, 2, or 4, thereby reducing the rate of progression a symptom of transthyretin amyloidosis in the human.

Further provided is a method for reversing degeneration indicated by a symptom associated with a transthyretin amyloidosis, administering to a human in need thereof a compound comprising a modified oligonucleotide consisting of 12 to 30 linked nucleosides, wherein said modified oligonucleotide specifically hybridizes to SEQ ID NO: 1, 2, or 4, thereby reversing degeneration indicated by a symptom of transthyretin amyloid disease in the human.

Further provided is a method for ameliorating a symptom of transthyretin amyloidosis, comprising administering to a human in need thereof a compound comprising a modified oligonucleotide consisting of 12 to 30 linked nucleosides and having a nucleobase sequence comprising at least 8 contiguous nucleobases of a nucleobase sequence recited in SEQ ID NO: 80, thereby ameliorating a symptom of transthyretin amyloidosis in the human.

Further embodiments provide a method of treating a human with transthyretin amyloidosis, administering to a human in need thereof a compound comprising a modified oligonucleotide consisting of 12 to 30 linked nucleosides and having a nucleobase sequence comprising at least 8 contiguous nucleobases of a nucleobase sequence recited in SEQ ID NO: 80, thereby treating transthyretin amyloidosis in a human.

In certain embodiments, the symptom is a physical, cognitive, psychiatric, or peripheral symptom. In certain embodiments, the symptom is a physical symptom selected from the group consisting of restlessness, lack of coordination, nystagmus, spastic paraparesis, lack of muscle coordination, impaired vision, insomnia, unusual sensations, myoclonus, blindness, loss of speech, Carpal tunnel syndrome, seizures, subarachnoid hemorrhages, stroke and bleeding in the brain, hydrocephalus, ataxia, and spastic paralysis, coma, sensory neuropathy, parathesia, hypesthesia, motor neuropathy, autonomic neuropathy, orthostatic hypotension, cyclic constipation, cyclic diarrhea, nausea, vomiting, reduced sweating, impotence, delayed gastric emptying, urinary retention, urinary incontinence, progressive cardiopathy, fatigue, shortness of breath, weight loss, lack of appetite, numbness, tingling, weakness, enlarged tongue, nephrotic syndrome, congestive heart failure, dyspnea on exertion, peripheral edema, arrhythmias, palpitations, lightheadedness, syncope, postural hypotension, peripheral nerve problems, sensory motor impairment, lower limb neuropathy, upper limb neuropathy, hyperalgesia, altered temperature sensation, lower extremity weakness, cachexia, peripheral edema, hepatomegaly, purpura, diastolic dysfunction, premature ventricular contractions, cranial neuropathy, diminished deep tendon reflexes, amyloid deposits in the corpus vitreum, vitreous opacity, dry eyes, glaucoma, scalloped appearance in the pupils, swelling of the feet due to water retention. In certain embodiments, the symptom is a cognitive symptom selected from the group consisting of impaired memory, impaired judgment, and thinking, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of dementia; anxiety, depression, blunted affect, egocentrisms, aggression, compulsive behavior, irritability, personality changes, including, impaired memory, judgment, and thinking and suicidal ideation.

In certain embodiments the symptom is at least one of at least one physical symptom, at least one cognitive symptom, at least one psychiatric symptom, and at least one peripheral symptom.

In certain embodiments the physical symptom is selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances.

In certain embodiments the cognitive symptom is selected from the group consisting of impaired memory, impaired judgment, and thinking, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia.

In certain embodiments the psychiatric symptom is selected from the group consisting of dementia; anxiety, depression, blunted affect, egocentrisms, aggression, compulsive behavior, irritability, personality changes, including, impaired memory, judgment, and thinking and suicidal ideation.

In certain embodiments the peripheral symptom is selected from the group consisting of reduced brain mass, muscle atrophy, cardiac failure, impaired glucose tolerance, weight loss, osteoporosis, and testicular atrophy.

Also provided are methods and compounds for the preparation of a medicament for the treatment, prevention, or amelioration of a central nervous system related disease.

Certain embodiments provide the use of a compound as described herein in the manufacture of a medicament for treating, ameliorating, or preventing a transthyretin amyloidosis.

Certain embodiments provide a compound as described herein for use in treating, preventing, or ameliorating transthyretin amyloidosis as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating transthyretin amyloidosis as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating transthyretin amyloidosis as described herein in a patient who is subsequently administered an additional agent or therapy as described herein.

Certain embodiments provide a kit for treating, preventing, or ameliorating transthyretin amyloidosis as described herein wherein the kit comprises:
(i) a compound as described herein; and alternatively
(ii) an additional agent or therapy as described herein.

A kit as described herein may further include instructions for using the kit to treat, prevent, or ameliorate transthyretin amyloidosis as described herein by combination therapy as described herein.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a transthyretin nucleic acid is 12 to 30 nucleotides in length. In other words, antisense compounds are from 12 to 30 linked nucleobases. In other embodiments, the antisense compound comprises a modified oligonucleotide consisting of 8 to 80, 12 to 50, 12 to 30, 15 to 30, 18 to 24, 18 to 21, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a transthyretin nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides or linked nucleosides that supports RNaseH cleavage is positioned between external regions having a plurality of nucleotides or linked nucleosides that are chemically distinct from the nucleotides or linked nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH2)n-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6 or 5-8-5.

In certain embodiments, the antisense compound as a "wingmer" motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to a transthyretin nucleic acid possess a 5-10-5 gapmer motif.

In certain embodiments, antisense compounds targeted to a transthyretin nucleic acid possess a 6-8-6 gapmer motif.

In certain embodiments, antisense compounds targeted to a transthyretin nucleic acid possess a 5-8-5 gapmer motif.

In certain embodiments, an antisense compound targeted to a transthyretin nucleic acid has a gap-widened motif.

In certain embodiments, a gap-widened antisense oligonucleotide targeted to a transthyretin nucleic acid has a gap segment of ten 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a transthyretin nucleic acid has a gap segment of eight 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a transthyretin nucleic acid has a gap segment of eight 2'-deoxyribonucleotides positioned immediately adjacent to and between wing segments of six chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

In certain embodiments, the transthyretin nucleic acid is any of the sequences set forth in GENBANK Accession No. NM_000371.2, first deposited with GENBANK® on Feb. 13, 2008 (incorporated herein as SEQ ID NO: 1), GENBANK Accession No. NT_010966.10 truncated from nucleotides 2009236 to 2017289, first deposited with GENBANK® on Aug. 1, 2002 (incorporated herein as SEQ ID NO: 2); exons 1-4 extracted from the rhesus monkey genomic sequence GENBANK Accession No. NW_001105671.1, based on similarity to human exons; and GENBANK Accession No. NW_001105671.1 truncated from nucleotides 628000 to 638000 (incorporated herein as SEQ ID NO: 4), first deposited with GENBANK® on Mar. 28, 2006.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) or ISIS NO indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for transthyretin can be obtained by accession number from sequence databases such as NCBI and such information is incorporated herein by reference. In certain embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in transthyretin mRNA levels are indicative of inhibition of transthyretin expression. Reductions in levels of a transthyretin protein are also indicative of inhibition of target mRNA expression. Further, phenotypic changes are indicative of inhibition of transthyretin expression. For example, increase in brain size to normal, improvement in motor coordination, decrease in continual muscular spasms (dystonia), decrease in irritability and/or anxiety, improvement of memory, or an increase in energy, among other phenotypic changes that may be assayed. Other phenotypic indications, e.g., symptoms associated with transthyretin amyloidosis, may also be assessed as described below.

Hybridization

In some embodiments, hybridization occurs between an antisense compound disclosed herein and a transthyretin nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a transthyretin nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a transthyretin nucleic acid).

An antisense compound may hybridize over one or more segments of a transthyretin nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a transthyretin nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a transthyretin nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a transthyretin nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a transthyretin nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a transthyretin nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds of the invention can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH$_3$, 2'-OCH$_2$CH$_3$, 2'-OCH$_2$CH$_2$F and 2'-O(CH$_2$)$_2$OCH$_3$ substituent groups. The substituent at the 2' position can also be selected from allyl, amino, azido, thio, O-allyl, O—C$_1$-C$_{10}$ alkyl, OCF$_3$, OCH$_2$F, O(CH$_2$)$_2$SCH$_3$, O(CH$_2$)$_2$—O—N(R$_m$)(R$_n$) O—CH$_2$—C(=O)—N(R$_m$)(R$_n$), and O—CH$_2$—C(=O)—N(R$_l$)—(CH$_2$)$_2$—N(R$_m$)(R$_n$), where each R$_l$, R$_m$ and R$_n$ is, independently, H or substituted or unsubstituted C$_1$-C$_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH(CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N(OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J. Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$)=C(R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_2$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{13}$ aminoalkyl, substituted C$_1$-C$_{12}$ aminoalkyl or a protecting group.

In certain embodiments, the bridge of a bicyclic sugar moiety is —[C(R$_a$)(R$_b$)]$_n$—, —[C(R$_a$)(R$_b$)]$_n$—O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 63 65-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

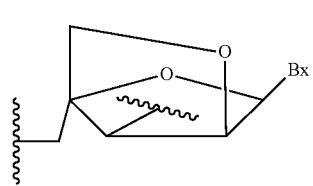

(A)

-continued (B) 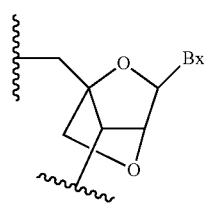

(C) 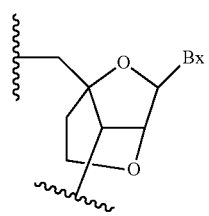

(D) 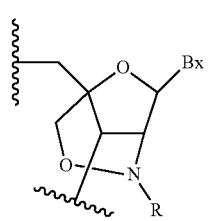

(E) 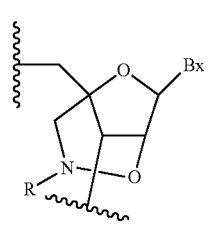

(F) 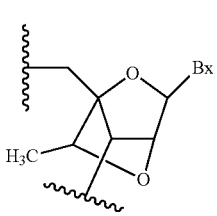

(G) 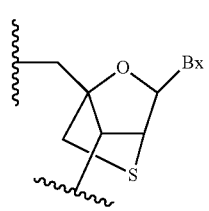

(H) 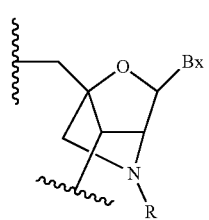

-continued (I) 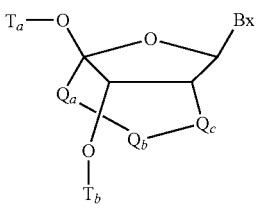

(J) 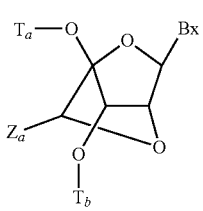

wherein Bx is the base moiety and R is independently H, a protecting group or $C_1$-$C_{12}$ alkyl.

In certain embodiments, bicyclic nucleosides are provided having Formula I:

$$\text{I}$$

wherein:
Bx is a heterocyclic base moiety;
-$Q_a$-$Q_b$-$Q_c$-is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

$$\text{II}$$

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

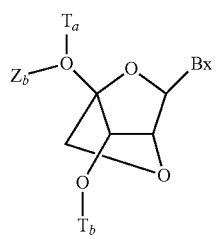

III wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

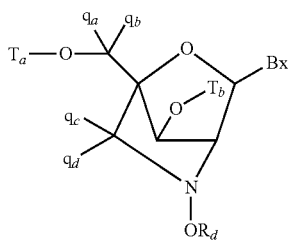

IV wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

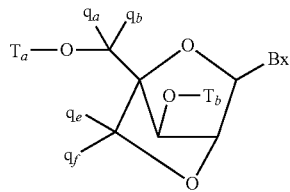

V wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

$q_a$, $q_b$, $q_e$ and $q_f$ of are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$;

or $q_e$ and $q_f$ together are =C($q_g$)($q_h$);

$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribonucleotide duplexes as substrates for nucleic acid polymerases has also been described (Wengel et al., WO 99/14226). Furthermore, synthesis of 2'-amino-BNA, a novel comformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

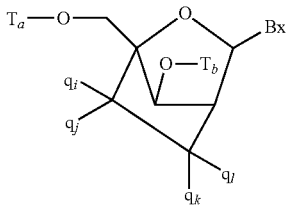

VI wherein:

Bx is a heterocyclic base moiety;

$T_a$ and $T_b$ are each, independently H, a hydroxyl protecting group, a conjugate group, a reactive phosphorus group, a phosphorus moiety or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, C(=O)$OJ_j$, C(=O)$NJ_jJ_k$, C(=O)$J_j$, O—C(=O)$NJ_jJ_k$, N(H)C(=NH)$NJ_jJ_k$, N(H)C(=O)$NJ_jJ_k$ or N(H)C(=S)$NJ_jJ_k$; and $q_i$ and $q_j$ or $q_l$ and $q_k$ together are =C($q_g$)($q_h$), wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-(CH$_2$)$_3$-2' bridge and the alkenyl analog bridge 4'-CH=CH—CH$_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$)]$_m$CH$_3$, O(CH$_2$)$_n$NH$_2$, O(CH$_2$)$_n$CH$_3$, O(CH$_2$)$_n$F, O(CH$_2$)$_n$ONH$_2$, OCH$_2$C(=O)N(H)CH$_3$, and O(CH$_2$)$_n$ON[(CH$_2$)$_n$CH$_3$]$_2$, where n and m are from 1 to about 10. Other 2'-substituent groups can also be selected from: $C_1$-$C_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.*, 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta*, 1995, 78, 486-504; Altmann et al., *Chimia*, 1996, 50, 168-176; Altmann et al., *Biochem. Soc. Trans.*, 1996, 24, 630-637; and Altmann et al., *Nucleosides Nucleotides*, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.*, 2002, 10, 841-854), fluoro HNA (F-HNA) or those compounds having Formula VII:

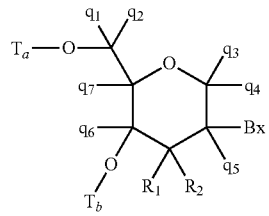

VII wherein independently for each of said at least one tetrahydropyran nucleoside analog of Formula VII:

Bx is a heterocyclic base moiety;

$T_a$ and $T_b$ are each, independently, an internucleoside linking group linking the tetrahydropyran nucleoside analog to the antisense compound or one of $T_a$ and $T_b$ is an internucleoside linking group linking the tetrahydropyran nucleoside analog to the antisense compound and the other of $T_a$ and $T_b$ is H, a hydroxyl protecting group, a linked conjugate group or a 5' or 3'-terminal group;

$q_1$, $q_2$, $q_3$, $q_4$, $q_5$, $q_6$ and $q_7$ are each independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl; and each of $R_1$ and $R_2$ is selected from hydrogen, hydroxyl, halogen, substituted or unsubstituted alkoxy, $NJ_1J_2$, $SJ_1$, $N_3$, OC(=X)$J_1$, OC(=X)$NJ_1J_2$, $NJ_3$C(=X)$NJ_1J_2$ and CN, wherein X is O, S or $NJ_1$ and each $J_1$, $J_2$ and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, $q_3$, $q_4$, $q_5$, $q_6$ and $q_7$ is methyl. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is fluoro. In certain embodiments, $R_1$ is fluoro and $R_2$ is H; $R_1$ is methoxy and $R_2$ is H, and $R_1$ is H and $R_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—$C_1$-$C_{10}$ alkyl, —OCF$_3$, O—(CH$_2$)$_2$—O—CH$_3$, 2'-O(CH$_2$)$_2$SCH$_3$, O—(CH$_2$)$_2$—O—N($R_m$)($R_n$), or O—CH$_2$—C(=O)—N($R_m$)($R_n$), where each $R_m$ and $R_n$ is, independently, H or substituted or unsubstituted $C_1$-$C_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "MOE" or "2'-MOE" or "2'-OCH$_2$CH$_2$OCH$_3$" or "2'-O-methoxyethyl" each refers to a nucleoside comprising a sugar comprising a —OCH$_2$CH$_2$OCH$_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.*, 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH$_3$)—O-2') bridging group. In certain embodiments, the (4'-CH(CH$_3$)—O-2') modified nucleosides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a transthyretin nucleic acid comprise one or more modified nucleobases. In certain embodiments, gap-widened antisense oligonucleotides targeted to a transthyretin nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a transthyretin nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a transthyretin nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of transthyretin nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a transthyretin nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a transthyretin nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of transthyretin nucleic acids can be assessed by measuring transthyretin protein levels. Protein levels of transthyretin can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat transthyretin are commercially available.

In Vivo Testing of Antisense Compounds

Antisense compounds, for example, antisense oligonucleotides, are tested in animals to assess their ability to inhibit expression of transthyretin and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in transthyretin nucleic acid expression are measured. Changes in transthyretin protein levels are also measured.

Certain Compounds

About two hundred and forty six newly designed antisense compounds of various lengths, motifs and backbone composition were tested for their effect on human transthyretin mRNA in vitro in several cell types. The new compounds were compared with about seventy nine previously designed compounds including ISIS NOs. 304267, 304268, 304280, 304284, 304285, 304286, 304287, 304288, 304289, 304290, 304291, 304292, 304293, 304294, 304296, 304297, 304298, 304299, 304300, 304301, 304302, 304303, 304304, 304307, 304308, 304309, 304311, and 304312 which have previously been determined to be some of the most potent antisense compounds in vitro (see e.g., U.S. Patent Publication Nos. US2005/0244869 and US2009/0082300). Of the about three hundred and twenty five newly designed and previously designed antisense compounds, about fifteen compounds were selected for further study based on in vitro potency. The selected compounds were tested for in vivo potency and tolerability in a transgenic mouse model (see Example 10). Of the fifteen compounds tested, eleven were selected and tested for systemic tolerability (see Example 11) and half-life measurement in liver (see Example 12) in CD1 mice, and also for systemic tolerability (see Example 13) and pharmacokinetic studies of oligonucleotide concentration in liver (see Example 14) in Sprague-Dawley rats. From these studies, seven compounds were tested for dose dependent inhibition and tolerability in transgenic mice (see Example 15). Furthermore, fifteen additional compounds were selected from Table 1 and six additional compounds with various motifs were designed with overlapping sequences to ISIS 420951, which displayed high potency and tolerability in the above-mentioned assays. These additional compounds were compared with ISIS 420951 for potency and tolerability in transgenic mice (see Example 16). Based on all these studies (Examples 10-16), twenty two compounds were selected and tested for systemic tolerability in CD1 mice (see Example 17). Seven compounds were considered tolerable in the mouse model and further tested for systemic tolerability in Sprague-Dawley rats (see Example 18) and for pharmacokinetic studies of oligonucleotide concentration in the liver and kidney (see Example 19). The seven compounds were also tested for dose-dependent potency in transgenic mice (see Example 20).

Final evaluation of these studies (Examples 16-20), led to the selection of nine compounds having a nucleobase sequence of a sequence recited in SEQ ID NO: 25, 78, 80, 86, 87, 115, 120, 122 and 124. By virtue of their complementary sequence, the compounds are complementary to the regions 505-524, 507-526, 508-527, 513-532, 515-534, 516-535, 580-599, 585-604, 587-606, or 589-608 of SEQ ID NO: 1. In certain embodiments, the compounds targeting the listed regions, as further described herein, comprise a modified oligonucleotide having some nucleobase portion of the sequence recited in the SEQ ID NOs, as further described herein, In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 304299, ISIS 420913, ISIS 420915, ISIS 420921, ISIS 420922, ISIS 420950, ISIS 420955, ISIS 420957, or ISIS 420959.

The nine compounds having a nucleobase sequence of a sequence recited in SEQ ID NO: 25, 78, 80, 86, 87, 115, 120, 122 and 124, were further tested for dose dependent inhibition in primary hepatocytes of cynomolgus monkey (See Example 21). These compounds were also tested for optimal viscosity (Example 22). The half life in the liver of CD1 mice of seven of the compounds having a nucleobase sequence of a sequence recited in SEQ ID NOs: 78, 86, 87. 115, 120 and 124 was also evaluated (Example 23).

Final evaluation of these studies (Examples 1-23), led to the selection of eight compounds having a nucleobase sequence of a sequence recited in SEQ ID NO: 25, 80, 86, 87, 115, 120, 122 and 124. By virtue of their complementary sequence, the compounds are complementary to the regions 504-523, 505-524, 512-531, 513-532, 577-596, 582-601, 584-603, and 586-605 of SEQ ID NO: 1. In certain embodiments, the compounds targeting the listed regions, as further described herein, comprise a modified oligonucleotide having some nucleobase portion of the sequence recited in the SEQ ID NOs, as further described herein, In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 304299, ISIS 420915, ISIS 420921, ISIS 420922, ISIS 420950, ISIS 420955, ISIS 420957, or ISIS 420959.

These eight compounds were tested for efficacy, pharmacokinetic profile and tolerability in cynomolgus monkeys (Example 24). The inhibition studies in these monkeys indicated that treatment with some of these compounds caused high inhibition of TTR mRNA in the liver. Specifically, treatment with ISIS 420950, ISIS 420955 and ISIS 420915 caused 91%, 79% and 78% inhibition, respectively compared to the PBS control. It was noted that ISIS 420915 caused greater inhibition of TTR (78%) mRNA compared to ISIS 304299 (59%), even though the two oligonucleotides differ from each other by a single base-pair shift of their target region on SEQ ID NO: 1. Protein analysis also complemented the RNA analysis data with treatment with ISIS 420915 causing 76% inhibition and treatment with ISIS 304299 causing 47% inhibition of TTR protein compared to the control. RBP4 protein levels, as a protein associated with transthyretin, was also expected to decrease after treatment with the antisense compounds. RBP4 protein levels decreased by 63% after treatment with ISIS 420915. Treatment with ISIS 304299 decreased RBP4 protein levels by 19%. Additionally, ISIS 420915 was more tolerable than ISIS 304299, as indicated in the monkey study (Example 24) Transaminase levels of monkeys treated with ISIS 304299 (ALT 81 IU/L and AST 101 IU/L) were higher than those treated with ISIS 420915 (ALT 68 IU/L and AST 62 IU/L). The complement C3 levels of monkeys treated with ISIS 304299 (96 mg/dL) were lower than that of monkeys treated with ISIS 420915 (104 mg/dL).

Accordingly, provided herein are antisense compounds with any one or more of the improved characteristics. In a certain embodiments, provided herein are compounds comprising a modified oligonucleotide as further described herein targeted to or specifically hybridizable with the region of nucleotides of SEQ ID NO: 1.

Accordingly, provided herein are antisense compounds with any one or more of the improved characteristics. In a certain embodiments, provided herein are compounds comprising a modified oligonucleotide as further described herein targeted to or specifically hybridizable with the region of nucleotides of SEQ ID NO: 2.

Accordingly, provided herein are antisense compounds with any one or more of the improved characteristics. In a certain embodiments, provided herein are compounds comprising a modified oligonucleotide as further described herein targeted to or specifically hybridizable with the region of nucleotides of SEQ ID NO: 4.

In certain embodiments, the compounds as described herein are efficacious by virtue of having at least one of an in vitro $IC_{50}$ of less than 2.9 uM, less than 2.2 uM, less than 2.0 uM, less than 1.5 uM, less than 1.4 uM, less than 1.3 uM, less than 1.0 uM, less than 0.7 uM, less than 0.6 uM, when delivered to a cynomolgous monkey hepatocyte cell line using electroporation as described in Example 67. In certain embodiments, the compounds as described herein are highly tolerable as demonstrated by having at least one of an increase in ALT or AST value of no more than 4 fold, 3 fold, or 2 fold over saline treated animals; or an increase in liver, spleen or kidney weight of no more than 30%, 20%, 15%, 12%, 10%, 5% or 2%.

Certain Indications

In certain embodiments, provided herein are methods of treating an individual comprising administering one or more pharmaceutical compositions as described herein. In certain embodiments, the individual has central nervous system related disease.

As shown in the examples below, compounds targeted to transthyretin as described herein have been shown to reduce the severity of physiological symptoms of central nervous system related diseases. In certain of the experiments, the compounds reduced rate of amyloid plaque formation, e.g., the animals continued to experience symptoms, but the symptoms were less severe compared to untreated animals. In other of the experiments, however, the compounds appear to result in regeneration of function over time; e.g., animals treated for a longer period of time experienced less severe symptoms than those administered the compounds for a shorter period of time. The ability of the compounds exemplified below to restore function therefore demonstrates that symptoms of the disease may be reversed by treatment with a compound as described herein.

Accordingly, provided herein are methods for ameliorating a symptom associated with central nervous system related, cardiac, neuropathologic or gastrointestinal disease in a subject in need thereof. In certain embodiments, provided is a method for reducing the rate of onset of a symptom associated with central nervous system related, cardiac, neuropathologic or gastrointestinal disease. In certain embodiments, provided is a method for reducing the severity of a symptom associated with central nervous system related, cardiac, neuropathologic or gastrointestinal. In such embodiments, the methods comprise administering to an individual in need thereof a therapeutically effective amount of a compound targeted to a Transthyretin nucleic acid.

Transthyretin amyloidosis is characterized by numerous physical, neurological, psychiatric, and/or peripheral symptoms. Any symptom known to one of skill in the art to be associated with transthyretin amyloidosis can be ameliorated or otherwise modulated as set forth above in the methods described above. In certain embodiments, the symptom is a physical, cognitive, psychiatric, or peripheral symptom. In certain embodiments, the symptom is a physical symptom selected from the group consisting of restlessness, lack of coordination, nystagmus, spastic paraparesis, lack of muscle coordination, impaired vision, insomnia, unusual sensations, myoclonus, blindness, loss of speech, Carpal tunnel syndrome, seizures, subarachnoid hemorrhages, stroke and bleeding in the brain, hydrocephalus, ataxia, and spastic paralysis, coma, sensory neuropathy, parathesia, hypesthesia, motor neuropathy, autonomic neuropathy, orthostatic hypotension, cyclic constipation, cyclic diarrhea, nausea, vomiting, reduced sweating, impotence, delayed gastric emptying, urinary retention, urinary incontinence, progressive cardiopathy, fatigue, shortness of breath, weight loss, lack of appetite, numbness, tingling, weakness, enlarged tongue, nephrotic syndrome, congestive heart failure, dyspnea on exertion, peripheral edema, arrhythmias, palpitations, light-headedness, syncope, postural hypotension, peripheral nerve problems, sensory motor impairment, lower limb neuropathy, upper limb neuropathy, hyperalgesia, altered temperature sensation, lower extremity weakness, cachexia, peripheral edema, hepatomegaly, purpura, diastolic dysfunction, premature ventricular contractions, cranial neuropathy, diminished deep tendon reflexes, amyloid deposits in the corpus vitreum, vitreous opacity, dry eyes, glaucoma, scalloped appearance in the pupils, swelling of the feet due to water retention. In certain embodiments, the symptom is a cognitive symptom selected from the group consisting of impaired memory, impaired judgment, and thinking, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of dementia; anxiety, depression, blunted affect, egocentrisms, aggression, compulsive behavior, irritability, personality changes, including, impaired memory, judgment, and thinking and suicidal ideation.

In certain embodiments, the symptom is restlessness. In certain embodiments, the symptom is lack of coordination. In certain embodiments, the symptom is nystagmus. In certain embodiments, the symptom is spastic paraparesis. In certain embodiments, the symptom is lack of muscle coordination. In certain embodiments, the symptom is impaired vision. In certain embodiments, the symptom is insomnia. In certain embodiments, the symptom is unusual sensations. In certain embodiments, the symptom is myoclonus. In certain embodiments, the symptom is blindness. In certain embodiments, the symptom is loss of speech. In certain embodiments, the symptom is Carpal tunnel syndrome. In certain embodiments, the symptom is seizures. In certain embodiments, the symptom is subarachnoid hemorrhages. In certain embodiments, the symptom is stroke. In certain embodiments, the symptom is bleeding in the brain. In certain embodiments, the symptom is hydrocephalus. In certain embodiments, the symptom is ataxia. In certain embodiments, the symptom is spastic paralysis. In certain embodiments, the symptom is coma. In certain embodiments, the symptom is sensory neuropathy. In certain embodiments, the symptom is parathesia. In certain embodiments, the symptom is hypesthesia. In certain embodiments, the symptom is motor neuropathy. In certain embodiments, the symptom is autonomic neuropathy. In certain embodiments, the symptom is orthostatic hypotension. In certain embodiments, the symptom is cyclic constipation. In certain embodiments, the symptom is cyclic diarrhea. In certain embodiments, the symptom is nausea. In certain embodiments, the symptom is vomiting. In certain embodiments, the symptom is reduced sweating. In certain embodiments, the symptom is impotence. In certain embodiments, the symptom is delayed gastric emptying. In certain embodiments, the symptom is urinary retention. In certain embodiments, the symptom is urinary incontinence. In certain embodiments, the symptom is progressive cardiopathy. In certain embodiments, the symptom is fatigue. In certain embodiments, the symptom is shortness of breath. In certain embodiments, the symptom is weight loss. In certain embodiments, the symptom is numbness. In certain embodiments, the symptom is tingling. In certain embodiments, the symptom is weakness. In certain embodiments, the symptom is enlarged tongue. In certain embodiments, the symptom is nephrotic syndrome. In certain embodiments, the symptom is congestive heart failure. In certain embodiments, the symptom is dyspnea on exertion. In certain embodiments, the symptom is peripheral edema. In certain embodiments, the symptom is arrhythmias. In certain embodiments, the symptom is palpitations. In certain embodiments, the symptom is light-headedness. In certain embodiments, the symptom is syncope. In certain embodiments, the symptom is postural hypotension. In certain embodiments, the symptom is peripheral nerve problems. In certain embodiments, the symptom is sensory motor impairment. In certain embodiments, the symptom is lower limb neuropathy. In certain embodiments, the symptom is upper limb neuropathy. In certain embodiments, the symptom is hyperalgesia. In certain embodiments, the symptom is altered temperature sensation. In certain embodiments, the symptom is lower extremity weakness. In certain embodiments, the symptom is cachexia. In certain embodiments, the symptom is edema. In certain embodiments, the symptom is hepatomegaly. In certain embodiments, the symptom is purpura. In certain embodiments, the symptom is diastolic dysfunction. In certain embodiments, the symptom is premature ventricular contractions. In certain embodiments, the symptom is cranial neuropathy. In certain embodiments, the symptom is diminished deep tendon reflexes. In certain embodiments, the symptom is amyloid deposits in the corpus vitreum. In certain embodiments, the symptom is vitreous opacity. In certain embodiments, the symptom is dry eyes. In certain embodiments, the symptom is glaucoma. In certain embodiments, the symptom is scalloped appearance in the pupils. In certain embodiments, the symptom is swelling of the feet due to water retention.

In certain embodiments, the symptom is impaired memory. In certain embodiments, the symptom is impaired judgment, and thinking. In certain embodiments, the symptom is impaired planning. In certain embodiments, the symptom is impaired flexibility. In certain embodiments, the symptom is impaired abstract thinking. In certain embodiments, the symptom is impaired rule acquisition. In certain embodiments, the symptom is impaired initiation of appropriate actions. In certain embodiments, the symptom is impaired inhibition of inappropriate actions. In certain embodiments, the symptom is impaired short-term memory. In certain embodiments, the symptom is impaired long-term memory. In certain embodiments, the symptom is paranoia. In certain embodiments, the symptom is disorientation. In certain embodiments, the symptom is confusion. In certain embodiments, the symptom is hallucination. In certain embodiments, the symptom is dementia.

In certain embodiments, the symptom is dementia. In certain embodiments, the symptom is anxiety. In certain embodiments, the symptom is depression. In certain embodiments, the symptom is blunted affect. In certain embodiments, the symptom is egocentrisms. In certain embodiments, the symptom is aggression. In certain embodiments, the symptom is compulsive behavior. In certain embodiments, the symptom is irritability. In certain embodiments, the symptom is personality changes. In certain embodiments, the symptom is suicidal ideation.

In certain embodiments, provided are methods of treating an individual comprising administering one or more pharmaceutical compositions as described herein. In certain embodiments, the individual has central nervous system related disease.

In certain embodiments, administration of an antisense compound targeted to a transthyretin nucleic acid results in reduction of transthyretin expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to transthyretin are used for the preparation of a medicament for treating a patient suffering or susceptible to central nervous system related disease.

In certain embodiments, the methods described herein include administering a compound comprising a modified oligonucleotide having a contiguous nucleobases portion as described herein of a sequence recited in SEQ ID NO: 25, 78, 80, 86, 87, 115, 120, 122 and 124.

Administration

In certain embodiments, the compounds and compositions as described herein may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, oral or parenteral. The compounds and compositions as described herein can be delivered in a manner to target a particular tissue, such as the liver or brain.

In certain embodiments, the compounds and compositions as described herein are administered parenterally. "Parenteral administration" means administration through injection or infusion. Parenteral administration includes subcutaneous administration, intravenous administration, intramuscular administration, intraarterial administration, intraperitoneal administration, or intracranial administration, e.g. intracerebral administration, intrathecal administration, intraventricular administration, ventricular administration, intracerebroventricular administration, cerebral intraventricular administration or cerebral ventricular administration. Administration can be continuous, or chronic, or short or intermittent.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, parenteral administration is subcutaneous.

In further embodiments, the formulation for administration is the compounds described herein and saline.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal into multiple regions of the central nervous system (e.g., into multiple regions of the brain, and/or into the spinal cord) by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, the present invention includes pharmaceutical compositions that can be delivered by injection directly into the brain. The injection can be by stereotactic injection into a particular region of the brain (e.g., the substantia nigra, choroid plexus, cortex, hippocampus, striatum, choroid plexus or globus pallidus). The compound can also be delivered into diffuse regions of the brain (e.g., diffuse delivery to the cortex of the brain).

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

In certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

The half-life of MOE gapmer oligonucleotides in CD1 mice liver tissue is about 21 days (see Examples 12).

In certain embodiments, an antisense oligonucleotide is delivered by injection or infusion once every month, every two months, every 90 days, every 3 months, every 6 months, twice a year or once a year.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, the second compound is administered prior to administration of a pharmaceutical composition of the present invention. In certain embodiments, the second compound is administered following administration of a pharmaceutical composition of the present invention. In certain embodiments, the second compound is administered at the same time as a pharmaceutical composition of the present invention. In certain embodiments, the dose of a co-administered second compound is the same as the dose that would be administered if the second compound was administered alone. In certain embodiments, the dose of a co-administered second compound is lower than the dose that would be administered if the second compound was administered alone. In certain embodiments, the dose of a co-administered second compound is greater than the dose that would be administered if the second compound was administered alone.

In certain embodiments, the co-administration of a second compound enhances the effect of a first compound, such that co-administration of the compounds results in an effect that is greater than the effect of administering the first compound alone. In certain embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

In certain embodiments, pharmaceutical agents that may be co-administered with a pharmaceutical composition of the present invention include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, ramelteon, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

In certain embodiments, pharmaceutical agents that may be co-administered with a pharmaceutical composition of the present invention include analgesics, such as, paracetamol (acetaminophen); non-steroidal anti-inflammatory drugs (NSAIDs), such as, salicylates; narcotic drugs, such as, morphine, and synthetic drugs with narcotic properties such as tramadol.

In certain embodiments, pharmaceutical agents that may be co-administered with a pharmaceutical composition of the present invention include muscle relaxants, such as, benzodiapines and methocarbamol.

Formulations

The compounds of the invention may also be admixed, conjugated or otherwise associated with other molecules, molecule structures or mixtures of compounds, as for example, liposomes, receptor-targeted molecules, or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety. Sodium salts have been shown to be suitable forms of oligonucleotide drugs.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be parenteral. Parenteral administration includes intravenous, intraarterial, subcutaneous, intraperitoneal or intramuscular injection or infusion; or intracranial, e.g., intracerebral administration, intrathecal administration, intraventricular administration, ventricular administration, intracerebroventricular administration, cerebral intraventricular administration or cerebral ventricular administration.

Administration intraventricularly, is preferred to target transthyretin expression in the choroid plexus. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 µm in diameter. Emulsions may contain additional components in addition to the dispersed phases, and the active drug which may be present as a solution in the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Liposomes and their uses are further described in U.S. Pat. No. 6,287,860, which is incorporated herein in its entirety.

In another embodiment of the invention, formulations of the present invention include saline formulations. In certain embodiment of the invention, a formulation consists of the compounds described herein and saline. In certain embodiments, a formulation consists essentially of the compounds described herein and saline. In certain embodiments, the saline is pharmaceutically acceptable grade saline. In certain embodiments, the saline is buffered saline. In certain embodiments, the saline is phosphate buffered saline (PBS).

In certain embodiments, a formulation excludes liposomes. In certain embodiments, the formulation excludes sterically stabilized liposomes. In certain embodiments, a formulation excludes phospholipids. In certain embodiments, the formulation consists essentially of the compounds described herein and saline and excludes liposomes.

The pharmaceutical formulations and compositions of the present invention may also include surfactants. Surfactants and their uses are further described in U.S. Pat. No. 6,287,860, which is incorporated herein in its entirety.

In one embodiment, the present invention employs various penetration enhancers to affect the efficient delivery of nucleic acids, particularly oligonucleotides. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

Compositions and formulations for parenteral administration, including intravenous, intraarterial, subcutaneous, intraperitoneal, intramuscular injection or infusion, or intracranial may include sterile aqueous solutions which may also contain buffers, diluents and other suitable additives such as, but not limited to, penetration enhancers, carrier compounds and other pharmaceutically acceptable carriers or excipients.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual oligonucleotides, and can generally be estimated based on $EC_{50}$s found to be effective in in vitro and in vivo animal models. In general, dosage is from 0.01 µg to 100 g per kg of body weight, and may be given once or more daily, weekly, monthly or yearly, or at desired intervals. Following successful treatment, it may be desirable to have the patient undergo maintenance therapy to prevent the recurrence of the disease state, wherein the oligonucleotide is administered in maintenance doses, ranging from 0.01 µg to 100 g per kg of body weight, once or more daily.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Transthyretin in HepG2 Cells

Antisense oligonucleotides were designed targeting a transthyretin nucleic acid and were tested for their effects on transthyretin mRNA in vitro. Cultured HepG2 cells at a density of 10,000 cells per well were transfected using lipofectin reagent with 50 nM antisense oligonucleotide. After a treatment period of approximately 24 hours, RNA was isolated from the cells and transthyretin mRNA levels were measured by quantitative real-time PCR. Human primer probe set RTS1396 (forward sequence CCCTGCTGAGCCCCTACTC, designated herein as SEQ ID NO: 5; reverse sequence TCCCTCATTCCTTGGGATTG, designated herein as SEQ ID NO: 6; probe sequence ATTCCACCACGGCTGTCGTCAX, designated herein as SEQ ID NO: 7). Transthyretin mRNA levels were adjusted according to total RNA content, as measured by RIBOGREEN®. Results are presented as percent inhibition of transthyretin, relative to untreated control cells.

The chimeric antisense oligonucleotides in Tables 1 and 2 were designed as 5-10-5 MOE gapmers. The gapmers are 20 nucleotides in length, wherein the central gap segment is comprised of ten 2'-deoxynucleotides and is flanked on both sides (in the 5' and 3' directions) by wings comprising five nucleotides each. Each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. "Human Target start site" indicates the 5'-most nucleotide to which the gapmer is targeted in the human gene sequence. "Human Target stop site" indicates the 3'-most nucleotide to which the gapmer is targeted human gene sequence. Each gapmer listed in Table 1 is targeted to human transthyretin mRNA, designated herein as SEQ ID NO: 1 (GENBANK Accession No. NM_000371.2). Certain gapmers were also designed which targeted intronic sequences or intron-exon junctions of the human transthyretin genomic sequence, designated herein as SEQ ID NO: 2 (GENBANK Accession No. NT_010966.10 truncated from nucleotides 2009236 to 2017289) and are listed in Table 2.

The human oligonucleotides of Tables 1 and 2 are also cross-reactive with rhesus monkey gene sequences. 'Mismatches' indicate the number of nucleobases by which the human oligonucleotide is mismatched with a rhesus monkey gene sequence. The greater the complementarity between the human oligonucleotide and the rhesus monkey sequence, the more likely the human oligonucleotide can cross-react with the rhesus monkey sequence. The human oligonucleotides in Table 1 were compared to exons 1-4 extracted from the rhesus monkey genomic sequence GENBANK Accession No. NW_001105671.1, based on similarity to human exons. The human oligonucleotides in Table 2 were compared to the rhesus monkey genomic sequence, designated herein as SEQ ID NO: 4 (GENBANK Accession No. NW_001105671.1 truncated from nucleotides 628000 to 638000). "Rhesus monkey Target start site" indicates the 5'-most nucleotide to which the gapmer is targeted in the rhesus monkey gene sequence. "Rhesus monkey Target stop site" indicates the 3'-most nucleotide to which the gapmer is targeted rhesus monkey gene sequence.

TABLE 1

Inhibition of human transthyretin mRNA levels by chimeric antisense oligonucleotides having 5-10-5 MOE wings and deoxy gap targeted to SEQ ID NO: 1 and SEQ ID NO: 4

| ISIS NO | Human Start Site | Human Stop Site | Region | Sequence | % inhibition | Rhesus monkey start site | Rhesus monkey stop site | Mismatches | SEQ ID NO |
|---|---|---|---|---|---|---|---|---|---|
| 304267 | 217 | 236 | coding | ACTGGTTTTCCCAGAGGCAA | 53 | 217 | 236 | 0 | 8 |
| 304268 | 222 | 241 | coding | GACTCACTGGTTTTCCCAGA | 16 | 222 | 241 | 0 | 9 |
| 304280 | 353 | 372 | coding | TGAATACCACCTCTGCATGC | 51 | 353 | 372 | 0 | 10 |
| 304284 | 425 | 444 | coding | CCGTGGTGGAATAGGAGTAG | 82 | 425 | 444 | 0 | 11 |
| 304285 | 427 | 446 | coding | AGCCGTGGTGGAATAGGAGT | 89 | 427 | 446 | 0 | 12 |
| 304286 | 431 | 450 | coding | CGACAGCCGTGGTGGAATAG | 63 | 431 | 450 | 0 | 13 |
| 304287 | 438 | 457 | coding | TTGGTGACGACAGCCGTGGT | 88 | 438 | 457 | 0 | 14 |
| 304288 | 440 | 459 | coding | GATTGGTGACGACAGCCGTG | 82 | 440 | 459 | 0 | 15 |

TABLE 1-continued

Inhibition of human transthyretin mRNA levels by
chimeric antisense oligonucleotides having 5-10-5
MOE wings and deoxy gap targeted to SEQ ID NO: 1
and SEQ ID NO: 4

| ISIS NO | Human Start Site | Human Stop Site | Region | Sequence | % inhibition | Rhesus monkey start site | Rhesus monkey stop site | Mis-matches | SEQ ID NO |
|---|---|---|---|---|---|---|---|---|---|
| 304289 | 442 | 461 | coding | GGGATTGGTGACGACAGCCG | 78 | 442 | 461 | 0 | 16 |
| 304290 | 443 | 462 | coding | TGGGATTGGTGACGACAGCC | 85 | 443 | 462 | 0 | 17 |
| 304291 | 449 | 468 | coding-stop codon | ATTCCTTGGGATTGGTGACG | 52 | 449 | 468 | 0 | 18 |
| 304292 | 450 | 469 | coding-stop codon | CATTCCTTGGGATTGGTGAC | 34 | 450 | 469 | 0 | 19 |
| 304293 | 451 | 470 | coding-stop codon | TCATTCCTTGGGATTGGTGA | 29 | 451 | 470 | 0 | 20 |
| 304294 | 460 | 479 | coding-stop codon-3'-UTR | AGAAGTCCCTCATTCCTTGG | 32 | 460 | 479 | 0 | 21 |
| 304296 | 481 | 500 | 3'-UTR | GTCCTTCAGGTCCACTGGAG | 84 | 478 | 497 | 2 | 22 |
| 304297 | 489 | 508 | 3'-UTR | CATCCCTCGTCCTTCAGGTC | 0 | 486 | 505 | 1 | 23 |
| 304298 | 501 | 520 | 3'-UTR | TACATGAAATCCCATCCCTC | 26 | 498 | 517 | 0 | 24 |
| 304299 | 507 | 526 | 3'-UTR | CTTGGTTACATGAAATCCCA | 85 | 504 | 523 | 0 | 25 |
| 304300 | 513 | 532 | 3'-UTR | AATACTCTTGGTTACATGAA | 49 | 510 | 529 | 0 | 26 |
| 304301 | 526 | 545 | 3'UTR | TTAGTAAAAATGGAATACTC | 0 | 523 | 542 | 0 | 27 |
| 304302 | 532 | 551 | 3'UTR | ACTGCTTTAGTAAAAATGGA | 42 | 529 | 548 | 0 | 28 |
| 304303 | 539 | 558 | 3'UTR | TGAAAACACTGCTTTAGTAA | 41 | 536 | 555 | 0 | 29 |
| 304304 | 546 | 565 | 3'UTR | TATGAGGTGAAAACACTGCT | 49 | 543 | 562 | 0 | 30 |
| 304307 | 564 | 583 | 3'UTR | TGGACTTCTAACATAGCATA | 73 | 561 | 580 | 2 | 31 |
| 304308 | 572 | 591 | 3'UTR | TCTCTGCCTGGACTTCTAAC | 55 | 569 | 588 | 1 | 32 |
| 304309 | 578 | 597 | 3'-UTR | TTATTGTCTCTGCCTGGACT | 77 | 575 | 594 | 0 | 33 |
| 304311 | 597 | 616 | 3'-UTR | TGCCTTTCACAGGAATGTTT | 80 | 594 | 613 | 0 | 34 |
| 304312 | 598 | 617 | 3'-UTR | GTGCCTTTCACAGGAATGTT | 71 | 595 | 614 | 0 | 35 |
| 420871 | 36 | 55 | coding | CAGAGGAGGAGCAGACGATG | 48 | 36 | 55 | 0 | 36 |
| 420872 | 120 | 139 | coding | TCTAGAACTTTGACCATCAG | 55 | 120 | 139 | 0 | 37 |

TABLE 1-continued

Inhibition of human transthyretin mRNA levels by
chimeric antisense oligonucleotides having 5-10-5
MOE wings and deoxy gap targeted to SEQ ID NO: 1
and SEQ ID NO: 4

| ISIS NO | Human Start Site | Human Stop Site | Region | Sequence | % inhibition | Rhesus monkey start site | Rhesus monkey stop site | Mis-matches | SEQ ID NO |
|---|---|---|---|---|---|---|---|---|---|
| 420873 | 212 | 231 | coding | TTTTCCCAGAGGCAAATGGC | 54 | 212 | 231 | 0 | 38 |
| 420874 | 226 | 245 | coding | TCCAGACTCACTGGTTTTCC | 63 | 226 | 245 | 0 | 39 |
| 420875 | 271 | 290 | coding | TATCCCTTCTACAAATTCCT | 40 | 271 | 290 | 0 | 40 |
| 420876 | 285 | 304 | coding | ATTTCCACTTTGTATATCCC | 42 | 285 | 304 | 0 | 41 |
| 420877 | 293 | 312 | coding | TGGTGTCTATTTCCACTTTG | 76 | 293 | 312 | 0 | 42 |
| 420878 | 303 | 322 | coding | CAGTAAGATTTGGTGTCTAT | 80 | 303 | 322 | 0 | 43 |
| 420879 | 307 | 326 | coding | CTTCCAGTAAGATTTGGTGT | 73 | 307 | 326 | 0 | 44 |
| 420880 | 347 | 366 | coding | CCACCTCTGCATGCTCATGG | 76 | 347 | 366 | 0 | 45 |
| 420881 | 355 | 374 | coding | TGTGAATACCACCTCTGCAT | 58 | 355 | 374 | 0 | 46 |
| 420882 | 357 | 376 | coding | GCTGTGAATACCACCTCTGC | 69 | 357 | 376 | 0 | 47 |
| 420883 | 362 | 381 | coding | CGTTGGCTGTGAATACCACC | 64 | 362 | 381 | 0 | 48 |
| 420884 | 428 | 447 | coding | CAGCCGTGGTGGAATAGGAG | 93 | 428 | 447 | 0 | 49 |
| 420885 | 430 | 449 | coding | GACAGCCGTGGTGGAATAGG | 93 | 430 | 449 | 0 | 50 |
| 420886 | 432 | 451 | coding | ACGACAGCCGTGGTGGAATA | 92 | 432 | 451 | 0 | 51 |
| 420887 | 433 | 452 | coding | GACGACAGCCGTGGTGGAAT | 93 | 433 | 452 | 0 | 52 |
| 420888 | 434 | 453 | coding | TGACGACAGCCGTGGTGGAA | 95 | 434 | 453 | 0 | 53 |
| 420889 | 435 | 454 | coding | GTGACGACAGCCGTGGTGGA | 93 | 435 | 454 | 0 | 54 |
| 420890 | 436 | 455 | coding | GGTGACGACAGCCGTGGTGG | 97 | 436 | 455 | 0 | 55 |
| 420891 | 437 | 456 | coding | TGGTGACGACAGCCGTGGTG | 97 | 437 | 456 | 0 | 56 |
| 420892 | 439 | 458 | coding | ATTGGTGACGACAGCCGTGG | 93 | 439 | 458 | 0 | 57 |
| 420893 | 441 | 460 | coding | GGATTGGTGACGACAGCCGT | 96 | 441 | 460 | 0 | 58 |
| 420894 | 444 | 463 | coding | TTGGGATTGGTGACGACAGC | 88 | 444 | 463 | 0 | 59 |
| 420895 | 445 | 464 | coding | CTTGGGATTGGTGACGACAG | 95 | 445 | 464 | 0 | 60 |

TABLE 1-continued

Inhibition of human transthyretin mRNA levels by
chimeric antisense oligonucleotides having 5-10-5
MOE wings and deoxy gap targeted to SEQ ID NO: 1
and SEQ ID NO: 4

| ISIS NO | Human Start Site | Human Stop Site | Region | Sequence | % inhibition | Rhesus monkey start site | Rhesus monkey stop site | Mis-matches | SEQ ID NO |
|---|---|---|---|---|---|---|---|---|---|
| 420896 | 446 | 465 | coding | CCTTGGGATTGGTGACGACA | 95 | 446 | 465 | 0 | 61 |
| 420897 | 447 | 466 | coding | TCCTTGGGATTGGTGACGAC | 94 | 447 | 466 | 0 | 62 |
| 420898 | 448 | 467 | coding-stop codon | TTCCTTGGGATTGGTGACGA | 86 | 448 | 467 | 0 | 63 |
| 420899 | 452 | 471 | coding-stop codon-3'UTR | CTCATTCCTTGGGATTGGTG | 94 | 452 | 471 | 0 | 64 |
| 420900 | 453 | 472 | coding-stop codon-3'UTR | CCTCATTCCTTGGGATTGGT | 92 | 453 | 472 | 0 | 65 |
| 420901 | 454 | 473 | coding-stop codon-3'UTR | CCCTCATTCCTTGGGATTGG | 93 | 454 | 473 | 0 | 66 |
| 420902 | 455 | 474 | coding-stop codon-3'UTR | TCCCTCATTCCTTGGGATTG | 75 | 455 | 474 | 0 | 67 |
| 420903 | 456 | 475 | coding-stop codon-3'UTR | GTCCCTCATTCCTTGGGATT | 57 | 456 | 475 | 0 | 68 |
| 420904 | 457 | 476 | coding-stop codon-3'UTR | AGTCCCTCATTCCTTGGGAT | 62 | 457 | 476 | 0 | 69 |
| 420905 | 458 | 477 | coding-stop codon-3'UTR | AAGTCCCTCATTCCTTGGGA | 58 | 458 | 477 | 0 | 70 |
| 420906 | 459 | 478 | coding-stop codon-3'UTR | GAAGTCCCTCATTCCTTGGG | 79 | 459 | 478 | 0 | 71 |
| 420907 | 461 | 480 | coding-stop codon-3'UTR | GAGAAGTCCCTCATTCCTTG | 59 | 461 | 480 | 0 | 72 |
| 420908 | 462 | 481 | coding-stop codon-3'UTR | GGAGAAGTCCCTCATTCCTT | 75 | 462 | 481 | 0 | 73 |
| 420909 | 500 | 519 | 3'UTR | ACATGAAATCCCATCCCTCG | 82 | 497 | 516 | 0 | 74 |
| 420910 | 502 | 521 | 3'UTR | TTACATGAAATCCCATCCCT | 74 | 499 | 518 | 0 | 75 |
| 420911 | 503 | 522 | 3'UTR | GTTACATGAAATCCCATCCC | 81 | 500 | 519 | 0 | 76 |

TABLE 1-continued

Inhibition of human transthyretin mRNA levels by
chimeric antisense oligonucleotides having 5-10-5
MOE wings and deoxy gap targeted to SEQ ID NO: 1
and SEQ ID NO: 4

| ISIS NO | Human Start Site | Human Stop Site | Region | Sequence | % inhibition | Rhesus monkey start site | Rhesus monkey stop site | Mis-matches | SEQ ID NO |
|---|---|---|---|---|---|---|---|---|---|
| 420912 | 504 | 523 | 3'UTR | GGTTACATGAAATCCCATCC | 92 | 501 | 520 | 0 | 77 |
| 420913 | 505 | 524 | 3'UTR | TGGTTACATGAAATCCCATC | 95 | 502 | 521 | 0 | 78 |
| 420914 | 506 | 525 | 3'UTR | TTGGTTACATGAAATCCCAT | 93 | 503 | 522 | 0 | 79 |
| 420915 | 508 | 527 | 3'UTR | TCTTGGTTACATGAAATCCC | 92 | 505 | 524 | 0 | 80 |
| 420916 | 509 | 528 | 3'UTR | CTCTTGGTTACATGAAATCC | 88 | 506 | 525 | 0 | 81 |
| 420917 | 510 | 529 | 3'UTR | ACTCTTGGTTACATGAAATC | 92 | 507 | 526 | 0 | 82 |
| 420918 | 511 | 530 | 3'UTR | TACTCTTGGTTACATGAAAT | 88 | 508 | 527 | 0 | 83 |
| 420919 | 512 | 531 | 3'UTR | ATACTCTTGGTTACATGAAA | 89 | 509 | 528 | 0 | 84 |
| 420920 | 514 | 533 | 3'UTR | GAATACTCTTGGTTACATGA | 87 | 511 | 530 | 0 | 85 |
| 420921 | 515 | 534 | 3'UTR | GGAATACTCTTGGTTACATG | 92 | 512 | 531 | 0 | 86 |
| 420922 | 516 | 535 | 3'UTR | TGGAATACTCTTGGTTACAT | 95 | 513 | 532 | 0 | 87 |
| 420923 | 517 | 536 | 3'UTR | ATGGAATACTCTTGGTTACA | 90 | 514 | 533 | 0 | 88 |
| 420924 | 518 | 537 | 3'UTR | AATGGAATACTCTTGGTTAC | 75 | 515 | 534 | 0 | 89 |
| 420925 | 519 | 538 | 3'UTR | AAATGGAATACTCTTGGTTA | 87 | 516 | 535 | 0 | 90 |
| 420926 | 520 | 539 | 3'UTR | AAAATGGAATACTCTTGGTT | 88 | 517 | 536 | 0 | 91 |
| 420927 | 521 | 540 | 3'UTR | AAAAATGGAATACTCTTGGT | 50 | 518 | 537 | 0 | 92 |
| 420928 | 522 | 541 | 3'UTR | TAAAAATGGAATACTCTTGG | 26 | 519 | 538 | 0 | 93 |
| 420929 | 523 | 542 | 3'UTR | GTAAAAATGGAATACTCTTG | 56 | 520 | 539 | 0 | 94 |
| 420930 | 524 | 543 | 3'UTR | AGTAAAAATGGAATACTCTT | 18 | 521 | 540 | 0 | 95 |
| 420931 | 525 | 544 | 3'UTR | TAGTAAAAATGGAATACTCT | 12 | 522 | 541 | 0 | 96 |
| 420932 | 527 | 546 | 3'UTR | TTTAGTAAAAATGGAATACT | 1 | 524 | 543 | 0 | 97 |
| 420933 | 528 | 547 | 3'UTR | CTTTAGTAAAAATGGAATAC | 0 | 525 | 544 | 0 | 98 |
| 420934 | 529 | 548 | 3'UTR | GCTTTAGTAAAAATGGAATA | 6 | 526 | 545 | 0 | 99 |

TABLE 1-continued

Inhibition of human transthyretin mRNA levels by
chimeric antisense oligonucleotides having 5-10-5
MOE wings and deoxy gap targeted to SEQ ID NO: 1
and SEQ ID NO: 4

| ISIS NO | Human Start Site | Human Stop Site | Region | Sequence | % inhibition | Rhesus monkey start site | Rhesus monkey stop site | Mis-matches | SEQ ID NO |
|---|---|---|---|---|---|---|---|---|---|
| 420935 | 530 | 549 | 3'UTR | TGCTTTAGTAAAAATGGAAT | 0 | 527 | 546 | 0 | 100 |
| 420936 | 531 | 550 | 3'UTR | CTGCTTTAGTAAAAATGGAA | 40 | 528 | 547 | 0 | 101 |
| 420937 | 533 | 552 | 3'UTR | CACTGCTTTAGTAAAAATGG | 47 | 530 | 549 | 0 | 102 |
| 420938 | 534 | 553 | 3'UTR | ACACTGCTTTAGTAAAAATG | 30 | 531 | 550 | 0 | 103 |
| 420939 | 535 | 554 | 3'UTR | AACACTGCTTTAGTAAAAAT | 0 | 532 | 551 | 0 | 104 |
| 420940 | 536 | 555 | 3'UTR | AAACACTGCTTTAGTAAAAA | 0 | 533 | 552 | 0 | 105 |
| 420941 | 537 | 556 | 3'UTR | AAAACACTGCTTTAGTAAAA | 0 | 534 | 553 | 0 | 106 |
| 420942 | 538 | 557 | 3'UTR | GAAAACACTGCTTTAGTAAA | 0 | 535 | 554 | 0 | 107 |
| 420943 | 540 | 559 | 3'UTR | GTGAAAACACTGCTTTAGTA | 14 | 537 | 556 | 0 | 108 |
| 420944 | 541 | 560 | 3'UTR | GGTGAAAACACTGCTTTAGT | 43 | 538 | 557 | 0 | 109 |
| 420945 | 542 | 561 | 3'UTR | AGGTGAAAACACTGCTTTAG | 41 | 539 | 558 | 0 | 110 |
| 420946 | 543 | 562 | 3'UTR | GAGGTGAAAACACTGCTTTA | 20 | 540 | 559 | 0 | 111 |
| 420947 | 544 | 563 | 3'UTR | TGAGGTGAAAACACTGCTTT | 69 | 541 | 560 | 0 | 112 |
| 420948 | 545 | 564 | 3'UTR | ATGAGGTGAAAACACTGCTT | 63 | 542 | 561 | 0 | 113 |
| 420949 | 579 | 598 | 3'UTR | TTTATTGTCTCTGCCTGGAC | 84 | 576 | 595 | 0 | 114 |
| 420950 | 580 | 599 | 3'UTR | TTTTATTGTCTCTGCCTGGA | 69 | 577 | 596 | 0 | 115 |
| 420951 | 581 | 600 | 3'UTR | GTTTTATTGTCTCTGCCTGG | 87 | 578 | 597 | 0 | 116 |
| 420952 | 582 | 601 | 3'UTR | TGTTTTATTGTCTCTGCCTG | 67 | 579 | 598 | 0 | 117 |
| 420953 | 583 | 602 | 3'UTR | ATGTTTTATTGTCTCTGCCT | 51 | 580 | 599 | 0 | 118 |
| 420954 | 584 | 603 | 3'UTR | AATGTTTTATTGTCTCTGCC | 60 | 581 | 600 | 0 | 119 |
| 420955 | 585 | 604 | 3'UTR | GAATGTTTTATTGTCTCTGC | 65 | 582 | 601 | 0 | 120 |
| 420956 | 586 | 605 | 3'UTR | GGAATGTTTTATTGTCTCTG | 67 | 583 | 602 | 0 | 121 |
| 420957 | 587 | 606 | 3'UTR | AGGAATGTTTTATTGTCTCT | 68 | 584 | 603 | 0 | 122 |

TABLE 1-continued

Inhibition of human transthyretin mRNA levels by
chimeric antisense oligonucleotides having 5-10-5
MOE wings and deoxy gap targeted to SEQ ID NO: 1
and SEQ ID NO: 4

| ISIS NO | Human Start Site | Human Stop Site | Region | Sequence | % inhibition | Rhesus monkey start site | Rhesus monkey stop site | Mis-matches | SEQ ID NO |
|---|---|---|---|---|---|---|---|---|---|
| 420958 | 588 | 607 | 3'UTR | CAGGAATGTTTTATTGTCTC | 45 | 585 | 604 | 0 | 123 |
| 420959 | 589 | 608 | 3'UTR | ACAGGAATGTTTTATTGTCT | 28 | 586 | 605 | 0 | 124 |

TABLE 2

Inhibition of human transthyretin mRNA levels by
chimeric antisense oligonucleotides having 5-10-5
MOE wings and deoxy gap targeted to SEQ ID NO: 2
and SEQ ID NO: 4

| ISIS NO | Human Start Site | Human Stop Site | Region | Sequence | % inhibition | Rhesus monkey start site | Rhesus monkey stop site | Mis-matches | SEQ ID NO |
|---|---|---|---|---|---|---|---|---|---|
| 420960 | 606 | 625 | exon 1-intron 1 | GATGTCACAGAAACACTCAC | 13 | 1755 | 1774 | 0 | 125 |
| 420961 | 665 | 684 | intron 1 | GCAAAGCTGGAAGGAGTCAC | 7 | 1814 | 1833 | 0 | 126 |
| 420962 | 748 | 767 | intron 1 | GAACTTCATTCTTTTTGAAG | 0 | 1897 | 1916 | 0 | 127 |
| 420963 | 882 | 901 | intron 1 | AGCTTCCTTAATATCATATC | 0 | 2031 | 2050 | 0 | 128 |
| 420964 | 966 | 985 | intron 1 | TATAGGGCCAGAATATAATC | 10 | 2115 | 2134 | 0 | 129 |
| 420965 | 1010 | 1029 | intron 1 | ACTAAGCCTTTTAAAGATTA | 17 | 2159 | 2178 | 0 | 130 |
| 420966 | 1208 | 1227 | intron 1 | TGGAATTACTGAAAAGATGT | 35 | 2356 | 2375 | 0 | 131 |
| 420967 | 1289 | 1308 | intron 1 | ACCAGGGATGTGTATAATGA | 43 | 2437 | 2456 | 0 | 132 |
| 420968 | 1364 | 1383 | intron 1 | TCCCTACTCAGTATAACACA | 0 | 2512 | 2531 | 0 | 133 |
| 420969 | 1472 | 1491 | intron 1 | GATCAGAGTGAAAGGATTTA | 0 | 2620 | 2639 | 0 | 134 |
| 420970 | 1687 | 1706 | intron 2 | GGGAAGATAAAACCAAGTCC | 46 | 2826 | 2845 | 0 | 135 |
| 420971 | 1739 | 1758 | intron 2 | TAAATTCTTTAGCAGATGAT | 0 | 2878 | 2897 | 0 | 136 |
| 420972 | 1842 | 1861 | intron 2 | AATGATGCTCAGGTTCCTGG | 23 | 2980 | 2999 | 0 | 137 |
| 420973 | 2051 | 2070 | intron 2 | TTGGTGTTACCCAGGGACAC | 0 | 3187 | 3206 | 0 | 138 |
| 420974 | 2207 | 2226 | intron 2 | AAAGTGTTCATTAGGCAAAA | 29 | 3344 | 3363 | 0 | 139 |
| 420975 | 2655 | 2674 | intron 2 | GGCATTTTATATAAACATAA | 0 | 3798 | 3817 | 0 | 140 |

TABLE 2-continued

Inhibition of human transthyretin mRNA levels by chimeric antisense oligonucleotides having 5-10-5 MOE wings and deoxy gap targeted to SEQ ID NO: 2 and SEQ ID NO: 4

| ISIS NO | Human Start Site | Human Stop Site | Region | Sequence | % inhibition | Rhesus monkey start site | Rhesus monkey stop site | Mismatches | SEQ ID NO |
|---|---|---|---|---|---|---|---|---|---|
| 420976 | 2733 | 2752 | intron 2 | AAGAACATTGGAATATTTTT | 0 | 3876 | 3895 | 0 | 141 |
| 420977 | 2874 | 2893 | intron 2 | GTTGGAAATTGCTTCCCATT | 9 | 4017 | 4036 | 0 | 142 |
| 420978 | 3015 | 3034 | intron 2 | AGTGGAAAACCTAAAGTAGG | 0 | 4156 | 4175 | 0 | 143 |
| 420979 | 3618 | 3637 | intron 2 | TTCCCCTCAACTAAGTCAGA | 0 | 4795 | 4814 | 0 | 144 |
| 420980 | 3735 | 3754 | intron 2-exon 3 | CCTATAAGGTGTGAAAGTCT | 0 | 4930 | 4949 | 0 | 145 |
| 420981 | 4096 | 4115 | intron 3 | TGTAAGTTCAAGTCATGTTA | 0 | 5291 | 5310 | 0 | 146 |
| 420982 | 4306 | 4325 | intron 3 | GTGTTGCCAAGAATCACTTG | 0 | 5502 | 5521 | 0 | 147 |
| 420983 | 4404 | 4423 | intron 3 | AAAACACTTATAATTGTGTC | 0 | 5600 | 5619 | 0 | 148 |
| 420984 | 4518 | 4537 | intron 3 | CTTTGACAAGTTATTTGACT | 0 | 5714 | 5733 | 0 | 149 |
| 420985 | 4880 | 4899 | intron 3 | ATCCATGACTAAGCCAGAGA | 0 | 6073 | 6092 | 0 | 150 |
| 420986 | 5185 | 5204 | intron 3 | ATGGTTCCCATCAGGCTGAG | 0 | 6379 | 6398 | 0 | 151 |
| 420987 | 5542 | 5561 | intron 3 | GCATTTATCAGAAGAAGCTG | 0 | 6732 | 6751 | 0 | 152 |
| 420988 | 6030 | 6049 | intron 3 | TTGACCTTCAGCCCACTTGA | 0 | 7226 | 7245 | 0 | 153 |
| 420989 | 6133 | 6152 | intron 3 | AGGAAGTGAGAATCACCTAA | 0 | 7641 | 7660 | 0 | 154 |
| 420990 | 6320 | 6339 | intron 3 | AGAAGACAGTAAAGATGTGT | 0 | 7828 | 7847 | 0 | 155 |
| 420991 | 6457 | 6476 | intron 3 | AAATTGTGGATCAAAATGCT | 0 | 7966 | 7985 | 0 | 156 |
| 420992 | 6736 | 6755 | intron 3 | AACCAGACTTGAATTATTGT | 0 | 8246 | 8265 | 0 | 157 |
| 420993 | 6811 | 6830 | intron 3 | AGTGGCTGCCAACCACAGAC | 0 | 8321 | 8340 | 0 | 158 |
| 420994 | 7106 | 7125 | intron 3 | GGAAGTCCAGTGCCAACTTA | 0 | 8615 | 8634 | 0 | 159 |
| 420995 | 7162 | 7181 | intron 3 | ATCCATTTCCACCAGAGCCC | 0 | 8670 | 8689 | 0 | 160 |

Due to the short length of the human transthyretin mRNA, a second primer probe set was designed away from the first primer probe set, RTS1396, to avoid amplicon oligonucleotides. The antisense oligonucleotides were also tested for their effects on transthyretin mRNA in vitro using new human primer probe set RTS3029 (forward sequence CTTGCTGGACTGGTATTTGTGTCT, designated herein as SEQ ID NO: 161, reverse sequence AGAACTTTGAC-CATCAGAGGACACT, designated herein as SEQ ID NO: 162; probe sequence CCCTACGGGCACCGGT-GAATCCX, designated herein as SEQ ID NO: 163). Cultured HepG2 cells at a density of 10,000 cells per well were transfected using lipofectin reagent with 50 nM antisense oligonucleotide. After a treatment period of approximately 24 hours, RNA was isolated from the cells and transthyretin mRNA levels were measured by quantitative real-time PCR. Transthyretin mRNA levels were adjusted according to total RNA content, as measured by RIBOGREEN®. Results are presented as percent inhibition of transthyretin, relative to untreated control cells. The results are presented in Table 3 as percent inhibition of the PBS control cell set.

TABLE 3

Inhibition of human transthyretin mRNA levels by chimeric antisense oligonucleotides having 5-10-5 MOE wings and deoxy gap with primer probe set RTS3029

| ISIS NO | Region | % inhibition |
| --- | --- | --- |
| 304267 | coding | 13 |
| 304268 | coding | 10 |
| 304280 | coding | 23 |
| 304284 | coding | 10 |
| 304285 | coding | 34 |
| 304286 | coding | 0 |
| 304287 | coding | 34 |
| 304288 | coding | 45 |
| 304289 | coding | 3 |
| 304290 | coding | 16 |
| 304291 | coding-stop codon | 4 |
| 304292 | coding-stop codon | 10 |
| 304293 | coding-stop codon | 14 |
| 304294 | stop codon-3' UTR | 30 |
| 304296 | exon 4 | 78 |
| 304297 | exon 4 | 29 |
| 304298 | exon 4 | 19 |
| 304299 | exon 4 | 85 |
| 304300 | exon 4 | 52 |
| 304301 | exon 4 | 15 |
| 304302 | exon 4 | 45 |
| 304303 | exon 4 | 51 |
| 304304 | exon 4 | 62 |
| 304307 | exon 4 | 76 |
| 304308 | exon 4 | 63 |
| 304309 | exon 4 | 75 |
| 304311 | exon 4 | 81 |
| 304312 | exon 4 | 68 |
| 420871 | coding | 0 |
| 420872 | coding | 5 |
| 420873 | coding | 19 |
| 420874 | coding | 0 |
| 420875 | coding | 6 |
| 420876 | coding | 20 |
| 420877 | coding | 28 |
| 420878 | coding | 37 |
| 420879 | coding | 34 |
| 420880 | coding | 36 |
| 420881 | coding | 10 |
| 420882 | coding | 27 |
| 420883 | coding | 13 |
| 420884 | coding | 28 |
| 420885 | coding | 4 |
| 420886 | coding | 21 |
| 420887 | coding | 39 |
| 420888 | coding | 37 |
| 420889 | coding | 9 |
| 420890 | coding | 27 |
| 420891 | coding | 39 |
| 420892 | coding | 43 |
| 420893 | coding | 39 |
| 420894 | coding | 0 |
| 420895 | coding | 0 |
| 420896 | coding | 24 |
| 420897 | coding | 31 |
| 420898 | coding- | 0 |
| 420899 | stop codon-3'UTR | 41 |
| 420900 | stop codon-3'UTR | 26 |
| 420901 | stop codon-3'UTR | 28 |
| 420902 | stop codon-3'UTR | 20 |
| 420903 | stop codon-3'UTR | 20 |
| 420904 | stop codon-3'UTR | 22 |
| 420905 | stop codon-3'UTR | 32 |
| 420906 | stop codon-3'UTR | 13 |

TABLE 3-continued

Inhibition of human transthyretin mRNA levels by chimeric antisense oligonucleotides having 5-10-5 MOE wings and deoxy gap with primer probe set RTS3029

| ISIS NO | Region | % inhibition |
| --- | --- | --- |
| 420907 | -stop codon-3'UTR | 0 |
| 420908 | stop codon-3'UTR | 45 |
| 420909 | 3'UTR | 41 |
| 420910 | 3'UTR | 14 |
| 420911 | 3'UTR | 45 |
| 420912 | 3'UTR | 62 |
| 420913 | 3'UTR | 81 |
| 420914 | 3'UTR | 68 |
| 420915 | 3'UTR | 71 |
| 420916 | 3'UTR | 54 |
| 420917 | 3'UTR | 50 |
| 420918 | 3'UTR | 43 |
| 420919 | 3'UTR | 65 |
| 420920 | 3'UTR | 61 |
| 420921 | 3'UTR | 65 |
| 420922 | 3'UTR | 68 |
| 420923 | 3'UTR | 62 |
| 420924 | 3'UTR | 9 |
| 420925 | 3'UTR | 17 |
| 420926 | 3'UTR | 47 |
| 420927 | 3'UTR | 57 |
| 420928 | 3'UTR | 51 |
| 420929 | 3'UTR | 46 |
| 420930 | 3'UTR | 39 |
| 420931 | 3'UTR | 14 |
| 420932 | 3'UTR | 6 |
| 420933 | 3'UTR | 1 |
| 420934 | 3'UTR | 48 |
| 420935 | 3'UTR | 13 |
| 420936 | 3'UTR | 62 |
| 420937 | 3'UTR | 65 |
| 420938 | 3'UTR | 48 |
| 420939 | 3'UTR | 7 |
| 420940 | 3'UTR | 3 |
| 420941 | 3'UTR | 31 |
| 420942 | 3'UTR | 0 |
| 420943 | 3'UTR | 40 |
| 420944 | 3'UTR | 78 |
| 420945 | 3'UTR | 58 |
| 420946 | 3'UTR | 52 |
| 420947 | 3'UTR | 71 |
| 420948 | 3'UTR | 73 |
| 420949 | 3'UTR | 88 |
| 420950 | 3'UTR | 82 |
| 420951 | 3'UTR | 90 |
| 420952 | 3'UTR | 82 |
| 420953 | 3'UTR | 71 |
| 420954 | 3'UTR | 67 |
| 420955 | 3'UTR | 73 |
| 420956 | 3'UTR | 65 |
| 420957 | 3'UTR | 74 |
| 420958 | 3'UTR | 69 |
| 420959 | 3'UTR | 63 |
| 420960 | exon1-intron1 | 14 |
| 420961 | intron 1 | 16 |
| 420962 | intron 1 | 0 |
| 420963 | intron 1 | 0 |
| 420964 | intron 1 | 14 |
| 420965 | intron 1 | 23 |
| 420966 | intron 1 | 25 |
| 420967 | intron 1 | 12 |
| 420968 | intron 1 | 0 |
| 420969 | intron 1 | 0 |
| 420970 | intron 2 | 25 |
| 420971 | intron 2 | 0 |
| 420972 | intron 2 | 25 |
| 420973 | intron 2 | 7 |
| 420974 | intron 2 | 28 |
| 420975 | intron 2 | 9 |
| 420976 | intron 2 | 21 |
| 420977 | intron 2 | 14 |
| 420978 | intron 2 | 37 |
| 420979 | intron 2 | 37 |
| 420980 | intron2-exon 3 | 16 |

TABLE 3-continued

Inhibition of human transthyretin mRNA levels by chimeric antisense oligonucleotides having 5-10-5 MOE wings and deoxy gap with primer probe set RTS3029

| ISIS NO | Region | % inhibition |
|---------|--------|--------------|
| 420981 | intron 3 | 0 |
| 420982 | intron 3 | 28 |
| 420983 | intron 3 | 0 |
| 420984 | intron 3 | 0 |
| 420985 | intron 3 | 0 |
| 420986 | intron 3 | 7 |
| 420987 | intron 3 | 0 |
| 420988 | intron 3 | 0 |
| 420989 | intron 3 | 0 |
| 420990 | intron 3 | 6 |
| 420991 | intron 3 | 15 |
| 420992 | intron 3 | 0 |
| 420993 | intron 3 | 0 |
| 420994 | intron 3 | 0 |
| 420995 | intron 3 | 10 |

Based on the inhibition results using the new primer probe set RTS3029, antisense oligonucleotides exhibiting 50% or more inhibition of transthyretin mRNA were selected for further studies.

Example 2: Antisense Inhibition of Human Transthyretin in HepG2 Cells by Oligonucleotides Designed by Microwalk Additional gapmers were designed based on the gapmers presented in Table 3 that demonstrated an inhibition of at least 50%. These gapmers were designed by creating gapmers shifted slightly upstream and downstream (i.e. "microwalk") of the original gapmers from Table 3. Gapmers were also created with various motifs, e.g. 5-10-5 MOE, 3-14-3 MOE, 2-13-5 MOE, and 4-11-5 MOE motifs. These gapmers were tested in vitro. Cultured HepG2 cells at a density of 10,000 cells per well were transfected using lipofectin reagent with 50 nM antisense oligonucleotide. After a treatment period of approximately 24 hours, RNA was isolated from the cells and transthyretin mRNA levels were measured by quantitative real-time PCR. The human primer probe set RTS3029 was used to measure transthyretin mRNA levels. Transthyretin mRNA levels were adjusted according to total RNA content, as measured by RIBOGREEN®. Results are presented as percent inhibition of transthyretin, relative to untreated control cells. The results are presented in Table 4.

The chimeric antisense oligonucleotides in Table 4 were designed as 5-10-5 MOE, 3-14-3 MOE, 2-13-5 MOE or 4-11-5 MOE gapmers. The gapmers designated with an asterisk (*) in Table 4 are the original gapmers from which gapmers, ISIS 425650-425763, were designed via microwalk. The 5-10-5 gapmers are 20 nucleotides in length, wherein the central gap segment is comprised often 2'-deoxynucleotides and is flanked on both sides (in the 5' and 3' directions) by wings comprising five nucleotides each. The 3-14-3 gapmers are 20 nucleotides in length, wherein the central gap segment is comprised of fourteen 2'-deoxynucleotides and is flanked on both sides (in the 5' and 3' directions) by wings comprising three nucleotides each. The 2-13-5 gapmers are 20 nucleotides in length, wherein the central gap segment is comprised of thirteen 2'-deoxynucleotides and is flanked on the 5' and the 3' directions with wings comprising two and five nucleotides respectively. The 4-11-5 gapmers are 20 nucleotides in length, wherein the central gap segment is comprised of eleven 2'-deoxynucleotides and is flanked on the 5' and the 3' directions with wings comprising four and five nucleotides respectively. For each of the motifs (5-10-5, 3-14-3, 2-113-5, and 4-11-5), each nucleotide in the 5' wing segment and each nucleotide in the 3' wing segment has a 2'-MOE modification. The internucleoside linkages throughout each gapmer are phosphorothioate (P=S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 4 is targeted to the target region spanning nucleobases 481-619 of SEQ ID NO: 1 (GENBANK Accession No. NM_000371.2).

As shown in Table 4, several of the gapmers exhibited at least 50% inhibition, including ISIS numbers: 304296, 425655, 425695, 425735, 425649, 425656, 425696, 425736, 420912, 425657, 425697, 425737, 420913, 425658, 425698, 425738, 420914, 425659, 425699, 425739, 304299, 425660, 425700, 425740, 420915, 420916, 425662, 425702, 420919, 425703, 420920, 425664, 425704, 425742, 420921, 425665, 425705, 425743, 420922, 425666, 425706, 420923, 420937, 420944, 425669, 425709, 425746, 425710, 425711, 425747, 420948, 425712, 425748, 425673, 425713, 425749, 425651, 425675, 425715, 425751, 304309, 425676, 425716, 425752, 420949, 425677, 425717, 425753, 420950, 425678, 425718, 425754, 420951, 425679, 425719, 425755, 420952, 425680, 425720, 425756, 420953, 425681, 425721, 425757, 420954, 425722, 425758, 420955, 425759, 425724, 425760, 425762, 304310, 425729, 425764, 425653, 425690, 425730, 425765, 304311, 425691, 425731, 425766, 304312, 425692, 425732, 425767, 425654, 425693, 425733, 425768, 304313, 425734, and 425769.

Several of the gapmers exhibited at least 60% inhibition, including ISIS numbers: 304296, 425655, 425695, 425735, 425649, 425656, 425696, 425736, 420912, 425657, 425697, 425737, 420913, 425658, 425698, 425738, 420914, 425659, 425739, 304299, 425740, 420915, 425702, 420919, 420920, 425742, 420921, 425665, 425705, 425706, 420923, 425746, 425711, 425747, 420948, 425712, 425748, 425651, 425715, 425751, 304309, 425716, 425752, 425677, 425717, 425753, 420950, 425718, 425754, 420951, 425679, 425719, 425755, 420952, 425680, 425720, 420953, 425681, 425721, 425757, 420954, 425722, 425758, 420955, 425724, 425760, 425764, 425653, 425690, 425730, 425765, 304311, 425691, 425731, 425766, 304312, 425692, 425732, 425767, 425654, 425693, 425733, 304313, and 425769.

Several of the gapmers exhibited at least 70% inhibition, including ISIS numbers: 304296, 425655, 425695, 425735, 425649, 425656, 425696, 425736, 420912, 425657, 425737, 420913, 425738, 420914, 425659, 304299, 420915, 420920, 425742, 425712, 425748, 425716, 425754, 420951, 425679, 425719, 425755, 425680, 425721, 425757, 425760, 425653, 425690, 425730, 425765, 304311, 425691, 425731, 425766, 304312, 425767, 425693, and 304313.

Several of the gapmers exhibited at least 80% inhibition, including ISIS numbers: 304296, 425655, 425695, 425736, 420913, 425659, 304299, 420915, 425716, 425754, 425719, 425757, 425765, and 425767.

Several of the gapmers exhibited at least 85% inhibition, including ISIS numbers: 420913, 425716, 425754, and 425719.

One gapmer, ISIS 425719, exhibited 90% inhibition.

TABLE 4

Inhibition of human transthyretin rnRNA levels by chimeric antisense oligonucleotides targeted to SEQ ID NO: 1 (GENBANK Accession No. NM_000371.2)

| Oligo ID | Start Site | Stop Site | Sequence | Motif | % inhibition | SEQ ID NO |
|---|---|---|---|---|---|---|
| *304296 | 481 | 500 | GTCCTTCAGGTCCACTGGAG | 5-10-5 | 83 | 22 |
| 425655 | 481 | 500 | GTCCTTCAGGTCCACTGGAG | 3-14-3 | 80 | 22 |
| 425695 | 481 | 500 | GTCCTTCAGGTCCACTGGAG | 2-13-5 | 80 | 22 |
| 425735 | 481 | 500 | GTCCTTCAGGTCCACTGGAG | 4-11-5 | 72 | 22 |
| 425649 | 482 | 501 | CGTCCTTCAGGTCCACTGGA | 5-10-5 | 75 | 170 |
| 425656 | 482 | 501 | CGTCCTTCAGGTCCACTGGA | 3-14-3 | 78 | 170 |
| 425696 | 482 | 501 | CGTCCTTCAGGTCCACTGGA | 2-13-5 | 74 | 170 |
| 425736 | 482 | 501 | CGTCCTTCAGGTCCACTGGA | 4-11-5 | 83 | 170 |
| *420912 | 504 | 523 | GGTTACATGAAATCCCATCC | 5-10-5 | 73 | 77 |
| 425657 | 504 | 523 | GGTTACATGAAATCCCATCC | 3-14-3 | 76 | 77 |
| 425697 | 504 | 523 | GGTTACATGAAATCCCATCC | 2-13-5 | 69 | 77 |
| 425737 | 504 | 523 | GGTTACATGAAATCCCATCC | 4-11-5 | 78 | 77 |
| *420913 | 505 | 524 | TGGTTACATGAAATCCCATC | 5-10-5 | 89 | 78 |
| 425658 | 505 | 524 | TGGTTACATGAAATCCCATC | 3-14-3 | 69 | 78 |
| 425698 | 505 | 524 | TGGTTACATGAAATCCCATC | 2-13-5 | 61 | 78 |
| 425738 | 505 | 524 | TGGTTACATGAAATCCCATC | 4-11-5 | 78 | 78 |
| *420914 | 506 | 525 | TTGGTTACATGAAATCCCAT | 5-10-5 | 70 | 79 |
| 425659 | 506 | 525 | TTGGTTACATGAAATCCCAT | 3-14-3 | 83 | 79 |
| 425699 | 506 | 525 | TTGGTTACATGAAATCCCAT | 2-13-5 | 56 | 79 |
| 425739 | 506 | 525 | TTGGTTACATGAAATCCCAT | 4-11-5 | 69 | 79 |
| *304299 | 507 | 526 | CTTGGTTACATGAAATCCCA | 5-10-5 | 83 | 25 |
| 425660 | 507 | 526 | CTTGGTTACATGAAATCCCA | 3-14-3 | 59 | 25 |
| 425700 | 507 | 526 | CTTGGTTACATGAAATCCCA | 2-13-5 | 52 | 25 |
| 425740 | 507 | 526 | CTTGGTTACATGAAATCCCA | 4-11-5 | 69 | 25 |
| *420915 | 508 | 527 | TCTTGGTTACATGAAATCCC | 5-10-5 | 81 | 80 |
| 425661 | 508 | 527 | TCTTGGTTACATGAAATCCC | 3-14-3 | 48 | 80 |
| 425701 | 508 | 527 | TCTTGGTTACATGAAATCCC | 2-13-5 | 41 | 80 |
| 425741 | 508 | 527 | TCTTGGTTACATGAAATCCC | 4-11-5 | 37 | 80 |
| *420916 | 509 | 528 | CTCTTGGTTACATGAAATCC | 5-10-5 | 52 | 81 |
| 425662 | 509 | 528 | CTCTTGGTTACATGAAATCC | 3-14-3 | 57 | 81 |
| 425702 | 509 | 528 | CTCTTGGTTACATGAAATCC | 2-13-5 | 63 | 81 |
| *420919 | 512 | 531 | ATACTCTTGGTTACATGAAA | 5-10-5 | 69 | 84 |
| 425663 | 512 | 531 | ATACTCTTGGTTACATGAAA | 3-14-3 | 46 | 84 |
| 425703 | 512 | 531 | ATACTCTTGGTTACATGAAA | 2-13-5 | 52 | 84 |
| *420920 | 514 | 533 | GAATACTCTTGGTTACATGA | 5-10-5 | 71 | 85 |
| 425664 | 514 | 533 | GAATACTCTTGGTTACATGA | 3-14-3 | 57 | 85 |
| 425704 | 514 | 533 | GAATACTCTTGGTTACATGA | 2-13-5 | 58 | 85 |

TABLE 4-continued

Inhibition of human transthyretin rnRNA levels by
chimeric antisense oligonucleotides targeted to
SEQ ID NO: 1 (GENBANK Accession No. NM_000371.2)

| Oligo ID | Start Site | Stop Site | Sequence | Motif | % inhibition | SEQ ID NO |
|---|---|---|---|---|---|---|
| 425742 | 514 | 533 | GAATACTCTTGGTTACATGA | 4-11-5 | 71 | 85 |
| *420921 | 515 | 534 | GGAATACTCTTGGTTACATG | 5-10-5 | 68 | 86 |
| 425665 | 515 | 534 | GGAATACTCTTGGTTACATG | 3-14-3 | 65 | 86 |
| 425705 | 515 | 534 | GGAATACTCTTGGTTACATG | 2-13-5 | 60 | 86 |
| 425743 | 515 | 534 | GGAATACTCTTGGTTACATG | 4-11-5 | 56 | 86 |
| *420922 | 516 | 535 | TGGAATACTCTTGGTTACAT | 5-10-5 | 54 | 87 |
| 425666 | 516 | 535 | TGGAATACTCTTGGTTACAT | 3-14-3 | 56 | 87 |
| 425706 | 516 | 535 | TGGAATACTCTTGGTTACAT | 2-13-5 | 64 | 87 |
| 425744 | 516 | 535 | TGGAATACTCTTGGTTACAT | 4-11-5 | 39 | 87 |
| *420923 | 517 | 536 | ATGGAATACTCTTGGTTACA | 5-10-5 | 62 | 88 |
| 425667 | 517 | 536 | ATGGAATACTCTTGGTTACA | 3-14-3 | 44 | 88 |
| 425707 | 517 | 536 | ATGGAATACTCTTGGTTACA | 2-13-5 | 30 | 88 |
| *420937 | 533 | 552 | CACTGCTTTAGTAAAAATGG | 5-10-5 | 59 | 102 |
| 425668 | 533 | 552 | CACTGCTTTAGTAAAAATGG | 3-14-3 | 37 | 102 |
| 425708 | 533 | 552 | CACTGCTTTAGTAAAAATGG | 2-13-5 | 32 | 102 |
| 425745 | 533 | 552 | CACTGCTTTAGTAAAAATGG | 4-11-5 | 43 | 102 |
| *420944 | 541 | 560 | GGTGAAAACACTGCTTTAGT | 5-10-5 | 52 | 109 |
| 425669 | 541 | 560 | GGTGAAAACACTGCTTTAGT | 3-14-3 | 54 | 109 |
| 425709 | 541 | 560 | GGTGAAAACACTGCTTTAGT | 2-13-5 | 54 | 109 |
| 425746 | 541 | 560 | GGTGAAAACACTGCTTTAGT | 4-11-5 | 60 | 109 |
| *420945 | 542 | 561 | AGGTGAAAACACTGCTTTAG | 5-10-5 | 38 | 110 |
| 425670 | 542 | 561 | AGGTGAAAACACTGCTTTAG | 3-14-3 | 38 | 110 |
| 425710 | 542 | 561 | AGGTGAAAACACTGCTTTAG | 2-13-5 | 52 | 110 |
| *420947 | 544 | 563 | TGAGGTGAAAACACTGCTTT | 5-10-5 | 34 | 112 |
| 425671 | 544 | 563 | TGAGGTGAAAACACTGCTTT | 3-14-3 | 27 | 112 |
| 425711 | 544 | 563 | TGAGGTGAAAACACTGCTTT | 2-13-5 | 68 | 112 |
| 425747 | 544 | 563 | TGAGGTGAAAACACTGCTTT | 4-11-5 | 61 | 112 |
| *420948 | 545 | 564 | ATGAGGTGAAAACACTGCTT | 5-10-5 | 66 | 113 |
| 425672 | 545 | 564 | ATGAGGTGAAAACACTGCTT | 3-14-3 | 47 | 113 |
| 425712 | 545 | 564 | ATGAGGTGAAAACACTGCTT | 2-13-5 | 70 | 113 |
| 425748 | 545 | 564 | ATGAGGTGAAAACACTGCTT | 4-11-5 | 71 | 113 |
| *304304 | 546 | 565 | TATGAGGTGAAAACACTGCT | 5-10-5 | 46 | 30 |
| 425673 | 546 | 565 | TATGAGGTGAAAACACTGCT | 3-14-3 | 51 | 30 |
| 425713 | 546 | 565 | TATGAGGTGAAAACACTGCT | 2-13-5 | 50 | 30 |
| 425749 | 546 | 565 | TATGAGGTGAAAACACTGCT | 4-11-5 | 58 | 30 |
| 425650 | 547 | 566 | ATATGAGGTGAAAACACTGC | 5-10-5 | 28 | 171 |

TABLE 4-continued

Inhibition of human transthyretin rnRNA levels by chimeric antisense oligonucleotides targeted to SEQ ID NO: 1 (GENBANK Accession No. NM_000371.2)

| Oligo ID | Start Site | Stop Site | Sequence | Motif | % inhibition | SEQ ID NO |
|---|---|---|---|---|---|---|
| 425674 | 547 | 566 | ATATGAGGTGAAAACACTGC | 3-14-3 | 40 | 171 |
| 425714 | 547 | 566 | ATATGAGGTGAAAACACTGC | 2-13-5 | 44 | 171 |
| 425750 | 547 | 566 | ATATGAGGTGAAAACACTGC | 4-11-5 | 47 | 171 |
| 425651 | 577 | 596 | TATTGTCTCTGCCTGGACTT | 5-10-5 | 65 | 172 |
| 425675 | 577 | 596 | TATTGTCTCTGCCTGGACTT | 3-14-3 | 55 | 172 |
| 425715 | 577 | 596 | TATTGTCTCTGCCTGGACTT | 2-13-5 | 65 | 172 |
| 425751 | 577 | 596 | TATTGTCTCTGCCTGGACTT | 4-11-5 | 62 | 172 |
| *304309 | 578 | 597 | TTATTGTCTCTGCCTGGACT | 5-10-5 | 66 | 33 |
| 425676 | 578 | 597 | TTATTGTCTCTGCCTGGACT | 3-14-3 | 59 | 33 |
| 425716 | 578 | 597 | TTATTGTCTCTGCCTGGACT | 2-13-5 | 87 | 33 |
| 425752 | 578 | 597 | TTATTGTCTCTGCCTGGACT | 4-11-5 | 67 | 33 |
| *420949 | 579 | 598 | TTTATTGTCTCTGCCTGGAC | 5-10-5 | 57 | 114 |
| 425677 | 579 | 598 | TTTATTGTCTCTGCCTGGAC | 3-14-3 | 67 | 114 |
| 425717 | 579 | 598 | TTTATTGTCTCTGCCTGGAC | 2-13-5 | 68 | 114 |
| 425753 | 579 | 598 | TTTATTGTCTCTGCCTGGAC | 4-11-5 | 69 | 114 |
| *420950 | 580 | 599 | TTTTATTGTCTCTGCCTGGA | 5-10-5 | 61 | 115 |
| 425678 | 580 | 599 | TTTTATTGTCTCTGCCTGGA | 3-14-3 | 59 | 115 |
| 425718 | 580 | 599 | TTTTATTGTCTCTGCCTGGA | 2-13-5 | 69 | 115 |
| 425754 | 580 | 599 | TTTTATTGTCTCTGCCTGGA | 4-11-5 | 86 | 115 |
| *420951 | 581 | 600 | GTTTTATTGTCTCTGCCTGG | 5-10-5 | 78 | 116 |
| 425679 | 581 | 600 | GTTTTATTGTCTCTGCCTGG | 3-14-3 | 73 | 116 |
| 425719 | 581 | 600 | GTTTTATTGTCTCTGCCTGG | 2-13-5 | 90 | 116 |
| 425755 | 581 | 600 | GTTTTATTGTCTCTGCCTGG | 4-11-5 | 73 | 116 |
| *420952 | 582 | 601 | TGTTTTATTGTCTCTGCCTG | 5-10-5 | 61 | 117 |
| 425680 | 582 | 601 | TGTTTTATTGTCTCTGCCTG | 3-14-3 | 77 | 117 |
| 425720 | 582 | 601 | TGTTTTATTGTCTCTGCCTG | 2-13-5 | 67 | 117 |
| 425756 | 582 | 601 | TGTTTTATTGTCTCTGCCTG | 4-11-5 | 57 | 117 |
| *420953 | 583 | 602 | ATGTTTTATTGTCTCTGCCT | 5-10-5 | 65 | 118 |
| 425681 | 583 | 602 | ATGTTTTATTGTCTCTGCCT | 3-14-3 | 61 | 118 |
| 425721 | 583 | 602 | ATGTTTTATTGTCTCTGCCT | 2-13-5 | 77 | 118 |
| 425757 | 583 | 602 | ATGTTTTATTGTCTCTGCCT | 4-11-5 | 83 | 118 |
| *420954 | 584 | 603 | AATGTTTTATTGTCTCTGCC | 5-10-5 | 63 | 119 |
| 425682 | 584 | 603 | AATGTTTTATTGTCTCTGCC | 3-14-3 | 42 | 119 |
| 425722 | 584 | 603 | AATGTTTTATTGTCTCTGCC | 2-13-5 | 69 | 119 |
| 425758 | 584 | 603 | AATGTTTTATTGTCTCTGCC | 4-11-5 | 61 | 119 |
| *420955 | 585 | 604 | GAATGTTTTATTGTCTCTGC | 5-10-5 | 65 | 120 |
| 425683 | 585 | 604 | GAATGTTTTATTGTCTCTGC | 3-14-3 | 30 | 120 |

TABLE 4-continued

Inhibition of human transthyretin rnRNA levels by chimeric antisense oligonucleotides targeted to SEQ ID NO: 1 (GENBANK Accession No. NM_000371.2)

| Oligo ID | Start Site | Stop Site | Sequence | Motif | % inhibition | SEQ ID NO |
|---|---|---|---|---|---|---|
| 425723 | 585 | 604 | GAATGTTTTATTGTCTCTGC | 2-13-5 | 44 | 120 |
| 425759 | 585 | 604 | GAATGTTTTATTGTCTCTGC | 4-11-5 | 50 | 120 |
| *420956 | 586 | 605 | GGAATGTTTTATTGTCTCTG | 5-10-5 | 47 | 121 |
| 425684 | 586 | 605 | GGAATGTTTTATTGTCTCTG | 3-14-3 | 44 | 121 |
| 425724 | 586 | 605 | GGAATGTTTTATTGTCTCTG | 2-13-5 | 65 | 121 |
| *420957 | 587 | 606 | AGGAATGTTTTATTGTCTCT | 5-10-5 | 37 | 122 |
| 425685 | 587 | 606 | AGGAATGTTTTATTGTCTCT | 3-14-3 | 46 | 122 |
| 425725 | 587 | 606 | AGGAATGTTTTATTGTCTCT | 2-13-5 | 43 | 122 |
| 425760 | 587 | 606 | AGGAATGTTTTATTGTCTCT | 4-11-5 | 78 | 122 |
| *420958 | 588 | 607 | CAGGAATGTTTTATTGTCTC | 5-10-5 | 41 | 123 |
| 425686 | 588 | 607 | CAGGAATGTTTTATTGTCTC | 3-14-3 | 6 | 123 |
| 425726 | 588 | 607 | CAGGAATGTTTTATTGTCTC | 2-13-5 | 41 | 123 |
| 425761 | 588 | 607 | CAGGAATGTTTTATTGTCTC | 4-11-5 | 39 | 123 |
| *420959 | 589 | 608 | ACAGGAATGTTTTATTGTCT | 5-10-5 | 43 | 124 |
| 425687 | 589 | 608 | ACAGGAATGTTTTATTGTCT | 3-14-3 | 22 | 124 |
| 425727 | 589 | 608 | ACAGGAATGTTTTATTGTCT | 2-13-5 | 25 | 124 |
| 425762 | 589 | 608 | ACAGGAATGTTTTATTGTCT | 4-11-5 | 57 | 124 |
| 425652 | 590 | 609 | CACAGGAATGTTTTATTGTC | 5-10-5 | 23 | 173 |
| 425688 | 590 | 609 | CACAGGAATGTTTTATTGTC | 3-14-3 | 11 | 173 |
| 425728 | 590 | 609 | CACAGGAATGTTTTATTGTC | 2-13-5 | 37 | 173 |
| 425763 | 590 | 609 | CACAGGAATGTTTTATTGTC | 4-11-5 | 38 | 173 |
| 304310 | 595 | 614 | CCTTTCACAGGAATGTTTTA | 5-10-5 | 57 | 174 |
| 425689 | 595 | 614 | CCTTTCACAGGAATGTTTTA | 3-14-3 | 38 | 174 |
| 425729 | 595 | 614 | CCTTTCACAGGAATGTTTTA | 2-13-5 | 58 | 174 |
| 425764 | 595 | 614 | CCTTTCACAGGAATGTTTTA | 4-11-5 | 60 | 174 |
| 425653 | 596 | 615 | GCCTTTCACAGGAATGTTTT | 5-10-5 | 79 | 175 |
| 425690 | 596 | 615 | GCCTTTCACAGGAATGTTTT | 3-14-3 | 73 | 175 |
| 425730 | 596 | 615 | GCCTTTCACAGGAATGTTTT | 2-13-5 | 76 | 175 |
| 425765 | 596 | 615 | GCCTTTCACAGGAATGTTTT | 4-11-5 | 83 | 175 |
| *304311 | 597 | 616 | TGCCTTTCACAGGAATGTTT | 5-10-5 | 71 | 34 |
| 425691 | 597 | 616 | TGCCTTTCACAGGAATGTTT | 3-14-3 | 74 | 34 |
| 425731 | 597 | 616 | TGCCTTTCACAGGAATGTTT | 2-13-5 | 73 | 34 |
| 425766 | 597 | 616 | TGCCTTTCACAGGAATGTTT | 4-11-5 | 79 | 34 |
| *304312 | 598 | 617 | GTGCCTTTCACAGGAATGTT | 5-10-5 | 71 | 35 |
| 425692 | 598 | 617 | GTGCCTTTCACAGGAATGTT | 3-14-3 | 69 | 35 |
| 425732 | 598 | 617 | GTGCCTTTCACAGGAATGTT | 2-13-5 | 67 | 35 |

TABLE 4-continued

Inhibition of human transthyretin rnRNA levels by
chimeric antisense oligonucleotides targeted to
SEQ ID NO: 1 (GENBANK Accession No. NM_000371.2)

| Oligo ID | Start Site | Stop Site | Sequence | Motif | % inhibition | SEQ ID NO |
|---|---|---|---|---|---|---|
| 425767 | 598 | 617 | GTGCCTTTCACAGGAATGTT | 4-11-5 | 83 | 35 |
| 425654 | 599 | 618 | AGTGCCTTTCACAGGAATGT | 5-10-5 | 64 | 176 |
| 425693 | 599 | 618 | AGTGCCTTTCACAGGAATGT | 3-14-3 | 79 | 176 |
| 425733 | 599 | 618 | AGTGCCTTTCACAGGAATGT | 2-13-5 | 68 | 176 |
| 425768 | 599 | 618 | AGTGCCTTTCACAGGAATGT | 4-11-5 | 50 | 176 |
| 304313 | 600 | 619 | AAGTGCCTTTCACAGGAATG | 5-10-5 | 73 | 177 |
| 425694 | 600 | 619 | AAGTGCCTTTCACAGGAATG | 3-14-3 | 45 | 177 |
| 425734 | 600 | 619 | AAGTGCCTTTCACAGGAATG | 2-13-5 | 55 | 177 |
| 425769 | 600 | 619 | AAGTGCCTTTCACAGGAATG | 4-11-5 | 62 | 177 |

Example 3: Dose-Dependent Antisense Inhibition of Human Transthyretin in HepG2 Cells Gapmers from Example 2 exhibiting significant in vitro inhibition of human transthyretin were tested at various doses in HepG2 cells. Cells were plated at a density of 20,000 cells per well and transfected using electroporation with 625 nM, 1250 nM, 2500 nM, 5000 nM and 10000 nM concentrations of antisense oligonucleotide, as specified in Table 5. After a treatment period of approximately 16 hours, RNA was isolated from the cells and transthyretin mRNA levels were measured by quantitative real-time PCR. Human transthyretin primer probe set RTS3029 was used to measure mRNA levels. Transthyretin mRNA levels were adjusted according to total RNA content, as measured by RIBOGREEN®. Results are presented as percent inhibition of transthyretin, relative to untreated control cells.

The half maximal inhibitory concentration ($IC_{50}$) of each oligonucleotide is also presented in Table 5 and was calculated by plotting the concentrations of oligonucleotides used versus the percent inhibition of transthyretin mRNA expression achieved at each concentration, and noting the concentration of oligonucleotide at which 50% inhibition of transthyretin mRNA expression was achieved compared to the control. As illustrated in Table 5, transthyretin mRNA levels were significantly reduced in a dose-dependent manner in antisense oligonucleotide treated cells.

TABLE 5

Dose-dependent antisense inhibition of human transthyretin
in HepG2 cells using electroporation

| ISIS NO | 625 nM | 1250 nM | 2500 nM | 5000 nM | 10000 nM | $IC_{50}$ (µM) |
|---|---|---|---|---|---|---|
| 304296 | 57 | 74 | 83 | 91 | 96 | <0.625 |
| 304299 | 43 | 76 | 82 | 95 | 94 | 0.627 |
| 420913 | 59 | 75 | 90 | 88 | 98 | <0.625 |
| 420915 | 60 | 85 | 91 | 95 | 99 | <0.625 |
| 420951 | 64 | 77 | 90 | 97 | 99 | <0.625 |
| 425653 | 70 | 86 | 86 | 88 | 82 | <0.625 |
| 425655 | 48 | 80 | 85 | 97 | 96 | <0.625 |
| 425656 | 70 | 89 | 92 | 92 | 96 | <0.625 |
| 425659 | 46 | 56 | 68 | 82 | 93 | 0.8 |
| 425679 | 63 | 77 | 72 | 94 | 97 | <0.625 |
| 425680 | 28 | 79 | 85 | 93 | 98 | 0.8 |
| 425693 | 2 | 64 | 74 | 76 | 81 | 1.7 |
| 425695 | 74 | 87 | 91 | 97 | 98 | <0.625 |
| 425716 | 69 | 84 | 95 | 97 | 98 | <0.625 |
| 425719 | 58 | 84 | 92 | 96 | 98 | <0.625 |
| 425721 | 40 | 75 | 89 | 95 | 98 | 0.7 |
| 425736 | 64 | 71 | 86 | 93 | 93 | <0.625 |
| 425737 | 78 | 93 | 95 | 97 | 98 | <0.625 |
| 425738 | 40 | 77 | 88 | 94 | 95 | 0.7 |
| 425754 | 56 | 75 | 87 | 96 | 99 | <0.625 |
| 425755 | 58 | 84 | 88 | 94 | 97 | <0.625 |
| 425757 | 62 | 82 | 94 | 97 | 99 | <0.625 |
| 425760 | 58 | 42 | 74 | 85 | 93 | <0.625 |
| 425765 | 81 | 86 | 87 | 83 | 88 | <0.625 |
| 425766 | 83 | 89 | 81 | 75 | 74 | <0.625 |
| 425767 | 56 | 75 | 83 | 81 | 80 | <0.625 |

Gapmers from Example 2 were also tested at various doses in HepG2 cells using the transfection reagent, lipofectin. Cells were plated at a density of 10,000 cells per well and transfected using electroporation with 6.25 nM, 12.5 nM, 25 nM, 50 nM and 100 nM concentrations of antisense oligonucleotide, as specified in Table 6. After a treatment period of approximately 16 hours, RNA was isolated from the cells and transthyretin mRNA levels were measured by quantitative real-time PCR. Human transthyretin primer probe set RTS3029 was used to measure mRNA levels. Transthyretin mRNA levels were adjusted according to total RNA content, as measured by RIBOGREEN®. Results are presented as percent inhibition of transthyretin, relative to untreated control cells. As illustrated in Table 6, transthyretin mRNA levels were significantly reduced in a dose-dependent manner in antisense oligonucleotide treated cells.

TABLE 6

Dose-dependent antisense inhibition of human transthyretin in HepG2 cells using lipofectin reagent

| ISIS NO | 6.25 nM | 12.5 nM | 25 nM | 50 nM | 100 nM | IC$_{50}$ (nM) |
|---|---|---|---|---|---|---|
| 304296 | 26 | 41 | 43 | 52 | 65 | 39 |
| 304299 | 22 | 70 | 43 | 74 | 83 | 20 |
| 420913 | 4 | 60 | 60 | 68 | 82 | 30 |
| 420915 | 36 | 31 | 46 | 64 | 67 | 28 |
| 420951 | 10 | 37 | 56 | 85 | 84 | 19 |
| 425653 | 25 | 38 | 60 | 74 | 77 | 18 |
| 425655 | 27 | 15 | 62 | 79 | 81 | 16 |
| 425656 | 37 | 62 | 47 | 69 | 82 | 15 |
| 425659 | 17 | 35 | 33 | 79 | 73 | 30 |
| 425679 | 32 | 6 | 63 | 79 | 77 | 14 |
| 425680 | 16 | 48 | 41 | 84 | 84 | 28 |
| 425693 | 10 | 19 | 51 | 66 | 61 | 26 |
| 425695 | 36 | 23 | 54 | 76 | 84 | 28 |
| 425716 | 57 | 52 | 36 | 85 | 81 | 38 |
| 425719 | 25 | 39 | 28 | 60 | 76 | 45 |
| 425721 | 0 | 22 | 38 | 73 | 75 | 32 |
| 425736 | 25 | 60 | 30 | 77 | 80 | 22 |
| 425737 | 36 | 52 | 50 | 60 | 76 | 14 |
| 425738 | 13 | 15 | 19 | 65 | 70 | 27 |
| 425754 | 8 | 18 | 38 | 75 | 71 | 42 |
| 425755 | 26 | 46 | 54 | 77 | 86 | 20 |
| 425757 | 0 | 37 | 81 | 83 | 71 | 19 |
| 425760 | 28 | 46 | 72 | 70 | 80 | 18 |
| 425765 | 0 | 52 | 48 | 66 | 69 | 29 |
| 425766 | 24 | 19 | 48 | 69 | 71 | 29 |
| 425767 | 41 | 49 | 48 | 65 | 75 | 14 |

Example 4: Dose-Dependent Antisense Inhibition of Human Transthyretin in HepG2 Cells Gapmers selected from Example 3 were tested at various doses in HepG2 cells. Cells were plated at a density of 20,000 cells per well and transfected using electroporation with 0.0617 µM, 0.1852 µM, 0.5556 µM, 1.6667 µM and 5 µM concentrations of antisense oligonucleotide, as specified in Table 7. After a treatment period of approximately 16 hours, RNA was isolated from the cells and transthyretin mRNA levels were measured by quantitative real-time PCR. Human transthyretin primer probe set RTS3029 was used to measure mRNA levels. Transthyretin mRNA levels were adjusted according to total RNA content, as measured by RIBOGREEN®. Results are presented as percent inhibition of transthyretin, relative to untreated control cells. As illustrated in Table 7, transthyretin mRNA levels were reduced in a dose-dependent manner in antisense oligonucleotide treated cells.

TABLE 7

Dose-dependent antisense inhibition of human transthyretin in HepG2 cells using electroporation

| ISIS NO | 0.0617 µM | 0.1852 µM | 0.5556 µM | 1.6667 µM | 5 µM | IC$_{50}$ (µM) |
|---|---|---|---|---|---|---|
| 304296 | 0 | 6 | 44 | 58 | 83 | 1.2 |
| 304299 | 38 | 10 | 57 | 83 | 92 | 0.6 |
| 420913 | 51 | 51 | 54 | 73 | 93 | 0.2 |
| 420915 | 33 | 35 | 62 | 65 | 93 | 0.2 |
| 420951 | 40 | 33 | 36 | 82 | 96 | 0.4 |
| 425653 | 55 | 58 | 74 | 72 | 84 | <0.06 |
| 425655 | 8 | 35 | 54 | 57 | 90 | 0.5 |
| 425656 | 12 | 43 | 43 | 78 | 94 | 0.4 |
| 425659 | 14 | 35 | 19 | 46 | 82 | 0.6 |
| 425679 | 30 | 13 | 23 | 69 | 91 | 0.8 |
| 425680 | 0 | 35 | 45 | 74 | 84 | 0.7 |
| 425693 | 0 | 6 | 14 | 32 | 59 | 3.4 |
| 425695 | 15 | 47 | 61 | 81 | 91 | 0.3 |
| 425716 | 20 | 17 | 53 | 77 | 91 | 0.6 |
| 425719 | 0 | 14 | 45 | 78 | 94 | 0.8 |
| 425721 | 0 | 0 | 22 | 74 | 84 | 0.9 |
| 425736 | 42 | 43 | 56 | 76 | 91 | 0.3 |
| 425737 | 21 | 29 | 61 | 81 | 97 | 0.3 |
| 425738 | 14 | 39 | 57 | 74 | 93 | 0.4 |
| 425754 | 29 | 34 | 45 | 78 | 94 | 0.4 |
| 425755 | 8 | 21 | 57 | 78 | 95 | 0.5 |
| 425757 | 29 | 28 | 62 | 83 | 95 | 0.4 |
| 425760 | 3 | 6 | 9 | 56 | 77 | 1.4 |
| 425765 | 24 | 51 | 75 | 77 | 88 | 0.3 |
| 425766 | 7 | 41 | 59 | 73 | 77 | 0.3 |
| 425767 | 1 | 18 | 49 | 66 | 79 | 1.0 |

Example 5: Dose Response Confirmation of Antisense Oligonucleotides Targeting Human Transthyretin in Hep3B Cells Gapmers from Example 4 exhibiting significant in vitro inhibition of human transthyretin were tested at various doses in Hep3B cells. Cells were plated at a density of 20,000 cells per well and transfected using electroporation with 0.0206 µM, 0.062 µM, 0.185 µM, 0.556 µM, 1.667 µM and 5 µM concentrations of antisense oligonucleotide, as specified in Table 8. After a treatment period of approximately 16 hours, RNA was isolated from the cells and transthyretin mRNA levels were measured by quantitative real-time PCR. Human transthyretin primer probe set RTS1396 was used to measure mRNA levels. Transthyretin mRNA levels were adjusted according to total RNA content, as measured by RIBOGREEN®. Results are presented as percent inhibition of transthyretin, relative to untreated control cells. As illustrated in Table 8, transthyretin mRNA levels were reduced in a dose-dependent manner in antisense oligonucleotide treated cells. The IC$_{50}$ of each oligonucleotide is also presented in Table 8.

TABLE 8

Dose-dependent antisense inhibition of human transthyretin in Hep3B cells using electroporation

| ISIS NO | 0.0206 µM | 0.062 µM | 0.185 µM | 0.556 µM | 1.667 µM | 5 µM | IC$_{50}$ (µM) |
|---|---|---|---|---|---|---|---|
| 304299 | 27 | 2 | 25 | 52 | 76 | 96 | 0.5 |
| 420915 | 0 | 12 | 27 | 30 | 69 | 93 | 0.8 |
| 425653 | 23 | 13 | 55 | 86 | 88 | 91 | 0.1 |
| 425655 | 3 | 30 | 32 | 62 | 84 | 94 | 0.3 |
| 425656 | 0 | 0 | 29 | 66 | 82 | 95 | 0.5 |
| 425679 | 0 | 21 | 36 | 71 | 92 | 97 | 0.3 |
| 425695 | 37 | 23 | 63 | 79 | 94 | 98 | 0.1 |
| 425736 | 31 | 43 | 40 | 64 | 82 | 95 | 0.1 |
| 425737 | 0 | 13 | 62 | 82 | 95 | 98 | 0.2 |
| 425755 | 17 | 8 | 18 | 69 | 86 | 98 | 0.4 |
| 425757 | 22 | 47 | 53 | 79 | 96 | 98 | 0.2 |

Example 6: Dose Response Confirmation of Antisense Oligonucleotides Targeting Human Transthyretin in Human Transthyretin-Transgenic Mouse Primary Hepatocytes Gapmers from Example 5 were also tested at various doses in primary hepatocytes of human transthyretin-transgenic mice. ISIS 304309, ISIS 304311, ISIS 304312 and ISIS 420951 (see Example 2) were also retested along with these gapmers under the same culture conditions. Cells were plated at a density of 10,000 cells per well and transfected using cytofectin with 18.75 nM, 37.5 nM, 75 nM, 150 nM and 300 nM concentrations of antisense oligonucleotide, as specified in Table 9. After a treatment period of approximately 16 hours, RNA was isolated from the cells and transthyretin mRNA levels were measured by quantitative real-time PCR. Human transthyretin primer probe set RTS1396 was used to measure mRNA levels. Transthyretin mRNA levels were adjusted according to total RNA content, as measured by RIBOGREEN®. Results are presented as percent inhibition of transthyretin, relative to untreated control cells. As illustrated in Table 9, transthyretin mRNA levels were reduced in a dose-dependent manner in antisense oligonucleotide treated cells.

TABLE 9

Dose-dependent antisense inhibition of human transthyretin in mouse primary hepatocytes using cytofectin

| ISIS NO | 18.75 nM | 37.5 nM | 75 nM | 150 nM | 300 nM | Motif |
|---|---|---|---|---|---|---|
| 304299 | 54 | 79 | 97 | 98 | 99 | 5-10-5 |
| 304309 | 48 | 77 | 94 | 99 | 99 | 5-10-5 |
| 304311 | 45 | 79 | 92 | 96 | 98 | 5-10-5 |
| 304312 | 33 | 71 | 89 | 96 | 98 | 5-10-5 |
| 420915 | 40 | 70 | 92 | 98 | 99 | 5-10-5 |
| 420951 | 41 | 86 | 96 | 98 | 99 | 5-10-5 |
| 425653 | 44 | 81 | 93 | 96 | 99 | 5-10-5 |
| 425655 | 61 | 88 | 96 | 99 | 99 | 3-14-3 |
| 425656 | 61 | 84 | 94 | 98 | 99 | 3-14-3 |
| 425679 | 74 | 78 | 97 | 98 | 99 | 3-14-3 |
| 425695 | 66 | 84 | 96 | 98 | 99 | 2-13-5 |
| 425736 | 58 | 84 | 95 | 98 | 99 | 4-11-5 |
| 425737 | 57 | 77 | 95 | 98 | 99 | 4-11-5 |
| 425755 | 61 | 82 | 96 | 99 | 99 | 4-11-5 |
| 425757 | 37 | 77 | 93 | 98 | 98 | 4-11-5 |

Example 7: Dose Response Confirmation of Antisense Oligonucleotides Targeting Human Transthyretin in HepG2 Cells Gapmers from Example 6 were tested at various doses in HepG2 Cells. Cells were plated at a density of 10,000 cells per well and transfected using electroporation with 0.062 µM, 0.185 µM, 0.556 µM, 1.66 µM and 5000 µM concentrations of antisense oligonucleotide, as specified in Table 10. After a treatment period of approximately 16 hours, RNA was isolated from the cells and transthyretin mRNA levels were measured by quantitative real-time PCR. Human transthyretin primer probe set RTS1396 was used to measure mRNA levels. Transthyretin mRNA levels were adjusted according to total RNA content, as measured by RIBOGREEN®. Results are presented as percent inhibition of transthyretin, relative to untreated control cells. As illustrated in Table 10, transthyretin mRNA levels were reduced in a dose-dependent manner in antisense oligonucleotide treated cells.

TABLE 10

Dose-dependent antisense inhibition of human transthyretin in HepG2 cells using electroporation

| ISIS NO | 0.062 µM | 0.185 µM | 0.556 µM | 1.667 µM | 5.000 µM | $IC_{50}$ (µM) | Motif |
|---|---|---|---|---|---|---|---|
| 304299 | 55 | 66 | 72 | 87 | 96 | 0.037 | 5-10-5 |
| 304309 | 41 | 65 | 72 | 91 | 96 | 0.087 | 5-10-5 |
| 304311 | 57 | 83 | 88 | 89 | 83 | 0.001 | 5-10-5 |
| 304312 | 46 | 69 | 74 | 84 | 81 | 0.038 | 5-10-5 |
| 420915 | 38 | 62 | 80 | 90 | 98 | 0.096 | 5-10-5 |
| 420951 | 45 | 71 | 84 | 93 | 97 | 0.049 | 5-10-5 |
| 425653 | 48 | 73 | 87 | 88 | 82 | 0.017 | 5-10-5 |
| 425655 | 40 | 57 | 77 | 85 | 95 | 0.105 | 3-14-3 |
| 425656 | 28 | 54 | 70 | 94 | 97 | 0.177 | 3-14-3 |
| 425679 | 43 | 51 | 81 | 95 | 99 | 0.106 | 3-14-3 |
| 425695 | 49 | 67 | 90 | 96 | 99 | 0.043 | 2-13-5 |
| 425736 | 32 | 63 | 85 | 95 | 98 | 0.108 | 4-11-5 |
| 425737 | 42 | 71 | 90 | 98 | 99 | 0.053 | 4-11-5 |
| 425755 | 24 | 63 | 85 | 95 | 99 | 0.137 | 4-11-5 |
| 425757 | 21 | 62 | 86 | 96 | 99 | 0.148 | 4-11-5 |

Example 8: Dose Response Confirmation of Antisense Oligonucleotides Targeting Human Transthyretin in Human Transthyretin-Transgenic Mouse Primary Hepatocytes Gapmers from Example 6 were also tested at various doses in primary hepatocytes of human transthyretin-transgenic mice. Cells were plated at a density of 10,000 cells per well and transfected using cytofectin with 5 nM, 10 nM, 20 nM, 40 nM and 80 nM concentrations of antisense oligonucleotide, as specified in Table 11. After a treatment period of approximately 16 hours, RNA was isolated from the cells and transthyretin mRNA levels were measured by quantitative real-time PCR. Human transthyretin primer probe set RTS3029 was used to measure mRNA levels. Transthyretin mRNA levels were adjusted according to total RNA content, as measured by RIBOGREEN®. Results are presented as percent inhibition of transthyretin, relative to untreated control cells. As illustrated in Table 11, transthyretin mRNA levels were reduced in a dose-dependent manner in antisense oligonucleotide treated cells.

TABLE 11

Dose-dependent antisense inhibition of human transthyretin in mouse primary hepatocytes using cytofectin

| ISIS NO | 5 nM | 10 nM | 20 nM | 40 nM | 80 nM | Motif |
|---|---|---|---|---|---|---|
| 304299 | 0 | 8 | 37 | 69 | 90 | 5-10-5 |
| 304309 | 0 | 9 | 39 | 75 | 93 | 5-10-5 |
| 304311 | 1 | 13 | 43 | 70 | 81 | 5-10-5 |
| 304312 | 0 | 3 | 32 | 64 | 76 | 5-10-5 |
| 420915 | 0 | 0 | 34 | 59 | 87 | 5-10-5 |
| 420951 | 0 | 12 | 57 | 84 | 92 | 5-10-5 |
| 425653 | 0 | 9 | 44 | 72 | 84 | 5-10-5 |
| 425655 | 0 | 19 | 45 | 80 | 91 | 3-14-3 |
| 425656 | 0 | 2 | 33 | 70 | 93 | 3-14-3 |
| 425679 | 0 | 13 | 42 | 72 | 90 | 3-14-3 |
| 425695 | 3 | 12 | 33 | 70 | 90 | 2-13-5 |
| 425736 | 2 | 7 | 37 | 70 | 89 | 4-11-5 |
| 425737 | 0 | 4 | 36 | 65 | 89 | 4-11-5 |
| 425755 | 0 | 25 | 50 | 75 | 94 | 4-11-5 |
| 425757 | 0 | 5 | 43 | 72 | 92 | 4-11-5 |

Gapmers were also tested using electroporation as the transfection agent. Cells were plated at a density of 35,000 cells per well and transfected using electroporation with 148.148 nM, 444.444 nM, 1,333.333 nM, 4,000 nM and 12,000 nM concentrations of antisense oligonucleotide, as specified in Table 12. After a treatment period of approximately 16 hours, RNA was isolated from the cells and transthyretin mRNA levels were measured by quantitative real-time PCR. Human transthyretin primer probe set RTS3029 was used to measure mRNA levels. Transthyretin mRNA levels were adjusted according to total RNA content, as measured by RIBOGREEN®. Results are presented as percent inhibition of transthyretin, relative to untreated control cells.

TABLE 12

Dose-dependent antisense inhibition of human transthyretin in mouse primary hepatocytes using electroporation

| ISIS NO | 148.148 nM | 444.444 nM | 1333.333 nM | 4000 nM | 12000 nM | Motif |
|---|---|---|---|---|---|---|
| 304299 | 75 | 96 | 98 | 98 | 99 | 5-10-5 |
| 304309 | 72 | 96 | 98 | 98 | 98 | 5-10-5 |
| 304311 | 68 | 92 | 93 | 94 | 97 | 5-10-5 |
| 304312 | 50 | 84 | 92 | 93 | 97 | 5-10-5 |
| 420915 | 55 | 89 | 96 | 96 | 97 | 5-10-5 |
| 420951 | 65 | 92 | 95 | 96 | 98 | 5-10-5 |
| 425653 | 68 | 89 | 91 | 93 | 95 | 5-10-5 |
| 425655 | 63 | 94 | 96 | 96 | 96 | 3-14-3 |
| 425656 | 69 | 93 | 98 | 98 | 98 | 3-14-3 |
| 425679 | 63 | 92 | 97 | 98 | 98 | 3-14-3 |
| 425695 | 69 | 92 | 96 | 96 | 95 | 2-13-5 |
| 425736 | 75 | 93 | 96 | 96 | 96 | 4-11-5 |
| 425737 | 71 | 94 | 96 | 96 | 95 | 4-11-5 |
| 425755 | 70 | 93 | 95 | 95 | 95 | 4-11-5 |
| 425757 | 61 | 91 | 95 | 95 | 95 | 4-11-5 |

Example 9: Dose Response Confirmation of Antisense Oligonucleotides Targeting Human Transthyretin in Cynomolgus Monkey Primary Hepatocytes Gapmers from Example 6 were also tested at various doses in primary hepatocytes of cynomolgus monkeys. Cells were plated at a density of 35,000 cells per well and transfected using electroporation with 1,250 nM, 2,500 nM, 5,000 nM, 10,000 nM and 20,000 nM concentrations of antisense oligonucleotide, as specified in Table 13. After a treatment period of approximately 16 hours, RNA was isolated from the cells and transthyretin mRNA levels were measured by quantitative real-time PCR. Human transthyretin primer probe set RTS1396 was used to measure mRNA levels. Transthyretin mRNA levels were adjusted according to total RNA content, as measured by RIBOGREEN®. Results are presented as percent inhibition of transthyretin, relative to untreated control cells. As illustrated in Table 13, transthyretin mRNA levels were reduced in a dose-dependent manner in hepatocytes treated with ISIS oligonucleotides.

In absence of a complete cynomolgus monkey gene sequence in the NCBI database, the oligonucleotides were tested for cross-reactivity against the rhesus monkey gene sequence, since the two species are from the same genus, 'Macaca'. The human oligonucleotides are cross-reactive with rhesus monkey transthyretin gene, designated herein as SEQ ID NO: 4 (exons 1-4 extracted from GENBANK Accession No. NW_001105671.1). 'Mismatches' indicates the number of mismatches between the human oligonucleotide and the rhesus monkey transthyretin gene. 'n/a' indicates that the human oligonucleotide has more than 3 mismatches with the rhesus monkey transthyretin gene and therefore does not cross-react with it.

TABLE 13

Dose-dependent antisense inhibition of human transthyretin in Rhesus monkey primary hepatocytes using electroporation

| ISIS NO | 1,250 nM | 2,500 nM | 5,000 nM | 10,000 nM | 2,0000 nM | IC$_{50}$ (µM) | Rhesus monkey Target start site | Rhesus monkey Target stop site | Mismatches |
|---|---|---|---|---|---|---|---|---|---|
| 304299 | 21 | 45 | 69 | 80 | 95 | 3.1 | 504 | 523 | 0 |
| 304309 | 53 | 66 | 79 | 85 | 93 | <1.25 | 575 | 594 | 0 |
| 304311 | 75 | 78 | 82 | 86 | 90 | <1.25 | 594 | 613 | 0 |
| 304312 | 37 | 53 | 65 | 75 | 80 | 2.3 | 595 | 614 | 0 |
| 420915 | 59 | 54 | 77 | 87 | 94 | <1.25 | 505 | 524 | 0 |
| 420951 | 67 | 77 | 91 | 93 | 96 | <1.25 | 578 | 597 | 0 |
| 425653 | 56 | 72 | 84 | 83 | 85 | <1.25 | 593 | 612 | 0 |
| 425655 | 0 | 7 | 0 | 21 | 45 | >20 | 478 | 497 | 2 |
| 425656 | 41 | 20 | 38 | 53 | 51 | 8.7 | 479 | 498 | 2 |
| 425679 | 68 | 74 | 88 | 94 | 98 | <1.25 | 578 | 597 | 0 |
| 425695 | 42 | 29 | 41 | 49 | 65 | 25.8 | 478 | 497 | 2 |
| 425736 | 36 | 27 | 37 | 49 | 74 | 8.2 | 479 | 498 | 2 |
| 425737 | 76 | 78 | 89 | 95 | 97 | <1.25 | 501 | 520 | 0 |
| 425755 | 79 | 80 | 92 | 94 | 97 | <1.25 | 578 | 597 | 0 |
| 425757 | 68 | 74 | 88 | 95 | 96 | <1.25 | 580 | 599 | 0 |

Example 10: In Vivo Inhibition of Human Transthyretin in Human Transthyretin-Transgenic Mice Gapmers from Example 6, demonstrating significant inhibition of transthyretin mRNA, were tested in transgenic mice containing the human transthyretin gene and the efficacy of the gapmers was evaluated.

Treatment

Fifteen groups of four hTTR transgenic female mice each were administered subcutaneously twice a week for four weeks with 25 mg/kg of ISIS 304299, ISIS 304309, ISIS 304311, ISIS 304312, ISIS 420915, ISIS 420951, ISIS 425653, ISIS 425655, ISIS 425656, ISIS 425679, ISIS 425695, ISIS 425736, ISIS 425737, ISIS 425755, or ISIS 425757. Another group of four female hTTR transgenic mice was injected with 25 mg/kg of control oligonucleotide ISIS 141923 (CCTTCCCTGAAGGTTCCTCC, designated herein as SEQ ID NO: 165) twice a week for four weeks. Another group of four hTTR transgenic female mice were injected subcutaneously with PBS twice a week for four weeks. The mice injected with PBS served as a control group. Blood samples were collected from all groups on weeks 0, 1, 2, 3, and 4 for plasma transthyretin level analysis. The mice were sacrificed two days after the last dose and livers were harvested for target mRNA analysis.

RNA Analysis

RNA was extracted from liver tissue for real-time PCR analysis of transthyretin using primer probe set RTS3029. Results are presented as percent inhibition of human transthyretin, relative to PBS control. As shown in Table 14, treatment with ISIS antisense oligonucleotides resulted in significant reduction of human transthyretin mRNA in comparison to the PBS control. Treatment with the control oligonucleotide, ISIS 141923 did not result in significant reduction of transthyretin, as expected.

TABLE 14

Inhibition of human transthyretin mRNA in the hTTR transgenic mice liver relative to the PBS control

| ISIS NO | % inhibition |
|---|---|
| 304299 | 79 |
| 304309 | 83 |
| 304311 | 63 |
| 304312 | 64 |
| 420915 | 82 |
| 420951 | 92 |
| 425653 | 66 |
| 425655 | 76 |
| 425656 | 76 |
| 425679 | 93 |
| 425695 | 82 |
| 425736 | 63 |
| 425737 | 76 |
| 425755 | 91 |
| 425757 | 91 |
| 141923 | 28 |

Protein Analysis

Human transthyretin protein levels were measured in transgenic mice plasma by ELISA using an anti-transthyretin polyclonal antibody (Abcam Ab37774) and a sheep anti-TTR horse radish peroxidase detection antibody (Abcam cat. no. 35217). The color reaction was developed by the ImmunoPure® TMB Substrate Kit and absorbance measured at 450 nm using a microtiter plate spectrophotometer. Plasma samples were taken predose and on days 7, 14 and 28. The results are presented in Table 15 expressed as percentage inhibition compared to the predose levels and demonstrate a time-dependent reduction in protein levels with treatment with ISIS oligonucleotides.

TABLE 15

Inhibition of human transthyretin protein in the hTTR transgenic mice plasma relative to predose levels

|  | PBS | ISIS 304299 | ISIS 304309 | ISIS 420915 | ISIS 420951 | ISIS 425679 | ISIS 425695 | ISIS 425755 | ISIS 141923 |
|---|---|---|---|---|---|---|---|---|---|
| Day 7 | 0 | 50 | 63 | 71 | 92 | 99 | 69 | 57 | 3 |
| Day 14 | 3 | 76 | 78 | 90 | 98 | 100 | 80 | 72 | 3 |
| Day 21 | 20 | 88 | 81 | 95 | 100 | 99 | 88 | 78 | 13 |
| Day 28 | 13 | 89 | 83 | 98 | 100 | 100 | 91 | 79 | 8 |

Body Weight and Organ Weight

The body weights of the mice were measured predose and at the end of the treatment period. The body weights are presented in Table 16 and are expressed as percent increase over the PBS control weight taken before the start of treatment. Liver, spleen and kidney weights were measured at the end of the study, and are also presented in Table 16 as a percent change over the respective organ weights of the PBS control. As shown in Table 16, there was no significant change in body or organ weights as a result of antisense oligonucleotide treatment.

TABLE 16

Percent change in body and organ weights of transgenic mice after antisense oligonucleotide treatment

|  | Body weight | Liver | Spleen | Kidney |
|---|---|---|---|---|
| PBS | 1.1 | 1.0 | 1.0 | 1.0 |
| ISIS 304299 | 1.1 | 1.1 | 1.0 | 0.8 |
| ISIS 304309 | 1.1 | 1.1 | 1.0 | 1.0 |
| ISIS 304311 | 1.1 | 1.2 | 1.0 | 1.2 |
| ISIS 304312 | 1.1 | 1.3 | 1.0 | 0.8 |
| ISIS 420915 | 1.1 | 1.1 | 1.0 | 1.1 |
| ISIS 420951 | 1.1 | 1.2 | 1.0 | 1.5 |
| ISIS 425653 | 1.1 | 1.1 | 0.9 | 1.0 |
| ISIS 425655 | 1.1 | 1.3 | 1.0 | 1.2 |
| ISIS 425656 | 1.2 | 1.3 | 1.0 | 1.3 |
| ISIS 425679 | 1.2 | 1.2 | 1.0 | 1.6 |
| ISIS 425695 | 1.1 | 1.3 | 1.0 | 1.0 |
| ISIS 425736 | 1.2 | 1.2 | 1.0 | 1.0 |
| ISIS 425737 | 1.1 | 1.2 | 1.1 | 1.2 |

TABLE 16-continued

Percent change in body and organ weights of transgenic mice after antisense oligonucleotide treatment

|  | Body weight | Liver | Spleen | Kidney |
|---|---|---|---|---|
| ISIS 425755 | 1.2 | 1.3 | 1.1 | 1.3 |
| ISIS 425757 | 1.1 | 1.9 | 1.0 | 1.5 |
| ISIS 141923 | 1.1 | 1.1 | 1.0 | 0.8 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 17, expressed in IU/L. Plasma levels of bilirubin were also measured using the same clinical chemistry analyzer; results are also presented in Table 17 and expressed in mg/dL.

TABLE 17

Effect of antisense oligonucleotide treatment on metabolic markers in the liver of transgenic mice

|  | ALT (IU/L) | AST (IU/L) | Bilirubin (mg/dL) |
|---|---|---|---|
| PBS | 31 | 78 | 0.23 |
| ISIS 304299 | 40 | 121 | 0.19 |
| ISIS 304309 | 38 | 119 | 0.20 |
| ISIS 304311 | 34 | 60 | 0.16 |
| ISIS 304312 | 43 | 67 | 0.17 |
| ISIS 420915 | 34 | 75 | 0.26 |
| ISIS 420951 | 75 | 124 | 0.17 |
| ISIS 425653 | 35 | 78 | 0.20 |
| ISIS 425655 | 131 | 109 | 0.16 |
| ISIS 425656 | 68 | 110 | 0.19 |
| ISIS 425679 | 119 | 180 | 0.20 |
| ISIS 425695 | 43 | 69 | 0.15 |
| ISIS 425736 | 23 | 58 | 0.16 |
| ISIS 425737 | 35 | 64 | 0.19 |
| ISIS 425755 | 109 | 162 | 0.16 |
| ISIS 425757 | 1904 | 937 | 0.24 |
| ISIS 141923 | 31 | 76 | 0.19 |

Kidney Function

To evaluate the effect of ISIS oligonucleotides on kidney function, plasma concentrations of blood urea nitrogen (BUN) were measured using an automated clinical chemistry analyzer (Hitachi Olympus AU400e, Melville, N.Y.). Results are presented in Table 18, expressed in mg/dL. The data indicates that antisense inhibition of transthyretin has no effect on BUN levels in these transgenic mice.

TABLE 18

Effect of antisense oligonucleotide treatment on BUN (mg/dL) in the kidney of transgenic mice

|  | BUN (mg/dL) |
|---|---|
| PBS | 26 |
| ISIS 304299 | 24 |
| ISIS 304309 | 29 |
| ISIS 304311 | 28 |
| ISIS 304312 | 26 |
| ISIS 420915 | 25 |
| ISIS 420951 | 25 |
| ISIS 425653 | 24 |
| ISIS 425655 | 28 |
| ISIS 425656 | 25 |
| ISIS 425679 | 26 |
| ISIS 425695 | 28 |
| ISIS 425736 | 25 |
| ISIS 425737 | 23 |
| ISIS 425755 | 24 |
| ISIS 425757 | 25 |
| ISIS 141923 | 23 |

Example 11: Tolerability of Antisense Oligonucleotides Targeting Human Transthyretin in CD1 Mice CD1® mice (Charles River, Mass.) are a multipurpose model of mice, frequently utilized for safety and efficacy testing. The mice were treated with ISIS antisense oligonucleotides selected from studies described in Example 10 and evaluated for changes in the levels of various metabolic markers.

Treatment

Groups of eight CD1 mice each were injected subcutaneously twice a week with 50 mg/kg of ISIS 304299, ISIS 304309, ISIS 420915, ISIS 420951, ISIS 425655, ISIS 425656, ISIS 425679, ISIS 425695, ISIS 425736, ISIS 425737, and ISIS 425755. Four mice from each group were evaluated at week 2 and week 6 of the treatment period. Three days after the last dose at each time point, body weights were taken, mice were euthanized and organs and plasma were harvested for further analysis.

Body and Organ Weights

The body weights of the mice were measured pre-dose and at the end of each treatment period (two weeks and six weeks). The body weights are presented in Tables 19 and 20, and are expressed as percent increase over the PBS control weight taken before the start of treatment. Liver, spleen and kidney weights were measured at the end of the study, and are also presented in Tables 19 and 20 as a percentage change over the respective organ weights of the PBS control.

TABLE 19

Change in body and organ weights of CD1 mice after antisense oligonucleotide treatment (%) at week 2

|  | Body weight | Liver | Spleen | Kidney |
|---|---|---|---|---|
| PBS | 1.1 | 1.0 | 1.0 | 1.0 |
| ISIS 304299 | 1.1 | 1.1 | 1.1 | 1.1 |
| ISIS 304309 | 1.1 | 1.1 | 1.1 | 1.0 |
| ISIS 420915 | 1.1 | 1.1 | 1.1 | 1.0 |
| ISIS 420951 | 1.1 | 1.3 | 1.7 | 1.2 |
| ISIS 425655 | 1.1 | 1.2 | 1.2 | 0.9 |
| ISIS 425656 | 1.1 | 1.1 | 1.1 | 1.0 |
| ISIS 425679 | 1.1 | 1.1 | 1.4 | 1.1 |
| ISIS 425695 | 1.1 | 1.1 | 0.9 | 1.1 |
| ISIS 425736 | 1.1 | 1.1 | 1.0 | 1.1 |
| ISIS 425737 | 1.2 | 1.1 | 1.1 | 1.1 |
| ISIS 425755 | 1.2 | 1.2 | 1.3 | 1.2 |

TABLE 20

Change in body and organ weights of CD1 mice after antisense oligonucleotide treatment (%) at week 6

|  | Body weight | Liver | Spleen | Kidney |
|---|---|---|---|---|
| PBS | 1.2 | 1.0 | 1.0 | 1.0 |
| ISIS 304299 | 1.3 | 1.2 | 1.4 | 1.0 |
| ISIS 304309 | 1.3 | 1.3 | 2.0 | 1.0 |
| ISIS 420915 | 1.3 | 1.1 | 1.5 | 0.9 |
| ISIS 420951 | 1.3 | 1.3 | 2.0 | 1.1 |
| ISIS 425655 | 1.4 | 1.3 | 1.7 | 0.9 |
| ISIS 425656 | 1.3 | 1.3 | 1.1 | 1.0 |
| ISIS 425679 | 1.3 | 1.4 | 2.3 | 1.2 |
| ISIS 425695 | 1.3 | 1.4 | 1.5 | 1.0 |
| ISIS 425736 | 1.3 | 1.1 | 1.2 | 0.9 |
| ISIS 425737 | 1.2 | 1.1 | 1.3 | 1.0 |
| ISIS 425755 | 1.3 | 1.3 | 2.1 | 1.0 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Tables 21 and 22 expressed in IU/L. Plasma levels of bilirubin and albumin were also measured using the same clinical chemistry analyzer and the results are also presented in Tables 21 and 22.

TABLE 21

Effect of antisense oligonucleotide treatment on metabolic markers in the liver of CD1 mice at week 2

|  | ALT (IU/L) | AST (IU/L) | Bilirubin (mg/dL) | Albumin (g/dL) |
|---|---|---|---|---|
| PBS | 38 | 66 | 0.19 | 5.0 |
| ISIS 304299 | 42 | 79 | 0.33 | 3.8 |
| ISIS 304309 | 52 | 77 | 0.22 | 3.2 |
| ISIS 420915 | 32 | 61 | 0.28 | 3.5 |
| ISIS 420951 | 1184 | 804 | 0.17 | 3.7 |
| ISIS 425655 | 60 | 70 | 0.20 | 3.9 |
| ISIS 425656 | 37 | 53 | 0.31 | 3.5 |
| ISIS 425679 | 88 | 147 | 0.23 | 3.7 |
| ISIS 425695 | 25 | 50 | 0.23 | 3.6 |
| ISIS 425736 | 31 | 79 | 0.23 | 3.2 |
| ISIS 425737 | 39 | 43 | 0.23 | 3.1 |
| ISIS 425755 | 104 | 85 | 0.29 | 3.6 |

TABLE 22

Effect of antisense oligonucleotide treatment on metabolic markers in the liver of CD1 mice at week 6

|  | ALT (IU/L) | AST (IU/L) | Bilirubin (mg/dL) | Albumin (g/dL) |
|---|---|---|---|---|
| PBS | 31 | 67 | 0.20 | 5.6 |
| ISIS 304299 | 54 | 71 | 0.20 | 5.2 |
| ISIS 304309 | 1211 | 504 | 0.30 | 5.2 |
| ISIS 420915 | 89 | 91 | 0.17 | 5.0 |
| ISIS 420951 | 872 | 319 | 0.20 | 3.6 |
| ISIS 425655 | 730 | 247 | 0.13 | 4.3 |
| ISIS 425656 | 502 | 261 | 0.17 | 4.3 |
| ISIS 425679 | 935 | 475 | 0.29 | 4.5 |
| ISIS 425695 | 1627 | 563 | 0.16 | 4.0 |
| ISIS 425736 | 41 | 47 | 0.15 | 4.1 |
| ISIS 425737 | 32 | 55 | 0.16 | 4.1 |
| ISIS 425755 | 233 | 176 | 0.16 | 4.3 |

Kidney Function

To evaluate the effect of ISIS oligonucleotides on kidney function, plasma concentrations of blood urea nitrogen (BUN) and creatinine were measured using an automated clinical chemistry analyzer (Hitachi Olympus AU400e, Melville, N.Y.). Results are presented in Tables 23 and 24, expressed in mg/dL.

TABLE 23

Effect of antisense oligonucleotide treatment on metabolic markers (mg/dL) in the kidney of CD1 mice at week 2

|  | BUN | Creatinine |
|---|---|---|
| PBS | 32 | 0.23 |
| ISIS 304299 | 26 | 0.21 |
| ISIS 304309 | 30 | 0.19 |
| ISIS 420915 | 30 | 0.22 |
| ISIS 420951 | 24 | 0.17 |
| ISIS 425655 | 29 | 0.22 |
| ISIS 425656 | 25 | 0.19 |
| ISIS 425679 | 28 | 0.19 |
| ISIS 425695 | 29 | 0.19 |
| ISIS 425736 | 24 | 0.19 |
| ISIS 425737 | 24 | 0.16 |
| ISIS 425755 | 27 | 0.17 |

TABLE 24

Effect of antisense oligonucleotide treatment on metabolic markers (mg/dL) in the kidney of CD1 mice at week 6

|  | BUN | Creatinine |
|---|---|---|
| PBS | 24 | 0.15 |
| ISIS 304299 | 19 | 0.11 |
| ISIS 304309 | 20 | 0.14 |
| ISIS 420915 | 24 | 0.18 |
| ISIS 420951 | 19 | 0.08 |
| ISIS 425655 | 22 | 0.11 |
| ISIS 425656 | 21 | 0.10 |
| ISIS 425679 | 20 | 0.06 |
| ISIS 425695 | 21 | 0.08 |
| ISIS 425736 | 22 | 0.07 |
| ISIS 425737 | 18 | 0.07 |
| ISIS 425755 | 22 | 0.09 |

Hematology Assays

Blood obtained from all mice groups were sent to Antech Diagnostics for hematocrit (HCT), mean corpuscular volume (MCV), mean corpuscular hemoglobin (MCH), and mean corpuscular hemoglobin concentration (MCHC) measurements and analyses, as well as measurements of the differential blood cell counts, such as that of WBC (neutrophils, lymphocytes, and monocytes), RBC, and platelets, and total hemoglobin content. The results are presented in Tables 25-28. Percentages given in the tables indicate the percent change in total blood cell count compared to the PBS control. Those antisense oligonucleotides which did not affect a decrease in platelet count less than 70% of the PBS control or an increase in monocyte count more than two-fold were selected for further studies.

TABLE 25

Effect of antisense oligonucleotide treatment on complete blood cell count (%) compared to the PBS control in CD1 mice at week 2

| ISIS NO. | WBC | RBC | Hemoglobin | HCT | MCV | MCH | MCHC |
|---|---|---|---|---|---|---|---|
| 304299 | −15 | −3 | −2 | 0 | +3 | +1 | −1 |
| 304309 | −13 | −4 | −7 | −6 | −2 | −4 | −2 |
| 420915 | +7 | −7 | −7 | −5 | +2 | +1 | −2 |

TABLE 25-continued

Effect of antisense oligonucleotide treatment on complete blood cell count (%) compared to the PBS control in CD1 mice at week 2

| ISIS NO. | WBC | RBC | Hemoglobin | HCT | MCV | MCH | MCHC |
|---|---|---|---|---|---|---|---|
| 420951 | +79 | −6 | −5 | −5 | +1 | +1 | 0 |
| 425655 | +56 | −3 | −5 | −4 | −1 | −2 | −1 |
| 425656 | +69 | −5 | −6 | −5 | 0 | −1 | −2 |
| 425679 | +30 | −6 | −7 | −7 | −1 | −1 | 0 |
| 425695 | +49 | −3 | −4 | −4 | 0 | 0 | +1 |
| 425736 | +15 | −6 | −6 | −4 | +1 | 0 | −2 |
| 425737 | +19 | −5 | −7 | −5 | −1 | −3 | −2 |
| 425755 | +85 | −3 | −6 | −6 | −4 | −3 | 0 |

TABLE 26

Effect of antisense oligonucleotide treatment on complete blood cell count (%) compared to the PBS control in CD1 mice at week 6

| ISIS NO. | WBC | RBC | Hemoglobin | HCT | MCV | MCH | MCHC |
|---|---|---|---|---|---|---|---|
| 304299 | −7 | −9 | −10 | −13 | −5 | 0 | +4 |
| 304309 | +10 | −12 | −11 | −15 | −5 | +1 | +6 |
| 420915 | +11 | −7 | −8 | −10 | −4 | −2 | +2 |
| 420951 | +81 | −12 | −20 | −19 | −9 | −9 | −1 |
| 425655 | +29 | −3 | −11 | −10 | −8 | −9 | −2 |
| 425656 | +72 | −1 | −5 | −6 | −4 | −5 | −1 |
| 425679 | +154 | −11 | −20 | −21 | −10 | −9 | +2 |
| 425695 | +118 | +3 | −9 | −9 | −2 | −12 | +3 |
| 425736 | +51 | +4 | −5 | −7 | 0 | −10 | +1 |
| 425737 | +30 | +8 | −1 | −2 | 0 | −8 | +1 |
| 425755 | +54 | −1 | −11 | −12 | −8 | −10 | 0 |

TABLE 27

Effect of antisense oligonucleotide treatment on differential blood cell count (%) compared to the PBS control in CD1 mice at week 2

| ISIS NO. | Neutrophils | Monocytes | Lymphocytes | Platelets |
|---|---|---|---|---|
| 304299 | 11 | −3 | 20 | 17 |
| 304309 | −11 | 5 | 8 | 14 |
| 420915 | 1 | 4 | −24 | 41 |
| 420951 | 18 | −7 | 32 | −9 |
| 425655 | 18 | −5 | 20 | 18 |
| 425656 | 31 | −7 | −4 | 24 |
| 425679 | 2 | −1 | 24 | −19 |
| 425695 | −50 | 15 | 20 | 29 |
| 425736 | 8 | −1 | 0 | 10 |
| 425737 | −29 | 10 | −8 | 24 |
| 425755 | −13 | 7 | −4 | 9 |

TABLE 28

Effect of antisense oligonucleotide treatment on differential blood cell count (%) compared to the PBS control in CD1 mice at week 6

| ISIS NO. | Neutrophils | Lymphocytes | Monocytes | Platelets |
|---|---|---|---|---|
| 304299 | −60 | +26 | +10 | −16 |
| 304309 | −28 | +12 | +30 | +2 |
| 420915 | −29 | +6 | +50 | −30 |
| 420951 | −26 | +11 | 0 | −40 |
| 425655 | −16 | +8 | −10 | −19 |
| 425656 | −22 | +16 | −50 | −25 |
| 425679 | −36 | +19 | −20 | −27 |
| 425695 | −25 | +9 | −15 | −49 |
| 425736 | −41 | +16 | −5 | −46 |
| 425737 | −53 | +23 | −20 | −65 |
| 425755 | −20 | +4 | +25 | −41 |

Example 12: Measurement of Half-Life of Antisense Oligonucleotide in CD1 Mouse Liver CD1 mice were treated with ISIS antisense oligonucleotides from studies described in Example 11 and the oligonucleotide half-life as well as the elapsed time for oligonucleotide degradation and elimination from the liver was evaluated.

Treatment

Groups of twelve CD1 mice each were injected subcutaneously twice per week for 2 weeks with 50 mg/kg of ISIS 304299, ISIS 304309, ISIS 420915, ISIS 420951, ISIS 425655, ISIS 425656, ISIS 425679, ISIS 425695, ISIS 425736, ISIS 425737, and ISIS 425755. Four mice from each group were sacrificed 3 days, 28 days and 56 days following the final dose. Livers were harvested for analysis.

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 166) was added prior to extraction. Tissue sample concentrations were calculated using calibration curves, with a lower limit of quantitation (LLOQ) of approximately 1.14 µg/g. Half-lives were then calculated using WinNonlin software (PHARSIGHT).

The results are presented in Tables 29 and 30, expressed as µg/g liver tissue. The half-life of each oligonucleotide is presented in Table 31. Antisense oligonucleotides with half-lives within 11-34 days were chosen for further studies.

TABLE 29

Full-length oligonucleotide concentration (µg/g) in the liver of CD1 mice

| ISIS NO. | 3 days | 28 days | 56 days |
|---|---|---|---|
| 304299 | 180 | 56 | 8 |
| 304309 | 317 | 254 | 106 |
| 420915 | 248 | 126 | 34 |
| 420951 | 173 | 109 | 49 |
| 425655 | 191 | 113 | 33 |
| 425656 | 256 | 73 | 29 |
| 425679 | 201 | 73 | 27 |
| 425695 | 315 | 194 | 65 |
| 425736 | 219 | 110 | 47 |
| 425737 | 190 | 40 | 9 |
| 425755 | 211 | 120 | 47 |

TABLE 30

Total oligonucleotide concentration (µg/g) in the liver of CD1 mice

| ISIS NO. | 3 days | 28 days | 56 days |
|---|---|---|---|
| 304299 | 268 | 168 | 38 |
| 304309 | 389 | 354 | 152 |
| 420915 | 314 | 229 | 83 |
| 420951 | 262 | 196 | 131 |
| 425655 | 298 | 217 | 87 |
| 425656 | 328 | 135 | 85 |
| 425679 | 333 | 161 | 103 |

TABLE 30-continued

Total oligonucleotide concentration (μg/g) in the liver of CD1 mice

| ISIS NO. | 3 days | 28 days | 56 days |
|---|---|---|---|
| 425695 | 364 | 263 | 143 |
| 425736 | 298 | 211 | 140 |
| 425737 | 266 | 117 | 31 |
| 425755 | 337 | 227 | 140 |

TABLE 31

Half-life of oligonucleotide (days) in the liver of CD1 mice

| ISIS NO. | Half-life (days) |
|---|---|
| 304299 | 12 |
| 304309 | 33 |
| 420915 | 19 |
| 420951 | 29 |
| 425655 | 21 |
| 425656 | 17 |
| 425679 | 18 |
| 425695 | 23 |
| 425736 | 24 |
| 425737 | 12 |
| 425755 | 24 |

Example 13: Tolerability of Antisense Oligonucleotides Targeting Human Transthyretin in Sprague-Dawley Rats Sprague-Dawley rats were treated with ISIS antisense oligonucleotides selected from studies described in Examples 11 and 12 and evaluated for changes in the levels of various metabolic markers.

Treatment

The body weights, complete blood count and different blood count, as well as the urine protein/creatinine ratio of the rats were evaluated pre-dose. Groups of four Sprague-Dawley rats each were injected subcutaneously twice a week with 50 mg/kg of ISIS 304299, ISIS 304309, ISIS 420915, ISIS 420951, ISIS 425655, ISIS 425656, ISIS 425679, ISIS 425695, ISIS 425736, ISIS 425737, and ISIS 425755. Three days after the last dose at each time point, body weights were taken, mice were euthanized and organs and plasma were harvested for further analysis.

Body and Organ Weights

The body weights of the rats were measured pre-dose and at the end of the treatment period. The body weights are presented in Table 32, and are expressed as percent increase over the PBS control weight taken before the start of treatment. Liver, spleen and kidney weights were measured at the end of the study, and are also presented in Table 32 as a percentage change over the respective organ weights of the PBS control.

TABLE 32

Change in body and organ weights of Sprague-Dawley rats after antisense oligonucleotide treatment (%)

|  | Body weight | Liver | Spleen | Kidney |
|---|---|---|---|---|
| PBS | 1.6 | 1.0 | 1.0 | 1.0 |
| ISIS 304299 | 1.2 | 1.7 | 4.9 | 1.6 |
| ISIS 304309 | 1.1 | 1.6 | 4.3 | 1.4 |
| ISIS 420915 | 1.4 | 1.4 | 3.3 | 1.3 |
| ISIS 420951 | 1.1 | 1.4 | 5.0 | 1.5 |
| ISIS 425655 | 1.2 | 1.5 | 3.4 | 1.3 |
| ISIS 425656 | 1.2 | 1.5 | 2.9 | 1.2 |
| ISIS 425679 | 1.0 | 1.9 | 6.4 | 1.7 |
| ISIS 425695 | 1.2 | 1.6 | 3.3 | 1.3 |
| ISIS 425736 | 1.3 | 1.5 | 2.9 | 1.2 |
| ISIS 425737 | 1.2 | 1.7 | 4.0 | 1.5 |
| ISIS 425755 | 1.0 | 1.5 | 5.4 | 1.5 |

As shown in Tables 32, certain compounds showed a less than a 4-fold increase in spleen weight.

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 33 expressed in IU/L. Plasma levels of bilirubin and albumin were also measured using the same clinical chemistry analyzer and the results are also presented in Table 33.

TABLE 33

Effect of antisense oligonucleotide treatment on metabolic markers in the liver of Sprague-Dawley rats

|  | ALT (IU/L) | AST (IU/L) | Bilirubin (mg/dL) | Albumin (g/dL) |
|---|---|---|---|---|
| PBS | 55 | 138 | 0.15 | 3.3 |
| ISIS 304299 | 69 | 154 | 0.15 | 2.7 |
| ISIS 304309 | 80 | 138 | 0.11 | 2.9 |
| ISIS 420915 | 43 | 95 | 0.11 | 3.0 |
| ISIS 420951 | 353 | 511 | 0.32 | 2.6 |
| ISIS 425655 | 312 | 497 | 0.47 | 2.6 |
| ISIS 425656 | 277 | 335 | 0.20 | 3.0 |
| ISIS 425679 | 537 | 659 | 0.38 | 2.7 |
| ISIS 425695 | 228 | 445 | 0.23 | 2.3 |
| ISIS 425736 | 362 | 553 | 0.32 | 2.9 |
| ISIS 425737 | 55 | 79 | 0.09 | 1.9 |
| ISIS 425755 | 271 | 303 | 0.41 | 2.8 |

Kidney Function

To evaluate the effect of ISIS oligonucleotides on kidney function, plasma concentrations of blood urea nitrogen (BUN) and creatinine were measured using an automated clinical chemistry analyzer (Hitachi Olympus AU400e, Melville, N.Y.). Results are presented in Table 34, expressed in mg/dL. The ratio of total urine protein to creatinine was also evaluated and presented in Table 35.

TABLE 34

Effect of antisense oligonucleotide treatment on metabolic markers (mg/dL) in the kidney of Sprague-Dawley rats

|  | BUN | Creatinine |
|---|---|---|
| PBS | 20 | 0.26 |
| ISIS 304299 | 30 | 0.40 |
| ISIS 304309 | 24 | 0.33 |
| ISIS 420915 | 20 | 0.26 |
| ISIS 420951 | 37 | 0.47 |
| ISIS 425655 | 28 | 0.40 |
| ISIS 425656 | 25 | 0.34 |
| ISIS 425679 | 46 | 0.42 |
| ISIS 425695 | 30 | 0.37 |

TABLE 34-continued

Effect of antisense oligonucleotide treatment on metabolic markers (mg/dL) in the kidney of Sprague-Dawley rats

|  | BUN | Creatinine |
|---|---|---|
| ISIS 425736 | 26 | 0.37 |
| ISIS 425737 | 30 | 0.36 |
| ISIS 425755 | 29 | 0.36 |

TABLE 35

Effect of antisense oligonucleotide treatment on total urine protein/creatinine in the kidney of Sprague-Dawley rats

|  | Pre-dose | Week 6 |
|---|---|---|
| PBS | 0.82 | 0.95 |
| ISIS 304299 | 0.95 | 7.57 |
| ISIS 304309 | 1.10 | 5.20 |
| ISIS 420915 | 0.91 | 5.30 |
| ISIS 420951 | 0.90 | 5.02 |
| ISIS 425655 | 0.78 | 6.03 |
| ISIS 425656 | 0.86 | 9.37 |
| ISIS 425679 | 0.91 | 7.80 |
| ISIS 425695 | 0.89 | 5.71 |
| ISIS 425736 | 1.00 | 5.85 |
| ISIS 425737 | 0.86 | 43.76 |
| ISIS 425755 | 0.78 | 3.70 |

As shown in Tables 34 and 35, certain compounds demonstrated a less than 7-fold increase in the total urine protein/creatinine in the kidney of these rats. Furthermore, certain compounds demonstrated a less than 6-fold increase in the total urine protein/creatinine in the kidney of these rats.

Hematology Assays

Blood obtained from all rat groups were sent to Antech Diagnostics for hematocrit (HCT), mean corpuscular volume (MCV), mean corpuscular hemoglobin (MCH), and mean corpuscular hemoglobin concentration (MCHC) measurements and analyses, as well as measurements of the differential blood cell counts, such as that of WBC (neutrophils, lymphocytes, and monocytes), RBC, and platelets, and total hemoglobin content. The results are presented in Tables 36 and 37. Percentages given in the tables indicate the percent change in total blood cell count compared to the PBS control.

TABLE 36

Effect of antisense oligonucleotide treatment on complete blood cell count (%) compared to the PBS control in Sprague-Dawley rats

| ISIS NO. | WBC | RBC | Hemoglobin | HCT | MCV | MCH | MCHC |
|---|---|---|---|---|---|---|---|
| 304299 | +4 | −5 | −3 | +2 | +11 | +5 | −5 |
| 304309 | −10 | −8 | −11 | −12 | −4 | −3 | +1 |
| 420915 | −9 | −16 | −20 | −17 | +1 | −3 | −3 |
| 420951 | +5 | −5 | −8 | −5 | +1 | −2 | −3 |
| 425655 | +22 | −17 | −18 | −19 | −2 | 0 | +2 |
| 425656 | −1 | −13 | −19 | −16 | −3 | −6 | −2 |
| 425679 | +49 | −42 | −32 | −28 | +26 | +19 | −5 |
| 425695 | −2 | −25 | −31 | −29 | −4 | −8 | −3 |
| 425736 | +18 | +1 | −3 | +2 | 0 | −4 | −4 |
| 425737 | −15 | −20 | −18 | −20 | +2 | +3 | +1 |
| 425755 | +35 | −31 | −27 | −23 | +14 | +8 | −4 |

TABLE 37

Effect of antisense oligonucleotide treatment on complete blood cell count (%) compared to the PBS control in Sprague-Dawley rats

| ISIS NO. | Neutrophils | Lymphocytes | Monocytes | Platelet |
|---|---|---|---|---|
| 304299 | −61 | +15 | −10 | −41 |
| 304309 | −35 | +8 | +10 | −37 |
| 420915 | −23 | +6 | 0 | −29 |
| 420951 | −62 | +15 | +10 | −67 |
| 425655 | +23 | −8 | +80 | −13 |
| 425656 | −14 | 0 | +70 | −15 |
| 425679 | −4 | −1 | +60 | −75 |
| 425695 | +68 | −20 | +80 | −5 |
| 425736 | 0 | −2 | +70 | −1 |
| 425737 | −6 | +1 | +20 | −21 |
| 425755 | −18 | +3 | +70 | −58 |

Example 14: Pharmacokinetic Studies of Antisense Oligonucleotide Concentration in Sprague-Dawley Rat Liver and Kidney Sprague Dawley rats were treated with ISIS antisense oligonucleotides from studies described in Example 13 and the oligonucleotide half-life as well as the elapsed time for oligonucleotide degradation and elimination from the liver and kidney was evaluated.

Treatment

Groups of four Sprague Dawley rats each were injected subcutaneously twice a week for 2 weeks with 20 mg/kg of ISIS 304299, ISIS 304309, ISIS 420915, ISIS 420951, ISIS 425655, ISIS 425656, ISIS 425679, ISIS 425695, ISIS 425736, ISIS 425737, and ISIS 425755. Three days after the last dose, the rats were sacrificed and livers and kidneys were collected for analysis.

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2′-O-methoxyethyl modified phosphorothioate oligonucleotide, GCGTTTGCTCTTCTTCTTGCGTTTTTT, designated herein as SEQ ID NO: 166) was added prior to extraction. Tissue sample concentrations were calculated using calibration curves, with a lower limit of quantitation (LLOQ) of approximately 1.14 µg/g. The results are presented in Tables 38 and 39, expressed as µg/g liver or kidney tissue. The kidney to liver ratio of full length oligonucleotide was also calculated and presented in Table 38.

TABLE 38

Full-length oligonucleotide concentration (µg/g) and ratio in the liver and kidney of Sprague-Dawley rats

| ISIS NO. | Liver | Kidney | Kidney/Liver Ratio |
|---|---|---|---|
| 304299 | 165 | 487 | 2.9 |
| 304309 | 344 | 606 | 1.8 |
| 420915 | 171 | 680 | 4.0 |
| 420951 | 214 | 389 | 1.8 |
| 425655 | 242 | 466 | 1.9 |
| 425656 | 286 | 595 | 2.1 |
| 425679 | 290 | 334 | 1.2 |
| 425695 | 266 | 566 | 2.1 |
| 425736 | 245 | 571 | 2.3 |

TABLE 38-continued

Full-length oligonucleotide concentration (µg/g)
and ratio in the liver and kidney of Sprague-Dawley rats

| ISIS NO. | Liver | Kidney | Kidney/Liver Ratio |
|---|---|---|---|
| 425737 | 167 | 477 | 2.9 |
| 425755 | 218 | 379 | 1.7 |

TABLE 39

Total oligonucleotide concentration (µg/g)
in the liver and kidney of Sprague-Dawley rats

| ISIS NO. | Liver | Kidney |
|---|---|---|
| 304299 | 208 | 653 |
| 304309 | 409 | 803 |
| 420915 | 196 | 844 |
| 420951 | 348 | 879 |
| 425655 | 340 | 764 |
| 425656 | 329 | 703 |
| 425679 | 461 | 710 |
| 425695 | 369 | 843 |
| 425736 | 282 | 738 |
| 425737 | 195 | 587 |
| 425755 | 351 | 886 |

Example 15: In Vivo Dose-Dependent Inhibition of Human Transthyretin in Transgenic Mice Transgenic mice containing the human transthyretin gene were dosed in increasing doses of ISIS oligonucleotides selected from studies described in Example 14 to evaluate the effect of dose-dependent inhibition of human transthyretin in these mice.

Treatment

Groups of four mice, two male and two female, each were injected subcutaneously twice a week for 4 weeks with 4 mg/kg, 10 mg/kg or 25 mg/kg of ISIS 304299, ISIS 420915, ISIS 420951, ISIS 425679, ISIS 425736, ISIS 425737, or ISIS 425755. One group of four mice, two male and two female, was injected subcutaneously twice a week for 4 weeks with 25 mg/kg of the control oligonucleotide, ISIS 141923. One control group of four mice, two male and two female, was injected subcutaneously twice a week for 4 weeks with PBS. Plasma samples were taken from each group at days 0, 7, 14, 21 and 28. Two days after the last dose, the mice were euthanized and organs were harvested for further analysis.

RNA Analysis

RNA was extracted from liver tissue for real-time PCR analysis of transthyretin using primer probe set RTS3029. Results are presented as percent inhibition of human transthyretin, relative to PBS control. As shown in Table 40, treatment with ISIS antisense oligonucleotides resulted in significant dose-dependent reduction of human transthyretin mRNA in comparison to the PBS control. Treatment with the control oligonucleotide, ISIS 141923 did not result in significant reduction of transthyretin, as expected.

TABLE 40

Inhibition of human transthyretin mRNA in the hTTR
transgenic mice liver relative to the PBS control

| ISIS NO. | Dose (mg/kg) | % inhibition |
|---|---|---|
| 304299 | 25 | 73 |
|  | 10 | 60 |
|  | 4 | 9 |
| 420915 | 25 | 78 |
|  | 10 | 57 |
|  | 4 | 43 |
| 420951 | 25 | 91 |
|  | 10 | 85 |
|  | 4 | 52 |
| 425679 | 25 | 94 |
|  | 10 | 88 |
|  | 4 | 42 |
| 425736 | 25 | 49 |
|  | 10 | 54 |
|  | 4 | 15 |
| 425737 | 25 | 82 |
|  | 10 | 59 |
|  | 4 | 21 |
| 425755 | 25 | 91 |
|  | 10 | 79 |
|  | 4 | 24 |
| 141923 | 25 | 0 |

Protein Analysis

Human transthyretin protein levels were measured in transgenic mice plasma by ELISA using an anti-transthyretin polyclonal antibody (Abcam Ab37774) and a sheep anti-TTR horse radish peroxidase detection antibody (Abcam cat. no. 35217). The color reaction was developed by the ImmunoPure® TMB Substrate Kit and absorbance measured at 450 nm using a microtiter plate spectrophotometer. Plasma samples were taken predose and on days 7, 14, 21 and 28. The results are presented in Table 41 expressed as percentage inhibition compared to the predose levels and demonstrate a time-dependent and dose-dependent reduction in protein levels on treatment with ISIS oligonucleotides.

TABLE 41

Inhibition of human transthyretin protein in transgenic
mice plasma relative to pre-dose levels

| ISIS NO. |  | Day 0 | Day 7 | Day 14 | Day 21 | Day 28 |
|---|---|---|---|---|---|---|
| 141923 | 25 | 0 | 0 | 20 | 77 | 41 |
| 304299 | 25 | 0 | 44 | 85 | 100 | 88 |
|  | 10 | 0 | 0 | 8 | 93 | 78 |
|  | 4 | 0 | 0 | 0 | 57 | 0 |
| 420915 | 25 | 0 | 0 | 67 | 86 | 91 |
|  | 10 | 0 | 21 | 39 | 70 | 71 |
|  | 4 | 0 | 25 | 0 | 0 | 0 |
| 420951 | 25 | 0 | 83 | 96 | 100 | 100 |
|  | 10 | 0 | 35 | 66 | 91 | 86 |
|  | 4 | 0 | 7 | 26 | 0 | 0 |
| 425679 | 25 | 0 | 93 | 97 | 96 | 98 |
|  | 10 | 0 | 38 | 80 | 96 | 95 |
|  | 4 | 0 | 0 | 0 | 0 | 0 |
| 425736 | 25 | 0 | 56 | 76 | 82 | 92 |
|  | 10 | 0 | 0 | 33 | 37 | 66 |
|  | 4 | 0 | 0 | 0 | 0 | 0 |
| 425737 | 25 | 0 | 90 | 96 | 99 | 98 |
|  | 10 | 0 | 51 | 80 | 88 | 89 |
|  | 4 | 0 | 29 | 21 | 37 | 31 |
| 425755 | 25 | 0 | 88 | 96 | 98 | 99 |
|  | 10 | 0 | 52 | 76 | 90 | 88 |
|  | 4 | 0 | 29 | 22 | 36 | 26 |

Body Weight and Organ Weight

The body weights of the mice were measured pre-dose and at the end of the treatment period. The body weights are presented in Table 42 and are expressed as percent increase over the PBS control weight taken before the start of treatment. Liver, spleen and kidney weights were measured at the end of the study, and are also presented in Table 42 as a percentage change over the respective organ weights of the PBS control.

TABLE 42

Change in body and organ weights of transgenic mice after antisense oligonucleotide treatment (%)

| | Dose (mg/kg) | Body weight | Liver | Spleen | Kidney |
|---|---|---|---|---|---|
| PBS | | +13 | 0 | 0 | 0 |
| ISIS 304299 | 25 | +17 | +16 | +3 | −2 |
| | 10 | +14 | +10 | −13 | −4 |
| | 4 | +17 | +2 | +17 | −2 |
| ISIS 420915 | 25 | +18 | +12 | −6 | −6 |
| | 10 | +16 | +6 | −4 | −5 |
| | 4 | +15 | +4 | +8 | −2 |
| ISIS 420951 | 25 | +22 | +23 | +32 | −2 |
| | 10 | +16 | +11 | +10 | −3 |
| | 4 | +24 | +7 | +19 | +5 |
| ISIS 425679 | 25 | +24 | +33 | +40 | −1 |
| | 10 | +14 | +5 | +9 | −2 |
| | 4 | +19 | +7 | +10 | 0 |
| ISIS 425736 | 25 | +16 | +15 | 0 | −5 |
| | 10 | +28 | +8 | −12 | −6 |
| | 4 | +20 | +10 | −9 | −2 |
| ISIS 425737 | 25 | +16 | +13 | 0 | −2 |
| | 10 | +19 | +6 | +18 | −3 |
| | 4 | +19 | +5 | +4 | +1 |
| ISIS 425755 | 25 | +21 | +25 | +34 | −5 |
| | 10 | +17 | +10 | +13 | −4 |
| | 4 | +22 | +3 | +27 | +4 |
| ISIS 141923 | 25 | +20 | +8 | −3 | −4 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 43 expressed in IU/L. Plasma levels of bilirubin were also measured using the same clinical chemistry analyzer; results are also presented in Table 43 and expressed in mg/dL.

TABLE 43

Effect of antisense oligonucleotide treatment on metabolic markers in the liver of transgenic mice

| | Dose (mg/kg) | ALT (IU/L) | AST (IU/L) | TBIL (mg/dL) |
|---|---|---|---|---|
| PBS | — | 48 | 112 | 0.20 |
| ISIS 304299 | 25 | 42 | 93 | 0.14 |
| | 10 | 37 | 56 | 0.18 |
| | 4 | 35 | 71 | 0.15 |
| ISIS 420915 | 25 | 63 | 181 | 0.22 |
| | 10 | 46 | 132 | 0.22 |
| | 4 | 35 | 114 | 0.22 |
| ISIS 420951 | 25 | 63 | 85 | 0.17 |
| | 10 | 42 | 107 | 0.21 |
| | 4 | 31 | 74 | 0.19 |
| ISIS 425679 | 25 | 156 | 150 | 0.13 |
| | 10 | 93 | 148 | 0.23 |
| | 4 | 38 | 119 | 0.22 |
| ISIS 425736 | 25 | 37 | 78 | 0.21 |
| | 10 | 33 | 62 | 0.20 |
| | 4 | 46 | 228 | 0.23 |
| ISIS | 25 | 55 | 121 | 0.20 |

TABLE 43-continued

Effect of antisense oligonucleotide treatment on metabolic markers in the liver of transgenic mice

| | Dose (mg/kg) | ALT (IU/L) | AST (IU/L) | TBIL (mg/dL) |
|---|---|---|---|---|
| 425737 | 10 | 41 | 94 | 0.18 |
| | 4 | 32 | 73 | 0.14 |
| ISIS 425755 | 25 | 74 | 160 | 0.17 |
| | 10 | 31 | 80 | 0.16 |
| | 4 | 45 | 122 | 0.21 |
| ISIS 141923 | 25 | 66 | 141 | 0.17 |

Kidney Function

To evaluate the effect of ISIS oligonucleotides on kidney function, plasma concentrations of blood urea nitrogen (BUN) were measured using an automated clinical chemistry analyzer (Hitachi Olympus AU400e, Melville, N.Y.). Results are presented in Table 44, expressed in mg/dL.

TABLE 44

Effect of antisense oligonucleotide treatment on BUN (mg/dL) in the kidney of transgenic mice

| | Dose (mg/kg) | BUN |
|---|---|---|
| PBS | | 22 |
| ISIS 304299 | 25 | 22 |
| | 10 | 22 |
| | 4 | 22 |
| ISIS 420915 | 25 | 24 |
| | 10 | 25 |
| | 4 | 20 |
| ISIS 420951 | 25 | 24 |
| | 10 | 25 |
| | 4 | 26 |
| ISIS 425679 | 25 | 26 |
| | 10 | 24 |
| | 4 | 22 |
| ISIS 425736 | 25 | 20 |
| | 10 | 22 |
| | 4 | 22 |
| ISIS 425737 | 25 | 21 |
| | 10 | 19 |
| | 4 | 23 |
| ISIS 425755 | 25 | 23 |
| | 10 | 21 |
| | 4 | 20 |
| ISIS 141923 | 25 | 21 |

Example 16: In Vivo Inhibition of Human Transthyretin in Human Transthyretin-Transgenic Mice Antisense oligonucleotides with 5-10-5 MOE motifs, ISIS 304313, ISIS 420913, ISIS 420919, ISIS 420921, ISIS 420922, ISIS 420937, ISIS 420944, ISIS 420947, ISIS 420949, ISIS 420950, ISIS 420951, ISIS 420952, ISIS 420953, ISIS 420955, ISIS 420957, and ISIS 420959 from Table 4. These antisense oligonucleotides exhibited 65% inhibition or more of transthyretin mRNA were selected and tested in transgenic mice containing the human transthyretin gene. Additional oligonucleotides with overlapping sequences to ISIS 420951 (GTTTTATTGTCTCTGCCTGG (SEQ ID NO: 116)), and with various motifs were also designed to test in the transgenic mice. These additional oligonucleotides were ISIS 450518 (TTTTAT-TGTCTCTGCCTG (SEQ ID NO: 5-8-5 MOE (SEQ ID NO: 167)), ISIS 450519 (GTTTTATTGTCTCTGCCTGG, 6-8-6

MOE (SEQ ID NO: 116)), ISIS 450520 (GTTTTAT-TGTCTCTGCCTGG, 3-10-7 MOE (SEQ ID NO: 116)), ISIS 450521 (GTTTTATTGTCTCTGCCTGG, 7-10-3 MOE (SEQ ID NO: 116)), ISIS 450522 (GTTTTAT-TGTCTCTGCCTGG, 2-10-8 MOE (SEQ ID NO: 116)), and ISIS 450523 (GTTTTATTGTCTCTGCCTGG, 8-10-2 MOE (SEQ ID NO: 116)).

Treatment

Groups of four hTTR transgenic mice each, two male and two female, were administered subcutaneously twice per week for four weeks with 25 mg/kg of ISIS 304313, ISIS 420913, ISIS 420919, ISIS 420921, ISIS 420922, ISIS 420937, ISIS 420944, ISIS 420947, ISIS 420949, ISIS 420950, ISIS 420951, ISIS 420952, ISIS 420953, ISIS 420955, ISIS 420957, ISIS 420959, ISIS 425518, ISIS 425519, ISIS 425520, ISIS 425521, ISIS 425522, or ISIS 425523. A control group four hTTR transgenic mice, two male and two female, were injected subcutaneously with PBS twice per week for four weeks. Blood samples were collected from all groups on days 0, 14 and 28 for plasma transthyretin level analysis. The mice were sacrificed two days after the last dose and livers were harvested for target mRNA analysis.

RNA Analysis

RNA was extracted from liver tissue for real-time PCR analysis of transthyretin using primer probe set RTS3029. Results are presented as percent inhibition of human transthyretin, relative to PBS control. As shown in Table 45, treatment with ISIS antisense oligonucleotides resulted in significant reduction of human transthyretin mRNA in comparison to the PBS control.

TABLE 45

Inhibition of human transthyretin mRNA in the hTTR transgenic mice liver relative to the PBS control

| ISIS NO. | % inhibition |
|---|---|
| 304313 | 68 |
| 420913 | 83 |
| 420919 | 64 |
| 420921 | 70 |
| 420922 | 82 |
| 420937 | 46 |
| 420944 | 58 |
| 420947 | 62 |
| 420949 | 87 |
| 420950 | 94 |
| 420952 | 95 |
| 420953 | 93 |
| 420955 | 93 |
| 420957 | 90 |
| 420959 | 73 |
| 450518 | 80 |
| 450519 | 87 |
| 450520 | 85 |
| 450521 | 94 |
| 450522 | 73 |
| 450523 | 94 |
| 420951 | 94 |

Protein Analysis

Human transthyretin protein levels were measured in transgenic mice plasma by ELISA using an anti-transthyretin transthyretin polyclonal antibody (Abcam Ab37774) and a sheep anti-TTR horse radish peroxidase detection antibody (Abcam cat. no. 35217). The color reaction was developed by the ImmunoPure® TMB Substrate Kit and absorbance measured at 450 nm using a microtiter plate spectrophotometer. Plasma samples were taken predose and on days 7, 14 and 28. The results are presented in Table 46 expressed as percentage inhibition compared to the pre-dose levels and demonstrate a time-dependent reduction in protein levels on treatment with ISIS oligonucleotides.

TABLE 46

Inhibition of human transthyretin protein in the hTTR transgenic mice plasma relative to pre-dose levels

| | Day 0 | Day 14 | Day 28 |
|---|---|---|---|
| PBS | 0 | 0 | 0 |
| ISIS 304313 | 0 | 62 | 77 |
| ISIS 420913 | 0 | 91 | 97 |
| ISIS 420919 | 0 | 70 | 82 |
| ISIS 420921 | 0 | 83 | 87 |
| ISIS 420922 | 0 | 95 | 97 |
| ISIS 420937 | 0 | 37 | 59 |
| ISIS 420944 | 0 | 57 | 72 |
| ISIS 420947 | 0 | 57 | 65 |
| ISIS 420949 | 0 | 93 | 99 |
| ISIS 420950 | 0 | 97 | 100 |
| ISIS 420952 | 0 | 98 | 100 |
| ISIS 420953 | 0 | 99 | 100 |
| ISIS 420955 | 0 | 89 | 100 |
| ISIS 420957 | 0 | 92 | 94 |
| ISIS 420959 | 0 | 69 | 87 |
| ISIS 450518 | 0 | 80 | 97 |
| ISIS 450519 | 0 | 94 | 100 |
| ISIS 450520 | 0 | 83 | 100 |
| ISIS 450521 | 0 | 100 | 100 |
| ISIS 450522 | 0 | 93 | 97 |
| ISIS 450523 | 0 | 100 | 100 |
| ISIS 420951 | 0 | 99 | 100 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 47 expressed in IU/L. Plasma levels of bilirubin were also measured using the same clinical chemistry analyzer; results are also presented in Table 47 and expressed in mg/dL.

TABLE 47

Effect of antisense oligonucleotide treatment on metabolic markers in the liver of transgenic mice

| | ALT (IU/L) | AST (IU/L) | Bilirubin (mg/dL) |
|---|---|---|---|
| PBS | 34 | 88 | 0.20 |
| ISIS 304313 | 42 | 79 | 0.16 |
| ISIS 420913 | 35 | 67 | 0.17 |
| ISIS 420919 | 63 | 177 | 0.20 |
| ISIS 420921 | 47 | 103 | 0.15 |
| ISIS 420922 | 42 | 128 | 0.16 |
| ISIS 420937 | 33 | 160 | 0.15 |
| ISIS 420944 | 38 | 84 | 0.15 |
| ISIS 420947 | 42 | 120 | 0.17 |
| ISIS 420949 | 46 | 125 | 0.15 |
| ISIS 420950 | 73 | 106 | 0.15 |
| ISIS 420952 | 151 | 271 | 0.19 |
| ISIS 420953 | 982 | 452 | 0.16 |
| ISIS 420955 | 47 | 80 | 0.15 |
| ISIS 420957 | 53 | 133 | 0.18 |
| ISIS 420959 | 31 | 89 | 0.11 |
| ISIS 450518 | 103 | 200 | 0.20 |
| ISIS 450519 | 64 | 81 | 0.12 |

TABLE 47-continued

Effect of antisense oligonucleotide treatment on
metabolic markers in the liver of transgenic mice

|  | ALT (IU/L) | AST (IU/L) | Bilirubin (mg/dL) |
|---|---|---|---|
| ISIS 450520 | 350 | 270 | 0.12 |
| ISIS 450521 | 104 | 226 | 0.13 |
| ISIS 450522 | 109 | 201 | 0.14 |
| ISIS 450523 | 80 | 170 | 0.19 |
| ISIS 420951 | 67 | 100 | 0.09 |

Kidney Function

To evaluate the effect of ISIS oligonucleotides on kidney function, plasma concentrations of blood urea nitrogen (BUN) were measured using an automated clinical chemistry analyzer (Hitachi Olympus AU400e, Melville, N.Y.). Results are presented in Table 48, expressed in mg/dL.

TABLE 48

Effect of antisense oligonucleotide treatment
on BUN (mg/dL) in the kidney of transgenic mice

| PBS | 35 |
|---|---|
| ISIS 304313 | 29 |
| ISIS 420913 | 30 |
| ISIS 420919 | 29 |
| ISIS 420921 | 29 |
| ISIS 420922 | 27 |
| ISIS 420937 | 29 |
| ISIS 420944 | 27 |
| ISIS 420947 | 26 |
| ISIS 420949 | 25 |
| ISIS 420950 | 34 |
| ISIS 420952 | 23 |
| ISIS 420953 | 34 |
| ISIS 420955 | 24 |
| ISIS 420957 | 23 |
| ISIS 420959 | 29 |
| ISIS 450518 | 28 |
| ISIS 450519 | 25 |
| ISIS 450520 | 29 |
| ISIS 450521 | 24 |
| ISIS 450522 | 29 |
| ISIS 450523 | 27 |
| ISIS 420951 | 25 |

Example 17: Tolerability of Antisense Oligonucleotides Targeting Human Transthyretin in CD1 Mice CD1 mice were treated with ISIS antisense oligonucleotides from Example 16 and evaluated for changes in the levels of various metabolic markers.

Treatment

Groups of eight CD1 mice each were injected subcutaneously twice a week with 50 mg/kg of ISIS 304313, ISIS 420913, ISIS 420919, ISIS 420921, ISIS 420922, ISIS 420937, ISIS 420944, ISIS 420947, ISIS 420949, ISIS 420950, ISIS 420951, ISIS 420952, ISIS 420953, ISIS 420955, ISIS 420957, ISIS 420959, ISIS 425518, ISIS 425519, ISIS 425520, ISIS 425521, ISIS 425522, or ISIS 425523. Three days after the last dose at each time point, body weights were taken, mice were euthanized and organs and plasma were harvested for further analysis.

Body and Organ Weights

The body weights of the mice were measured pre-dose and at the end of each treatment period (two weeks and six weeks). The body weights are presented in Table 49 and are expressed as percent increase over the PBS control weight taken before the start of treatment. Liver, spleen and kidney weights were measured at the end of the study, and are also presented in Table 49 as a percentage change over the respective organ weights of the PBS control.

TABLE 49

Change in body and organ weights of CD1 mice after
antisense oligonucleotide treatment (%) at week 6

|  | Body weight | Liver | Spleen | Kidney |
|---|---|---|---|---|
| PBS | 1.3 | 1.0 | 1.0 | 1.0 |
| ISIS 304313 | 1.2 | 1.2 | 1.4 | 1.2 |
| ISIS 420913 | 1.2 | 1.2 | 1.3 | 1.1 |
| ISIS 420919 | 1.3 | 1.2 | 1.9 | 1.1 |
| ISIS 420921 | 1.1 | 1.1 | 2.2 | 1.1 |
| ISIS 420922 | 1.1 | 1.0 | 1.6 | 0.9 |
| ISIS 420937 | 1.1 | 1.0 | 1.2 | 1.0 |
| ISIS 420944 | 1.1 | 1.1 | 2.0 | 1.0 |
| ISIS 420947 | 1.3 | 1.2 | 1.7 | 1.0 |
| ISIS 420949 | 1.3 | 1.2 | 1.8 | 1.1 |
| ISIS 420950 | 1.3 | 1.0 | 1.7 | 1.0 |
| ISIS 420952 | 1.4 | 1.3 | 2.1 | 0.9 |
| ISIS 420953 | 1.3 | 1.5 | 2.2 | 1.0 |
| ISIS 420955 | 1.2 | 1.2 | 2.2 | 1.0 |
| ISIS 420957 | 1.1 | 1.1 | 1.8 | 1.1 |
| ISIS 420959 | 1.3 | 1.2 | 3.2 | 1.1 |
| ISIS 450518 | 1.4 | 1.3 | 1.8 | 1.1 |
| ISIS 450519 | 1.3 | 1.5 | 2.4 | 1.0 |
| ISIS 450520 | 1.4 | 1.4 | 2.2 | 1.0 |
| ISIS 450521 | 1.2 | 1.2 | 1.9 | 1.1 |
| ISIS 450522 | 1.3 | 1.5 | 2.3 | 1.1 |
| ISIS 450523 | 1.2 | 1.3 | 2.4 | 1.1 |
| ISIS 420951 | 1.3 | 1.2 | 1.9 | 1.0 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 50 expressed in IU/L. Plasma levels of bilirubin and albumin were also measured using the same clinical chemistry analyzer and the results are also presented in Table 50.

TABLE 50

Effect of antisense oligonucleotide treatment
on metabolic markers in the liver of CD1 mice

|  | ALT | AST | TBIL |
|---|---|---|---|
| PBS | 34 | 88 | 0.20 |
| ISIS 304313 | 42 | 79 | 0.16 |
| ISIS 420913 | 35 | 67 | 0.17 |
| ISIS 420919 | 63 | 177 | 0.20 |
| ISIS 420921 | 47 | 103 | 0.15 |
| ISIS 420922 | 42 | 128 | 0.16 |
| ISIS 420937 | 33 | 160 | 0.15 |
| ISIS 420944 | 38 | 84 | 0.15 |
| ISIS 420947 | 42 | 120 | 0.17 |
| ISIS 420949 | 46 | 125 | 0.15 |
| ISIS 420950 | 73 | 106 | 0.15 |
| ISIS 420952 | 151 | 271 | 0.19 |
| ISIS 420953 | 982 | 452 | 0.16 |
| ISIS 420955 | 47 | 80 | 0.15 |
| ISIS 420957 | 53 | 133 | 0.18 |
| ISIS 420959 | 31 | 89 | 0.11 |
| ISIS 450518 | 103 | 200 | 0.20 |
| ISIS 450519 | 64 | 81 | 0.12 |
| ISIS 450520 | 350 | 270 | 0.12 |

TABLE 50-continued

Effect of antisense oligonucleotide treatment on metabolic markers in the liver of CD1 mice

|  | ALT | AST | TBIL |
|---|---|---|---|
| ISIS 450521 | 104 | 226 | 0.13 |
| ISIS 450522 | 109 | 201 | 0.14 |
| ISIS 450523 | 80 | 170 | 0.19 |
| ISIS 420951 | 67 | 100 | 0.09 |

Kidney Function

To evaluate the effect of ISIS oligonucleotides on kidney function, plasma concentrations of blood urea nitrogen (BUN) and creatinine were measured using an automated clinical chemistry analyzer (Hitachi Olympus AU400e, Melville, N.Y.). Results are presented in Table 51, expressed in mg/dL.

TABLE 51

Effect of antisense oligonucleotide treatment on BUN (mg/dL) in the kidney of CD1 mice

|  | BUN |
|---|---|
| PBS | 35 |
| ISIS 304313 | 29 |
| ISIS 420913 | 30 |
| ISIS 420919 | 29 |
| ISIS 420921 | 29 |
| ISIS 420922 | 27 |
| ISIS 420937 | 29 |
| ISIS 420944 | 27 |
| ISIS 420947 | 26 |
| ISIS 420949 | 25 |
| ISIS 420950 | 34 |
| ISIS 420952 | 23 |
| ISIS 420953 | 34 |
| ISIS 420955 | 24 |
| ISIS 420957 | 23 |
| ISIS 420959 | 29 |
| ISIS 450518 | 28 |
| ISIS 450519 | 25 |
| ISIS 450520 | 29 |
| ISIS 450521 | 24 |
| ISIS 450522 | 29 |
| ISIS 450523 | 27 |
| ISIS 420951 | 25 |

Hematology Assays

Blood obtained from all mice groups were sent to Antech Diagnostics for hematocrit (HCT), mean corpuscular volume (MCV), mean corpuscular hemoglobin (MCH), and mean corpuscular hemoglobin concentration (MCHC) measurements and analyses, as well as measurements of the differential blood cell counts, such as that of WBC (neutrophils, lymphocytes, and monocytes), RBC, and platelets, and total hemoglobin content. The results are presented in Table 52 and 53. Percentages given in the tables indicate the percent change in total blood cell count compared to the PBS control.

TABLE 52

Effect of antisense oligonucleotide treatment on complete blood cell count (%) compared to the PBS control in CD1 mice

|  | WBC | RBC | Hemoglobin | HCT | MCV | MCH | MCHC |
|---|---|---|---|---|---|---|---|
| ISIS 304313 | +80 | −5 | −7 | −9 | −4 | −2 | +4 |
| ISIS 420913 | −10 | −1 | −3 | −5 | −4 | −2 | +3 |
| ISIS 420919 | +26 | −2 | −7 | −9 | −7 | −5 | +4 |
| ISIS 420921 | +60 | −9 | −12 | −15 | −6 | −3 | +5 |
| ISIS 420922 | +18 | −6 | −11 | −16 | −11 | −6 | +6 |
| ISIS 420937 | +42 | −3 | −4 | −7 | −5 | −1 | +5 |
| ISIS 420944 | +49 | −5 | −9 | −13 | −8 | −4 | +6 |
| ISIS 420947 | +36 | −2 | −2 | −5 | −3 | 0 | +4 |
| ISIS 420949 | +61 | −4 | −6 | −9 | −7 | −3 | +5 |
| ISIS 420950 | +56 | −14 | −16 | −19 | −7 | −3 | +6 |
| ISIS 420952 | +36 | −20 | −24 | −25 | −7 | −5 | +4 |
| ISIS 420953 | +105 | −21 | −24 | −26 | −6 | −4 | +4 |
| ISIS 420955 | +107 | −14 | −19 | −21 | −9 | −5 | +6 |
| ISIS 420957 | +79 | −5 | −10 | −13 | −9 | −6 | +5 |
| ISIS 420959 | +92 | −8 | −14 | −18 | −11 | −7 | +6 |
| ISIS 450518 | +138 | −5 | −10 | −12 | −7 | −4 | +4 |
| ISIS 450519 | +118 | −17 | −21 | −24 | −9 | −5 | +6 |
| ISIS 450520 | +151 | −18 | −21 | −23 | −7 | −4 | +4 |
| ISIS 450521 | +118 | −15 | −21 | −23 | −11 | −7 | +5 |
| ISIS 450522 | +63 | −22 | −28 | −31 | −12 | −8 | +6 |
| ISIS 450523 | +116 | −22 | −27 | −29 | −11 | −7 | +6 |
| ISIS 420951 | +54 | −15 | −21 | −24 | −10 | −6 | +5 |

TABLE 53

Effect of antisense oligonucleotide treatment on differential blood cell count (%) compared to the PBS control in CD1 mice

|  | Neutrophils | Lymphocytes | Monocytes | Platelets |
|---|---|---|---|---|
| ISIS 304313 | −54 | +49 | −45 | +36 |
| ISIS 420913 | −46 | +39 | −21 | −2 |
| ISIS 420919 | −57 | +49 | −21 | +19 |
| ISIS 420921 | −55 | +47 | −24 | +25 |
| ISIS 420922 | −53 | +46 | −31 | +24 |
| ISIS 420937 | −63 | +57 | −48 | +20 |
| ISIS 420944 | −40 | +37 | −28 | +18 |
| ISIS 420947 | −55 | +49 | −38 | −9 |
| ISIS 420949 | −30 | +24 | +7 | +17 |
| ISIS 420950 | −50 | +40 | 0 | +6 |
| ISIS 420952 | −34 | +33 | −28 | +13 |
| ISIS 420953 | −37 | +35 | −34 | +11 |
| ISIS 420955 | −37 | +34 | −21 | +30 |
| ISIS 420957 | −71 | +61 | −28 | +16 |
| ISIS 420959 | −52 | +45 | −24 | −1 |
| ISIS 450518 | −56 | +49 | −28 | +18 |
| ISIS 450519 | −18 | +11 | +41 | +55 |
| ISIS 450520 | −41 | +34 | 0 | +7 |
| ISIS 450521 | −41 | +36 | −14 | +21 |
| ISIS 450522 | −41 | +31 | +17 | +58 |
| ISIS 450523 | −28 | +19 | +31 | +51 |
| ISIS 420951 | −28 | +24 | 0 | +26 |

Example 18: Tolerability of Antisense Oligonucleotides Targeting Human Transthyretin in Sprague-Dawley Rats ISIS oligonucleotides selected from studies described in Example 17 were also tested in Sprague-Dawley rats and evaluated for changes in the levels of various metabolic markers.

Treatment

The body weights, complete blood count and different blood count, as well as the urine protein/creatinine ratio of the rats were evaluated pre-dose. Groups of four Sprague-Dawley rats each were injected subcutaneously twice a week with 50 mg/kg of ISIS 420913, ISIS 420921, ISIS 420922, ISIS 420950, ISIS 420955, ISIS 420957, and ISIS 420959. Three days after the last dose at each time point, body weights were taken, mice were euthanized and organs and plasma were harvested for further analysis.

Body and Organ Weights

The body weights of the rats were measured pre-dose and at the end of the treatment period. The body weights are presented in Table 54, and are expressed as percent increase over the PBS control weight taken before the start of treatment. Liver, spleen and kidney weights were measured at the end of the study, and are also presented in Table 54 as a percentage change over the respective organ weights of the PBS control.

TABLE 54

Change in body and organ weights of Sprague-Dawley rats after antisense oligonucleotide treatment (%)

|  | Body weight | Liver | Spleen | Kidney |
| --- | --- | --- | --- | --- |
| PBS | 2.1 | 1.0 | 1.0 | 1.0 |
| ISIS 420913 | 1.5 | 1.5 | 4.7 | 1.1 |
| ISIS 420921 | 1.6 | 1.5 | 4.2 | 1.3 |
| ISIS 420922 | 1.3 | 1.5 | 4.4 | 1.4 |
| ISIS 420950 | 1.4 | 1.5 | 6.4 | 1.7 |
| ISIS 420955 | 1.5 | 1.6 | 5.9 | 1.4 |
| ISIS 420957 | 1.4 | 1.4 | 6.8 | 1.3 |
| ISIS 420959 | 1.5 | 1.4 | 5.5 | 1.4 |

As shown in Table 54, the compounds demonstrated a less than 10-fold increase in organ weight of these rats. Furthermore, certain compounds demonstrated a less than 7-fold increase in organ weight of these rats. While certain compounds demonstrated a less than 6-fold increase in organ weight of these rats. Certain compounds demonstrated a less than 5-fold increase in organ weight of these rats.

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 55 expressed in IU/L. Plasma levels of bilirubin and albumin were also measured using the same clinical chemistry analyzer and the results are also presented in Table 55.

TABLE 55

Effect of antisense oligonucleotide treatment on metabolic markers in the liver of Sprague-Dawley rats

|  | ALT (IU/L) | AST (IU/L) | TBIL (mg/dL) | Albumin (g/dL) |
| --- | --- | --- | --- | --- |
| PBS | 26 | 66 | 0.09 | 4.5 |
| ISIS 420913 | 38 | 95 | 0.08 | 3.3 |
| ISIS 420921 | 65 | 151 | 0.11 | 3.2 |
| ISIS 420922 | 40 | 121 | 0.11 | 4.0 |
| ISIS 420950 | 398 | 327 | 0.19 | 4.0 |
| ISIS 420955 | 78 | 241 | 0.18 | 4.1 |
| ISIS 420957 | 84 | 244 | 0.14 | 3.7 |
| ISIS 420959 | 82 | 405 | 0.17 | 4.6 |

Kidney Function

To evaluate the effect of ISIS oligonucleotides on kidney function, plasma concentrations of blood urea nitrogen (BUN) and creatinine were measured using an automated clinical chemistry analyzer (Hitachi Olympus AU400e, Melville, N.Y.). Results are presented in Table 56, expressed in mg/dL. The ratio of total urine protein to creatinine was also evaluated and presented in Table 56.

TABLE 56

Effect of antisense oligonucleotide treatment on metabolic markers (mg/dL) in the kidney of Sprague-Dawley rats

|  | BUN | Creatinine |
| --- | --- | --- |
| PBS | 14 | 0.05 |
| ISIS 420913 | 22 | 0.09 |
| ISIS 420921 | 23 | 0.07 |
| ISIS 420922 | 21 | 0.08 |
| ISIS 420950 | 20 | 0.11 |
| ISIS 420955 | 22 | 0.06 |
| ISIS 420957 | 23 | 0.18 |
| ISIS 420959 | 24 | 0.17 |

TABLE 57

Effect of antisense oligonucleotide treatment on total urine protein/creatinine in the kidney of Sprague-Dawley rats

|  | Urine protein/creatinine ratio |
| --- | --- |
| PBS | 1.50 |
| ISIS 420913 | 19.51 |
| ISIS 420921 | 5.07 |
| ISIS 420922 | 4.72 |
| ISIS 420950 | 5.61 |
| ISIS 420955 | 5.57 |
| ISIS 420957 | 5.40 |
| ISIS 420959 | 4.39 |

Hematology Assays

Blood obtained from all rat groups were sent to Antech Diagnostics for hematocrit (HCT), mean corpuscular volume (MCV), mean corpuscular hemoglobin (MCH), and mean corpuscular hemoglobin concentration (MCHC) measurements and analyses, as well as measurements of the differential blood cell counts, such as that of WBC (neutrophils, lymphocytes, and monocytes), RBC, and platelets, and total hemoglobin content. The results are presented in Tables 58 and 59. Percents given in the tables indicate the percent change in total blood cell count compared to the PBS control.

TABLE 58

Effect of antisense oligonucleotide treatment on complete blood cell count (%) compared to the PBS control in Sprague-Dawley rats

|  | WBC | RBC | Hemoglobin | HCT | MCV | MCH | MCHC |
| --- | --- | --- | --- | --- | --- | --- | --- |
| PBS | 1.0 | 1.0 | 1.0 | 1.0 | 1.0 | 1.0 | 1.0 |
| ISIS 420913 | 1.7 | 0.9 | 0.9 | 0.9 | 0.9 | 0.9 | 1.0 |
| ISIS 420921 | 1.6 | 0.9 | 0.9 | 0.9 | 1.0 | 1.0 | 1.0 |
| ISIS 420922 | 1.6 | 0.9 | 0.9 | 0.8 | 1.0 | 1.0 | 1.0 |
| ISIS 420950 | 2.2 | 0.7 | 0.7 | 0.7 | 1.0 | 1.0 | 1.0 |
| ISIS 420955 | 1.9 | 0.7 | 0.8 | 0.7 | 1.1 | 1.2 | 1.0 |
| ISIS 420957 | 3.1 | 0.8 | 0.8 | 0.8 | 1.0 | 1.0 | 1.0 |
| ISIS 420959 | 2.2 | 0.8 | 0.8 | 0.8 | 1.0 | 1.0 | 1.0 |

TABLE 59

Effect of antisense oligonucleotide treatment on differential blood cell count (%) compared to the PBS control in Sprague-Dawley rats

|  | Neutrophils | Lymphocytes | Monocytes | Platelet |
| --- | --- | --- | --- | --- |
| PBS | 1.0 | 1.0 | 1.0 | 1.0 |
| ISIS 420913 | 0.5 | 1.1 | 1.7 | 0.7 |
| ISIS 420921 | 0.7 | 1.0 | 1.6 | 0.6 |
| ISIS 420922 | 0.5 | 1.1 | 1.3 | 0.7 |
| ISIS 420950 | 0.8 | 1.0 | 2.3 | 0.7 |

TABLE 59-continued

Effect of antisense oligonucleotide treatment on differential blood cell count (%) compared to the PBS control in Sprague-Dawley rats

| | Neutrophils | Lymphocytes | Monocytes | Platelet |
|---|---|---|---|---|
| ISIS 420955 | 0.5 | 1.0 | 2.4 | 0.7 |
| ISIS 420957 | 0.7 | 1.0 | 1.6 | 0.3 |
| ISIS 420959 | 0.5 | 1.1 | 1.3 | n.d. |

Example 19: Pharmacokinetic Studies of Half-Life of Antisense Oligonucleotide Concentration in Sprague-Dawley Rat Liver and Kidney Sprague Dawley rats were treated with ISIS antisense oligonucleotides targeting from studies described in Example 18 and the oligonucleotide half-life as well as the elapsed time for oligonucleotide degradation and elimination from the liver and kidney was evaluated.

Treatment

Groups of four Sprague Dawley rats each were injected subcutaneously twice a week for 2 weeks with 20 mg/kg of ISIS 420913, ISIS 420921, ISIS 420922, ISIS 420950, ISIS 420955, ISIS 420957, and ISIS 420959. Three days after the last dose, the rats were sacrificed and livers and kidneys were collected for analysis.

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 166) was added prior to extraction. Tissue sample concentrations were calculated using calibration curves, with a lower limit of quantitation (LLOQ) of approximately 1.14 µg/g. The results are presented in Tables 60 and 61, expressed as µg/g liver or kidney tissue. The kidney to liver ratio of oligonucleotide concentration was also calculated and presented in Tables 60 and 61.

TABLE 60

Full-length oligonucleotide concentration (µg/g) and ratio in the liver and kidney of Sprague-Dawley rats

| ISIS NO. | Liver | Kidney | Kidney/Liver ratio |
|---|---|---|---|
| 420913 | 154 | 285 | 1.9 |
| 420921 | 147 | 293 | 2.0 |
| 420922 | 226 | 497 | 2.2 |
| 420950 | 161 | 411 | 2.6 |
| 420955 | 152 | 383 | 2.5 |
| 420957 | 235 | 453 | 1.9 |
| 420959 | 187 | 513 | 2.7 |

TABLE 61

Total oligonucleotide concentration (µg/g) in the liver and kidney of Sprague-Dawley rats

| ISIS NO. | Liver | Kidney | Kidney/Liver ratio |
|---|---|---|---|
| 420913 | 180 | 310 | 1.7 |
| 420921 | 159 | 305 | 1.9 |
| 420922 | 238 | 544 | 2.3 |
| 420950 | 168 | 466 | 2.8 |
| 420955 | 156 | 442 | 2.8 |
| 420957 | 244 | 551 | 2.3 |
| 420959 | 202 | 534 | 2.6 |

Example 20: In Vivo Dose-Dependent Inhibition of Human Transthyretin in Transgenic Mice ISIS 420913, ISIS 420921, ISIS 420922, ISIS 420957 and ISIS 420959, which exhibited good efficacy and tolerability, as demonstrated in Examples 16-19, were chosen for the study of dose-dependent target knockdown in transgenic mice containing the human transthyretin gene. ISIS 420950 and ISIS 420955, which demonstrated 90% or more target knockdown, but which also demonstrated toxicity in CD1 mice (Examples 16-19) were also chosen for this study for comparison.

Treatment

Groups of four mice, two male and two female, each were injected subcutaneously twice a week for 4 weeks with 4 mg/kg, 10 mg/kg or 25 mg/kg of ISIS 420913, ISIS 420921, ISIS 420922, ISIS 420950, ISIS 420955, ISIS 420957, or ISIS 420959. One group of four mice, two male and two female, was injected subcutaneously twice a week for 4 weeks with 25 mg/kg of the control oligonucleotide, ISIS 141923. One control group of four mice, two male and two female, was injected subcutaneously twice a week for 4 weeks with PBS. Plasma samples were taken from each group at days 0, 14 and 28. Two days after the last dose, the mice were euthanized and organs were harvested for further analysis.

RNA Analysis

RNA was extracted from liver tissue for real-time PCR analysis of transthyretin using primer probe set RTS3029. Results are presented as percent inhibition of human transthyretin, relative to PBS control. As shown in Table 62, treatment with ISIS antisense oligonucleotides resulted in significant dose-dependent reduction of human transthyretin mRNA in comparison to the PBS control. Treatment with the control oligonucleotide, ISIS 141923 did not result in significant reduction of transthyretin, as expected.

TABLE 62

Inhibition of human transthyretin mRNA in the hTTR transgenic mice liver relative to the PBS control

| ISIS NO. | Dose (mg/kg) | % inhibition |
|---|---|---|
| 420913 | 25 | 78 |
| | 10 | 65 |
| | 4 | 32 |
| 420921 | 25 | 76 |
| | 10 | 64 |
| | 4 | 13 |

TABLE 62-continued

Inhibition of human transthyretin mRNA in the hTTR transgenic mice liver relative to the PBS control

| ISIS NO. | Dose (mg/kg) | % inhibition |
|---|---|---|
| 420922 | 25 | 80 |
|  | 10 | 53 |
|  | 4 | 21 |
| 420950 | 25 | 92 |
|  | 10 | 77 |
|  | 4 | 57 |
| 420955 | 25 | 88 |
|  | 10 | 56 |
|  | 4 | 23 |
| 420957 | 25 | 85 |
|  | 10 | 72 |
|  | 4 | 32 |
| 420959 | 25 | 75 |
|  | 10 | 26 |
|  | 4 | 11 |
| 141923 | 25 | 0 |

Protein Analysis

Human transthyretin protein levels were measured in transgenic mice plasma by ELISA using an anti-transthyretin transthyretin polyclonal antibody (Abcam Ab37774) and a sheep anti-TTR horse radish peroxidase detection antibody (Abcam cat. no. 35217). The color reaction was developed by the ImmunoPure® TMB Substrate Kit and absorbance measured at 450 nm using a microtiter plate spectrophotometer. Plasma samples were taken predose and on days 7, 14, 21 and 28. The results are presented in Table 63 expressed as percentage inhibition compared to the predose levels and demonstrate a time-dependent and dose-dependent reduction in protein levels on treatment with ISIS oligonucleotides.

TABLE 63

Inhibition of human transthyretin protein in the hTTR transgenic mice plasma relative to predose levels

| ISIS NO. | Dose (mg/kg) | d 0 | d 14 | d 28 |
|---|---|---|---|---|
| 420913 | 25 | 0 | 73 | 93 |
|  | 10 | 0 | 27 | 96 |
|  | 4 | 0 | 25 | 54 |
| 420921 | 25 | 0 | 73 | 90 |
|  | 10 | 0 | 63 | 79 |
|  | 4 | 0 | 42 | 67 |
| 420922 | 25 | 0 | 63 | 96 |
|  | 10 | 0 | 57 | 89 |
|  | 4 | 0 | 38 | 77 |
| 420950 | 25 | 0 | 95 | 97 |
|  | 10 | 0 | 71 | 96 |
|  | 4 | 0 | 29 | 53 |
| 420955 | 25 | 0 | 84 | 96 |
|  | 10 | 0 | 53 | 91 |
|  | 4 | 0 | 20 | 30 |
| 420957 | 25 | 0 | 83 | 93 |
|  | 10 | 0 | 51 | 66 |
|  | 4 | 0 | 32 | 49 |
| 420959 | 25 | 0 | 74 | 80 |
|  | 10 | 0 | 31 | 58 |
|  | 4 | 0 | 0 | 0 |
| 141923 | 25 | 0 | 22 | 0 |

Body Weight and Organ Weight

The body weights of the mice were measured pre-dose and at the end of the treatment period. The body weights are presented in Table 64 and are expressed as percent increase over the PBS control weight taken before the start of treatment. Liver, spleen and kidney weights were measured at the end of the study, and are also presented in Table 64 as a percentage change over the respective organ weights of the PBS control.

TABLE 64

Change in body and organ weights of transgenic mice after antisense oligonucleotide treatment (%)

|  |  | Body weight | Liver | Spleen | Kidney |
|---|---|---|---|---|---|
| PBS |  | 6.4 | 0.0 | 0.0 | 0.0 |
| ISIS 420913 | 25 | 8.1 | 0.3 | 11.4 | 4.1 |
|  | 10 | 10.6 | −8.6 | 14.3 | 13.6 |
|  | 4 | 7.4 | 3.7 | 5.0 | 12.0 |
| ISIS 420921 | 25 | 10.5 | 8.8 | 25.6 | −0.1 |
|  | 10 | 9.7 | 5.7 | 10.8 | 4.0 |
|  | 4 | 8.7 | −4.4 | 16.0 | 11.0 |
| ISIS 420922 | 25 | 8.4 | 5.6 | 18.0 | 1.7 |
|  | 10 | 9.2 | −1.7 | 27.1 | 6.3 |
|  | 4 | 8.1 | −2.1 | −11.4 | 5.1 |
| ISIS 420950 | 25 | 12.8 | 14.3 | 22.8 | 1.7 |
|  | 10 | 8.4 | 4.3 | −2.8 | 0.6 |
|  | 4 | 9.1 | 0.4 | 14.2 | 1.5 |
| ISIS 420955 | 25 | 10.1 | 14.6 | 17.7 | −4.4 |
|  | 10 | 11.8 | 5.6 | −0.3 | 1.4 |
|  | 4 | 7.9 | 4.7 | −12.3 | 4.5 |
| ISIS 420957 | 25 | 12.8 | 6.4 | 33.1 | 2.8 |
|  | 10 | 14.5 | 13.9 | −6.3 | 9.7 |
|  | 4 | 7.4 | −5.4 | 12.2 | 6.2 |
| ISIS 420959 | 25 | 10.0 | 2.4 | 72.7 | 23.3 |
|  | 10 | 7.2 | −5.4 | 40.2 | 9.8 |
|  | 4 | 4.1 | −4.4 | 27.8 | −6.6 |
| ISIS 141923 | 25 | 9.2 | −1.3 | 20.4 | −5.5 |

Liver Function

To evaluate the effect of ISIS oligonucleotides on hepatic function, plasma concentrations of transaminases were measured using an automated clinical chemistry analyzer (Hitachi Olympus AU400e, Melville, N.Y.). Plasma concentrations of ALT (alanine transaminase) and AST (aspartate transaminase) were measured and the results are presented in Table 65 expressed in IU/L. Plasma levels of bilirubin were also measured using the same clinical chemistry analyzer; results are also presented in Table 65 and expressed in mg/dL.

TABLE 65

Effect of antisense oligonucleotide treatment on metabolic markers in the liver of transgenic mice

|  | Dose (mg/kg) | ALT (IU/L) | AST (IU/L) | TBIL (mg/dL) |
|---|---|---|---|---|
| PBS |  | 47 | 63 | 0.16 |
| ISIS 420913 | 25 | 42 | 69 | 0.13 |
|  | 10 | 49 | 90 | 0.17 |
|  | 4 | 42 | 59 | 0.18 |
| ISIS 420921 | 25 | 56 | 96 | 0.12 |
|  | 10 | 51 | 68 | 0.22 |
|  | 4 | 42 | 75 | 0.14 |
| ISIS 420922 | 25 | 50 | 76 | 0.12 |
|  | 10 | 40 | 170 | 0.14 |
|  | 4 | 37 | 48 | 0.13 |
| ISIS 420950 | 25 | 74 | 116 | 0.14 |
|  | 10 | 37 | 67 | 0.13 |
|  | 4 | 34 | 64 | 0.11 |
| ISIS 420955 | 25 | 46 | 117 | 0.15 |
|  | 10 | 54 | 76 | 0.16 |
|  | 4 | 50 | 153 | 0.17 |

TABLE 65-continued

Effect of antisense oligonucleotide treatment on
metabolic markers in the liver of transgenic mice

|  | Dose (mg/kg) | ALT (IU/L) | AST (IU/L) | TBIL (mg/dL) |
|---|---|---|---|---|
| ISIS 420957 | 25 | 40 | 73 | 0.13 |
|  | 10 | 36 | 63 | 0.20 |
|  | 4 | 37 | 61 | 0.12 |
| ISIS 420959 | 25 | 51 | 92 | 0.19 |
|  | 10 | 48 | 69 | 0.13 |
|  | 4 | 37 | 67 | 0.13 |
| ISIS 141923 | 25 | 44 | 79 | 0.12 |

Kidney Function

To evaluate the effect of ISIS oligonucleotides on kidney function, plasma concentrations of blood urea nitrogen (BUN) were measured using an automated clinical chemistry analyzer (Hitachi Olympus AU400e, Melville, N.Y.). Results are presented in Table 66, expressed in mg/dL.

TABLE 66

Effect of antisense oligonucleotide treatment
on BUN (mg/dL) in the kidney of transgenic mice

|  | Dose (mg/kg) | BUN |
|---|---|---|
| PBS | — | 23 |
| ISIS 420913 | 25 | 24 |
|  | 10 | 22 |
|  | 4 | 20 |
| ISIS 420921 | 25 | 24 |
|  | 10 | 22 |
|  | 4 | 23 |
| ISIS 420922 | 25 | 23 |
|  | 10 | 22 |
|  | 4 | 24 |
| ISIS 420950 | 25 | 22 |
|  | 10 | 26 |
|  | 4 | 23 |
| ISIS 420955 | 25 | 23 |
|  | 10 | 24 |
|  | 4 | 25 |
| ISIS 420957 | 25 | 20 |
|  | 10 | 22 |
|  | 4 | 20 |
| ISIS 420959 | 25 | 25 |
|  | 10 | 22 |
|  | 4 | 22 |
| ISIS 141923 | 25 | 19 |

Example 21: Dose Response Confirmation of Antisense Oligonucleotides Targeting Human Transthyretin in Cynomolgus Monkey Primary Hepatocytes Gapmers showing tolerability in CD1 mice and Sprague Dawley rats (studies described in Examples 17-19) as well as potency in transgenic mice (studies described in Examples 16 and 20) were selected and tested at various doses in primary hepatocytes of cynomolgus monkeys. Cells were plated at a density of 35,000 cells per well and transfected using electroporation with 156.25 nM, 312.5 nM, 625 nM, 1,250 nM 2,500 nM, 5,000 nM, 10,000 nM and 20,000 nM concentrations of antisense oligonucleotide, as specified in Table 67. After a treatment period of approximately 16 hours, RNA was isolated from the cells and transthyretin mRNA levels were measured by quantitative real-time PCR. Human transthyretin primer probe set RTS1396 was used to measure mRNA levels. Transthyretin mRNA levels were adjusted according to total RNA content, as measured by RIBOGREEN®. Results are presented as percent inhibition of transthyretin, relative to untreated control cells. As illustrated in Table 67, transthyretin mRNA levels were reduced in a dose-dependent manner in hepatocytes treated with all the ISIS oligonucleotides, which are cross-reactive with rhesus monkey transthyretin gene, designated herein as SEQ ID NO: 4 (exons 1-4 extracted from GENBANK Accession No. NW_001105671.1).

TABLE 67

Dose-dependent antisense inhibition of human transthyretin in
cynomolgus monkey primary hepatocytes using electroporation

| ISIS No. | 156.25 nM | 312.5 nM | 625 nM | 1250 nM | 2500 nM | 5000 nM | 10000 nM | 20000 nM | $IC_{50}$ (µM) | Target Start Site |
|---|---|---|---|---|---|---|---|---|---|---|
| 304299 | 0 | 0 | 25 | 42 | 89 | 95 | 98 | 99 | 1.4 | 504 |
| 420913 | 0 | 0 | 42 | 49 | 84 | 96 | 98 | 98 | 1.2 | 502 |
| 420915 | 0 | 8 | 46 | 58 | 84 | 94 | 97 | 99 | 1 | 505 |
| 420921 | 0 | 0 | 26 | 30 | 53 | 74 | 94 | 97 | 2 | 512 |
| 420922 | 4 | 0 | 13 | 29 | 38 | 69 | 87 | 97 | 2.9 | 513 |
| 420950 | 23 | 27 | 60 | 71 | 88 | 94 | 98 | 98 | 0.6 | 577 |
| 420955 | 19 | 0 | 25 | 50 | 74 | 86 | 93 | 97 | 1.4 | 582 |
| 420957 | 0 | 0 | 15 | 34 | 65 | 72 | 87 | 94 | 2.2 | 584 |
| 420959 | 3 | 12 | 10 | 37 | 71 | 88 | 94 | 94 | 1.5 | 586 |

Example 22: Measurement of Viscosity of ISIS Antisense Oligonucleotides Targeting Human Transthyretin The viscosity of antisense oligonucleotides from studies described in Example 21 was measured with the aim of screening out antisense oligonucleotides which have a viscosity more than 40 cP. Oligonucleotides having a viscosity greater than 40 cP would be too viscous to be administered to any subject.

ISIS oligonucleotides (32-35 mg) were weighed into a glass vial, 120 μL of water was added and the antisense oligonucleotide was dissolved into solution by heating the vial at 50° C. Part of (75 μL) the pre-heated sample was pipetted to a micro-viscometer (Cambridge). The temperature of the micro-viscometter was set to 25° C. and the viscosity of the sample was measured. Another part (20 μL) of the pre-heated sample was pipetted into 10 mL of water for UV reading at 260 nM at 85° C. (Cary UV instrument). The results are presented in Table 68 and indicate that all the antisense oligonucleotides solutions are optimal in their viscosity under the criterion stated above.

TABLE 68

Viscosity and concentration of ISIS antisense oligonucleotides targeting human transthyretin

| ISIS No. | Viscosity (cP) | Concentration (mg/mL) |
|---|---|---|
| 304299 | 9.9 | 169 |
| 420913 | 6.5 | 178 |
| 420915 | 8.4 | 227 |
| 420921 | 8.2 | 234 |
| 420922 | 5.3 | 191 |
| 420950 | 12.5 | 297 |
| 420955 | 15.7 | 259 |
| 420957 | 12.9 | 233 |
| 420959 | 18.7 | 276 |

Example 23: Measurement of Half-Life of Antisense Oligonucleotide in CD1 Mouse Liver CD1 mice were treated with ISIS antisense oligonucleotides from studies described in Example 22 and the oligonucleotide half-life as well as the elapsed time for oligonucleotide degradation and elimination from the liver was evaluated.

Treatment

Groups of twelve CD1 mice each were injected subcutaneously twice per week for 2 weeks with 50 mg/kg of ISIS 420913, ISIS 420921, ISIS 420922, ISIS 420950, ISIS 420955, ISIS 420957, and ISIS 420959. Four mice from each group were sacrificed 3 days, 28 days and 56 days following the final dose. Livers were harvested for analysis.

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 166) was added prior to extraction. Tissue sample concentrations were calculated using calibration curves, with a lower limit of quantitation (LLOQ) of approximately 1.14 μg/g. Half-lives were then calculated using WinNonlin software (PHARSIGHT).

The results are presented in Tables 69, expressed as μg/g liver tissue. The half-life of each oligonucleotide is presented in Table 70.

TABLE 69

Full-length oligonucleotide concentration (μg/g) in the liver of CD1 mice

| ISIS No. | 3 days | 28 days | 56 days |
|---|---|---|---|
| 420913 | 243 | 109 | 33 |
| 420921 | 225 | 49 | 6 |
| 420922 | 310 | 129 | 53 |
| 420950 | 254 | 88 | 62 |
| 420955 | 308 | 137 | 79 |
| 420957 | 325 | 129 | 49 |
| 420959 | 258 | 97 | 37 |

TABLE 70

Half-life of oligonucleotide (days) in the liver of CD1 mice

| ISIS No. | Half-life (days) |
|---|---|
| 420913 | 18.5 |
| 420921 | 10.0 |
| 420922 | 20.7 |
| 420950 | 26.4 |
| 420955 | 27.2 |
| 420957 | 19.5 |
| 420959 | 18.9 |

Example 24: Effect of ISIS Antisense Oligonucleotides Targeting Human Transthyretin in Cynomolgus Monkeys Cynomolgus monkeys were treated with ISIS antisense oligonucleotides from studies described in Examples 21, 22 and 23. Antisense oligonucleotide efficacy and tolerability, as well as their pharmacokinetic profile in the liver and kidney, were evaluated.

Treatment

Prior to the study, the monkeys were kept in quarantine for a 30-day time period, during which standard panels of serum chemistry and hematology, examination of fecal samples for ova and parasites, and a tuberculosis test, were conducted to screen out abnormal or ailing monkeys. Nine groups of four randomly assigned male cynomolgus monkeys each were injected subcutaneously thrice per week for the first week, and subsequently twice a week for the next 11 weeks, with 25 mg/kg of ISIS 304299, ISIS 420915, ISIS 420921, ISIS 420922, ISIS 420950, ISIS 420955, ISIS 420957, or ISIS 420959. A control group of 4 cynomolgus monkeys was injected with PBS subcutaneously thrice per week for the first week, and subsequently twice a week for the next 11 weeks. Blood samples were collected 5 days before the treatment as well as on various days of the study period and analyzed. The animals were fasted for at least 13 hours (overnight) prior to blood collection. Terminal sacrifices of all groups were conducted on day 86, which was 48 hours after the last dose.

During the study period, the monkeys were observed daily for signs of illness or distress. Any animal showing adverse effects to the treatment was removed and referred to the veterinarian and Study Director. All the animals treated with ISIS 420955 were removed from the study on day 31 due to symptoms of illness displayed by 2 monkeys in the group. Similarly, one monkey each from groups treated with ISIS 420957 and ISIS 420950 was removed from the study on days 44 and 76, respectively, due to signs of illness.

Inhibition Studies

RNA Analysis

On day 86, RNA was extracted from liver tissue for real-time PCR analysis of transthyretin using primer probe set RTS3029. Results are presented as percent inhibition of transthyretin, relative to PBS control, normalized to cyclophilin. Similar results were obtained on normalization with RIBOGREEN®. As shown in Table 71, treatment with ISIS antisense oligonucleotides resulted in significant reduction of transthyretin mRNA in comparison to the PBS control. Specifically, treatment with ISIS 420915 caused greater inhibition of TTR mRNA than treatment with ISIS 304299, even though the two oligonucleotides differ from each other by a single base-pair shift. The data for animals treated with ISIS 420955 was taken at day 31.

TABLE 71

Inhibition of transthyretin mRNA in the cynomolgus monkey liver relative to the PBS control

| ISIS No | % inhibition |
| --- | --- |
| 304299 | 59 |
| 420915 | 78 |
| 420921 | 54 |
| 420922 | 61 |
| 420950 | 91 |
| 420955* | 79 |
| 420957 | 64 |
| 420959 | 55 |

(*Data of day 31)

Protein Analysis

The monkeys were fasted overnight prior to blood collection. Approximately 1 mL of blood was collected from all available animals and placed in tubes containing the potassium salt of EDTA. The tubes were centrifuged (3000 rpm for 10 min at room temperature) to obtain plasma. Transthyretin protein levels were measured in the plasma using a clinical analyzer. Plasma samples were taken predose (on day −5) and on days 1, 9, 16, 23, 30, 44, 58, 72, and 86. The results are presented in Table 72 expressed as percentage inhibition compared to the predose levels and demonstrate a time-dependent reduction in protein levels with treatment with ISIS oligonucleotides. The final plasma TTR levels are presented in Table 73 and demonstrate the strong correlation between TTR protein level reduction and TTR mRNA inhibition (Table 71). Specifically, treatment with ISIS 420915 caused greater inhibition of TTR plasma protein than treatment with ISIS 304299 (76% inhibition vs. 47% inhibition), even though the two oligonucleotides differ from each other by a single base-pair shift.

TABLE 72

Time course of transthyretin protein level reduction in the cynomolgus monkey plasma relative to predose levels

| ISIS No. | Day 0 | Day 9 | Day 16 | Day 23 | Day 30 | Day 44 | Day 58 | Day 72 | Day 86 |
| --- | --- | --- | --- | --- | --- | --- | --- | --- | --- |
| 304299 | 4 | 15 | 21 | 23 | 26 | 27 | 31 | 38 | 47 |
| 420915 | 2 | 8 | 23 | 34 | 42 | 54 | 63 | 70 | 76 |
| 420921 | 5 | 11 | 21 | 31 | 23 | 27 | 30 | 40 | 50 |
| 420922 | 0 | 17 | 37 | 42 | 49 | 49 | 50 | 49 | 54 |
| 420950 | 0 | 39 | 63 | 68 | 72 | 79 | 85 | 82 | 87 |
| 420955 | 0 | 42 | 63 | 80 | 81 | n/a | n/a | n/a | n/a |
| 420957 | 2 | 18 | 28 | 26 | 26 | 35 | 35 | 41 | 50 |
| 420959 | 0 | 25 | 29 | 28 | 32 | 38 | 42 | 43 | 50 | n/a = study was terminated on day 31 for animals treated with ISIS 420955; therefore data for subsequent days is not available.

TABLE 73

Day 86 transthyretin protein level reduction in the cynomolgus monkey plasma relative to predose levels

| ISIS No. | % reduction |
| --- | --- |
| 304299 | 47 |
| 420915 | 76 |
| 420921 | 50 |
| 420922 | 54 |
| 420950 | 87 |
| 420957 | 50 |
| 420959 | 50 |

RBP4 protein levels were also measured in the plasma using an ELISA kit. Plasma samples were taken predose (on day −5) and on days 9, 16, 23, 30, 44, 58, 72, and 86. The results are presented in Table 74 expressed as percentage inhibition compared to the predose levels. Some of the ISIS oligonucleotides (ISIS 420915, ISIS 420922, ISIS 420950, ISIS 420955 and ISIS 420959) demonstrate a time-dependent reduction in protein levels, concomitant with TTR reduction. The final plasma RBP4 levels are presented in Table 75 and also demonstrate the strong correlation between RBP4 and TTR protein level reductions (Table 73) on treatment with the above-mentioned oligonucleotides. Specifically, treatment with ISIS 420915 caused greater inhibition of RBP4 plasma protein than treatment with ISIS 304299 (63% inhibition vs. 19% inhibition), even though the two oligonucleotides differ from each other by a single base-pair shift.

TABLE 74

Time course of RBP4 protein level reduction in the cynomolgus monkey plasma relative to predose levels

| ISIS No. | Day 9 | Day 16 | Day 23 | Day 30 | Day 44 | Day 58 | Day 72 | Day 86 |
| --- | --- | --- | --- | --- | --- | --- | --- | --- |
| 304299 | 0 | 6 | 10 | 4 | 1 | 9 | 13 | 19 |
| 420915 | 5 | 22 | 22 | 30 | 38 | 47 | 54 | 63 |
| 420921 | 0 | 0 | 0 | 0 | 0 | 0 | 6 | 24 |
| 420922 | 4 | 19 | 16 | 34 | 33 | 29 | 15 | 32 |
| 420950 | 30 | 44 | 46 | 47 | 52 | 54 | 47 | 48 |
| 420955 | 6 | 36 | 53 | 65 | n/a | n/a | n/a | n/a |
| 420957 | 0 | 10 | 0 | 0 | 0 | 0 | 3 | 27 |
| 420959 | 18 | 22 | 14 | 17 | 19 | 25 | 22 | 34 | n/a = study was terminated on day 31 for animals treated with ISIS 420955; therefore data for subsequent days is not available.

TABLE 75

Day 86 RBP4 protein level reduction in the cynomolgus
monkey plasma relative to predose levels

| ISIS No. | % reduction |
|---|---|
| 304299 | 19 |
| 420915 | 63 |
| 420921 | 24 |
| 420922 | 32 |
| 420950 | 48 |
| 420957 | 27 |
| 420959 | 34 |

Tolerability Studies

Body and Organ Weight Measurements

To evaluate the effect of ISIS oligonucleotides on the overall health of the animals, body and organ weights were measured at day 86. The data for animals treated with ISIS 420955 was taken at day 31. Body weights were measured and compared to that at pre-dose levels. Organ weights were measured and treatment group weights were compared to the corresponding PBS control weights. The data is presented in Table 76.

TABLE 76

Final body and organ weight % changes in the
cynomolgus monkey relative to predose levels

| ISIS No. | Body weight | Liver weight | Kidney weight | Spleen weight |
|---|---|---|---|---|
| 304299 | +6 | +27 | +37 | +53 |
| 420915 | +6 | +37 | +26 | +41 |
| 420921 | +4 | +42 | +43 | +22 |
| 420922 | +4 | +45 | +39 | +63 |
| 420950 | 0 | +204 | +166 | +297 |
| 420955* | −3 | +36 | +81 | +70 |
| 420957 | −6 | +55 | +184 | +109 |
| 420959 | 0 | +57 | +101 | +112 |

(*Data of day 31)

Liver Function

To evaluate the effect of ISIS oligonucleotides on hepatic function, blood samples were collected from all the study groups. The blood samples were collected in tubes without any anticoagulant for serum separation. The tubes were kept at room temperature for 90 min and then centrifuged (3000 rpm for 10 min at room temperature) to obtain serum. Concentrations of transaminases were measured using a Toshiba 200FR NEO chemistry analyzer (Toshiba Co., Japan). Plasma concentrations of ALT (alanine transaminase) and AST (aspartate transaminase) were measured on day 86 and the results are presented in Table 77, expressed in IU/L. Alkaline phosphatase, which is synthesized in increased amounts by damaged liver cells, is also a marker of liver disease and was similarly measured. C-reactive protein (CRP), which is synthesized in the liver and which serves as a marker of inflammation, was also similarly measured on day 86. Both alkaline phosphatase and CRP data are also presented in Table 77. Bilirubin is also a liver metabolic marker and was similarly measured and is presented in Table 77, expressed in mg/dL.

TABLE 77

Effect of antisense oligonucleotide treatment on liver
metabolic markers in cynomolgus monkey plasma

| | AST (IU/L) | ALT (IU/L) | ALP (IU/L) | CRP (mg/L) | Bilirubin (mg/dL) |
|---|---|---|---|---|---|
| PBS | 60 | 54 | 955 | 2.4 | 0.24 |
| ISIS 304299 | 81 | 101 | 747 | 3.3 | 0.17 |
| ISIS 420915 | 68 | 62 | 672 | 1.6 | 0.15 |
| ISIS 420921 | 98 | 107 | 832 | 3.2 | 0.14 |
| ISIS 420922 | 94 | 96 | 907 | 2.4 | 0.15 |
| ISIS 420950 | 132 | 94 | 1032 | 12.9 | 0.11 |
| ISIS 420957 | 100 | 73 | 868 | 23.5 | 0.15 |
| ISIS 420959 | 70 | 63 | 811 | 16.0 | 0.13 |

Kidney Function

To evaluate the effect of ISIS oligonucleotides on kidney function, blood samples were collected from all the study groups. The blood samples were collected in tubes without any anticoagulant for serum separation. The tubes were kept at room temperature for 90 min and then centrifuged (3000 rpm for 10 min at room temperature) to obtain serum. Concentrations of BUN and creatinine were measured at day 86 using a Toshiba 200FR NEO chemistry analyzer (Toshiba Co., Japan). Results are presented in Table 78, expressed in mg/dL.

Urine samples were collected by drainage from special stainless-steel cage pans on day 5 before the study, and subsequently on days 25 and 84. Urine total protein to creatinine ratio was measured using a Toshiba 200FR NEO chemistry analyzer (Toshiba Co., Japan) and the results are presented in Table 79.

TABLE 78

Effect of antisense oligonucleotide treatment on plasma
BUN and creatinine levels (mg/dL) in cynomolgus monkeys

| | BUN | Creatinine |
|---|---|---|
| PBS | 28 | 0.86 |
| ISIS 304299 | 27 | 0.85 |
| ISIS 420915 | 25 | 0.90 |
| ISIS 420921 | 33 | 0.99 |
| ISIS 420922 | 28 | 0.86 |
| ISIS 420950 | 36 | 0.97 |
| ISIS 420957 | 35 | 0.86 |
| ISIS 420959 | 27 | 0.89 |

TABLE 79

Effect of antisense oligonucleotide treatment on urine
protein to creatine ratio in cynomolgus monkeys

| | Day −5 | Day 25 | Day 84 |
|---|---|---|---|
| PBS | 0.003 | 0.01 | 0.00 |
| ISIS 304299 | 0.000 | 0.01 | 0.00 |
| ISIS 420915 | 0.003 | 0.00 | 0.00 |
| ISIS 420921 | 0.033 | 0.13 | 0.09 |
| ISIS 420922 | 0.010 | 0.05 | 0.02 |
| ISIS 420950 | 0.008 | 0.29 | 0.21 |

TABLE 79-continued

Effect of antisense oligonucleotide treatment on urine protein to creatine ratio in cynomolgus monkeys

|  | Day −5 | Day 25 | Day 84 |
|---|---|---|---|
| ISIS 420955 | 0.000 | 0.61 | n/a |
| ISIS 420957 | 0.000 | 0.48 | 0.36 |
| ISIS 420959 | 0.005 | 0.08 | 0.03 | n/a = study was terminated on day 31 for animals treated with ISIS 420955; therefore data for subsequent days is not available.

Hematology

To evaluate any inflammatory effect of ISIS oligonucleotides in cynomolgus monkeys, blood samples were approximately 0.5 mL of blood was collected from each of the available study animals in tubes containing the potassium salt of EDTA. Samples were analyzed for red blood cell (RBC) count, white blood cells (WBC) count, individual white blood cell percentages, such as that of monocytes, neutrophils, lymphocytes, as well as for platelet count and hematocrit (%), using an ADVIA120 hematology analyzer (Bayer, USA). The data is presented in Table 80.

TABLE 80

Effect of antisense oligonucleotide treatment on hematologic parameters in cynomolgus monkeys

|  | WBC (×10³/μL) | RBC (×10⁶/μL) | Platelet (×1000/μL) | Hematocrit (%) | Lymphocytes (%) | Neutrophil (%) | Monocytes (%) |
|---|---|---|---|---|---|---|---|
| PBS | 9.6 | 5.3 | 415 | 40 | 62 | 35 | 1.8 |
| ISIS 304299 | 11.6 | 5.2 | 395 | 38 | 68 | 26 | 3.1 |
| ISIS 420915 | 10.3 | 5.1 | 382 | 36 | 72 | 22 | 3.5 |
| ISIS 420921 | 9.8 | 5.2 | 385 | 36 | 60 | 34 | 2.5 |
| ISIS 420922 | 11.6 | 5.2 | 396 | 37 | 62 | 29 | 5.4 |
| ISIS 420950 | 13.7 | 4.4 | 260 | 33 | 51 | 34 | 7.8 |
| ISIS 420957 | 18.6 | 4.7 | 298 | 33 | 52 | 35 | 9.1 |
| ISIS 420959 | 7.7 | 4.8 | 306 | 32 | 62 | 29 | 5.5 |

Analysis of Factors of Inflammation

To evaluate the effect of ISIS oligonucleotides on factors involved in inflammation, blood was collected on day 86 from all available animals for complement C3 analysis, as well as for measurement of cytokine levels. For complement C3 analysis, the blood samples were collected in tubes without anticoagulant for serum separation. The tubes were kept at room temperature for 90 min and then centrifuged (3000 rpm for 10 min at room temperature) to obtain serum. Complement C3 was measured using an automatic analyzer (Toshiba 200 FR NEO chemistry analyzer, Toshiba co., Japan). The data is presented in Table 81, expressed in mg/dL.

For cytokine level analyses, blood was collected in tubes containing EDTA for plasma separation. The tubes were then centrifuged (3000 rpm for 10 min at room temperature) to obtain plasma. Plasma samples were sent to Aushon Biosystems Inc. (Billerica, Mass.) for measurement of chemokine and cytokine levels. Levels of TNF-α were measured using the respective primate antibodies and levels of MIP-1α, MCP-1, and MIP-1β were measured using the respective cross-reacting human antibodies. Measurements were taken 5 days before the start of treatment and on days 3 and 86. The results are presented in Tables 82-85.

TABLE 81

Effect of antisense oligonucleotide treatment on complement C3 (mg/dL) in cynomolgus monkeys

|  | C3 |
|---|---|
| PBS | 133 |
| ISIS 304299 | 96 |
| ISIS 420915 | 104 |
| ISIS 420921 | 91 |
| ISIS 420922 | 102 |
| ISIS 420950 | 70 |
| ISIS 420957 | 69 |
| ISIS 420959 | 95 |

TABLE 82

Effect of antisense oligonucleotide treatment on MCP-1 (pg/mL) in cynomolgus monkeys

|  | Day −5 | Day 3 | Day 86 |
|---|---|---|---|
| PBS | 232 | 362 | 206 |
| ISIS 304299 | 219 | 292 | 427 |
| ISIS 420915 | 204 | 342 | 400 |
| ISIS 420921 | 281 | 407 | 2120 |
| ISIS 420922 | 215 | 482 | 838 |
| ISIS 420950 | 170 | 370 | 3355 |
| ISIS 420957 | 208 | 308 | 3485 |
| ISIS 420959 | 237 | 715 | 2035 |

TABLE 83

Effect of antisense oligonucleotide treatment on TNF-α (pg/mL) in cynomolgus monkeys

|  | Day −5 | Day 3 | Day 86 |
|---|---|---|---|
| PBS | 60 | 46 | 16 |
| ISIS 304299 | 46 | 35 | 24 |
| ISIS 420915 | 113 | 83 | 30 |
| ISIS 420921 | 57 | 50 | 56 |
| ISIS 420922 | 30 | 59 | 46 |
| ISIS 420950 | 48 | 54 | 266 |
| ISIS 420957 | 29 | 33 | 87 |
| ISIS 420959 | 22 | 77 | 74 |

TABLE 84

Effect of antisense oligonucleotide treatment on MIP-1α (pg/mL) in cynomolgus monkeys

|  | Day −5 | Day 3 | Day 86 |
|---|---|---|---|
| PBS | 6 | 7 | 7 |
| ISIS 304299 | 6 | 7 | 9 |
| ISIS 420915 | 5 | 5 | 10 |
| ISIS 420921 | 8 | 11 | 9 |
| ISIS 420922 | 9 | 8 | 5 |
| ISIS 420950 | 7 | 9 | 5 |
| ISIS 420957 | 6 | 6 | 6 |
| ISIS 420959 | 9 | 6 | 5 |

TABLE 85

Effect of antisense oligonucleotide treatment on MIP-1β (pg/mL) in cynomolgus monkeys

|  | Day −5 | Day 3 | Day 86 |
|---|---|---|---|
| PBS | 13 | 19 | 42 |
| ISIS 304299 | 17 | 23 | 54 |
| ISIS 420915 | 15 | 27 | 72 |
| ISIS 420921 | 23 | 43 | 112 |
| ISIS 420922 | 9 | 41 | 70 |
| ISIS 420950 | 8 | 25 | 126 |
| ISIS 420957 | 16 | 27 | 182 |
| ISIS 420959 | 36 | 46 | 117 |

Coagulation Tests

To evaluate the effect of ISIS oligonucleotides on factors involved in the coagulation pathway, the standard tests for coagulation were employed. PT and aPTT were measured using platelet poor plasma (PPP) from the monkeys over a period of 48 hrs. PT and aPTT values are provided in Tables 86 and 87 and expressed in seconds. Fibrinogen levels on the plasma were also quantitated over a period of 48 hrs and the data is presented in Table 88. As shown in Tables 86-88, PT, aPTT and fibrinogen were not significantly altered in monkeys treated with ISIS oligonucleotides compared to the PBS control.

TABLE 86

Effect of antisense oligonucleotide treatment on PT (sec)

|  | 0 hr | 1 hr | 4 hr | 8 hr | 24 hr | 48 hr |
|---|---|---|---|---|---|---|
| PBS | 10.08 | 10.38 | 10.10 | 10.33 | 9.83 | 9.40 |
| ISIS 304299 | 10.38 | 10.30 | 10.48 | 10.20 | 9.95 | 9.53 |
| ISIS 420915 | 10.15 | 10.13 | 10.38 | 9.93 | 9.75 | 9.48 |
| ISIS 420921 | 10.28 | 10.13 | 10.43 | 10.18 | 9.80 | 9.55 |
| ISIS 420922 | 9.95 | 10.00 | 10.05 | 9.70 | 9.48 | 9.28 |
| ISIS 420950 | 10.30 | 10.47 | 10.57 | 10.27 | 9.63 | 9.50 |
| ISIS 420957 | 10.63 | 10.47 | 10.60 | 10.77 | 10.33 | 10.27 |
| ISIS 420959 | 10.08 | 10.10 | 10.20 | 10.15 | 9.80 | 9.55 |

TABLE 87

Effect of antisense oligonucleotide treatment on aPTT (sec)

|  | 0 hr | 1 hr | 4 hr | 8 hr | 24 hr | 48 hr |
|---|---|---|---|---|---|---|
| PBS | 19.40 | 19.70 | 20.13 | 20.20 | 19.43 | 17.30 |
| ISIS 304299 | 21.83 | 24.35 | 27.05 | 25.73 | 22.40 | 18.78 |
| ISIS 420915 | 20.05 | 22.83 | 23.83 | 24.00 | 21.78 | 17.90 |
| ISIS 420921 | 24.15 | 26.68 | 31.78 | 31.90 | 27.80 | 22.15 |
| ISIS 420922 | 25.28 | 29.48 | 34.83 | 33.90 | 29.13 | 25.08 |
| ISIS 420950 | 28.13 | 31.40 | 35.40 | 35.40 | 31.40 | 28.37 |
| ISIS 420957 | 29.13 | 33.27 | 39.13 | 37.40 | 36.50 | 29.93 |
| ISIS 420959 | 22.45 | 24.73 | 29.18 | 28.38 | 25.50 | 20.65 |

TABLE 88

Effect of antisense oligonucleotide treatment on fibrinogen (mg/dL)

|  | 0 hr | 1 hr | 4 hr | 8 hr | 24 hr | 48 hr |
|---|---|---|---|---|---|---|
| PBS | 212 | 203 | 240 | 247 | 282 | 272 |
| ISIS 304299 | 175 | 172 | 198 | 207 | 227 | 200 |
| ISIS 420915 | 213 | 196 | 204 | 258 | 257 | 215 |
| ISIS 420921 | 208 | 209 | 230 | 237 | 301 | 249 |
| ISIS 420922 | 278 | 277 | 335 | 338 | 400 | 304 |
| ISIS 420950 | 293 | 295 | 348 | 376 | 390 | 296 |
| ISIS 420957 | 280 | 299 | 344 | 330 | 434 | 328 |
| ISIS 420959 | 276 | 211 | 354 | 326 | 414 | 320 |

Thyroid Panel Analysis

To evaluate the effect of ISIS oligonucleotides on thyroid hormones, monkeys were fasted overnight and 3.5 mL of blood was drawn from each of the available study animals 5 days prior to the start of treatment and on days 51 and 86. Collected blood samples were kept in tubes without anticoagulant for serum separation. The tubes were kept for 90 min at room temperature, after which they were centrifuged (3000 rpm for 10 min at room temperature) to obtain serum. Serum samples were sent to the Biomarkers Core Laboratory of Emory University (Atlanta, Ga.) for thyroid panel analysis. The results for thyroid stimulating hormone (TSH) are provided in Table 89 and expressed μL/mL. The results for total and free T3 hormone are provided in Tables 90 and 91. The results for total and free T4 hormone are provided in Tables 92 and 93. Overall, the thyroid panel analysis showed that all the animals remained within acceptable hormone levels even though transthyretin expression levels were reduced, demonstrating that the transthyretin antisense oligonucleotides did not affect hormone levels.

TABLE 89

Effect of antisense oligonucleotide treatment on TSH (μL/mL)

|  | Day −5 | Day 51 | Day 86 |
|---|---|---|---|
| PBS | 0.8 | 0.7 | 1.0 |
| ISIS 304299 | 1.4 | 1.0 | 2.2 |
| ISIS 420915 | 1.4 | 1.5 | 2.5 |
| ISIS 420921 | 0.7 | 0.6 | 1.0 |
| ISIS 420922 | 1.0 | 1.2 | 1.9 |
| ISIS 420950 | 0.6 | 2.2 | 5.4 |
| ISIS 420957 | 0.6 | 2.6 | 4.9 |
| ISIS 420959 | 0.9 | 1.6 | 4.7 |

TABLE 90

Effect of antisense oligonucleotide treatment on total T3 (ng/dL)

|  | Day −5 | Day 51 | Day 86 |
|---|---|---|---|
| PBS | 177 | 248 | 140 |
| ISIS 304299 | 202 | 226 | 176 |

TABLE 90-continued

Effect of antisense oligonucleotide treatment on total T3 (ng/dL)

|  | Day −5 | Day 51 | Day 86 |
|---|---|---|---|
| ISIS 420915 | 156 | 206 | 156 |
| ISIS 420921 | 217 | 204 | 137 |
| ISIS 420922 | 188 | 177 | 131 |
| ISIS 420950 | 260 | 208 | 105 |
| ISIS 420957 | 266 | 160 | 78 |
| ISIS 420959 | 299 | 219 | 137 |

TABLE 91

Effect of antisense oligonucleotide treatment on free T3 (pg/mL)

|  | Day −5 | Day 51 | Day 86 |
|---|---|---|---|
| PBS | 7.7 | 5.8 | 5.2 |
| ISIS 304299 | 9.2 | 6.0 | 4.7 |
| ISIS 420915 | 8.9 | 5.6 | 4.5 |
| ISIS 420921 | 10.2 | 4.8 | 4.0 |
| ISIS 420922 | 8.9 | 5.4 | 3.7 |
| ISIS 420950 | 7.2 | 3.8 | 2.1 |
| ISIS 420957 | 8.8 | 4.0 | 2.4 |
| ISIS 420959 | 8.3 | 4.9 | 3.3 |

TABLE 92

Effect of antisense oligonucleotide treatment on total T4 (ng/dL)

|  | Day −5 | Day 51 | Day 86 |
|---|---|---|---|
| PBS | 5.8 | 4.9 | 4.4 |
| ISIS 304299 | 8.1 | 5.5 | 6.1 |
| ISIS 420915 | 8.3 | 5.7 | 5.5 |
| ISIS 420921 | 7.6 | 6.1 | 5.6 |
| ISIS 420922 | 7.3 | 6.1 | 5.8 |
| ISIS 420950 | 6.1 | 6.3 | 5.7 |
| ISIS 420957 | 6.3 | 4.4 | 5.0 |
| ISIS 420959 | 7.9 | 5.9 | 8.1 |

TABLE 93

Effect of antisense oligonucleotide treatment on free T4 (pg/mL)

|  | Day −5 | Day 51 | Day 86 |
|---|---|---|---|
| PBS | 3.4 | 2.4 | 1.7 |
| ISIS 304299 | 3.2 | 2.5 | 1.7 |
| ISIS 420915 | 5.0 | 1.8 | 1.7 |
| ISIS 420921 | 2.6 | 1.5 | 1.5 |
| ISIS 420922 | 3.5 | 1.6 | 1.5 |
| ISIS 420950 | 2.5 | 1.2 | 1.1 |
| ISIS 420957 | 2.4 | 1.2 | 1.2 |
| ISIS 420959 | 3.8 | 1.4 | 1.5 |

Pharmacokinetic Studies

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 166) was added prior to extraction. Tissue sample concentrations were calculated using calibration curves, with a lower limit of quantitation (LLOQ) of approximately 1.14 µg/g. The ratio of the concentrations in the kidney versus the liver was calculated. The results are presented in Tables 94 and 95, expressed as µg/g tissue.

TABLE 94

Full-length oligonucleotide concentration (µg/g) in the liver of cynomolgus monkey

| ISIS No. | Kidney | Liver | Kidney/Liver ratio |
|---|---|---|---|
| 304299 | 2179 | 739 | 2.9 |
| 420915 | 2439 | 1064 | 2.3 |
| 420921 | 4617 | 1521 | 3.0 |
| 420922 | 3957 | 1126 | 3.5 |
| 420950 | 3921 | 1082 | 3.6 |
| 420955 | 2444 | 1111 | 2.2 |
| 420957 | 3619 | 1230 | 2.9 |
| 420959 | 3918 | 1158 | 3.4 |

TABLE 95

Total oligonucleotide concentration (µg/g) in the liver of cynomolgus monkey

| ISIS No. | Kidney | Liver | Kidney/Liver ratio |
|---|---|---|---|
| 304299 | 3098 | 992 | 3.1 |
| 420915 | 3024 | 1266 | 2.4 |
| 420921 | 6100 | 1974 | 3.1 |
| 420922 | 4861 | 1411 | 3.4 |
| 420950 | 6003 | 1553 | 3.9 |
| 420955 | 2763 | 1208 | 2.3 |
| 420957 | 5420 | 1582 | 3.4 |
| 420959 | 5498 | 1501 | 3.7 |

What is claimed is:

1. A compound comprising a modified oligonucleotide consisting of 15 to 30 linked nucleosides wherein the linked nucleosides comprise at least a 15 contiguous nucleobase portion that is complementary to an equal length nucleobase portion within nucleotides 120-139 of SEQ ID NO: 1;
   wherein the modified oligonucleotide comprises:
   a gap segment consisting of linked deoxynucleosides;
   a 5' wing segment consisting of linked nucleosides; and
   a 3' wing segment consisting of linked nucleosides;
   wherein the gap segment is positioned between the 5' wing segment and the 3' wing segment, and wherein at least one nucleoside comprises a modified sugar.

2. The compound of claim 1, wherein the modified oligonucleotide has at least an 16, at least an 17, at least an 18, at least an 19, or at least a 20 contiguous nucleobase portion of which is complementary within nucleotides 120-139 of SEQ ID NO: 1.

3. The compound of claim 1, wherein the nucleobase sequence of the modified oligonucleotide is at least 95% complementary over its entire length to a nucleobase sequence of SEQ ID NO: 1, 2, or 4.

4. The compound of claim 1, wherein the modified oligonucleotide has at least one modified internucleoside linkage.

5. The compound of claim 4, wherein the modified internucleoside linkage is a phosphorothioate internucleoside linkage.

6. The compound of claim 1, wherein each nucleoside of each wing segment comprises a modified sugar.

7. The compound of claim 6, wherein the modified sugar is a bicyclic sugar comprising a 4'-CH(CH$_3$)—O-2' bridge or the modified sugar comprises a 2'-O-methoxyethyl moiety.

8. The compound of claim 1, wherein each nucleoside of each wing segment comprises a 2'-O-methoxyethyl sugar, wherein each internucleoside linkage is a phosphorothioate linkage, and wherein each cytosine of the modified oligonucleotide is a 5-methylcytosine.

9. A composition comprising the compound of claim 1, or a salt thereof, and a pharmaceutically acceptable carrier or diluent.

10. A method of treating transthyretin amyloidosis in an animal comprising administering to the animal a compound comprising a modified oligonucleotide consisting of 15 to 30 linked nucleosides wherein the linked nucleosides comprise at least a 15 contiguous nucleobase portion that is complementary to an equal length nucleobase portion within nucleotides 120-139 of SEQ ID NO: 1.

* * * * *

SEQUENCE LISTING

<160> NUMBER OF SEQ ID NOS: 177

<210> SEQ ID NO 1
<211> LENGTH: 650
<212> TYPE: DNA
<213> ORGANISM: Homo sapiens
<220> FEATURE:
<221> NAME/KEY: CDS
<222> LOCATION: (27)..(470)

<400> SEQUENCE: 1

```
acagaagtcc actcattctt ggcagg atg gct tct cat cgt ctg ctc ctc ctc      53
                             Met Ala Ser His Arg Leu Leu Leu Leu
                             1               5 tgc ctt gct gga ctg gta ttt gtg tct gag gct ggc cct acg ggc acc      101
Cys Leu Ala Gly Leu Val Phe Val Ser Glu Ala Gly Pro Thr Gly Thr
10              15                  20                  25 ggt gaa tcc aag tgt cct ctg atg gtc aaa gtt cta gat gct gtc cga      149
Gly Glu Ser Lys Cys Pro Leu Met Val Lys Val Leu Asp Ala Val Arg
                30                  35                  40 ggc agt cct gcc atc aat gtg gcc gtg cat gtg ttc aga aag gct gct      197
Gly Ser Pro Ala Ile Asn Val Ala Val His Val Phe Arg Lys Ala Ala
            45                  50                  55 gat gac acc tgg gag cca ttt gcc tct ggg aaa acc agt gag tct gga      245
Asp Asp Thr Trp Glu Pro Phe Ala Ser Gly Lys Thr Ser Glu Ser Gly
        60                  65                  70 gag ctg cat ggg ctc aca act gag gag gaa ttt gta gaa ggg ata tac      293
Glu Leu His Gly Leu Thr Thr Glu Glu Glu Phe Val Glu Gly Ile Tyr
    75                  80                  85 aaa gtg gaa ata gac acc aaa tct tac tgg aag gca ctt ggc atc tcc      341
Lys Val Glu Ile Asp Thr Lys Ser Tyr Trp Lys Ala Leu Gly Ile Ser
90                  95                  100                 105 cca ttc cat gag cat gca gag gtg gta ttc aca gcc aac gac tcc ggc      389
Pro Phe His Glu His Ala Glu Val Val Phe Thr Ala Asn Asp Ser Gly
                110                 115                 120 ccc cgc cgc tac acc att gcc gcc ctg ctg agc ccc tac tcc tat tcc      437
Pro Arg Arg Tyr Thr Ile Ala Ala Leu Leu Ser Pro Tyr Ser Tyr Ser
            125                 130                 135 acc acg gct gtc gtc acc aat ccc aag gaa tga gggacttctc ctccagtgga    490
Thr Thr Ala Val Val Thr Asn Pro Lys Glu
        140                 145 cctgaaggac gagggatggg atttcatgta accaagagta ttccattttt actaaagcag    550
tgttttcacc tcatatgcta tgttagaagt ccaggcagag acaataaaac attcctgtga    610
aaggcacttt tcattccaaa aaaaaaaaaa aaaaaaaaa                           650

<210> SEQ ID NO 2
<211> LENGTH: 8054
<212> TYPE: DNA
<213> ORGANISM: Homo sapiens

<400> SEQUENCE: 2
ttgttgaccc atggatccat caagtgcaaa cattttctaa tgcactatat ttaagcctgt     60
gcagctagat gtcattcaac atgaaataca ttattacaac ttgcatctgt ctaaatctt    120 gcatctaaaa tgagagacaa aaaatctata aaaatggaaa acatgcatag aaatatgtga    180
gggaggaaaa aattacccc aagaatgtta gtgcacgcag tcacacaggg agaagactat     240
ttttgttttg ttttgattgt tttgtttttgt ttggttgtt ttgttttggt gacctaactg    300
gtcaaatgac ctattaagaa tatttcatag aacgaatgtt ccgatgctct aatctctcta    360
gacaaggttc atatttgtat gggttactta ttctctcttt gttgactaag tcaataatca    420
gaatcagcag gtttgcagtc agattggcag ggataagcag cctagctcag gagaagtgag    480
tataaaagcc ccaggctggg agcagccatc acagaagtcc actcattctt ggcaggatgg    540
cttctcatcg tctgctcctc ctctgccttg ctggactggt atttgtgtct gaggctggcc    600
ctacggtgag tgtttctgtg acatcccatt cctacattta agattcacgc taaatgaagt    660
agaagtgact ccttccagct ttgccaacca gcttttatta ctagggcaag ggtacccagc    720
atctattttt aatataatta attcaaactt caaaaagaat gaagttccac tgagcttact    780
```

```
gagctgggac ttgaactctg agcattctac ctcattgctt tggtgcatta ggtttgtaat    840
atctggtacc tctgtttcct cagatagatg atagaaataa agatatgata ttaaggaagc    900
tgttaatact gaattttcag aaaagtatcc ctccataaaa tgtatttggg ggacaaactg    960
caggagatta tattctggcc ctatagttat tcaaaacgta tttattgatt aatcttaaa    1020
aggcttagtg aacaatattc tagtcagata tctaattctt aaatcctcta gaagaattaa   1080
ctaatactat aaaatgggtc tggatgtagt tctgacatta ttttataaca actggtaaga   1140
gggagtgact atagcaacaa ctaaaatgat ctcaggaaaa cctgtttggc cctatgtatg   1200
gtacattaca tcttttcagt aattccactc aaatggagac tttaacaaa gcaactgttc    1260
tcagggacc tattttctcc cttaaaattc attatacaca tccctggttg atagcagtgt    1320
gtctggaggc agaaaccatt cttgctttgg aaacaattac gtctgtgtta tactgagtag   1380
ggaagctcat taattgtcga cacttacgtt cctgataatg ggatcagtgt gtaattcttg   1440
tttcgctcca gatttctaat accacaaaga ataaatcctt tcactctgat caattttgtt   1500
aacttctcac gtgtcttctc tacacccagg gcaccggtga atccaagtgt cctctgatgg   1560
tcaaagttct agatgctgtc cgaggcagtc ctgccatcaa tgtggccgtg catgtgttca   1620
gaaaggctgc tgatgacacc tgggagccat tgcctctgg gtaagttgcc aaagaaccct   1680
cccacaggac ttggttttat cttcccgttt gcccctcact tggtagagag aggctcacat   1740
catctgctaa agaatttaca agtagattga aaaacgtagg cagaggtcaa gtatgccctc   1800
tgaaggatgc cctcttttg ttttgcttag ctaggaagtg accaggaacc tgagcatcat   1860
ttagggcag acagtagaga aaagaaggaa tcagaactcc tctcctctag ctgtggtttg   1920
caacccttt gggtcacaga acactttatg taggtgatga aaagtaaaca ttctatgccc   1980
agaaaaatg cacagataca cacacataca aaatcatata tgtgatttta ggagtttcac    2040
agattccctg gtgtccctgg gtaacaccaa agctaagtgt ccttgtctta gaattttagg   2100
aaaaggtata atgtgtatta acccattaac aaaaggaaag gaattcagaa atattattaa   2160
ccaggcatct gtctgtagtt aatatggatc acccaaaacc caaggctttt gcctaatgaa   2220
cactttgggg cacctactgt gtgcaaggct gggggctgtc aagctcagtt aaaaaaaaaa   2280
agatagaaga gatggatcca tgaggcaaag tacagccccca ggctaatccc acgatcaccc   2340
gacttcatgt ccaagagtgg cttctcacct tcattagcca gttcacaatt tcatggagt    2400
ttttctacct gcactagcaa aaacttcaag gaaaatacat attaataaat ctaagcaaag   2460
tgaccagaag acagagcaat caggagaccc tttgcatcca gcagaagagg aactgctaag   2520
tatttacatc tccacagaga agaatttctg ttgggttta attgaacccc aagaaccaca   2580
tgattcttca accattattg ggaagatcat tttcttaggt ctggttttaa ctggcttttt   2640
atttgggaat tcatttatgt ttatataaaa tgccaagcat aacatgaaaa gtggttacag   2700
gactattcta agggagagac agaatggaca ccaaaaatat tccaatgttc ttgtgaatct   2760
tttccttgca ccaggacaaa aaaaaaaaga agtgaaaaga agaaaggagg aggggcataa   2820
tcagagtcag taaagacaac tgctattttt atctatcgta gctgttgcag tcaaatggga   2880
agcaatttcc aacattcaac tatggagctg gtacttacat ggaaatagaa gttgcctagt   2940
gtttgttgct ggcaaagagt tatcagagag gttaaatata taaagggaa aagagtcaga    3000
tacaggttct tcttcctact ttaggttttc cactgtgtgt gcaaatgata ctccctggtg   3060
gtgtgcagat gcctcaaagc tatcctcaca ccacaaggga gaggagcgag atcctgctgt   3120
```

-continued

```
cctggagaag tgcagagtta gaacagctgt ggccacttgc atccaatcat caatcttgaa    3180
tcacagggac tctttcttaa gtaaacatta tacctggccg ggcacggtgg ctcacgcctg    3240
taatcccagc actttgggat gccaaagtgg gcatatcatc tgaggtcagg agttcaagac    3300
cagcctggcc aacatggcaa aactccgtct ttatgaaaaa tacaaaaatt agccaggcat    3360
ggtggcaggc gcctgtaatc ccagctaatt gggaggctga ggctggagaa tcccttgaat    3420
ctaggaggca gaggttgcag tgagctgaga tcgtgccatt gcactccagc ctgggtgaca    3480
agagtaaaac tctgtctcaa aaaaaaaaaa ttatacctac attctcttct tatcagagaa    3540
aaaaatctac agtgagcttt tcaaaaagtt tttacaaact ttttgccatt taatttcagt    3600
taggagttttt ccctacttct gacttagttg aggggaaatg ttcataacat gtttataaca    3660
tgtttatgtg tgttagttgg tggggtgtgta ttactttgcc atgccatttg tttcctccat    3720
gcgtaactta atccagactt tcacaccttta taggaaaacc agtgagtctg gagagctgca    3780
tgggctcaca actgaggagg aatttgtaga agggatatac aaagtggaaa tagacaccaa    3840
atcttactgg aaggcacttg gcatctcccc attccatgag catgcagagg tgagtataca    3900
gaccttcgag ggttgttttg gttttggttt ttgcttttgg cattccagga aatgcacagt    3960
tttactcagt gtaccacaga aatgtcctaa ggaaggtgat gaatgaccaa aggttccctt    4020
tcctattata caagaaaaaa ttcacaaacac tctgagaagc aaatttcttt ttgactttga    4080
tgaaaatcca cttagtaaca tgacttgaac ttacatgaaa ctactcatag tctattcatt    4140
ccactttata tgaatattga tgtatctgct gttgaaataa tagtttatga ggcagccctc    4200
cagaccccac gtagagtgta tgtaacaaga gatgcaccat tttatttctc gaaaacccgt    4260
aacattcttc attccaaaac acatctggct tctcggaggt ctggacaagt gattcttggc    4320
aacacatacc tatagagaca ataaaatcaa agtaataatg gcaacacaat agataacatt    4380
taccaagcat acaccatgtg gcagacacaa ttataagtgt tttccatatt taacctactt    4440
aatcctcagg aataagccac tgaggtcagt cctattatta tccccatctt atagatgaag    4500
aaaatgaggc accaggaagt caaataactt gtcaaaggtc acaagactag gaaatacaca    4560
agtagaaatg tttacaatta aggcccaggc tgggtttgcc ctcagttctg ctatgcctcg    4620
cattatgccc caggaaactt tttccctttgt gaaagccaag cttaaaaaaa gaaaagccac    4680
atttgtaacg tgctctgttc ccctgcctat ggtgaggatc ttcaaacagt tatacatgga    4740
cccagtcccc ctgccttctc cttaatttct taagtcattt gaaacagatg gctgtcatgg    4800
aaatagaatc cagacatgtt ggtcagagtt aaagatcaac taattccatc aaaaatagct    4860
cggcatgaaa gggaactatt ctctggctta gtcatggatg agactttcaa ttgctataaa    4920
gtggttcctt tattagacaa tgttaccagg gaaacaacag gggtttgttt gacttctggg    4980
gcccacaagt caacaagaga gccccatcta ccaaggagca tgtccctgac taccctcag    5040
ccagcagcaa gacatggacc ccagtcaggg caggagcagg gtttcggcgg cgcccagcac    5100
aagacattgc cctagagtc tcagccccta ccctcgagta atagatctgc ctacctgaga    5160
ctgttgtttg cccaagagct gggtctcagc ctgatgggaa ccatataaaa aggttcactg    5220
acatactgcc cacatgttgt tctctttcat tagatcttag cttccttgtc tgctcttcat    5280
tcttgcagta ttcattcaac aaacattaaa aaaaaaaaaa agcattctat gtgtggaaca    5340
ctctgctaga tgctgtggat ttagaaatga aaatacatcc cgaccctggg aatggaaggg    5400
aaaggactga agtaagacag attaagcagg accgtcagcc cagcttgaag cccagataaa    5460
tacggagaac aagagagagc gagtagtgag agatgagtcc caatgcctca ctttggtgac    5520
```

```
gggtgcgtgg tgggcttcat gcagcttctt ctgataaatg cctccttcag aactggtcaa   5580
ctctaccttg gccagtgacc caggtggtca tagtagattt accaagggaa aatggaaact   5640
tttattagga gctcttaggc ctcttcactt catggatttt ttttccttt tttttgaga    5700 tggagttttg ccctgtcacc caggctggaa tgcagtggtg caatctcagc tcactgcaac   5760
ctccgcctcc caggttcaag caattctcct gcctcagcct cccgagtagc tgggactaca   5820
ggtgtgcgcc accacccag gctaatttt gtatttttg taaagacagg ttttcaccac     5880
gttggccagg ctggtctgaa ctccagacct caggtgattc acctgtctca gcctcccaaa   5940
gtgctgggat tacaggtgtg agccaccgtg cccggctact tcatggattt ttgattacag   6000
attatgcctc ttacaatttt taagaagaat caagtgggct gaaggtcaat gtcaccataa   6060
gacaaaagac attttatta gttgattcta gggaattggc cttaagggga gcccttctt    6120 cctaagagat tcttaggtga ttctcacttc ctcttgcccc agtattattt ttgtttttgg   6180
tatggctcac tcagatcctt ttttcctcct atccctaagt aatccgggtt tcttttccc    6240 atatttagaa caaaatgtat ttatgcagag tgtgtccaaa cctcaaccca aggcctgtat   6300
acaaaataaa tcaaattaaa cacatcttta ctgtcttcta cctctttcct gacctcaata   6360
tatcccaact tgcctcactc tgagaaccaa ggctgtccca gcacctgagt cgcagatatt   6420
ctactgattt gacagaactg tgtgactatc tggaacagca ttttgatcca caatttgccc   6480
agttacaaag cttaaatgag ctctagtgca tgcatatata tttcaaaatt ccaccatgat   6540
cttccacact ctgtattgta aatagagccc tgtaatgctt ttacttcgta tttcattgct   6600
tgttatacat aaaaatatac ttttcttctt catgttagaa aatgcaaaga ataggagggt   6660 ggggaatct ctgggcttgg agacaggaga cttgccttcc tactatggtt ccatcagaat    6720
gtagactggg acaatacaat aattcaagtc tggtttgctc atctgtaaat gggaagaat    6780 gtttccagct ccagaatgct aaatctctaa gtctgtggtt ggcagccact attgcagcag   6840
ctcttcaatg actcaatgca gttttgcatt ctccctacct tttttttcta aaaccaataa   6900
aatagataca gcctttaggc tttctgggat ttcccttagt caagctaggg tcatcctgac   6960
tttcggcgtg aatttgcaaa acaagacctg actctgtact cctgctctaa ggactgtgca   7020
tggttccaaa ggcttagctt gccagcatat ttgagctttt tccttctgtt caaactgttc   7080
caaaatataa aagaataaaa ttaattaagt tggcactgga cttccggtgg tcagtcatgt   7140
gtgtcatctg tcacgttttt cgggctctgg tggaaatgga tctgtctgtc ttctctcata   7200
ggtggtattc acagccaacg actccggccc ccgccgctac accattgccg ccctgctgag   7260
cccctactcc tattccacca cggctgtcgt caccaatccc aaggaatgag ggacttctcc   7320
tccagtggac ctgaaggacg agggatggga tttcatgtaa ccaagagtat tccattttta   7380
ctaaagcagt gttttcacct catatgctat gttagaagtc caggcagaga caataaaaca   7440
ttcctgtgaa aggcactttt cattccactt taacttgatt ttttaaattc ccttattgtc   7500
ccttccaaaa aaaagagaat caaaattta caaagaatca aaggaattct agaaagtatc    7560
tgggcagaac gctaggagag atccaaattt ccattgtctt gcaagcaaag cacgtattaa   7620
atatgatctg cagccattaa aaagacacat tctgtaaatg agagagcctt attttcctgt   7680
aaccttcagc aaatagcaaa agacacattc caagggccca cttctttact gtgggcattt   7740
cttttttttt ctttttttct tttttccttt tttgagacaa agtctcactc tgttgcccag   7800
gctagaatgc agtggtgtaa tctcagctca ctgcaacctc tgcttcctgg gttcaagcga   7860
```

| | |
|---|---:|
| ttctcctgcc tcagcctccc aagtaactgg gattacaggc gcatgccacc acgcctagct | 7920 |
| cattttttgta tttttagtag agatgggatt ttgccatgtt ggctaggctg gtctacgaac | 7980 |
| tcctgacctc aggtgatcca cctgcctcag cctcccaaag tgctgggatt acaggcatga | 8040 |
| gccactacac ccgg | 8054 |

<210> SEQ ID NO 3

<400> SEQUENCE: 3

000

<210> SEQ ID NO 4
<211> LENGTH: 10001
<212> TYPE: DNA
<213> ORGANISM: Macaca mulatta

<400> SEQUENCE: 4

| | |
|---|---:|
| gactctattc ctagttatgg tctcaactac atttgctcat tgctgtgagg ggtgagccca | 60 |
| cctcccggag tcctctcctg cacattccta tgttcctgaa aggactttcc atcccttcca | 120 |
| ctactccctg aaaactcctg tgcttcatga tttcttgttg aattttttct aatctgactc | 180 |
| tatcagttat gggaatgttc cctcaactct tagtgctcca gactggactc gctcttggca | 240 |
| tgtatttgtc caaaatattt gtctgctcta tgtcttctac atatttgtct tataaggaac | 300 |
| aaacacctga tttgtttatc catgaacaaa gccacacatg ctagtgcaca cgcacataca | 360 |
| cacacacaca tacacacaga ggattctgta cgtgattaat gaatcatcaa atcatcataa | 420 |
| tttctggact tgtattaata cgtcggccag gaggaaaaga atccgttgtc aatcatggct | 480 |
| tctggttctc acggtcatct ctactttctt ccagcaagtt tgattctgtc aaacaccagc | 540 |
| tggcagcttt gttccggcat gcccagtgca ggagagtcag taaagaagat ttcattctct | 600 |
| gtatttcagc gtcgtcaatg ccaggttgaa atacgctatt ctggcccagc tcagtggctc | 660 |
| acacgtgtaa tcccagcact ttggaaggcc aaggcaggca gatcgcttga gcccaggaat | 720 |
| tcgagaccag cctgggcaag aggctgaggt gggaggatga cctgagcccg ggaggtcaag | 780 |
| gctgcagcca gctgtgatca tgtcactgca ctcaagccag ggcgtcggag tgagaccgtg | 840 |
| tcaaaaaaaa aggaaggaaa gaaggaagga aggaaggaag gaaggaagga aggaaggaag | 900 |
| gaaggaagga aggaagggag ggaggaggg agggaggag gaaggaagga aggaagtatg | 960 |
| taaggaagga aggaaggaag gaagggaggg acggagggcg ggaggaagg aagatgccat | 1020 |
| tcttagattg aagtggacct tatgtgggca gaacacacac acacacacac acattgtgga | 1080 |
| gaaattgctg actaagcaaa gcttccaaat gactgagttt ggctaaaacg taggctttta | 1140 |
| aaaatgtgag cactgccaag ggtttttcct tgttgaccca tggatccatc aagtgcaaac | 1200 |
| attttctaat gcactatatt taagcctgtg cagccaaatg tcattcaaca tgaaatgcat | 1260 |
| tattacaact tgcatctgtc taaaatcttg catcaaaaat gaaagacaaa aatgtataaa | 1320 |
| aatggaaaac atgcatagaa atatgtgagg gaggaaaaaa atatccccag gaatgttagt | 1380 |
| gcacggagtc acacagggag aagactattt ttgtttttgtt ttgattgttt tgttctggtg | 1440 |
| acctcactgg tcaaatgacc tattaagaat atttttgtaga gctaatgttc cgatgctcta | 1500 |
| atctctctag acaaggttca tatttgtatg ggttacttat tctctctttg ttgactaagt | 1560 |
| caataatcag aatcagcagg tttggagtca gattggcagg gataagcagc ctagctcagg | 1620 |
| agaagtgggt ataaaagccc caggctggga gcagccatca cagaagtcca ctcgttcttg | 1680 |

```
gcaggatggc ttctcatcgt ctgctcctcc tctgcctcgc tggactggta tttgtgtctg      1740
aggctggtcc tacggtgagt gtttctgtga catctcgctc ctacatttaa aatgcacgct      1800
aaatgaggta ggagtgactc cttccagctt tgccaagcag cttttgttac tagggcaagg      1860
gtacccagca tctattttta atatcattta ttcaaacttc aaaaagaatg aagttccact      1920
gagcttactg agctgggact tgaactctgg ggattctgcc tcattgcttt ggtgcattgg      1980
gtttgtaatg tctggtatct ccacttcctc agatcgatga tagagataaa gatatgatat      2040
taaggaagct gttaatcctg aattttcaga aaagtatccc tttataaaat gtatttgggg      2100
ggcaaactgc atgagattat attctggccc tatagctaat caaaatgtat ttaccgatta      2160
atctttaaaa ggcttagtga acaatatttt agtcagatat ctaattctta aatactctag      2220
aaggattaac taatctataa aatgggtctg gatatagtct gacataattt tataacaacc      2280
ggtaagaggg agtgactaga gcaacaacta aaatcatctc aggaaaaact gttttggtcc      2340
tatgtatggt acgttacatc tttttcagtaa ttccattcaa atggagaagt ttaacaaggc      2400
aactgttctc aggggggccta ttctctccct taaaattcat tatacacatc cctggttgat      2460
agcagtgtgt ctggaggcag aaaccattct tgctttggaa acaattatgt ctgtgttata      2520
ctgagtaggg aagctcatta actgtcaaca cttatgttct tcataatgga atcagtgtgt      2580
aattcttgtt ttgttccaga tttctaacac cataaagaat aaatcctttc actctgatca      2640
atgttgttaa cttctcactt gtcttctcta tacccagggc gttgatgaat ccaagtgtcc      2700
tctgatggtc aaagttctag atgccgtccg aggcagtcct gccgtcaatg tggctgtgaa      2760
cgtgttcaaa aaggctgctg atgagacctg ggcgccattt gcctctgggt aagaaccctc      2820
ccacgggact tggttttatc ttcccattgg cccctcagtt ggtagacaga ggctcacatc      2880
atctgctaaa gaatttacaa gtagattgaa aaacgtgagc agaggtcaag tatgccctct      2940
gaagatgccc tcttttttgtt ttgcttagct aggaagggac caggaacctg agcatcattt      3000
aggggcagac agtagagaaa agaaggaatc agaactcttc ccctctagct gtggtgtgca      3060 accccttttgg gtcacagacc actttatgta ggtgataaaa actaaagatt ctatgcccag      3120
aaaaaatgta cagatacaca cacacaaaac catatatgtg atttttaggag tttcacagat      3180 tccctggtgt ccctgggtaa caccaaaggt gagagtcctc gtcttagaat tttaggaaag      3240
aggtgcaatg tgtattaacc cactaacgaa aggaaaggga ttcagaaata ttattgacta      3300
ggcatctgtc tgtagttcat ttggatcacc ccaaacccag ggcttttgcc taatgaacac      3360
tttggggcac ctactgtgtg cagggctgga ggctgtcaag ctcagttaaa acaaatgtaa      3420
aaaaagacag aagaaatgga tccatgaggc aaagtacagc cccagactaa tcccatgatc      3480
acccaacttc atgtgcaaga gtgacttcta accttcatga gccagtttac aatttttcatg      3540 gagttttttct acctacacta caaaaactcc aaggaaaata tatattaata aacctaagcg      3600
aattgaccga aagacagagc aataaggaga cccttcgcac ccagcagaag ggaactgtt      3660 aagtacttac ttctcctcag agaagaattt ctgttgtatt ttaattgaac cccaagaacc      3720
acacgattct tcaaccatta ttggtaagat catttcttta ggtctggttt taactgactt      3780
tttatttggt aattcattta tgtttatata aaatgccaag cataacatga aaagtggtta      3840
caggactatt ctaagggaga gagaaaatgg ataccaaaaa tattccaatg ttcttatgaa      3900
tcttttccct tgcgtcagga caaaaaaaaa aaaatgtaa agaagaaagg aggagatgca      3960
caatcagagt cagtaaagac aactgctatt tttatctgtc atagctgttg cagtctaatg      4020
ggaagcaatt tccaacattc aactatggag ctggtactta catggaaata gaagttgcct      4080
```

```
agtgtttgtt gctggcaaag agttatcaga gaggttaaat atataaaagg gaagagtcag   4140
atacaggttc ttcttcctac tttaggtttt ccactgtgtg tgcaaatgac cctccctggt   4200
ggtgtgcaga tgctctgaaa ggtatcctca caccacaagg cagaggagcg agaccctgct   4260
gtcctggaga agtgcagagt tagaacagct gtggccactt ccagggatgg tcacaacatc   4320
ccatctaatc atcaatcttg aacaacaagg actctttctt aagaaaacat tatacccagc   4380
cgggcgcggt ggctcacacc tgtaaatctc agcgctttgg gaggctgaaa tgggcatatc   4440
atctgaggtc gagagctcaa gaccaacctg gccaacatgg caaaactccg tctctatgaa   4500
aaatacaaaa attagccagg catggtggca ggcacctgta atcccggcta ctcgggaggc   4560
tgagactgga gaatcccttg aacctggagg cagaggttgc agtgagctga gatcacgcca   4620
ctgcactcca gcctgggtga ctagagtaaa actctgtctc aaaaataaaa aaaaatttaa   4680
aaaattatac ctacattctc ttcttatcag agaaaaatat ctacagtgag cttttcaaaa   4740
gttttttacaa acttttttgcc atttaatttc agacagttat gagttttccc tacttctgac   4800
ttagttgagg ggaaatgtat ataacacatt tatgtgtgtt gtgtatataa cacatataac   4860
acgtttatgt gtgttggtgg gggtattact ttgccatgcc atttgtttcc tccatgccta   4920
acttaaccca gactttcaca ccttatagga aaccagtga gtctggagag ctgcatgggc   4980
tcacaactga ggaggaattt gtagaaggga tatacaaagt ggaaatagac accaaatctt   5040
actggaagtc acttggcatc tccccattcc atgagcatgc agaggtgagt atataaacct   5100
tcgagggttg ttttggtttt ggttttttgct tttggcatcc caggaaatgc acagttttac   5160
ttagcatacc acagaaatgt cctaagaag gtgatgaatg accaaaggtt ccctctcctc   5220
ttatacaaga acaaattcac aacactctga gaagcacatt tcttttttgac tttgaggaaa   5280
acccatttag taacatgact tgaacttaca tgacactatt catagtctac tcattccatt   5340
ttatatgaat attgatgtat ttgccgttga aataacatgt ttatgaggca gacctccaga   5400
ccccacgtag agtgtatgaa acaagagatg caccattta ttctctaaa acctgtaaca   5460
ttcttcattc caaaacacat ctggctcctc ggaggtttgg acaagtgatt cttggcaaca   5520
catacataga gagacaataa aatcaaagta ataatggcaa cacaacagat aacatttact   5580
aagcatacac catgtggcag acacaattat aagtgttttc tatatttaac ctacttcatc   5640
ctcagggaca agccactgag gtcagtccta ttattatccc catctcatag atgaagcaag   5700
tgaggcacca ggaagtcaaa taacttgtca aaggtcacaa ggctaggaaa cacacaagta   5760
gagatgttta caaacaaggc ccaggctggg tttgccctca attctgctct gcctcgcatt   5820
gcgacccagg aaatttgttc ccctgtgaaa agccaagctt aaaaaagaa aagccacatt   5880
tgtaacgtgc tctgttcccc tgcctatggt gaggatcttc gaacagttat acagctccct   5940
gtcttcccct tgtcttaatt tcttcagtca tttgaaacag atggctgtca tggaaataga   6000
atccagacat gttggtcaga gttaaagatc aactaattcc atcaaaaata gctcagcatg   6060
aaagggaact attctctggc ttagtcatgg atgagacttt caattgctat aaagtggttc   6120
ctttattagg caatgttacc agggaaacaa taggggcttg tttgacttct ggggcccaca   6180
agtcaccaag ggagccccat ctaccaagaa gcatgtccct gactacccg cagccaggca   6240
gcaagacacg gacgccggtc agggcagcag cagggtttca gtggtgccca gcacaagaca   6300
ttgctcctag agtctcagcc cctacccttg agtagtagaa ctgcctacct gagaccgttg   6360
tttgcctaag acctgggtct cagcctgatg ggaaccatct aaaaagttca tcgccatact   6420
```

```
gcccacgtgt tgttctcttt cattagatct cagcttcctt gactgctctt cactcttgtt    6480
tattcattca acaaacattt aaaaaataaa agcattctat gtgtggaaca ctctgataga    6540
ggctggagat tcagaaatga aaatacatcc ctacccttgg aatggagggg aaaggactga    6600
agtaagacag actaggcagg cccgtcagcc cagcttgaag cccagataaa tatggagaac    6660
aagagtgagt gagtagtgag agatgagtcc cagtgcctca ctttggtgac tggtgcatgg    6720
tgggcttcat gcagcttctt ctgataaatg cctccttcag aaccggtcac ctctaccttg    6780
gccagtgacc caagtggtca tattagattt accaagggaa attggaaact tttattagga    6840
gctcttaggc ctcttcactt catggaattt tttcttttttt ctttttttttt tgagatggag    6900 ttttgctctg tcacccaggc tggaatgcag tggtgcaatc ttggctcact gcaacccttta   6960 cttcccaggt tcaagcaatt cttctgcctc agcctcccga gtagctggga ctacaggtgc    7020
acgccaccat acccagctaa gttttgtatt tttcatagag acagggtttc gccatgttgg    7080
ccaggctggt ctcgaactcc agacctcagg tgattcaccc acctcagcct cccaaagtgc    7140
tggcattaca ggtgtgagcc agtacaccca gctacttcat ggattttga tcacagatta    7200 tgcctcttat aattttaag aagaatcaag tgggctgaag gtcaatgtca ccataagata    7260
aaagatattt ttattagttg attctaggga gttggcctta aggggagccc tttcttctta    7320
agagattctt ggccgggcgc ggtggctcaa gcctgtaatc ccagcacttt gggaggccga    7380
gacgggtgga tcatgaggtc aggagatcga accatcctg gtaacacggt gaaacccgt     7440 ctctactaaa aatacaaaa aaactagccg ggtgagttgg cgggcgcctg tagtcccagc    7500
tactcgggag gctgaggcag gagaatggcg taaacccggg aggcggagct tgcagtgagc    7560
tgagatctgg ccactgcact ccagcccggg tgacagagcg agactccgtc tcaaaaaaaa   7620
aaaaaaaaaa aaagagattc ttaggtgatt ctcacttcct cttgcccaa tattatttt    7680 gtttttggta tggctcactc agctcctttt tccctcctat ccctaagtaa tccgggtttc    7740
ttttccccat atttggaaca aaatgtattt atgcagagtg tgtccaaaac tcaacccaag    7800
gcccgtatac aaaataaatc aaattaaaca catctttact gtcttctacc tctttcctga    7860
cctcaattta tcccaacttg cctcactctg agaatcaagc ctgtcccagc acatgagttg    7920
cagatactct actgaatttg acagaactgt gtgactatct ggaacagcat tttgatccac    7980
aatttgccca gttacaaagc ttaaatgaag tctagtgcat gcatgtatat ttcaaaattc    8040
caccatgctc ttccacactc tgtattgtaa atagagccct gaaatgcttt tggttcatat    8100
ttcattgctt gctatacata aaatatact ttttcttctt catgttagaa aatgcaaaga    8160 atagtgggt gggggaatct ctgggcttgg agacaggaga cttaccttcc tactgtggtt     8220
ccatcagtat gtagactggg gcaatacaat aattcaagtc tggtttgctc atctgtaaaa    8280
tgggaagaat gtttccagct ccagaatgct aagtctctaa gtctgtggtt ggcagccact    8340
attgcagcag cttttcaatg actcagtgca ttttttccatt ctccccacct tttttttttc    8400
taaaaccaac aaaatagata cagcctttag gctctctggg atttccctta gtcaagctag    8460
ggccatcctg acttttgatg tgaatttgca aaacaagacc tggttctgta ctcctgctct    8520
aagggctgtg catggttcca aaggcttggc ttgccagtgt atttgagctt tttccttctg    8580
ttcaaacttc aaaatataa agaataaaat taattaagtt ggcactggac ttccggtggt    8640
cagtcatgtg tgtcatctgt acggttttcg ggctctggtg gaaatggata ctgtctgtct    8700
tctctcatag gtggtattca cagccaacga ttccggcccc cgccactaca ccatcgccgc    8760
cctgctgagc ccctactcct attccaccac ggctgtcgtc accaatccca aggaatgagg    8820
```

```
gacttctcca gaggatctga aggacgaggg atgggatttc atgtaaccaa gagtattcca    8880
tttttactaa agcagtgttt tcacctcata agctatgtta ggagtccagg cagagacaat    8940
aaaacattcc tgtgaaaggc acttttcatt ccattttaac ttgattttt aaattccctt     9000 attgtccctt ccaaaaaac aagaatcaaa attctacaaa gaagcaaagg aattctagaa    9060
cgtatctggg cagaacgcta ggagagatcc aaatttccaa tttattgcaa gcaaagcaca    9120
tattaaatat gatctgcagt catcaaaaag acacattctg taaatgagaa agccttattt    9180
tcctgtaacc ttcagtgaat agcaaaagac acattctaag ggcccacttc tttactgtgg    9240
gcatttcttt tcttttcttt tttttttttt cttttctttt ccttttttga dacaaagtct    9300
cactctgtcg cccaggctag aatgcagtgg tgtgatctca gctcactgca acctctgctt    9360
ccgggttcaa gcgattctcc tgcctcagcc tcccaagcag ctgggattac aggcgcccgc    9420
caccacacct ggctaatttt tctacttgta gtagagatgg ggtttcgcca tgttggctag    9480
gctggcctcg aactcctgac ctcaggtgat ccacctgcct cagcctccca aagtgctggg    9540
attacaggca tgagccacta cacccggccc ctactctggg catttctttg atttaagaga    9600
agggcagctc caacaagaca cacctgcaga gactcaggcc atccgatcag ttcaggctag    9660
atccacgctg caatcagcca ggtcagggac aaaccaaaga accccacaca cccaatttac    9720
ttaggctgat ccaaaatcca tgtatggaga actcacatgc agcaggcact attttaggtg    9780
atctgaacat aaagaatagg acccagtacc tgcatttatt taaagaactc acaatctttt    9840
gaaaagataa ctgtttcatc atggtttggc aggaggctat ggtacaaggc acagcaaagg    9900
taagaaggag aaaaaaccaa caccctagag aaatcagaaa atgactctga ataggtgtca    9960
cttaatctga gtgttggtaa tttgtcagat agacaaggga a                       10001
```

```
<210> SEQ ID NO 5
<211> LENGTH: 19
<212> TYPE: DNA
<213> ORGANISM: Artificial sequence
<220> FEATURE:
<223> OTHER INFORMATION: Primer

<400> SEQUENCE: 5
ccctgctgag cccctactc                                                  19

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
tccctcattc cttgggattg                                                 20

<210> SEQ ID NO 7
<211> LENGTH: 21
<212> TYPE: DNA
<213> ORGANISM: Artificial sequence
<220> FEATURE:
<223> OTHER INFORMATION: Probe

<400> SEQUENCE: 7
attccaccac ggctgtcgtc a                                               21

<210> SEQ ID NO 8
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
actggttttc ccagaggcaa                                           20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
gactcactgg ttttcccaga                                           20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
tgaataccac ctctgcatgc                                           20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
ccgtggtgga ataggagtag                                           20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
agccgtggtg gaataggagt                                           20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
cgacagccgt ggtggaatag                                           20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
```
ttggtgacga cagccgtggt                                                    20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 15
gattggtgac gacagccgtg                                                    20

<210> SEQ ID NO 16
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 16
gggattggtg acgacagccg                                                    20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
tgggattggt gacgacagcc                                                    20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
attccttggg attggtgacg                                                    20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
cattccttgg gattggtgac                                                    20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
tcattccttg ggattggtga                                                    20

<210> SEQ ID NO 21
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 21
agaagtccct cattccttgg                                                    20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
gtccttcagg tccactggag                                                    20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
catccctcgt ccttcaggtc                                                    20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
tacatgaaat cccatccctc                                                    20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
cttggttaca tgaaatccca                                                    20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
aatactcttg gttacatgaa                                                    20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 27
ttagtaaaaa tggaatactc                                                    20
```

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
actgctttag taaaaatgga                                          20

<210> SEQ ID NO 29
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 29
tgaaaacact gctttagtaa                                          20

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
tatgaggtga aaacactgct                                          20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
tggacttcta acatagcata                                          20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
tctctgcctg gacttctaac                                          20

<210> SEQ ID NO 33
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 33
ttattgtctc tgcctggact                                          20

<210> SEQ ID NO 34
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 34
tgcctttcac aggaatgttt                                              20

<210> SEQ ID NO 35
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 35
gtgcctttca caggaatgtt                                              20

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
cagaggagga gcagacgatg                                              20

<210> SEQ ID NO 37
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 37
tctagaactt tgaccatcag                                              20

<210> SEQ ID NO 38
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 38
ttttcccaga ggcaaatggc                                              20

<210> SEQ ID NO 39
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 39
tccagactca ctggttttcc                                              20

<210> SEQ ID NO 40
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 40
tatcccttct acaaattcct                                              20

```
<210> SEQ ID NO 41
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 41
atttccactt tgtatatccc                                               20

<210> SEQ ID NO 42
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 42
tggtgtctat ttccactttg                                               20

<210> SEQ ID NO 43
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 43
cagtaagatt tggtgtctat                                               20

<210> SEQ ID NO 44
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 44
cttccagtaa gatttggtgt                                               20

<210> SEQ ID NO 45
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 45
ccacctctgc atgctcatgg                                               20

<210> SEQ ID NO 46
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 46
tgtgaatacc acctctgcat                                               20

<210> SEQ ID NO 47
<211> LENGTH: 20
<212> TYPE: DNA
<213> ORGANISM: Artificial sequence
<220> FEATURE:
<223> OTHER INFORMATION: Synthetic oligonucleotide
```

<400> SEQUENCE: 47
gctgtgaata ccacctctgc                                              20

<210> SEQ ID NO 48
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 48
cgttggctgt gaataccacc                                              20

<210> SEQ ID NO 49
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 49
cagccgtggt ggaataggag                                              20

<210> SEQ ID NO 50
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 50
gacagccgtg gtggaatagg                                              20

<210> SEQ ID NO 51
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 51
acgacagccg tggtggaata                                              20

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
gacgacagcc gtggtggaat                                              20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
tgacgacagc cgtggtggaa                                              20

<210> SEQ ID NO 54
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 54
gtgacgacag ccgtggtgga                                          20

<210> SEQ ID NO 55
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 55
ggtgacgaca gccgtggtgg                                          20

<210> SEQ ID NO 56
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 56
tggtgacgac agccgtggtg                                          20

<210> SEQ ID NO 57
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 57
attggtgacg acagccgtgg                                          20

<210> SEQ ID NO 58
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 58
ggattggtga cgacagccgt                                          20

<210> SEQ ID NO 59
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 59
ttgggattgg tgacgacagc                                          20

<210> SEQ ID NO 60
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 60
```
cttgggattg gtgacgacag                    20

<210> SEQ ID NO 61
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 61
ccttgggatt ggtgacgaca                    20

<210> SEQ ID NO 62
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 62
tccttgggat tggtgacgac                    20

<210> SEQ ID NO 63
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 63
ttccttggga ttggtgacga                    20

<210> SEQ ID NO 64
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 64
ctcattcctt gggattggtg                    20

<210> SEQ ID NO 65
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 65
cctcattcct tgggattggt                    20

<210> SEQ ID NO 66
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 66
ccctcattcc ttgggattgg                    20

<210> SEQ ID NO 67
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 67
tccctcattc cttgggattg                                               20

<210> SEQ ID NO 68
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 68
gtccctcatt ccttgggatt                                               20

<210> SEQ ID NO 69
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 69
agtccctcat tccttgggat                                               20

<210> SEQ ID NO 70
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 70
aagtccctca ttccttggga                                               20

<210> SEQ ID NO 71
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 71
gaagtccctc attccttggg                                               20

<210> SEQ ID NO 72
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 72
gagaagtccc tcattccttg                                               20

<210> SEQ ID NO 73
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 73
ggagaagtcc ctcattcctt                                               20
```

<210> SEQ ID NO 74
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 74
acatgaaatc ccatccctcg                                               20

<210> SEQ ID NO 75
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 75
ttacatgaaa tcccatccct                                               20

<210> SEQ ID NO 76
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 76
gttacatgaa atcccatccc                                               20

<210> SEQ ID NO 77
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 77
ggttacatga aatcccatcc                                               20

<210> SEQ ID NO 78
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 78
tggttacatg aaatcccatc                                               20

<210> SEQ ID NO 79
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 79
ttggttacat gaaatcccat                                               20

<210> SEQ ID NO 80
<211> LENGTH: 20
<212> TYPE: DNA
<213> ORGANISM: Artificial sequence
<220> FEATURE:
<223> OTHER INFORMATION: Synthetic oligonucleotide

```
<400> SEQUENCE: 80
tcttggttac atgaaatccc                                              20

<210> SEQ ID NO 81
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 81
ctcttggtta catgaaatcc                                              20

<210> SEQ ID NO 82
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 82
actcttggtt acatgaaatc                                              20

<210> SEQ ID NO 83
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 83
tactcttggt tacatgaaat                                              20

<210> SEQ ID NO 84
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 84
atactcttgg ttacatgaaa                                              20

<210> SEQ ID NO 85
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 85
gaatactctt ggttacatga                                              20

<210> SEQ ID NO 86
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 86
ggaatactct tggttacatg                                              20

<210> SEQ ID NO 87
```

```
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 87
tggaatactc ttggttacat                                              20

<210> SEQ ID NO 88
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 88
atggaatact cttggttaca                                              20

<210> SEQ ID NO 89
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 89
aatggaatac tcttggttac                                              20

<210> SEQ ID NO 90
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 90
aaatggaata ctcttggtta                                              20

<210> SEQ ID NO 91
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 91
aaaatggaat actcttggtt                                              20

<210> SEQ ID NO 92
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 92
aaaaatggaa tactcttggt                                              20

<210> SEQ ID NO 93
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 93
```
taaaaatgga atactcttgg 20

<210> SEQ ID NO 94
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 94
gtaaaaatgg aatactcttg 20

<210> SEQ ID NO 95
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 95
agtaaaaatg gaatactctt 20

<210> SEQ ID NO 96
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 96
tagtaaaaat ggaatactct 20

<210> SEQ ID NO 97
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 97
tttagtaaaa atggaatact 20

<210> SEQ ID NO 98
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 98
ctttagtaaa aatggaatac 20

<210> SEQ ID NO 99
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 99
gctttagtaa aaatggaata 20

<210> SEQ ID NO 100
<211> LENGTH: 20
<212> TYPE: DNA

```
<213> ORGANISM: Artificial sequence
<220> FEATURE:
<223> OTHER INFORMATION: Synthetic oligonucleotide

<400> SEQUENCE: 100
tgctttagta aaaatggaat                                                  20

<210> SEQ ID NO 101
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 101
ctgctttagt aaaaatggaa                                                  20

<210> SEQ ID NO 102
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 102
cactgcttta gtaaaaatgg                                                  20

<210> SEQ ID NO 103
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 103
acactgcttt agtaaaaatg                                                  20

<210> SEQ ID NO 104
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 104
aacactgctt tagtaaaaat                                                  20

<210> SEQ ID NO 105
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 105
aaacactgct ttagtaaaaa                                                  20

<210> SEQ ID NO 106
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 106
aaaacactgc tttagtaaaa                                                  20
```

<210> SEQ ID NO 107
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 107
gaaaacactg ctttagtaaa                                         20

<210> SEQ ID NO 108
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 108
gtgaaaacac tgctttagta                                         20

<210> SEQ ID NO 109
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 109
ggtgaaaaca ctgctttagt                                         20

<210> SEQ ID NO 110
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 110
aggtgaaaac actgctttag                                         20

<210> SEQ ID NO 111
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 111
gaggtgaaaa cactgcttta                                         20

<210> SEQ ID NO 112
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 112
tgaggtgaaa acactgcttt                                         20

<210> SEQ ID NO 113
<211> LENGTH: 20
<212> TYPE: DNA
<213> ORGANISM: Artificial sequence
<220> FEATURE:

<223> OTHER INFORMATION: Synthetic oligonucleotide

<400> SEQUENCE: 113
atgaggtgaa aacactgctt                                         20

<210> SEQ ID NO 114
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 114
tttattgtct ctgcctggac                                         20

<210> SEQ ID NO 115
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 115
ttttattgtc tctgcctgga                                         20

<210> SEQ ID NO 116
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 116
gttttattgt ctctgcctgg                                         20

<210> SEQ ID NO 117
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 117
tgttttattg tctctgcctg                                         20

<210> SEQ ID NO 118
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 118
atgttttatt gtctctgcct                                         20

<210> SEQ ID NO 119
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 119
aatgttttat tgtctctgcc                                         20

```
<210> SEQ ID NO 120
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 120
gaatgtttta ttgtctctgc                                              20

<210> SEQ ID NO 121
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 121
ggaatgtttt attgtctctg                                              20

<210> SEQ ID NO 122
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 122
aggaatgttt tattgtctct                                              20

<210> SEQ ID NO 123
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 123
caggaatgtt ttattgtctc                                              20

<210> SEQ ID NO 124
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 124
acaggaatgt tttattgtct                                              20

<210> SEQ ID NO 125
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 125
gatgtcacag aaacactcac                                              20

<210> SEQ ID NO 126
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 126
gcaaagctgg aaggagtcac                                                   20

<210> SEQ ID NO 127
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 127
gaacttcatt ctttttgaag                                                   20

<210> SEQ ID NO 128
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 128
agcttcctta atatcatatc                                                   20

<210> SEQ ID NO 129
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 129
tatagggcca gaatataatc                                                   20

<210> SEQ ID NO 130
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 130
actaagcctt ttaaagatta                                                   20

<210> SEQ ID NO 131
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 131
tggaattact gaaaagatgt                                                   20

<210> SEQ ID NO 132
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 132
accagggatg tgtataatga                                                   20

<210> SEQ ID NO 133
<211> LENGTH: 20
```

```
<212> TYPE: DNA
<213> ORGANISM: Artificial sequence
<220> FEATURE:
<223> OTHER INFORMATION: Synthetic oligonucleotide

<400> SEQUENCE: 133
tccctactca gtataacaca                                        20

<210> SEQ ID NO 134
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 134
gatcagagtg aaaggattta                                        20

<210> SEQ ID NO 135
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 135
gggaagataa aaccaagtcc                                        20

<210> SEQ ID NO 136
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 136
taaattcttt agcagatgat                                        20

<210> SEQ ID NO 137
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 137
aatgatgctc aggttcctgg                                        20

<210> SEQ ID NO 138
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 138
ttggtgttac ccagggacac                                        20

<210> SEQ ID NO 139
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 139
```
aaagtgttca ttaggcaaaa                                               20

<210> SEQ ID NO 140
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 140
ggcattttat ataaacataa                                               20

<210> SEQ ID NO 141
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 141
aagaacattg gaatattttt                                               20

<210> SEQ ID NO 142
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 142
gttggaaatt gcttcccatt                                               20

<210> SEQ ID NO 143
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 143
agtggaaaac ctaaagtagg                                               20

<210> SEQ ID NO 144
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 144
ttcccctcaa ctaagtcaga                                               20

<210> SEQ ID NO 145
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 145
cctataaggt gtgaaagtct                                               20

<210> SEQ ID NO 146
<211> LENGTH: 20
<212> TYPE: DNA
<213> ORGANISM: Artificial sequence

```
<220> FEATURE:
<223> OTHER INFORMATION: Synthetic oligonucleotide

<400> SEQUENCE: 146
tgtaagttca agtcatgtta                                                  20

<210> SEQ ID NO 147
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 147
gtgttgccaa gaatcacttg                                                  20

<210> SEQ ID NO 148
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 148
aaaacactta taattgtgtc                                                  20

<210> SEQ ID NO 149
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 149
ctttgacaag ttatttgact                                                  20

<210> SEQ ID NO 150
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 150
atccatgact aagccagaga                                                  20

<210> SEQ ID NO 151
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 151
atggttccca tcaggctgag                                                  20

<210> SEQ ID NO 152
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 152
gcatttatca gaagaagctg                                                  20
```

```
<210> SEQ ID NO 153
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 153
ttgaccttca gcccacttga                                                   20

<210> SEQ ID NO 154
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 154
aggaagtgag aatcacctaa                                                   20

<210> SEQ ID NO 155
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 155
agaagacagt aaagatgtgt                                                   20

<210> SEQ ID NO 156
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 156
aaattgtgga tcaaaatgct                                                   20

<210> SEQ ID NO 157
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 157
aaccagactt gaattattgt                                                   20

<210> SEQ ID NO 158
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 158
agtggctgcc aaccacagac                                                   20

<210> SEQ ID NO 159
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 159
ggaagtccag tgccaactta                                                  20

<210> SEQ ID NO 160
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 160
atccatttcc accagagccc                                                  20

<210> SEQ ID NO 161
<211> LENGTH: 24
<212> TYPE: DNA
<213> ORGANISM: Artificial sequence
<220> FEATURE:
<223> OTHER INFORMATION: Primer

<400> SEQUENCE: 161
cttgctggac tggtatttgt gtct                                             24

<210> SEQ ID NO 162
<211> LENGTH: 25
<212> TYPE: DNA
<213> ORGANISM: Artificial sequence
<220> FEATURE:
<223> OTHER INFORMATION: Primer

<400> SEQUENCE: 162
agaactttga ccatcagagg acact                                            25

<210> SEQ ID NO 163
<211> LENGTH: 22
<212> TYPE: DNA
<213> ORGANISM: Artificial sequence
<220> FEATURE:
<223> OTHER INFORMATION: Probe

<400> SEQUENCE: 163
ccctacgggc accggtgaat cc                                               22

<210> SEQ ID NO 164
<211> LENGTH: 612
<212> TYPE: DNA
<213> ORGANISM: Macaca fascicularis
<220> FEATURE:
<221> NAME/KEY: CDS
<222> LOCATION: (27)..(470)

<400> SEQUENCE: 164
acagaagtcc actcgttctt ggcagg atg gct tct cat cgt ctg ctc ctt ctc       53
                            Met Ala Ser His Arg Leu Leu Leu Leu
                              1               5 tgc ctc gct gga ctg gta ttt gtg tct gaa gct ggt cct acg ggc gtt       101
Cys Leu Ala Gly Leu Val Phe Val Ser Glu Ala Gly Pro Thr Gly Val
 10              15                  20                  25 gat gaa tcc aag tgt cct ctg atg gtc aaa gtt cta gat gcc gtc cga       149
Asp Glu Ser Lys Cys Pro Leu Met Val Lys Val Leu Asp Ala Val Arg
                 30                  35                  40 ggc agt cct gcc gtc aat gtg gct gtg aac gtg ttc aaa aag gct gct       197
Gly Ser Pro Ala Val Asn Val Ala Val Asn Val Phe Lys Lys Ala Ala
             45                  50                  55
```

```
gat gag acc tgg gcg cca ttt gcc tct ggg aaa acc agt gag tct gga      245
Asp Glu Thr Trp Ala Pro Phe Ala Ser Gly Lys Thr Ser Glu Ser Gly
         60                  65                  70 gag ctg cat ggg ctc aca act gag gag gaa ttt gta gaa ggg ata tac      293
Glu Leu His Gly Leu Thr Thr Glu Glu Glu Phe Val Glu Gly Ile Tyr
 75                  80                  85 aaa gtg gaa ata gac acc aaa tct tac tgg aag tca ctt ggc atc tcc      341
Lys Val Glu Ile Asp Thr Lys Ser Tyr Trp Lys Ser Leu Gly Ile Ser
 90                  95                 100                 105 cca ttc cat gag cat gca gag gtg gta ttc aca gcc aac gat tcc ggc      389
Pro Phe His Glu His Ala Glu Val Val Phe Thr Ala Asn Asp Ser Gly
             110                 115                 120 ccc cgc cac tac acc atc gcc cgc ctg ctg agc ccc tac tcc tat tcc      437
Pro Arg His Tyr Thr Ile Ala Arg Leu Leu Ser Pro Tyr Ser Tyr Ser
             125                 130                 135 acc acg gct gtc gtc acc aat ccc aag gaa tga gggacttctc cagaggatct    490
Thr Thr Ala Val Val Thr Asn Pro Lys Glu
             140                 145 gaaggacgag ggatgggatt tcatgtaacc aagagtattc cattttttact aaagcagtgt   550 tttcacctca taagctatgt taggagtcca ggcagagaca ataaaacatt cctgtgaaag    610
gc                                                                   612

<210> SEQ ID NO 165
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 165
ccttccctga aggttcctcc                                                 20

<210> SEQ ID NO 166
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 166
gcgtttgctc ttcttcttgc gttttttt                                        27

<210> SEQ ID NO 167
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 167
ttttattgtc tctgcctg                                                   18

<210> SEQ ID NO 168
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 168
tacaaatggg atgctactgc                                                 20
```

```
<210> SEQ ID NO 169
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 169
ggaatcccaa gcctcaaacg                                                    20

<210> SEQ ID NO 170
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 170
cgtccttcag gtccactgga                                                    20

<210> SEQ ID NO 171
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 171
atatgaggtg aaaacactgc                                                    20

<210> SEQ ID NO 172
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 172
tattgtctct gcctggactt                                                    20

<210> SEQ ID NO 173
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 173
cacaggaatg ttttattgtc                                                    20

<210> SEQ ID NO 174
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 174
cctttcacag gaatgtttta                                                    20

<210> SEQ ID NO 175
<211> LENGTH: 20
<212> TYPE: DNA
<213> ORGANISM: Artificial sequence
<220> FEATURE:
<223> OTHER INFORMATION: Synthetic oligonucleotide
```

```
<400> SEQUENCE: 175
gcctttcaca ggaatgtttt                                                        20

<210> SEQ ID NO 176
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 176
agtgcctttc acaggaatgt                                                        20

<210> SEQ ID NO 177
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 177
aagtgccttt cacaggaatg                                                        20
```